United States Patent
Siegrist et al.

(10) Patent No.: US 10,065,929 B2
(45) Date of Patent: *Sep. 4, 2018

(54) PYRAZOLE COMPOUNDS AND THEIR USE AS T-TYPE CALCIUM CHANNEL BLOCKERS

(71) Applicant: IDORSIA PHARMACEUTICALS LTD, Allschwil (CH)

(72) Inventors: Romain Siegrist, Allschwil (CH); Bibia Heidmann, Allschwil (CH); Simon Stamm, Allschwil (CH); John Gatfield, Allschwil (CH); Olivier Bezencon, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/847,611

(22) Filed: Dec. 19, 2017

(65) Prior Publication Data

US 2018/0105496 A1 Apr. 19, 2018

Related U.S. Application Data

(63) Continuation of application No. 15/316,100, filed as application No. PCT/IB2015/054164 on Jun. 2, 2015, now Pat. No. 9,932,314.

(30) Foreign Application Priority Data

Jun. 3, 2014 (WO) .................. PCT/IB2014/061901

(51) Int. Cl.
| | |
|---|---|
| *A61K 31/4155* | (2006.01) |
| *A61K 31/4439* | (2006.01) |
| *A61K 31/415* | (2006.01) |
| *A61P 3/10* | (2006.01) |
| *A61P 9/00* | (2006.01) |
| *A61P 15/00* | (2006.01) |
| *C07D 231/40* | (2006.01) |
| *C07D 403/06* | (2006.01) |
| *C07D 471/04* | (2006.01) |
| *C07D 413/12* | (2006.01) |
| *C07D 405/12* | (2006.01) |
| *C07D 401/12* | (2006.01) |
| *C07D 401/06* | (2006.01) |
| *C07D 405/14* | (2006.01) |
| *C07D 401/14* | (2006.01) |
| *C07D 403/12* | (2006.01) |

(52) U.S. Cl.
CPC ......... *C07D 231/40* (2013.01); *C07D 401/06* (2013.01); *C07D 401/12* (2013.01); *C07D 401/14* (2013.01); *C07D 403/06* (2013.01); *C07D 403/12* (2013.01); *C07D 405/12* (2013.01); *C07D 405/14* (2013.01); *C07D 413/12* (2013.01); *C07D 471/04* (2013.01)

(58) Field of Classification Search
CPC combination set(s) only.
See application file for complete search history.

(56) References Cited

U.S. PATENT DOCUMENTS

| | | | |
|---|---|---|---|
| 7,935,699 B2 | 5/2011 | Berthel et al. | |
| 8,501,955 B2* | 8/2013 | Bhuniya | C07D 213/80 546/114 |
| 2008/0146625 A1 | 6/2008 | Berthel et al. | |
| 2009/0239845 A1* | 9/2009 | Conway | C07D 231/14 514/217.01 |
| 2009/0325987 A1 | 12/2009 | Muthuppalniappan et al. | |
| 2010/0094006 A1 | 4/2010 | Nam et al. | |
| 2010/0197591 A1 | 8/2010 | Aspnes et al. | |
| 2010/0310493 A1 | 12/2010 | Bhuniya et al. | |

(Continued)

FOREIGN PATENT DOCUMENTS

| | | |
|---|---|---|
| EP | 2 402 327 | 1/2012 |
| EP | 2 530 078 | 12/2012 |

(Continued)

OTHER PUBLICATIONS

U.S. Appl. No. 15/510,980, filed Mar. 13, 2017, Bezencon et al.

(Continued)

*Primary Examiner* — Amanda L Aguirre
(74) *Attorney, Agent, or Firm* — Hoxie & Associates LLC

(57) ABSTRACT

The invention relates to compounds of formula (I)

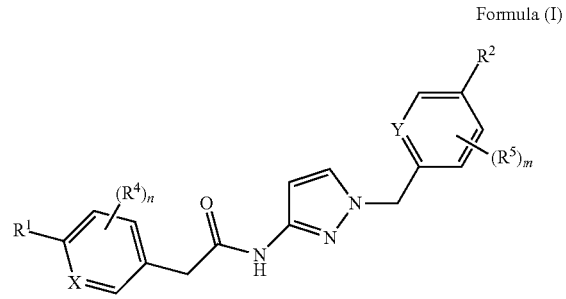

Formula (I)

wherein X, Y, $R^1$, $R^2$, $(R^4)_n$, and $(R^5)_m$ are as defined in the description, and to pharmaceutically acceptable salts of such compounds. These compounds are useful as calcium T-channel blockers.

30 Claims, No Drawings

(56) References Cited

U.S. PATENT DOCUMENTS

| | | | |
|---|---|---|---|
| 2012/0289698 | A1 | 11/2012 | Ashcraft et al. |
| 2015/0329533 | A1 | 11/2015 | Nam et al. |
| 2016/0106102 | A1 | 4/2016 | Kuebbeler et al. |
| 2017/0096399 | A1 | 4/2017 | Siegrist et al. |

FOREIGN PATENT DOCUMENTS

| | | |
|---|---|---|
| EP | 2 848 615 | 3/2015 |
| JP | 2012-524754 | 10/2012 |
| JP | 2012-524755 | 10/2012 |
| JP | 2013-507350 | 3/2013 |
| WO | WO 1996/000218 | 1/1996 |
| WO | WO 1998/028269 | 7/1998 |
| WO | WO 2002/000651 | 1/2002 |
| WO | WO 2002/053101 | 7/2002 |
| WO | WO 2002/053160 | 7/2002 |
| WO | WO 2003/037274 | 5/2003 |
| WO | WO 2003/051315 | 6/2003 |
| WO | WO 2003/051833 | 6/2003 |
| WO | WO 2003/101423 | 12/2003 |
| WO | WO 2004/089303 | 10/2004 |
| WO | WO 2004/089306 | 10/2004 |
| WO | WO 2004/099154 | 11/2004 |
| WO | WO 2005/056532 | 6/2005 |
| WO | WO 2006/018725 | 2/2006 |
| WO | WO 2006/066968 | 6/2006 |
| WO | WO 2006/114274 | 11/2006 |
| WO | WO 2006/114313 | 11/2006 |
| WO | WO 2007/073497 | 6/2007 |
| WO | WO 2007/120729 | 10/2007 |
| WO | WO 2008/012227 | 1/2008 |
| WO | WO 2008/085888 | 7/2008 |
| WO | WO 2008/156726 | 12/2008 |
| WO | WO 2009/054982 | 4/2009 |
| WO | WO 2009/054983 | 4/2009 |
| WO | WO 2009/054984 | 4/2009 |
| WO | WO 2009/118596 | 10/2009 |
| WO | WO 2009/121623 | 10/2009 |
| WO | WO 2010/073011 | 7/2010 |
| WO | WO 2010/075376 | 7/2010 |
| WO | WO 2010/122088 | 10/2010 |
| WO | WO 2010/122089 | 10/2010 |
| WO | WO 2010/139731 | 12/2010 |
| WO | WO 2011/022315 | 2/2011 |
| WO | WO 2011/042797 | 4/2011 |
| WO | WO 2011/053542 | 5/2011 |
| WO | WO 2011/084402 | 7/2011 |
| WO | WO 2012/027322 | 3/2012 |
| WO | WO 2012/077932 | 6/2012 |
| WO | WO 2012/120397 | 9/2012 |
| WO | WO 2013/011033 | 1/2013 |
| WO | WO 2013/134142 | 9/2013 |
| WO | WO 2014/179564 | 11/2014 |
| WO | WO 2014/187928 | 11/2014 |
| WO | WO 2016/041892 | 3/2016 |
| WO | WO 2016/123533 | 8/2016 |
| WO | WO 2016/138472 | 9/2016 |

OTHER PUBLICATIONS

Anderson et al., "Thalamic Cav3.1 T-type Ca2 channel plays a crucial role in stabilizing sleep", PNAS, vol. 102(5), p. 1743-1748, (2005).
Bateman et al., "The discovery of MK-0674, an orally bioavailable cathepsin K inhibitor", Bioorg. Med. Chem. Lett., vol. 20, p. 887-892, (2010).
Becker et al., "Transcriptional Upregulation of Cav3.2 Mediates Epileptogenesis in the Pilocarpine Model of Epilepsy", J. Neurosci., vol. 28(49), p. 13341-13353, (2008).
Benoff et al., "The Effect of calcium ion channel blockers on sperm fertilization potential", Fertility and Sterility, vol. 62, p. 606-617, (1994).
Berg et al., "Revised terminology and concepts for organization of seizures and epilepsies: Report of the ILAE Commission on Classification and Terminology", Epilepsia, vol. 51(4), p. 676-685, (2010).
Brave et al., "Posttranslational Mechanisms of Peripheral Sensitization", J. Neurobiol., vol. 61, p. 88-106, (2004).
Bourinet et al., "Silencing of the Cav3.2 T-type calcium channel gene in sensory neurons demonstrates its major role in nociception", The Embo Journal, vol. 24(2), p. 315-324, (2005).
Broicher et al., "Spike in the Thalamus of a Rat Model of Absence Epilepsy", Molecular and Cellular Neuroscience, vol. 39(3), p. 1-66, (2008).
Cavelier et al., "Participation of low-threshold Ca2+ spike in the Pukinje cells complex spike", Neuroreport., vol. 19(3), p. 299-303, (2008).
Cheong et al., "T-type Ca2+ channels in absence epilepsy", Eur J Physiol., vol. 466(4), p. 719-734, (2014).
Cho et al., "The SAR analysis of TRPV1 agonists with the a-methylated B-region", Bioorg. Med. Chem. Lett., vol. 22, p. 5227-5231, (2012).
Coderre et al. "Contribution of central neuroplasticity to pathological Pain : Review of clinical and experimental evidence", Pain, vol. 52, p. 259-285, (1993).
Destexhe et al., "A Model of Spindle Rhythmicity in the Isolated Thalamic Reticular Nucleus", Journal of Neurophysiology, vol. 72(2), p. 803-818, (1994).
Flatters et al., "T-type calcium channels: a potential target for the treatment of chronic pain", Drugs of the Future, vol. 30(6), p. 573-580, (2005).
Giordanetto et al., "T-type calcium channels inhibitors: a patent review", Expert Opin. Ther. Patents, vol. 21(1), p. 85-101, (2011).
Graef et al., "An Acquired Channelopathy Involving Thalamic T-Type Ca2+ Channels after Status Epilepticus", J. Neurosci., vol. 29(14), p. 4430-4441, (2009).
Greene et al., "Protective Groups in Organic Synthesis", P.G.M. Wuts, Wiley-Interscience, (1999).
Gutnick et al., "Low threshold calcium spikes, intrinsic neuronal oscillation and rhythm generation in the CNS", J. Neurosci. Methods, vol. 28, p. 93-99, (1989).
Hall et al., "Non-acidic pyrazole EP1 receptor antagonists with in vivo analgesic efficacy", Bioorg. Med. Chem. Lett., vol. 18, p. 3392-3399, (2008).
Hall et al., "Voltage-dependent calcium currents are enhanced in dorsal root ganglion neurones from the Bio Bred/Worchester diabetic rat", J. Physiol., vol. 486(2), p. 313-322, (1995).
Heron et al., "Extended Spectrum of Idiopathic Generalized Epilepsies Associated with CACNA1H Functional Variants", Ann Neurol., vol. 62(6), p. 560-568, (2007).
Huguenard et al., "Intrathalamic Rhythmicity Studied in vitro: Nominal T-Current Modulation Causes Robust Antioscillatory Effects", The Journal of Neuroscience, vol. 14(9), p. 5485-5502, (1994).
Iftinca et al., "Neuronal T-type calcium channels: What's new?", Journal of Medicine and Life, vol. 4(2), p. 126-138, (2011).
Iftinca et al., "Regulation of neuronal T-type calcium channels", Trends Pharmacol. Sci., vol. 30(1), p. 32-40, (2009).
International Search Report of International Appliction No. PCT/IB2015/054164, dated Aug. 3, 20i5, 3 pages.
Jagodic et al., "Upregulation of the T-Type Calcium Current in Small Rat Sensory Neurons After Chronic Constrictive Injury of the Sciatic Nerve", J. Neurophysiol., vol. 99, p. 3151-3156, (2008).
Jagodic et al., "Cell-SpecificAlterations of T-Type Calcium Current in Painful Diabetic Neuropathy Enhance Excitability of SensoryNeurons", The Journal of Neuroscience, vol. 27(12), p. 3305-3316, (2007).
Jeanmonod et al., "Low-threshold calcium spike bursts in the human thalamus Common physiopathology for sensory, motor and limbic positive symptoms", Brain, vol. 119, p. 363-375, (1996).
Jevtovic-Todorovic et al., "The role of Peripheral T-type calcium channels in pain transmission", Cell Calcium, vol. 40, p. 197-203, (2006).

(56) References Cited

OTHER PUBLICATIONS

Khosravani et al., "Voltage-Gated Calcium Channels and Idiopathic Generalized Epilepsies", Physiol. Rev., vol. 86(3), p. 941-966, (2006).
Kim et al., "Lack of the Burst Firing of Thalamocortical Relay Neurons and Resistance to Absence Seizures in Mice Lacking 1G T-Type Ca2 Channels", Neuron, vol. 31(1), p. 35-45, (2001).
Kiss et al., "Discovery of a Long-Acting, Peripherally Selective Inhibitor of Catechol-O-methyltransferase", J. Med. Chem., vol. 53, p. 3396-3411, (2010).
Lambert et al., "The many faces of T-type calcium channels", Eur. J. Physiol., vol. 466(3), p. 415-423, (2014).
Latham et al., "Selective T-Type Calcium Channel Blockade Alleviates Hyperalgesia in ob/ob Mice Diabetes", vol. 58, p. 2656-2665, (2009).
Lee et al., "Lack of delta waves and sleep disturbances during non-rapid eye movement sleep in mice lacking 1G-subunit of T-type calcium channels", PNAS, vol. 101(52), p. 18195-18199, (2004).
Lee et al. "Synthesis and anti-proliferative activity evaluation of N3-acyl-N5-aryl-3, 5-diaminoindazole analogues as anti-head and neck cancer agent" J. Pharm. Sci., vol. 22, p. 4-9, (2014).
Llinas et al., "Oscillatory properties of guinea-pig inferior olivary neurones and their pharmacological modulation: an in vitro study", J. Physiol., vol. 376, p. 163-182, (1986).
Lory et al., "Calcium channelopathies in inherited neurological disorders: Relevance to drug screening for acquired channel disorders", IDrugs, vol. 13(7), p. 467-471, (2010).
Mcgivern et al., "Targeting N-type and T-type calcium channels for the treatment of pain", Drug Discovery Today, vol. 11(5-6), p. 245-253, (2006).
Messinger et al., "In vivo silencing of the CaV3.2 T-type calcium channels in sensory neurons alleviates hyperalgesia in rats with streptozocin-induced diabetic neuropathy", Pain, vol. 145, p. 1-12, (2009).
Miwa et al., "T-Type Calcium Channel as a New Therapeutic Target for Tremor", Cerebellum, vol. 10, p. 563-569, (2011).
Nelson et al., "The Role of T-Type Calcium Channels in Epilepsy and Pain", Curr. Pharm. Des., vol. 12, p. 2189-2197, (2006).
Page et al., "Novel benzimidazole derivatives as selective CB2 agonists", Bioorg. Med. Chem. Lett., vol. 18, p. 3695-3700, (2008).
Park et al., "Supporting Information", PNAS, vol. 107, p. 1-6, (2010).
Park et al., "Cav3.1 is a tremor rhythm pacemaker in the inferior olive", PNAS, vol. 107 (23), p. 10731-10736, (2010).
Powell et al., "ACav3.2 T-Type Calcium Channel Point Mutation Has Splice-Variant-Specific Effects on Function and Segregates with Seizure Expression in a Polygenic Rat Model of Absence Epilepsy", The Journal of Neuroscience, vol. 29(2), p. 371-380, (2009).
Reger et al., "Pyridyl amides as potent inhibitors of T-type calcium channels", Bioorg. Med. Chem. Lett., vol. 21, p. 1692-1696, (2011).
Remington, The Science and Practice of Pharmacy, 21st Edition (2005), Part 5, "Pharmaceutical Manufacturing" [published by Lippincott Williams & Wilkins].
Repka et al., "Enantioselective Synthesis of Pyrroloindolines by a Formal [3+2] Cycloaddition Reaction", J Am Chem. Soc., vol. 132(41), p. 14418-14420, (2010).
Song et al., "Role of the 1G T-Type Calcium Channel in Spontaneous Absence Seizures in Mutant Mice", Neurobiology of Disease, vol. 24(22), p. 5249-5257, (2004).

Stahl et al., "Handbook of Pharmaceutical Salts. Properties, Selection and Use," IUPAC, (2008).
Steriade et al., "Sleep, epilepsy and thalamic reticular inhibitory neurons", Trends in Neuroscience, vol. 28(6), p. 317-324, (2005).
Su et al., "Upregulation of a T-Type Ca2 Channel Causes a Long-Lasting Modification of Neuronal Firing Mode after Status Epilepticus", J. Neurosci., vol. 22(9), p. 3645-3655, (2002).
Talley et al., "Differential Distribution of Three Members of a Gene Family Encoding Low Voltage-Activated (T-Type) Calcium Channels", J. Neurosci., vol. 19(6), p. 1895-1911, (1999).
Talley et al., "Low-voltage-activated calcium channel subunit expression in a genetic model of absence epilepsy in the rat", Molecular Brain Research, vol. 75, p. 159-165, (2000).
Todorovic et al., "Regulation of T-Type Calcium Channels in the Peripheral Pain Pathway", Channels, vol. 1(4), p. 238-245, (2007).
Todorovic et al., "T-type voltage-gated calcium channels as targets for the development of novel pain therapies", Br. J. Pharmacol., vol. 163, p. 484-495, (2011).
Tsakiridou et al., "Selective Increase in T-Type Calcium Conductance of Reticular Thalamic Neurons in a Rat Model of Absence Epilepsy", The Journal of Neuroscience, vol. 15(4), p. 3110-3117, (1995).
Uslaner et al., "T-Type Calcium Channel Antagonism Decreases Motivation for Nicotine and Blocks Nicotine- and Cue-Induced Reinstatement for a Response Previously Reinforced with Nicotine", Biological Psychiatry, vol. 68(8), p. 712-718, (2010).
Wang et al., "Pd(II)-Catalyzed Hydroxyl-Directed C-H Activation/ C-O Cyclization: Expedient Construction of Dihydrobenzofurans", J. Am. Chem. Soc., vol. 132, p. 12203-12205, (2010).
Wen et al., "Intrathecal administration of Cav3.2 and Cav3.3 antisense oligonucleotide reverses tactile allodynia and thermal hyperalgesia in rats following chronic compression of dorsal root of ganglion", Acta. Pharmacol. Sin., vol. 27(12), p. 1547-1552, (2006).
Wildburger et al., "Neuroprotective effects of blockers for T-type calcium channels", Molecular Neurodegeneration, vol. 4, p. 1-8, (2009).
Woods et al., "SexRx: Calcium Channel Blockers and Your Sex Life" [Aug. 2013]: Winchester Hospital [retrieved on Feb. 13, 2017]. Retrieved from <http://www.winhosp.org/health-library/article?id=22043>.
Wouters et al., "Pharmaceutical Salts and Co-crystals", RSC Drug Discovery, (2012).
Xie et al., "Validation of High Throughput Screening Assays Against Three Subtypes of Cav3 T-Type Channels Using Molecular and Pharmacologic Approaches", Assay and Drug Development Technologies, vol. 5(2), p. 191-203, (2007).
Yaari et al., "Recruitment of apical dendritic T-type Ca2+ channels by backpropagating spikes underlies de novo intrinsic bursting in hippocampal epileptogenesis", J. Physiol., vol. 580, p. 435-450, (2007).
Yang et al., "The T-type calcium channel as a new therapeutic target for Parkinson's disease", Pflugers Arch- Eur J Physiol, vol. 466, p. 747-755, (2014).
Yang et al., "Short-Acting T-Type Calcium Channel Antagonists Significantly Modify Sleep Architecture in Rodents", Med. Chem. Lett., vol. 1, p. 504-509, (2010).
Zamponi et al., "Role of voltage-gated calcium channels in epilepsy", Eur. J. Phys., vol. 460(2), p. 395-403, (2010).

* cited by examiner

PYRAZOLE COMPOUNDS AND THEIR USE AS T-TYPE CALCIUM CHANNEL BLOCKERS

CROSS REFERENCE TO RELATED APPLICATIONS

This application is continuation application of U.S. application Ser. No. 15/316,100, filed on Dec. 2, 2016, which claims the benefit of United States Application under 35 U.S.C. 371 of PCT Application No. PCT/IB2015/054164, filed on Jun. 2, 2015, which claims the benefit of PCT Application No. PCT/IB2014/061901, filed on Jun. 3, 2014, the contents of each of which are incorporated herein by reference.

The present invention relates to novel pyrazole compounds and their use as T-type calcium channel blockers in the treatment or prevention of various diseases or disorders where calcium T channels are involved, to pharmaceutical compositions containing these derivatives, and to processes for their preparation.

Intracellular calcium concentrations control important life processes such as signal transduction pathways, hormones and neurotransmitter release, muscular contraction, gene expression and cell division. Control of calcium influx across the cellular membrane is in part regulated by a family of transmembrane proteins termed voltage-gated calcium channels (VOCs). They are activated by changes in electrical potential difference across the membrane and have been further classified into different subtypes based on biophysical and pharmacological considerations: Cav1.x (L-type for Long-lasting), Cav2.x (N-, P/Q- and R-types; N for Neuronal, P for Purkinje cells, Q (after P) and R for Remaining or Resistant) and Cav3.x (T-type for Transient). The L, N, P and Q-type channels activate at more positive potentials (high voltage activated) and display diverse kinetics and voltage-dependent properties. The T-type class (or "low voltage-activated") is characterized by fast inactivation (transient) and small conductance (tiny) and is composed of three members due to the different main pore-forming al subunits: Cav3.1 (α1 G), Cav3.2 (α1 H) and Cav3.3 (α1 I).

Nearly all "excitable" cells, such as neurons of the central nervous system (CNS), peripheral nerve cells and muscle cells, including those of skeletal muscles, cardiac muscles, and venous and arterial smooth muscles, have voltage-dependent calcium channels. In consequence, calcium T channels have been linked to various human diseases and disorders, such as especially epilepsy, pain, neuropathic pain, sleep disorders, sleep disturbances, schizophrenia, essential tremors, Parkinson's disease, neurodegenerative disorders, depression, anxiety, psychosis, autism, drug addiction, hypertension, cardiac arrhythmias, heart block, cancer, diabetes, infertility and sexual dysfunction (Bourinet, E.; Alloui, A.; Monteil, A.; Barrere, C.; Couette, B.; Poirot, O.; Pages, A.; McRory, J.; Snutch, T. P.; Eschalier, A.; Nargeot, J., *EMBO J* 2005, 24 (2), 315-324; Flatters, S. J. L., Drugs Fut. 2005, 30(6), 573-580; Giordanetto, F.; Knerr, L.; Wallberg, A., *Expert Opin Ther Pat* 2011, 21 (1), 85-101; Huguenard, J. R.; Prince, D. A., *J Neurosci* 1994, 14 (9), 5485-502; Lory, P.; Mezghrani, A., *IDrugs* 2010, 13 (7), 467-71; McGivern, J. G., *Drug Discov Today* 2006, 11 (5-6), 245-53; Uslaner, J. M.; Vardigan, J. D.; Drott, J. M.; Uebele, V. N.; Renger, J. J.; Lee, A.; Li, Z.; Le, A. D.; Hutson, P. H., *Biol Psychiatry* 2010, 68 (8), 712-8; Wildburger, N. C.; Lin-Ye, A.; Baird, M. A.; Lei, D.; Bao, J., Mol Neurodegener 2009, 4, 44).

In the brain, T-type calcium channels are essential for regulating neuronal excitability and burst firing, both in the central and peripheral nervous system (Lambert, R. C.; Bessaih, T.; Crunelli, V.; Leresche, N., *Pflugers Arch* 2014, 466 (3), 415-23.). They are linked to diseases or disorders where abnormal oscillatory activity occurs in the brain, as well as diseases or disorders where there is abnormal coupling of activity, particular through the thalamus. They are particularly linked to an increasing number of neurological disorders such as the epilepsy disorders and neuropathic pain.

T-type calcium channels play a role in regulating neuronal firing patterns under normal physiological conditions, such as during sleep rhythms (Anderson, M. P.; Mochizuki, T.; Xie, J.; Fischler, W.; Manger, J. P.; Talley, E. M.; Scammell, T. E.; Tonegawa, S., *Proc Natl Acad Sci USA* 2005, 102 (5), 1743-8; Destexhe, A.; Contreras, D.; Sejnowski, T. J.; Steriade, M., *J Neurophysiol* 1994, 72 (2), 803-18; Lee, J.; Kim, D.; Shin, H. S., *Proc Natl Acad Sci USA* 2004, 101 (52), 18195-9; Steriade, M., *Trends Neurosci* 2005, 28 (6), 317-24.). However, T-type calcium channels are also involved in pathophysiological conditions such as epilepsy, autism, hypertension, atrial fibrillation, congenital heart failure, pain, psychoses and cancer (for review, see Iftinca, M. C., *J Med Life* 2011, 4 (2), 126-38).

T-type calcium channels are critical players in the development of idiopathic generalized seizures in humans and animals (Cheong, E.; Shin, H. S., Pflugers Arch 2014, 466 (4), 719-34; Khosravani, H.; Zamponi, G. W., *Physiol Rev* 2006, 86 (3), 941-66; Zamponi, G. W.; Lory, P.; Perez-Reyes, E., *Pflugers Arch* 2010, 460 (2), 395-403). In animals, knockout of Cav3.1 calcium channels protects mice from absence seizures (Kim, D.; Song, I.; Keum, S.; Lee, T.; Jeong, M. J.; Kim, S. S.; McEnery, M. W.; Shin, H. S., *Neuron* 2001, 31 (1), 35-45; Song, I.; Kim, D.; Choi, S.; Sun, M.; Kim, Y.; Shin, H. S., *J Neurosci* 2004, 24 (22), 5249-57). In rat models of absence epilepsy (GAERS or WAG/Rij), a gain of function mutation of the Cav3.2 gene has been reported (Powell, K. L.; Cain, S. M.; Ng, C.; Sirdesai, S.; David, L. S.; Kyi, M.; Garcia, E.; Tyson, J. R.; Reid, C. A.; Bahlo, M.; Foote, S. J.; Snutch, T. P.; O'Brien, T. J., *J Neurosci* 2009, 29 (2), 371-80), as well as elevated levels of Cav3.1 and Cav3.2 mRNA and an increase in the amplitude of the T-type calcium current in comparison to normal rat strain (Broicher, T.; Kanyshkova, T.; Meuth, P.; Pape, H. C.; Budde, T., *Mol Cell Neurosci* 2008, 39 (3), 384-99; Talley, E. M.; Solorzano, G.; Depaulis, A.; Perez-Reyes, E.; Bayliss, D. A., *Brain Res Mol Brain Res* 2000, 75 (1), 159-65; Tsakiridou, E.; Bertollini, L.; de Curtis, M.; Avanzini, G.; Pape, H. C., *J Neurosci* 1995, 15(4), 3110-7; Powell, K. L.; Cain, S. M.; Ng, C.; Sirdesai, S.; David, L. S.; Kyi, M.; Garcia, E.; Tyson, J. R.; Reid, C. A.; Bahlo, M.; Foote, S. J.; Snutch, T. P.; O'Brien, T. J., *J Neurosci* 2009, 29 (2), 371-80). In human, number of mutations have been described in Cav3.2 channels in patients with childhood absence and other forms of idiopathic generalized epilepsies (Heron, S. E.; Khosravani, H.; Varela, D.; Bladen, C.; Williams, T. C.; Newman, M. R.; Scheffer, I. E.; Berkovic, S. F.; Mulley, J. C.; Zamponi, G. W., *Ann Neurol* 2007, 62 (6), 560-8; Khosravani, H.; Zamponi, G. W., *Physiol Rev* 2006, 86 (3), 941-66; Zamponi, G. W.; Lory, P.; Perez-Reyes, E., *Pflugers Arch* 2010, 460 (2), 395-403). Those mutations are predicted to cause a gain of function with increase in calcium current, or can trigger an alteration of the balance between excitatory and inhibitory neuronal elements. As direct consequence, it may result in an increased spiking behavior in neurons that exhibit this rebound bursting, thereby contributing to the generation of epileptiform discharges.

In another type of epilepsy, i.e. the temporal lobe epilepsy, it has been shown in the pilocarpine rodent model that T-type calcium currents were uppregulated after status epilepticus and suggest a role of this channel in long-lasting modification of neuronal firing mode (regular to burst firing) and potential contribution to the development and expression of an epileptic condition after SE (Yaari, Y.; Yue, C.; Su, H., *J Physiol* 2007, 580 (Pt. 2), 435-50; Becker, A. J.; Pitsch, J.; Sochivko, D.; Opitz, T.; Staniek, M.; Chen, C. C.; Campbell, K. P.; Schoch, S.; Yaari, Y.; Beck, H., *J Neurosci* 2008, 28 (49), 13341-53; Graef, J. D.; Nordskog, B. K.; Wiggins, W. F.; Godwin, D. W., *J Neurosci* 2009, 29 (14), 4430-41; Su, H.; Sochivko, D.; Becker, A.; Chen, J.; Jiang, Y.; Yaari, Y.; Beck, H., *J Neurosci* 2002, 22 (9), 3645-55).

Increased activity of T-type calcium channel has been associated to neuropathic and inflammatory pain states (for review, see Todorovic, S. M.; Jevtovic-Todorovic, V., *Br J Pharmacol* 2011, 163 (3), 484-95). When nociceptors are in an increased state of responsiveness, they often respond to normal sensory stimuli as if painful (allodynia) and to mildly painful stimuli as though they were acutely painful (hyperalgesia). The electrophysiological answer of these altered pain responses, include lower thresholds of activation, increased frequency of firing in response to suprathreshold stimuli and spontaneous firing (Coderre, T. J.; Katz, J.; Vaccarino, A. L.; Melzack, R., *Pain* 1993, 52 (3), 259-85; Bhave, G.; Gereau, R. W. t., *J Neurobiol* 2004, 61 (1), 88-106). T-type calcium channel are abundantly expressed in nociceptors, spinal dorsal horn and thalamic neurons (Talley, E. M.; Cribbs, L. L.; Lee, J. H.; Daud, A.; Perez-Reyes, E.; Bayliss, D. A., *J Neurosci* 1999, 19 (6), 1895-911) and increased T-type channel activity has been linked to neuropathic and inflammatory pain states in animals and humans (Jagodic, M. M.; Pathirathna, S.; Nelson, M. T.; Mancuso, S.; Joksovic, P. M.; Rosenberg, E. R.; Bayliss, D. A.; Jevtovic-Todorovic, V.; Todorovic, S. M., *J Neurosci* 2007, 27 (12), 3305-16; Todorovic, S. M.; Jevtovic-Todorovic, V., *Channels (Austin)* 2007, 1 (4), 238-45; Jagodic, M. M.; Pathirathna, S.; Joksovic, P. M.; Lee, W.; Nelson, M. T.; Naik, A. K.; Su, P.; Jevtovic-Todorovic, V.; Todorovic, S. M., *J Neurophysiol* 2008, 99 (6), 3151-6). T-channels may play a role in the decrease of the threshold for action potential firing in dorsal root ganglia (DRG) cells that express T-channels (Nelson, M. T.; Todorovic, S. M.; Perez-Reyes, E., *Curr Pharm Des* 2006, 12 (18), 2189-97; Jagodic, M. M.; Pathirathna, S.; Nelson, M. T.; Mancuso, S.; Joksovic, P. M.; Rosenberg, E. R.; Bayliss, D. A.; Jevtovic-Todorovic, V.; Todorovic, S. M., *J Neurosci* 2007, 27 (12), 3305-16). T-type calcium channels would play a role of amplifiers of peripheral pain signals. Pharmacological and molecular downregulation of the function of these channels in DRG neurons supports the notion that T-channels contribute to the chronic pain associated with peripheral axonal injury (Bourinet, E.; Alloui, A.; Monteil, A.; Barrere, C.; Couette, B.; Poirot, O.; Pages, A.; McRory, J.; Snutch, T. P.; Eschalier, A.; Nargeot, J., *EMBO J* 2005, 24 (2), 315-24; Wen, X. J.; Li, Z. J.; Chen, Z. X.; Fang, Z. Y.; Yang, C. X.; Li, H.; Zeng, Y. M., *Acta Pharmacol Sin* 2006, 27 (12), 1547-52) (or for review, see (Jevtovic-Todorovic, V.; Todorovic, S. M., *Cell Calcium* 2006, 40 (2), 197-203)).

In addition, T-type calcium channel activity is upregulated during diabetic neuropathy (Hall, K. E.; Sima, A. A.; Wiley, J. W., *J Physiol* 1995, 486 (2), 313-22; Jagodic, M. M.; Pathirathna, S.; Nelson, M. T.; Mancuso, S.; Joksovic, P. M.; Rosenberg, E. R.; Bayliss, D. A.; Jevtovic-Todorovic, V.; Todorovic, S. M., *J Neurosci* 2007, 27 (12), 3305-16). Selective knock-down of DRG Cav3.2 currents in vivo has effectively reversed mechanical and thermal hyperalgesia in STZ-induced diabetic neuropathy in rats (Messinger, R. B.; Naik, A. K.; Jagodic, M. M.; Nelson, M. T.; Lee, W. Y.; Choe, W. J.; Orestes, P.; Latham, J. R.; Todorovic, S. M.; Jevtovic-Todorovic, V., *Pain* 2009, 145 (1-2), 184-95). Furthermore, significant up-regulation of Cav3.2 T-channel mRNA in DRG tissue homogenates and concomitant up-regulation of Cav3.2 T-currents in nociceptive DRG cells has been reported in another model of painful diabetic neuropathy, leptin-deficient ob/ob mice (Latham, J. R.; Pathirathna, S.; Jagodic, M. M.; Choe, W. J.; Levin, M. E.; Nelson, M. T.; Lee, W. Y.; Krishnan, K.; Covey, D. F.; Todorovic, S. M.; Jevtovic-Todorovic, V., *Diabetes* 2009, 58 (11), 2656-65). In humans, extracellular recordings from the medial thalamus of patients with neurogenic pain have shown abnormalities of LTS-mediated bursts that could at least contribute to persistent pain (Jeanmonod, D.; Magnin, M.; Morel, A., *Brain* 1996, 119 (2), 363-75).

It has been shown that T-type calcium (Ca) channels in the CNS are closely associated with repetitive burst discharges or neuronal oscillations (Llinas, R.; Yarom, Y., *J Physiol* 1986, 376, 163-82; Gutnick, M. J.; Yarom, Y., *J Neurosci Methods* 1989, 28 (1-2), 93-9; Iftinca, M. C.; Zamponi, G. W., *Trends Pharmacol Sci* 2009, 30 (1), 32-40). Tremor is a common encountered involuntary movements, and it is associated with various neurological diseases or pathological conditions such as essential tremor (ET) and Parkinson's disease (PD) and its related disorders. As tremor-related neuronal activities may be closely related to repetitive or oscillatory activities in the CNS, controlling T-type Ca channels may have therapeutic effects. This hypothesis is supported by neuro-anotomical and functional expression of expression of T-type calcium channels in area involved pathophysiological mechanisms underlying harmaline-induced tremor, a pharmacological model of ET in rodents (Llinas, R.; Yarom, Y., *J Physiol* 1986, 376, 163-82; Cavelier, P.; Lohof, A. M.; Lonchamp, E.; Beekenkamp, H.; Mariani, J.; Bossu, J. L., *Neuroreport* 2008, 19 (3), 299-303). Moreover, animal data involving selective knockdown of the Cav3.1 gene or mice lacking the Cav3.1 gene showed that Cav3.1 channels play a specific role in ET (Park, Y. G.; Park, H. Y.; Lee, C. J.; Choi, S.; Jo, S.; Choi, H.; Kim, Y. H.; Shin, H. S.; Llinas, R. R.; Kim, D., *Proc Natl Acad Sci USA* 2010, 107 (23), 10731-6). On the other hand, the role of the other isoform of the T-type calcium channels (Cav3.2 and Cav 3.3) in this pathology is not known but cannot be excluded (Miwa, H.; Kondo, T., *Cerebellum* 2011, 10 (3), 563-9).

In Parkinson's disease (PD) patients, deep brain stimulation of the subthalamic nucleus has been shown to be an effective treatment for parkinsonian symptoms indicating a pivotal role of this area in the pathogenesis of PD: In patients, as well as in animal models of PD, this area seems to have an abnormal pattern of firing with an increase of the burst firing mode. And this burst firing mode has been shown to involve the T-type $Ca^{2+}$ channels (for review, see Yang, Y. C.; Tai, C. H.; Pan, M. K.; Kuo, C. C., *Pflugers Arch* 2014, 466 (4), 747-55).

The compounds of the present invention are potent calcium T channel blockers and therefore useful for the prevention or treatment of diseases or disorders where calcium T channels are involved.

1) A first aspect of the invention relates to novel compounds of the formula (I)

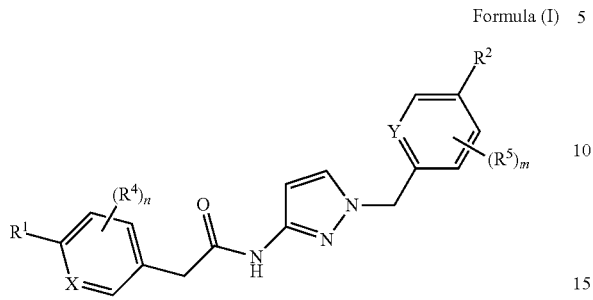

Formula (I)

wherein
X represents a ring carbon or a ring nitrogen atom;
R$^1$ represents
- (C$_{2-6}$)alkyl [in particular isopropyl, tert.-butyl, or isobutyl];
- (C$_{2-4}$)alkyl mono-substituted with cyano, or (C$_{1-3}$)alkoxy (especially methoxy); [in particular such group is 1-methoxy-ethyl, or 1-cyano-1-methyl-ethyl];
- (C$_{1-4}$)fluoroalkyl [in particular trifluoromethyl, 2,2,2-trifluoro-1,1-dimethyl-ethyl];
- (C$_{1-3}$)fluoroalkoxy [in particular trifluoromethoxy, 2,2,2-trifluoroethoxy, 3,3,3-trifluoropropoxy];
- pentafluoro-sulfanyl;
- (C$_{3-6}$)cycloalkyl-L$^1$- wherein
  said (C$_{3-6}$)cycloalkyl optionally contains one ring oxygen atom; wherein said (C$_{3-6}$)cycloalkyl is unsubstituted, or mono-substituted with fluoro, (C$_{1-3}$)alkyl (especially methyl), (C$_{1-3}$)alkoxy (especially methoxy), hydroxy, cyano, or (C$_{1-3}$)fluoroalkyl (especially trifluoromethyl), or di-substituted with fluoro, or tri-substituted with two fluoro substituents and a substituent selected from (C$_{1-3}$)alkyl (especially methyl) and cyano; and
  the linker L$^1$ represents a direct bond, (C$_{1-2}$)alkylene, oxygen, or (C$_{1-2}$)alkylene-oxy (which is attached to the rest of the molecule through the oxygen atom);
  [in particular such group (C$_{3-6}$)cycloalkyl-L$_1$- is cyclopropyl, 3-fluoro-oxetan-3-yl, 3-methoxy-oxetan-3-yl, 3-methyl-oxetan-3-yl, 3,3-difluoro-cyclobutyl, 1-cyano-3,3-difluoro-cyclobutyl, 1-trifluoromethyl-cyclopropyl, 2-trifluoromethyl-cyclopropyl, 1-methyl-cyclopropyl, 1-cyano-cyclopropyl, 1-hydroxy-cyclopropyl, 1-methoxy-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy; or it is cyclopropyl-methoxy, oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
- 5- or 6-membered heteroaryl, independently optionally mono-substituted with (C$_{1-3}$)alkyl (especially methyl); [in particular oxadiazolyl, pyrazinyl, pyrimidinyl, or pyridinyl];
- —NR$^{11}$R$^{12}$, wherein
  R$^{11}$ and R$^{12}$ independently represent hydrogen, (C$_{1-3}$)alkyl, (C$_{2-3}$)fluoroalkyl, (C$_{3-6}$)cycloalkyl, (C$_{3-6}$)cycloalkyl mono- or di-substituted with fluoro, (C$_{3-6}$)cycloalkyl-(C$_{1-3}$)alkyl, (C$_{1-3}$)alkoxy-(C$_{2-3}$)alkyl [in particular such group —NR$^{11}$R$^{12}$ is dimethylamino, ethyl-methyl-amino, diethylamino, cyclopropyl-methyl-amino, (2-methoxyethyl)-methyl-amino, (cyclopropylmethyl)-methyl-amino, or (2,2-difluoro-ethyl)-methyl-amino];
  or R$^{11}$ and R$^{12}$, together with the nitrogen atom to which they are attached to, form a 4- to- 6 membered ring optionally mono- or di-substituted with fluoro; a 2-oxo-pyrrolidinyl group; or a morpholinyl group [in particular such group —NR$^{11}$R$^{12}$ is azetidinyl, 3-fluoro-azetidinyl, 3,3-difluoro-azetidinyl, pyrrolidinyl, 3-fluoro-pyrrolidinyl, 3,3-difluoro-pyrrolidinyl, or 2-oxo-pyrrolidinyl];
and (R$^4$)$_n$ represents one or two optional substituents (i.e. n represents the integer 0, 1, or 2) independently selected from (C$_{1-4}$)alkyl (especially methyl, ethyl), (C$_{3-6}$)cycloalkyl (especially cyclopropyl), (C$_{1-4}$)alkoxy (especially methoxy), (C$_{1-3}$)fluoroalkyl (especially trifluoromethyl), (C$_{1-3}$)fluoroalkoxy (especially trifluoromethoxy), halogen (especially fluoro), and cyano [especially (R$^4$)$_n$ is absent (i.e. n=0); or (R$^4$)$_n$ represents one halogen or methyl substituent];
or R$^1$ together with (R$^4$)$_n$ forms a non-aromatic 5- or 6-membered ring which is fused to the phenyl/pyridine ring; wherein said 5- or 6-membered ring optionally contains one or two heteroatoms independently selected from oxygen and nitrogen; wherein said fused 5- or 6-membered non-aromatic ring independently is optionally further mono-substituted with oxo or (C$_{1-3}$)alkyl (especially methyl); di-substituted with (C$_{1-3}$)alkyl (especially methyl); or di-, tri-, or tetra-substituted wherein one substituent is oxo and the remaining are (C$_{1-3}$)alkyl (especially methyl); [in particular such non-aromatic 5- or 6-membered ring fused to the phenyl/pyridine ring forms, together with the phenyl/pyridine ring, a group selected from 2-oxo-2,3-dihydro-benzooxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3-dihydro-benzooxazol-6-yl, 3,3-dimethyl-2-oxo-2,3-dihydro-1H-indol-5-yl, 1,3,3-trimethyl-2-oxo-2,3-dihydro-1H-indol-5-yl, 2,2-dimethyl-2,3-dihydro-benzofuran-6-yl, 2,2-dimethyl-2,3-dihydro-benzofuran-5-yl, 3,3-dimethyl-2,3-dihydro-benzofuran-5-yl, 3,3-dimethyl-2,3-dihydro-benzofuran-6-yl, or 3-methylchroman-7-yl];
or R$^1$ together with (R$^4$)$_n$ forms an aromatic 5- or 6-membered ring which is fused to the phenyl/pyridine ring; wherein said 5- or 6-membered ring optionally contains one or two heteroatoms selected from nitrogen, wherein said fused 5- or 6-membered aromatic ring independently is optionally further mono- or di-substituted wherein the substituents are independently selected from (C$_{1-3}$)alkyl (especially methyl, ethyl, isopropyl), (C$_{3-6}$)cycloalkyl (especially cyclobutyl), (C$_1$)fluoroalkyl (especially trifluoromethyl), or cyano [in particular such aromatic 5- or 6-membered ring fused to the phenyl/pyridine ring forms, together with the phenyl/pyridine ring, a group selected from 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1- methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl-1H-benzoimidazol-6-yl, 1-methyl-1H-benzoimidazol-5-yl, 1-methyl-1H-benzoimidazol-6-yl, or quinolin-7-yl];

or $R^1$ represents methyl, or halogen (especially fluoro); and $(R^4)_n$ represents one substituent selected from $(C_{1-3})$fluoroalkoxy (especially 2,2,2-trifluoroethoxy) which is attached to the phenyl/pyridinyl ring in ortho or meta-position to the point of attachment of the —CH$_2$—CO—NH— group;

Y represents a ring carbon or a ring nitrogen atom; and $R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, isopropoxy); $(C_{3-6})$cycloalkyl-oxy (especially cyclopropyl-oxy); $(C_{1-3})$fluoroalkyl (especially trifluoromethyl); $(C_{1-3})$fluoroalkoxy (especially difluoromethoxy, trifluoromethoxy, 2,2,2-trifluoroethoxy); $(C_{1-3})$alkoxy-$(C_{2-3})$alkoxy (especially 2-methoxy-ethoxy); halogen; cyano; or —NR$^{21}$R$^{22}$, wherein $R^{21}$ and $R^{22}$ independently represent hydrogen, or $(C_{1-3})$alkyl (especially dimethylamino), or $R^{21}$ and $R^{22}$, together with the nitrogen atom to which they are attached to, form a 4- to- 6 membered ring optionally mono- or di-substituted with fluoro, or a morpholinyl group (especially azetidinyl, pyrrolidinyl, 3-fluoro-pyrrolidinyl); and $(R^5)_m$ represents one or two optional substituents (i.e. m represents the integer 0, 1, or 2) independently selected from $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen; cyano; $(C_{1-3})$fluoroalkyl (especially difluoromethyl, trifluoromethyl); and $(C_{1-3})$fluoroalkoxy (especially trifluoromethoxy, 2,2,2-trifluoroethoxy); [especially $(R^5)_m$ is absent (i.e. m=0), or $(R^5)_m$ represents one halogen substituent; preferably $(R^5)_m$ is absent].

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

Furthermore, in some instances, the compounds of the present invention may be present in tautomeric forms. Any such tautomeric form is encompassed. For example, it is well understood that, in case a benzimidazole moiety is unsubstituted on the ring nitrogen having a free valency such benzimidazole moiety represents tautomeric forms. Thus, further substituents of the benzimidazole moiety may be attached in the position(s) ortho to the bridgehead atoms (i.e. attached in position(s) 4 and/or 7), and/or in the position(s) meta to the bridgehead atoms, (i.e. attached in position(s) 5 and/or 6). It is understood that the two ortho, and, respectively, the two meta positions are considered equivalent. For example, the group 4-methyl-1H-benzoimidazol-2-yl is understood to signify the same group as 7-methyl-1H-benzoimidazol-2-yl and 4-methyl-3H-benzoimidazol-2-yl and 7-methyl-3H-benzoimidazol-2-yl.

The present invention also includes isotopically labelled, especially $^2$H (deuterium) labelled compounds of formula (I) according to embodiments 1) to 29), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, variably attached bonds may be used for substituents or groups (e.g. $(R^4)_n$ and $(R^5)_m$). In such case it is meant that any such substituent or group may be attached to any carbon atom of the ring system to which the variable attached bond is drawn into, provided that said carbon atom is not already substituted.

In this patent application, a bond drawn as a dotted line shows the point of attachment of the radical drawn. For example, the radical drawn below

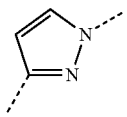

is a 1H-pyrazol-1,3-diyl group.

Where the plural form is used for compounds, salts, pharmaceutical compositions, diseases and the like, this is intended to mean also a single compound, salt, pharmaceutical composition, disease or the like.

Any reference to compounds of formula (I) according to embodiments 1) to 31) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 29), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, bromine, or iodine, preferably fluorine or chlorine, especially fluorine.

The term "cyano" refers to a group —CN.

The term "alkyl", used alone or in combination, refers to a saturated straight or branched chain hydrocarbon group containing one to six (especially one to four) carbon atoms.

The term "$(C_{x-y})$alkyl" (x and y each being an integer), refers to an alkyl group as defined before, containing x to y carbon atoms. In case a $(C_{x-y})$alkyl group (or, in general, a $(C_{x-y})$ alkyl group) is used in combination with another substituent, the term means that said substituent is linked through a $(C_{1-y})$alkyl group (or a $(C_{x-y})$alkyl group, respectively) to the rest of the molecule. In some instances such group is also referred to as $(C_{1-y})$alkylene. For example a $(C_{1-6})$alkyl group contains from one to six carbon atoms. Examples of $(C_{1-6})$alkyl groups are the $(C_{1-4})$alkyl groups methyl, ethyl, n-propyl, isopropyl, n-butyl, sec.-butyl, tert.-butyl, and isobutyl, as well as n-pentyl, and isopentyl. Preferred are methyl, ethyl, n-propyl, and isopropyl. Most preferred is methyl. For the substituent $R^1$ preferred examples of $(C_{2-6})$ alkyl are isopropyl, tert.-butyl, and isobutyl; especially tert.-butyl.

Examples of $(C_{2-4})$alkyl groups which are mono-substituted with cyano, or $(C_{1-3})$alkoxy as used for $R^1$ are 1-methoxy-ethyl, and 1-cyano-1-methyl-ethyl.

The term "alkoxy" means a group of the formula alkyl-O— in which the term alkyl has the previously given significance. The term "$(C_{x-y})$alkoxy" (x and y being an integer) refers to a straight or branched chain alkoxy group containing x to y carbon atoms. Examples of alkoxy groups are the $(C_{1-4})$alkoxy groups methoxy, ethoxy, n-propoxy, isopropoxy, n-butoxy, isobutoxy, sec-butoxy and tert.-butoxy. Preferred is methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. A preferred example is trifluoromethyl. Examples of $(C_{2-3})$fluoroalkyl groups include 2-fluoroethyl, 2,2-difluoroethyl and 2,2,2-trifluoroethyl (especially 2-fluoroethyl and 2,2,2-trifluoroethyl). In the specific case of $(C_{1-4})$fluoroalkyl groups, the fluoroalkyl group contains from one to four carbon atoms in which one to nine hydrogen atoms have been replaced with fluorine. Examples of $(C_{1-4})$fluoroalkyl groups as used for $R^1$ include trifluoromethyl, 2-fluoroethyl, 2,2-difluoroethyl, 2,2,2-trifluoroethyl, and 2,2,2-trifluoro-1,1-dimethyl-ethyl; especially trifluoromethyl, and 2,2,2-trifluoro-1,1-dimethyl-ethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Preferred examples are trifluoromethoxy, difluoromethoxy and 2,2,2-trifluoroethoxy. Representative examples of fluoroalkoxy groups as used for $R^1$ include trifluoromethoxy, difluoromethoxy, 2-fluoroethoxy, 2,2-difluoroethoxy and 2,2,2-trifluoroethoxy; especially 2,2,2-trifluoroethoxy. An additional example of $(C_{1-3})$fluoroalkoxy groups as used for $R^1$ is 3,3,3-trifluoropropoxy.

The term "cycloalkyl" refers to a saturated mono- or bicyclic carbocyclic ring containing three to eight carbon atoms. The term "$(C_{x-y})$cycloalkyl" (x and y each being an integer), refers to a cycloalkyl group as defined before containing x to y carbon atoms. For example a $(C_{3-6})$ cycloalkyl group refers to a saturated monocyclic carbocyclic ring containing three to six carbon atoms. Examples of cycloalkyl groups are cyclopropyl, cyclobutyl, cyclopentyl, and cyclohexyl. Preferred is cyclopropyl.

The term "$(C_{3-6})$cycloalkyl, wherein the cycloalkyl may optionally contain a ring oxygen atom", refers to a monocyclic cycloalkyl group as defined before. In addition, one ring carbon atom of said cycloalkyl may be replaced by an oxygen atom. For the substituent $R^1$, examples of such groups are especially cyclopropyl, cyclobutyl, and, in addition, oxetan-3-yl. Said groups are unsubstituted or substituted as explicitly defined.

The term "$(C_{3-6})$cycloalkyl-$(C_{1-3})$alkyl" refers to a $(C_{3-6})$cycloalkyl group as explicitly defined which group is linked to the rest of the molecule through a $(C_{1-3})$alkylene group as defined before. For the substituent $R^1$, the $(C_{1-2})$ alkylene group part of $(C_{3-6})$cycloalkyl-$(C_{1-2})$alkyl is in particular a methylene group.

The term "$(C_{3-6})$cycloalkyl-oxy" refers to a $(C_{3-6})$cycloalkyl group as explicitly defined which is linked to the rest of the molecule through an oxygen atom.

The term "$(C_{3-6})$cycloalkyl-$(C_{1-2})$alkylene-oxy" refers to a $(C_{3-6})$cycloalkyl group as explicitly defined which is linked to the rest of the molecule through a —$(CH_2)_{1-2}$—O— group. For the substituent $R^1$, the —$(C_{1-2})$alkylene-oxy group part of $(C_{3-6})$cycloalkyl-$(C_{1-2})$alkylene-oxy is in particular a —$CH_2$—O— group.

The term "$(C_{1-3})$alkoxy-$(C_{2-3})$alkoxy" refers to a $(C_{1-3})$ alkoxy-group as defined before which is attached to the rest of the molecule through a $(C_{2-3})$alkoxy group as defined before. An example is 2-methoxy-ethoxy.

The term "$(C_{1-3})$alkoxy-$(C_{2-3})$alkyl" means a $(C_{1-3})$ alkoxy-group as defined before which is attached to the rest of the molecule through a $(C_{2-3})$alkylene group as defined before. An example is 2-methoxy-ethyl.

The term "aryl", used alone or in combination, means phenyl or naphthyl, preferably phenyl. Likewise, an arylene group is an aryl group as defined before having two points of attachment to the respective rests of the molecule. The above-mentioned aryl/arylene groups are unsubstituted or substituted as explicitly defined.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are 5-membered heteroaryl such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl; 6-membered heteroaryl such as pyridinyl, pyrimidinyl, pyridazinyl, pyrazinyl; and bicyclic heteroaryl such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. Examples of heteroaryl groups as used for $R^1$ are especially oxadiazolyl, pyrazinyl, pyrimidinyl, and pyridinyl. The above-mentioned heteroaryl groups are unsubstituted or substituted as explicitly defined.

In case two substituents form an aromatic 5- or 6-membered ring optionally containing one or two nitrogen atoms which ring is fused to a phenyl/pyridine ring, examples of such thus formed bicyclic heteroaryl rings are pyrrolo[2,3-b]pyridinyl, indolyl, indazolyl, quinoxalinyl, benzoimidazolyl, and quinolinyl. The above-mentioned groups do not carry further substituents on the phenyl/pyridine part of the ring, whereas said aromatic 5- or 6-membered ring may be unsubstituted or substituted as explicitly defined.

In case two substituents form a non-aromatic 5- or 6-membered ring optionally containing one or two heteroatoms, which ring is fused to a phenyl/pyridine ring, examples of such thus formed bicyclic partially aromatic rings are 2,3-dihydro-benzooxazolyl, 3,4-dihydro-2H-benzo[1,4]oxazinyl, 2,3-dihydro-1H-indolyl, and 2,3-dihydro-benzofuranyl. A further example is chromanyl. The above-mentioned groups do not carry further substituents on the phenyl/pyridine part of the ring, whereas said non-aromatic 5- or 6-membered ring may be unsubstituted or substituted as explicitly defined.

Examples of —$NR^{11}R^{12}$ groups as used for $R^1$ are especially disubstituted amino groups wherein one substituent is methyl or ethyl, and the other is $(C_{1-3})$alkyl, $(C_{2-3})$fluoroalkyl, $(C_{3-6})$cycloalkyl, $(C_{3-6})$cycloalkyl mono- or di-substituted with fluoro, $(C_{3-6})$cycloalkyl-$(C_{1-3})$alkyl, $(C_{1-3})$alkoxy-$(C_{2-3})$alkyl. Examples are dimethylamino, ethyl-methyl-amino, diethylamino, cyclopropyl-methyl-amino, (2-methoxyethyl)-methyl-amino, (cyclopropylmethyl)-methyl-amino, and (2,2-difluoro-ethyl)-methyl-amino. Examples of —$NR^{11}R^{12}$ groups wherein $R^{11}$ and $R^{12}$, together with the nitrogen atom to which they are attached to, form a 4- to- 6 membered ring as used for $R^1$ are especially the four and five-membered rings azetidinyl, 3-fluoro-azetidinyl, 3,3-difluoro-azetidinyl, pyrrolidinyl, 3-fluoro-pyrrolidinyl, 3,3-difluoro-pyrrolidinyl.

An example of —$NR^{21}R^{22}$ groups as used for $R^2$ is dimethylamino. An example of —$NR^{21}R^{22}$ groups wherein $R^{21}$ and $R^{22}$, together with the nitrogen atom to which they are attached to, form a 4- to- 6 membered ring as used for $R^2$ is 3-fluoro-pyrrolidinyl. Further examples are azetidinyl and pyrrolidinyl.

Further embodiments of the invention are presented hereinafter:

2) A second embodiment relates to compounds according to embodiment 1), wherein
X represents a ring carbon or a ring nitrogen atom;
  $R^1$ represents
    $(C_{2-6})$alkyl [in particular isopropyl, tert.-butyl, or isobutyl];
    $(C_{2-4})$alkyl mono-substituted with cyano, or $(C_{1-3})$alkoxy (especially methoxy); [in particular such group is 1-methoxy-ethyl, or 1-cyano-1-methyl-ethyl];
    $(C_{1-4})$fluoroalkyl [in particular trifluoromethyl, 2,2,2-trifluoro-1,1-dimethyl-ethyl];
    $(C_{1-3})$fluoroalkoxy [in particular 2,2,2-trifluoroethoxy];
    pentafluoro-sulfanyl;
    $(C_{3-6})$cycloalkyl-$L^1$- wherein
      said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro, or tri-substituted with two fluoro substituents and a $(C_{1-3})$alkyl (especially methyl) substituent; and
      the linker $L^1$ represents a direct bond, $(C_{1-2})$alkylene, oxygen, or $(C_{1-2})$alkylene-oxy (which is attached to the rest of the molecule through the oxygen atom); [in particular such group $(C_{3-6})$cycloalkyl-$L$- is cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-cyano-cyclopropyl, 1-hydroxy-cyclopropyl, 1-cyano-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
    5- or 6-membered heteroaryl, independently optionally mono-substituted with $(C_{1-3})$alkyl (especially methyl); [in particular oxadiazolyl, pyrazinyl, pyrimidinyl, or pyridinyl];
    —$NR^{11}R^{12}$, wherein
      $R^{11}$ and $R^{12}$ independently represent hydrogen, $(C_{1-3})$alkyl, $(C_{2-3})$fluoroalkyl, $(C_{3-6})$cycloalkyl, $(C_{3-6})$cycloalkyl mono- or di-substituted with fluoro, $(C_{3-6})$cycloalkyl-$(C_{1-3})$alkyl, $(C_{1-3})$alkoxy-$(C_{2-3})$alkyl [in particular such group —$NR^{11}R^{12}$ is dimethylamino, ethyl-methyl-amino, diethylamino, cyclopropyl-methyl-amino, (2-methoxyethyl)-methyl-amino, (cyclopropylmethyl)-methyl-amino, or (2,2-difluoro-ethyl)-methyl-amino];
      or $R^{11}$ and $R^{12}$, together with the nitrogen atom to which they are attached to, form a 4-to- 6 membered ring optionally mono- or di-substituted with fluoro; a 2-oxo-pyrrolidinyl group; or a morpholinyl group [in particular such group —$NR^{11}R^{12}$ is azetidinyl, 3-fluoro-azetidinyl, 3,3-difluoro-azetidinyl, pyrrolidinyl, 3-fluoro-pyrrolidinyl, 3,3-difluoro-pyrrolidinyl, or 2-oxo-pyrrolidinyl];
and $(R^4)_n$ represents one or two optional substituents (i.e. n represents the integer 0, 1, or 2) independently selected from $(C_{1-4})$alkyl (especially methyl), $(C_{1-4})$alkoxy (especially methoxy), $(C_{1-3})$fluoroalkyl (especially trifluoromethyl), $(C_{1-3})$fluoroalkoxy (especially trifluoromethoxy), halogen (especially fluoro), and cyano [especially $(R^4)_n$ is absent (i.e. n=0); or $(R^4)_n$ represents one halogen or methyl substituent];
or $R^1$ together with $(R^4)_n$ forms a non-aromatic 5- or 6-membered ring which is fused to the phenyl/pyridine ring; wherein said 5- or 6-membered ring optionally contains one or two heteroatoms independently selected from oxygen and nitrogen; wherein said fused 5- or 6-membered non-aromatic ring independently is optionally further mono-substituted with oxo; or di-, tri-, or tetra-substituted wherein one substituent is oxo and the remaining are $(C_{1-3})$alkyl (especially methyl); [in particular such non-aromatic 5- or 6-membered ring fused to the phenyl/pyridine ring forms, together with the phenyl/pyridine ring, a group selected from 2-oxo-2,3-dihydro-benzooxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3-dihydro-benzooxazol-6-yl, 3,3-dimethyl-2-oxo-2,3-dihydro-1H-indol-5-yl, 1,3,3-trimethyl-2-oxo-2,3-dihydro-1H-indol-5-yl, 2,2-dimethyl-2,3-dihydro-benzofuran-6-yl, 2,2-dimethyl-2,3-dihydro-benzofuran-5-yl, or 3,3-dimethyl-2,3-dihydro-benzofuran-5-yl];
or $R^1$ together with $(R^4)_n$ forms an aromatic 5- or 6-membered ring which is fused to the phenyl/pyridine ring; wherein said 5- or 6-membered ring optionally contains one or two heteroatoms selected from nitrogen, wherein said fused 5- or 6-membered aromatic ring independently is optionally further mono- or di-substituted wherein the substituents are independently selected from $(C_{1-3})$alkyl (especially methyl, isopropyl), $(C_{3-6})$cycloalkyl (especially cyclobutyl), $(C_1)$fluoroalkyl (especially trifluoromethyl), or cyano [in particular such aromatic 5- or 6-membered ring fused to the phenyl/pyridine ring forms, together with the phenyl/pyridine ring, a group selected from 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl-1H-benzoimidazol-6-yl, 1-methyl-1H-benzoimidazol-5-yl, 1-methyl-1H-benzoimidazol-6-yl, or quinolin-7-yl];

or $R^1$ represents methyl, or halogen (especially fluoro); and $(R^4)_n$ represents one substituent selected from $(C_{1-3})$fluoroalkoxy (especially 2,2,2-trifluoroethoxy) which is attached to the phenyl/pyridinyl ring in ortho or meta-position to the point of attachment of the —$CH_2$—CO—NH— group;

Y represents a ring carbon or a ring nitrogen atom; and $R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, isopropoxy); $(C_{3-6})$cycloalkyl-oxy (especially cyclopropyl-oxy); $(C_{1-3})$fluoroalkyl (especially trifluoromethyl); $(C_{1-3})$fluoroalkoxy (especially difluoromethoxy, trifluoromethoxy, 2,2,2-trifluoroethoxy); $(C_{1-3})$alkoxy-$(C_{2-3})$alkoxy (especially 2-methoxy-ethoxy); halogen; cyano; or —$NR^{21}R^{22}$, wherein $R^{21}$ and $R^{22}$ independently represent hydrogen, or $(C_{1-3})$alkyl (especially dimethylamino), or $R^{21}$ and $R^{22}$, together with the nitrogen atom to which they are attached to, form a 4- to- 6 membered ring optionally mono- or di-substituted with fluoro, or a morpholinyl group (especially 3-fluoro-pyrrolidinyl); and $(R^5)_m$ represents one or two optional substituents (i.e. m represents the integer 0, 1, or 2) independently selected from $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen; cyano; $(C_{1-3})$fluoroalkyl (especially trifluoromethyl); and $(C_{1-3})$fluoroalkoxy (especially trifluoromethoxy, 2,2,2-trifluoroethoxy); [especially $(R^5)_m$ is absent (i.e. m=0), or $(R^5)_m$ represents one halogen substituent; preferably $(R^5)_m$ is absent].

3) Another embodiment relates to compounds according to any one of embodiments 1) or 2), wherein X represents a ring carbon atom.

4) Another embodiment relates to compounds according to any one of embodiments 1) or 2), wherein X represents a ring nitrogen atom.

5) Another embodiment relates to compounds according to any one of embodiments 1) to 4), wherein $R^1$ represents
- $(C_{2-6})$alkyl [in particular isopropyl, tert.-butyl, or isobutyl];
- $(C_{2-4})$alkyl mono-substituted with cyano, or $(C_{1-3})$alkoxy (especially methoxy); [in particular such group is 1-methoxy-ethyl, or 1-cyano-1-methyl-ethyl];
- $(C_{1-4})$fluoroalkyl [in particular trifluoromethyl, 2,2,2-trifluoro-1,1-dimethyl-ethyl];
- $(C_{1-3})$fluoroalkoxy [in particular 2,2,2-trifluoroethoxy]; pentafluoro-sulfanyl;
- $(C_{3-6})$cycloalkyl-$L_1$- wherein
  said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro, or tri-substituted with two fluoro substituents and a $(C_{1-3})$alkyl (especially methyl) substituent; and
  the linker $L^1$ represents a direct bond, $(C_{1-2})$alkylene, oxygen, or $(C_{1-2})$alkylene-oxy (which is attached to the rest of the molecule through the oxygen atom); [in particular such group $(C_{3-6})$cycloalkyl-$L_1$- is cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-hydroxy-cyclopropyl, 1-cyano-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
- 5- or 6-membered heteroaryl selected from oxadiazolyl, pyrazinyl, pyrimidinyl, and pyridinyl; wherein said heteroaryl independently is optionally mono-substituted with $(C_{1-3})$alkyl (especially methyl); or
- $NR^{11}R^{12}$, wherein
  $R^{11}$ and $R^{12}$ independently represent hydrogen, $(C_{1-3})$alkyl, $(C_{2-3})$fluoroalkyl, $(C_{3-6})$cycloalkyl, $(C_{3-6})$cycloalkyl mono- or di-substituted with fluoro, $(C_{3-6})$cycloalkyl-$(C_{1-3})$alkyl, $(C_{1-3})$alkoxy-$(C_{2-3})$alkyl [in particular such group —$NR^{11}R^{12}$ is dimethylamino, ethyl-methyl-amino, diethylamino, cyclopropyl-methyl-amino, (2-methoxyethyl)-methyl-amino, (cyclopropylmethyl)-methyl-amino, or (2,2-difluoro-ethyl)-methyl-amino];
  or $R^{11}$ and $R^{12}$, together with the nitrogen atom to which they are attached to, form an azetidinyl or a pyrrolidinyl ring, both independently optionally mono- or di-substituted with fluoro; or a 2-oxo-pyrrolidinyl group; [in particular such group —$NR^{11}R^{12}$ is azetidinyl, 3-fluoro-azetidinyl, 3,3-difluoro-azetidinyl, pyrrolidinyl, 3-fluoro-pyrrolidinyl, 3,3-difluoro-pyrrolidinyl, or 2-oxo-pyrrolidinyl];

and $(R^4)_n$ represents one optional substituent (i.e. n represents the integer 0, or 1) selected from $(C_{1-4})$alkyl (especially methyl), $(C_{1-4})$alkoxy (especially methoxy), $(C_{1-3})$fluoroalkyl (especially trifluoromethyl), $(C_{1-3})$fluoroalkoxy (especially trifluoromethoxy), halogen (especially fluoro), and cyano [especially $(R^4)_n$ is absent (i.e. n=0); or $(R^4)_n$ represents one halogen or methyl substituent];

or $R^1$ together with $(R^4)_n$ forms a non-aromatic 5- or 6-membered ring which is fused to the phenyl/pyridine ring to form a bicyclic ring system; wherein said bicyclic ring system is selected from 2,3-dihydro-benzooxazolyl, 3,4-dihydro-2H-benzo[1,4]oxazinyl, 2,3-dihydro-1H-indolyl, and 2,3-dihydro-benzofuranyl; wherein said non-aromatic 5- or 6-membered ring part of said bicyclic ring system independently is optionally further mono-substituted with oxo; or di-, tri-, or tetra-substituted wherein one substituent is oxo and the remaining are $(C_{1-3})$alkyl (especially methyl); [in particular such bicyclic ring system is a group selected from 2-oxo-2,3-dihydro-benzooxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3-dihydro-benzooxazol-6-yl, 3,3-dimethyl-2-oxo-2,3-dihydro-1H-indol-5-yl, 1,3,3-trimethyl-2-oxo-2,3-dihydro-1H-indol-5-yl, or 2,2-dimethyl-2,3-dihydro-benzofuran-6-yl, 2,2-dimethyl-2,3-dihydro-benzofuran-5-yl, or 3,3-dimethyl-2,3-dihydro-benzofuran-5-yl];

or $R^1$ together with $(R^4)_n$ forms an aromatic 5- or 6-membered ring which is fused to the phenyl/pyridine ring to form a bicyclic aromatic ring system selected from pyrrolo[2,3-b]pyridinyl, indolyl, indazolyl, quinoxalinyl, benzoimidazolyl, and quinolinyl (especially indolyl or indazolyl); wherein said fused 5- or 6-membered aromatic ring part of said aromatic bicyclic ring system independently is optionally further mono- or di-substituted wherein the substituents are independently selected from $(C_{1-3})$alkyl (especially methyl, isopropyl), $(C_{3-6})$cycloalkyl (especially cyclobutyl), (C)fluoroalkyl (especially trifluoromethyl), or cyano [in particular such aromatic part of said aromatic bicyclic ring system is a group selected from 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl-1H-benzoimidazol-6-yl, 1-methyl-1H-benzoimidazol-5-yl, 1-methyl-1H-benzoimidazol-6-yl, or quinolin-7-yl];

or $R^1$ represents methyl, or halogen (especially fluoro); and $(R^4)_n$ represents one substituent selected from $(C_{1-3})$fluoroalkoxy (especially 2,2,2-trifluoroethoxy) which is attached to the phenyl/pyridinyl ring in ortho or meta-position to the point of attachment of the —CH$_2$—CO—NH— group.

6) Another embodiment relates to compounds according to any one of embodiments 1) to 4), wherein $R^1$ represents
$(C_{2-6})$alkyl [in particular isopropyl, tert.-butyl, or isobutyl];
$(C_{2-4})$alkyl mono-substituted with cyano, or $(C_{1-3})$alkoxy (especially methoxy); [in particular such group is 1-methoxy-ethyl, or 1-cyano-1-methyl-ethyl]; S$(C_{1-4})$fluoroalkyl [in particular trifluoromethyl, 2,2,2-trifluoro-1,1-dimethyl-ethyl];
$(C_{1-3})$fluoroalkoxy [in particular 2,2,2-trifluoroethoxy];
pentafluoro-sulfanyl;
$(C_{3-6})$cycloalkyl-L$_1$- wherein
said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro, or tri-substituted with two fluoro substituents and a $(C_{1-3})$alkyl (especially methyl) substituent; and
the linker $L^1$ represents a direct bond, $(C_{1-2})$alkylene, oxygen, or $(C_{1-2})$alkylene-oxy (which is attached to the rest of the molecule through the oxygen atom); [in particular such group $(C_{3-6})$cycloalkyl-L$^1$- is cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-hydroxy-cyclopropyl, 1-cyano-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];
5- or 6-membered heteroaryl selected from oxadiazolyl, pyrazinyl, pyrimidinyl, and pyridinyl; wherein said heteroaryl independently is optionally mono-substituted with $(C_{1-3})$alkyl (especially methyl); or
—NR$^{11}$R$^{12}$, wherein
R$^{11}$ and R$^{12}$ independently represent $(C_{1-3})$alkyl, $(C_{2-3})$fluoroalkyl, $(C_{3-6})$cycloalkyl, $(C_{3-6})$cycloalkyl mono- or di-substituted with fluoro, $(C_{3-6})$cycloalkyl-$(C_{1-3})$alkyl, $(C_{1-3})$alkoxy-$(C_{2-3})$alkyl [in particular such group —NR$^{11}$R$^{12}$ is dimethylamino, ethyl-methyl-amino, diethylamino, cyclopropyl-methyl-amino, (2-methoxyethyl)-methyl-amino, (cyclopropylmethyl)-methyl-amino, or (2,2-difluoro-ethyl)-methyl-amino];
or R$^{11}$ and R$^{12}$, together with the nitrogen atom to which they are attached to, form an azetidinyl or a pyrrolidinyl ring, both independently optionally mono- or di-substituted with fluoro; [in particular such group —NR$^{11}$R$^{12}$ is azetidinyl, 3-fluoro-azetidinyl, 3,3-difluoro-azetidinyl, pyrrolidinyl, 3-fluoro-pyrrolidinyl, or 3,3-difluoro-pyrrolidinyl];
and $(R^4)_n$ represents one optional substituent (i.e. n represents the integer 0, or 1) selected from $(C_{1-4})$alkyl (especially methyl), $(C_{1-4})$alkoxy (especially methoxy), $(C_{1-3})$fluoroalkyl (especially trifluoromethyl), $(C_{1-3})$fluoroalkoxy (especially trifluoromethoxy), halogen (especially fluoro), and cyano [especially $(R^4)_n$ is absent (i.e. n=0); or $(R^4)_n$ represents one halogen or methyl substituent].

7) Another embodiment relates to compounds according to any one of embodiments 1) to 4), wherein $R^1$ represents
$(C_{2-6})$alkyl [in particular isopropyl, tert.-butyl, or isobutyl];
$(C_{1-4})$fluoroalkyl [in particular trifluoromethyl, 2,2,2-trifluoro-1,1-dimethyl-ethyl];
$(C_{1-3})$fluoroalkoxy [in particular 2,2,2-trifluoroethoxy];
$(C_{3-6})$cycloalkyl-L- wherein
said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro, or tri-substituted with two fluoro substituents and a $(C_{1-3})$alkyl (especially methyl) substituent; and
the linker $L^1$ represents a direct bond, $(C_{1-2})$alkylene, oxygen, or $(C_{1-2})$alkylene-oxy (which is attached to the rest of the molecule through the oxygen atom); [in particular such group $(C_{3-6})$cycloalkyl-L- is cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-hydroxy-cyclopropyl, 1-cyano-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy; or it is oxetan-3-yl-methoxy, (3-fluoro-oxetan-3-yl)-methoxy, (3,3-difluoro-cyclobutyl)-methoxy, (3-methyl-oxetan-3-yl)-methoxy, or (3,3-difluoro-1-methyl-cyclobutyl)-methoxy];

5- or 6-membered heteroaryl selected from oxadiazolyl, pyrazinyl, pyrimidinyl, and pyridinyl (especially oxadiazolyl, pyridinyl); wherein said heteroaryl independently is optionally mono-substituted with $(C_{1-3})$alkyl (especially methyl); or —$NR^{11}R^{12}$, wherein
  $R^{11}$ and $R^{12}$, together with the nitrogen atom to which they are attached to, form an azetidinyl or a pyrrolidinyl ring, both independently optionally mono- or di-substituted with fluoro; [in particular azetidinyl, 3-fluoro-azetidinyl, 3,3-difluoro-azetidinyl, pyrrolidinyl, 3-fluoro-pyrrolidinyl, or 3,3-difluoro-pyrrolidinyl];

and $(R^4)_n$ represents one optional substituent (i.e. n represents the integer 0, or 1) selected from $(C_{1-4})$alkyl (especially methyl), $(C_{1-4})$alkoxy (especially methoxy), $(C_{1-3})$fluoroalkyl (especially trifluoromethyl), $(C_{1-3})$fluoroalkoxy (especially trifluoromethoxy), halogen (especially fluoro), and cyano [especially $(R^4)_n$ is absent (i.e. n=0); or $(R^4)_n$ represents one halogen or methyl substituent].

8) Another embodiment relates to compounds according to any one of embodiments 1) to 4), wherein $R^1$ represents
  $(C_{2-6})$alkyl [in particular isopropyl, tert.-butyl, or isobutyl];
  $(C_{1-4})$fluoroalkyl [in particular trifluoromethyl, 2,2,2-trifluoro-1,1-dimethyl-ethyl];
  $(C_{1-3})$fluoroalkoxy [in particular 2,2,2-trifluoroethoxy];
  $(C_{3-6})$cycloalkyl wherein
    said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro; [in particular cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-hydroxy-cyclopropyl, 1-cyano-cyclopropyl, or 3-hydroxy-oxetan-3-yl];
  $(C_{3-6})$cycloalkyl-$(C_{1-2})$alkylene- [in particular cyclopropyl-methyl];
  $(C_{3-6})$cycloalkyl-oxy- wherein
    said $(C_{3-6})$cycloalkyl optionally contains one ring oxygen atom; wherein said $(C_{3-6})$cycloalkyl is unsubstituted, or mono- or di-substituted with fluoro; [in particular cyclopropyl-oxy, oxetan-3-yl-oxy, cyclobutyl-oxy, or 3,3-difluoro-cyclobutyl-oxy];
  $(C_{3-6})$cycloalkyl-$(C_{1-2})$alkylene-oxy- wherein
    said $(C_{3-6})$cycloalkyl optionally contains one ring oxygen atom; wherein said $(C_{3-6})$cycloalkyl is unsubstituted, or mono-substituted with fluoro, or $(C_{1-3})$alkyl (especially methyl), or di-substituted with fluoro; [in particular oxetan-3-yl-methoxy, (3-fluoro-oxetan-3-yl)-methoxy, (3,3-difluoro-cyclobutyl)-methoxy, or (3-methyl-oxetan-3-yl)-methoxy];

5- or 6-membered heteroaryl selected from oxadiazolyl, pyrazinyl, pyrimidinyl, and pyridinyl (especially oxadiazolyl, pyridinyl); wherein said heteroaryl independently is optionally mono-substituted with $(C_{1-3})$alkyl (especially methyl); or —$NR^{11}R^{12}$, wherein
  $R^{11}$ and $R^{12}$, together with the nitrogen atom to which they are attached to, form a pyrrolidinyl ring optionally mono- or di-substituted with fluoro [in particular pyrrolidinyl, 3-fluoro-pyrrolidinyl, 3,3-difluoro-pyrrolidinyl];

and $(R^4)_n$ represents one optional substituent (i.e. n represents the integer 0, or 1) selected from $(C_{1-4})$alkyl (especially methyl), $(C_{1-4})$alkoxy (especially methoxy), $(C_{1-3})$fluoroalkyl (especially trifluoromethyl), $(C_{1-3})$fluoroalkoxy (especially trifluoromethoxy), halogen (especially fluoro), and cyano [especially $(R^4)_n$ is absent (i.e. n=0); or $(R^4)_n$ represents one halogen or methyl substituent].

9) Another embodiment relates to compounds according to any one of embodiments 1) to 4), wherein $R^1$ represents
  $(C_{2-6})$alkyl [in particular isopropyl, tert.-butyl, or isobutyl, preferably tert.-butyl];
  $(C_{1-4})$fluoroalkyl [in particular trifluoromethyl, 2,2,2-trifluoro-1,1-dimethyl-ethyl; preferably 2,2,2-trifluoro-1,1-dimethyl-ethyl];
  $(C_{1-3})$fluoroalkoxy [in particular 2,2,2-trifluoroethoxy];
  $(C_{3-6})$cycloalkyl wherein
    said $(C_{3-6})$cycloalkyl optionally contains one ring oxygen atom; wherein said $(C_{3-6})$cycloalkyl is mono-substituted with fluoro or $(C_{1-3})$fluoroalkyl (especially trifluoromethyl), or di-substituted with fluoro; [in particular 3-fluoro-oxetan-3-yl, 3,3-difluoro-cyclobutyl, 1-trifluoromethyl-cyclopropyl, or 2-trifluoromethyl-cyclopropyl; especially 3-fluoro-oxetan-3-yl, 3,3-difluoro-cyclobutyl, or 1-trifluoromethyl-cyclopropyl; preferably 1-trifluoromethyl-cyclopropyl]; or
  $(C_{3-6})$cycloalkyl-oxy- wherein
    said $(C_{3-6})$cycloalkyl optionally contains one ring oxygen atom; wherein said $(C_{3-6})$cycloalkyl is unsubstituted, or di-substituted with fluoro; [in particular cyclopropyl-oxy, oxetan-3-yl-oxy, cyclobutyl-oxy, or 3,3-difluoro-cyclobutyl-oxy, especially 3,3-difluoro-cyclobutyl-oxy];

and $(R^4)_n$ represents one optional substituent (i.e. n represents the integer 0, or 1) selected from $(C_{1-4})$alkyl (especially methyl), or halogen (especially fluoro) [especially $(R^4)_n$ is absent (i.e. n=0); or $(R^4)_n$ represents one halogen or methyl substituent].

10) Another embodiment relates to compounds according to any one of embodiments 1) to 4), wherein
  $R^1$ together with $(R^4)_n$ forms a non-aromatic 5- or 6-membered ring which is fused to the phenyl/pyridine ring to form a bicyclic ring system; wherein said bicyclic ring system is selected from 2,3-dihydro-benzooxazolyl, 3,4-dihydro-2H-benzo[1,4]oxazinyl, 2,3-dihydro-1H-indolyl, and 2,3-dihydro-benzofuranyl; wherein said non-aromatic 5- or 6-membered ring part of said bicyclic ring system independently is optionally further mono-substituted with oxo; or di-, tri-, or tetra-substituted wherein one substituent is oxo and the remaining are $(C_{1-3})$alkyl (especially methyl); [in particular such bicyclic ring system is a group selected from 2-oxo-2,3-dihydro-benzooxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3- dihydro-benzooxazol-6-yl, 3,3-dimethyl-2-oxo-2,3-dihydro-1H-indol-5-yl, 1,3,3-trimethyl-2-oxo-2,3-dihydro-1H-indol-5-yl, 2,2-dimethyl-2,3-dihydro-benzofuran-6-yl, 2,2-dimethyl-2,3-dihydro-benzofuran-5-yl, or 3,3-dimethyl-2,3-dihydro-benzofuran-5-yl];

or (notably) $R^1$ together with $(R^4)_n$ forms an aromatic 5- or 6-membered ring which is fused to the phenyl/pyridine ring to form a bicyclic aromatic ring system selected from pyrrolo[2,3-b]pyridinyl, indolyl, indazolyl, quinoxalinyl, benzoimidazolyl, and quinolinyl; wherein said fused 5- or 6-membered aromatic ring part of said aromatic bicyclic ring system independently is optionally further mono- or di-substituted wherein the substituents are independently selected from $(C_{1-3})$alkyl (especially methyl, isopropyl), $(C_{3-6})$cycloalkyl (especially cyclobutyl), $(C_1)$fluoroalkyl (especially trifluoromethyl), or cyano [especially such aromatic bicyclic ring system is indolyl or indazolyl, both mono-substituted with methyl; in particular such aromatic bicyclic ring system is a group selected from 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl-1H-benzoimidazol-6-yl, 1-methyl-1H-benzoimidazol-5-yl, 1-methyl-1H-benzoimidazol-6-yl, or quinolin-7-yl].

11) Another embodiment relates to compounds according to any one of embodiments 1) to 4), wherein $R^1$ represents methyl, or halogen (especially fluoro); and $(R^4)_n$ represents one substituent selected from $(C_{1-3})$fluoroalkoxy (especially 2,2,2-trifluoroethoxy) which is attached to the phenyl/pyridinyl ring in ortho or meta-position to the point of attachment of the —CH$_2$—CO—NH— group.

12) Another embodiment relates to compounds according to any one of embodiments 1) to 4), wherein the fragment

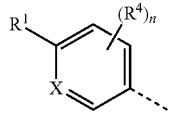

represents 4-cyclopropyl-phenyl, 4-isopropyl-phenyl, 4-dimethylamino-phenyl, 4-trifluoromethyl-phenyl, 4-tert.-butyl-phenyl, 4-isobutyl-phenyl, 4-(1-methoxy-ethyl)-phenyl, 4-(1-methyl-cyclopropyl)-phenyl, 4-(cyclopropyl-methyl)-phenyl, 4-(1-hydroxy-cyclopropyl)-phenyl, 4-(cyclopropyl-oxy)-phenyl, 4-(azetidin-1-yl)-phenyl, 4-(oxetan-3-yl-oxy)-phenyl, 4-(3-hydroxy-oxetan-3-yl)-phenyl, 4-(3-fluoro-oxetan-3-yl)-phenyl, 4-(cyclobutyl-oxy)-phenyl, 4-(3-methyl-oxetan-3-yl)-phenyl, 4-([1,2,4]oxadiazol-3-yl)-phenyl, 4-(5-methyl-[1,2,4]oxadiazol-3-yl)-phenyl, 4-(3-fluoro-azetidin-1-yl)-phenyl, 4-(1-cyano-cyclopropyl)-phenyl, 4-(1-cyano-1-methyl-ethyl)-phenyl, 4-(diethylamino)-phenyl, 4-(pentafluoro-sulfanyl)-phenyl, 4-(2,2,2-trifluoroethoxy)-phenyl, 3-methyl-4-(2,2,2-trifluoroethoxy)-phenyl, 3-fluoro-4-(2,2,2-trifluoroethoxy)-phenyl, 4-((2-methoxyethyl)-methyl-amino)-phenyl, 4-(3,3-difluoro-cyclobutyl)-phenyl, 4-(3-methoxy-oxetan-3-yl)-phenyl, 4-(oxetan-3-yl-methoxy)-phenyl, 4-(pyrazin-2-yl)-phenyl, 4-(3-methyl-pyrazin-2-yl)-phenyl, 4-(pyrimidin-4-yl)-phenyl, 4-(5-methyl-pyrimidin-4-yl)-phenyl, 4-(pyrimidin-2-yl)-phenyl, 4-(pyrimidin-5-yl)-phenyl, 4-(pyridin-4-yl)-phenyl, 4-(pyridin-3-yl)-phenyl, 4-(pyridin-2-yl)-phenyl, 4-(3-fluoro-pyrrolidin-1-yl)-phenyl, 4-(3,3-difluoro-azetidin-1-yl)-phenyl, 4-(2-oxo-pyrrolidin-1-yl)-phenyl, 4-(2-trifluoromethyl-cyclopropyl)-phenyl, 4-(1-trifluoromethyl-cyclopropyl)-phenyl, 4-((3-fluoro-oxetan-3-yl)-methoxy)-phenyl, 4-(3,3-difluoro-cyclobutyl-oxy)-phenyl, 4-(2,2,2-trifluoro-1,1-dimethyl-ethyl)-phenyl, 4-((3,3-difluoro-cyclobutyl)-methoxy)-phenyl, 4-((3,3-difluoro-1-methyl-cyclobutyl)-methoxy)-phenyl; 2-cyclopropyl-pyridin-5-yl, 2-dimethylamino-pyridin-5-yl, 2-isopropyl-pyridin-5-yl, 2-(ethyl-methyl-amino)-pyridin-5-yl, 2-(3-fluoro-azetidin-1-yl)-pyridin-5-yl, 2-(pyrrolidin-1-yl)-pyridin-5-yl, 2-(cyclopropyl-methyl-amino)-pyridin-5-yl, 2-(3-fluoro-oxetan-3-yl)-pyridin-5-yl, 2-(diethylamino)-pyridin-5-yl, 2-((2,2-difluoro-ethyl)-methyl-amino)-pyridin-5-yl, 2-((2-methoxyethyl)-methyl-amino)-pyridin-5-yl, 2-(2,2,2-trifluoroethoxy)-pyridin-5-yl, 3-fluoro-2-(2,2,2-trifluoroethoxy)-pyridin-5-yl, 3-fluoro-2-(pyrrolidin-1-yl)-pyridin-5-yl, 2-(3-fluoro-pyrrolidin-1-yl)-pyridin-5-yl, 2-((cyclopropylmethyl)-methyl-amino)-pyridin-5-yl, 2-(3,3-difluoro-azetidin-1-yl)-pyridin-5-yl, 2-(3-methoxy-oxetan-3-yl)-pyridin-5-yl, 2-(3,3-difluoro-pyrrolidin-1-yl)-pyridin-5-yl; 2-oxo-2,3-dihydro-benzooxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3-dihydro-benzooxazol-6-yl, 3,3-dimethyl-2-oxo-2,3-dihydro-1H-indol-5-yl, 1,3,3-trimethyl-2-oxo-2,3-dihydro-1H-indol-5-yl, 2,2-dimethyl-2,3-dihydro-benzofuran-6-yl, 2,2-dimethyl-2,3-dihydro-benzofuran-5-yl, 3,3-dimethyl-2,3-dihydro-benzofuran-5-yl; 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl-1H-benzoimidazol-6-yl, 1-methyl-1H-benzoimidazol-5-yl, 1-methyl-1H-benzoimidazol-6-yl, quinolin-7-yl; 4-methyl-3-(2,2,2-trifluoroethoxy)-phenyl; or 4-fluoro-2-(2,2,2-trifluoroethoxy)-phenyl.

13) Another embodiment relates to compounds according to any one of embodiments 1) to 12), wherein
Y represents a ring nitrogen atom; and
$R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, isopropoxy); $(C_{3-6})$cycloalkyl-oxy (especially cyclopropyl-oxy); $(C_{1-3})$fluoroalkyl (especially trifluoromethyl); $(C_{1-3})$fluoroalkoxy (especially difluoromethoxy, trifluoromethoxy, 2,2,2-trifluoroethoxy); $(C_{1-3})$alkoxy-$(C_{2-3})$alkoxy (especially 2-methoxy-ethoxy); halogen (especially fluoro); cyano; or —NR$^{21}$R$^{22}$, wherein R$^{21}$ and R$^{22}$ independently represent $(C_{1-3})$alkyl (especially dimethylamino), or R$^{21}$ and R$^{22}$, together with the nitrogen atom to which they are attached to, form a ring selected from azetidinyl optionally mono- or di-substituted with fluoro, pyrrolidinyl optionally mono- or di-substituted with fluoro, or piperidinyl optionally mono- or di-substituted with fluoro; and $(R^5)_m$ represents one or two optional substituents (i.e. m represents the integer 0, 1, or 2) independently selected from the group consisting of $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen (especially fluoro); cyano; $(C_{1-3})$fluoroalkyl (especially trifluoromethyl); and $(C_{1-3})$fluoroalkoxy (especially trifluoromethoxy, 2,2,2-trifluoroethoxy); [especially $(R^5)_m$ is absent (i.e. m=0), or $(R^5)_m$ represents one halogen substituent, preferably $(R^5)_m$ is absent]; or Y represents a ring carbon atom; and $R^2$ represents $(C_{1-4})$alkyl (especially methyl, ethyl, isopropyl, tert.-butyl); $(C_{3-6})$cycloalkyl (especially cyclopropyl); $(C_{1-4})$alkoxy (especially methoxy); $(C_{3-6})$cycloalkyl-oxy (especially cyclopropyl-oxy); $(C_{1-3})$fluoroalkyl (especially trifluoromethyl); $(C_{1-3})$fluoroalkoxy (especially difluoromethoxy, trifluoromethoxy); halogen (especially fluoro); or cyano; and $(R^5)_m$ represents one or two optional substituents (i.e. m represents the integer 0, 1, or 2) independently selected from the group consisting of $(C_{1-4})$alkyl (especially methyl); $(C_{3-6})$cycloalkyl (especially cyclopropyl); $(C_{1-4})$alkoxy (especially methoxy); halogen (especially fluoro); cyano; $(C_{1-3})$fluoroalkyl (especially trifluoromethyl); and $(C_{1-3})$fluoroalkoxy (especially trifluoromethoxy); [especially $(R^5)_m$ is absent (i.e. m=0), or $(R^5)_m$ represents one halogen substituent, preferably $(R^5)_m$ is absent].

14) Another embodiment relates to compounds according to any one of embodiments 1) to 12), wherein Y represents a ring nitrogen atom; and $R^2$ represents $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); $(C_{1-3})$fluoroalkyl (especially trifluoromethyl); $(C_{1-3})$fluoroalkoxy (especially 2,2,2-trifluoroethoxy); $(C_{1-3})$alkoxy-$(C_{2-3})$alkoxy (especially 2-methoxy-ethoxy); halogen (especially fluoro); or cyano; [in particular $R^2$ represents fluoro or cyano]; and $(R^5)_m$ represents one optional substituent (i.e. m represents the integer 0, or 1) independently selected from the group consisting of $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen (especially fluoro); cyano; $(C_{1-3})$fluoroalkyl (especially difluoromethyl, trifluoromethyl); and $(C_{1-3})$fluoroalkoxy (especially trifluoromethoxy, 2,2,2-trifluoroethoxy); [especially $(R^5)_m$ is absent (i.e. m=0), or $(R^5)_m$ represents one halogen substituent, preferably $(R^5)_m$ is absent]; or Y represents a ring carbon atom; and $R^2$ represents $(C_{1-4})$alkyl (especially methyl, ethyl, isopropyl, tert.-butyl); $(C_{3-6})$cycloalkyl (especially cyclopropyl); $(C_{1-4})$alkoxy (especially methoxy); $(C_{3-6})$cycloalkyl-oxy (especially cyclopropyl-oxy); $(C_{1-3})$fluoroalkyl (especially trifluoromethyl); $(C_{1-3})$fluoroalkoxy (especially difluoromethoxy, trifluoromethoxy); halogen (especially fluoro); or cyano; and $(R^5)_m$ represents one or two optional substituents (i.e. m represents the integer 0, 1, or 2) independently selected from the group consisting of $(C_{1-4})$alkyl (especially methyl); $(C_{1-4})$alkoxy (especially methoxy); halogen (especially fluoro); cyano; $(C_{1-3})$ fluoroalkyl (especially trifluoromethyl), and $(C_{1-3})$ fluoroalkoxy (especially trifluoromethoxy) [especially $(R^5)_m$ is absent (i.e. m=0), or $(R^5)_m$ represents one halogen substituent, preferably $(R^5)_m$ is absent].

15) Another embodiment relates to compounds according to any one of embodiments 1) to 12), wherein Y represents a ring nitrogen atom; and $R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, isopropoxy); $(C_{1-3})$fluoroalkyl (especially trifluoromethyl); $(C_{1-3})$fluoroalkoxy (especially difluoromethoxy, trifluoromethoxy, 2,2,2-trifluoroethoxy); $(C_{1-3})$alkoxy-$(C_{2-3})$alkoxy (especially 2-methoxy-ethoxy); halogen (especially fluoro); or (preferably) cyano; [in particular $R^2$ represents fluoro or cyano]; and $(R^5)_m$ represents one optional substituent (i.e. m represents the integer 0, or 1) independently selected from the group consisting of $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen (especially fluoro); cyano; $(C_{1-3})$ fluoroalkyl (especially difluoromethyl, trifluoromethyl), and $(C_{1-3})$fluoroalkoxy (especially trifluoromethoxy, 2,2,2-trifluoroethoxy) [especially $(R^5)_m$ is absent (i.e. m=0), or $(R^5)_m$ represents one halogen substituent, preferably $(R^5)_m$ is absent].

16) Another embodiment relates to compounds according to any one of embodiments 1) to 12), wherein the fragment

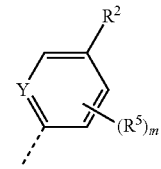

represents 4-fluorophenyl, 4-chlorophenyl, 4-bromophenyl, 4-methylphenyl, 4-ethylphenyl, 3-fluoro-4-methyl-phenyl, 4-fluoro-3-methyl-phenyl, 4-fluoro-3-cyano-phenyl, 4-fluoro-3,5-dimethylphenyl, 4-chloro-3-fluorophenyl, 3-chloro-4-fluorophenyl, 3,4-difluorophenyl, 3,5-difluoro-4-methoxy-phenyl, 4-cyano-3,5-difluoro-phenyl, 4-methoxyphenyl, 4-cyanophenyl, 4-cyclopropyl-phenyl, 3,4,5-trifluorophenyl, 4-tert.-butyl-phenyl, 4-isopropyl-phenyl, 4-(cyclopropyl-oxy)-phenyl, 4-chloro-3-trifluoromethyl-phenyl, 4-fluoro-3-trifluoromethyl-phenyl, 4-methoxy-3-trifluoromethyl-phenyl, 4-difluoromethoxy-phenyl, 4-trifluoromethoxy-phenyl, 4-chloro-3-trifluoromethoxy-phenyl, 4-fluoro-3-trifluoromethoxy-phenyl; 5-fluoro-pyridin-2-yl, 5-bromo-pyridin-2-yl, 5-cyano-pyridin-2-yl, 5-methyl-pyridin-2-yl, 5-ethyl-pyridin-2-yl, 5-methoxy-pyridin-2-yl, 6-chloro-5-fluoro-pyridin-2-yl, 5-cyclopropyl-pyridin-2-yl, 6-cyano-5-fluoro-pyridin-2-yl, 5-cyano-6-fluoro-pyridin-2-yl, 6-chloro-5-cyano-pyridin-2-yl, 5-chloro-6-cyano-pyridin-2-yl, 5-cyano-6-methyl-pyridin-2-yl, 5-cyano-4-methyl-pyridin-2-yl, 6-cyano-5-methyl-pyridin-2-yl, 5-cyano-6-isobutyl-pyridin-2-yl, 5-cyano-6-methoxy-pyridin-2-yl, 5-cyano-6-isopropoxy-pyridin-2-yl, 5-trifluoromethyl-pyridin-2-yl, 5-(2,2,2-trifluoroethoxy)-pyridin-2-yl, 5-cyano-6-(2,2,2-trifluoroethoxy)-pyridin-2-yl, 5-isobutyl-pyridin-2-yl, 5-isopropoxy-pyridin-2-yl, 5-dimethylamino-pyridine-2-yl, 4-cyclopropyl-5-cyano-

23 pyridin-2-yl, 5-(2-methoxy-ethoxy)-pyridin-2-yl, or 5-(3-fluoropyrrolidin-1-yl)-pyridin-2-yl.

17) Another embodiment relates to compounds according to embodiment 1), wherein X represents a ring carbon or a ring nitrogen atom;

$R^1$ represents

- $(C_{2-6})$alkyl [in particular isopropyl, tert.-butyl, or isobutyl];
- $(C_{2-4})$alkyl mono-substituted with cyano or $(C_{1-3})$alkoxy (especially methoxy); [in particular such group is 1-methoxy-ethyl, or 1-cyano-1-methyl-ethyl];
- $(C_{1-4})$fluoroalkyl [in particular trifluoromethyl, 2,2,2-trifluoro-1,1-dimethyl-ethyl];
- $(C_{1-3})$fluoroalkoxy [in particular trifluoromethoxy, 2,2,2-trifluoroethoxy, 3,3,3-trifluoropropoxy];
- $(C_{3-6})$cycloalkyl-$L^1$- wherein
    said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro; and
    the linker $L^1$ represents a direct bond, $(C_{1-2})$alkylene, or oxygen;
    [in particular such group $(C_{3-6})$cycloalkyl-$L_1$- is cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-cyano-cyclopropyl, 1-hydroxy-cyclopropyl, 1-methoxy-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy];
- 5- or 6-membered heteroaryl, independently optionally mono-substituted with $(C_{1-3})$alkyl (especially methyl); [in particular oxadiazolyl, pyrazinyl, pyrimidinyl, or pyridinyl];
- —$NR^{11}R^{12}$, wherein
    $R^{11}$ and $R^{12}$ independently represent hydrogen, $(C_{1-3})$alkyl, $(C_{3-6})$cycloalkyl, $(C_{3-6})$cycloalkyl-$(C_{1-3})$alkyl, $(C_{1-3})$alkoxy-$(C_{2-3})$alkyl [in particular such group —$NR^{11}R^{12}$ is dimethylamino, ethyl-methyl-amino, diethylamino, cyclopropyl-methyl-amino, (2-methoxyethyl)-methyl-amino, or (cyclopropylmethyl)-methyl-amino];
    or $R^{11}$ and $R^{12}$, together with the nitrogen atom to which they are attached to, form a 4-to- 6 membered ring optionally mono- or di-substituted with fluoro; [in particular such group —$NR^{11}R^{12}$ is azetidinyl, 3-fluoro-azetidinyl, 3,3-difluoro-azetidinyl, pyrrolidinyl, 3-fluoro-pyrrolidinyl, or 3,3-difluoro-pyrrolidinyl];

and $(R^4)_n$ represents one or two optional substituents (i.e. n represents the integer 0, 1, or 2) independently selected from $(C_{1-4})$alkyl (especially methyl, ethyl), $(C_{3-6})$cycloalkyl (especially cyclopropyl), $(C_{1-3})$fluoroalkyl (especially trifluoromethyl), $(C_{1-3})$fluoroalkoxy (especially trifluoromethoxy), halogen (especially fluoro), and cyano [especially $(R^4)_n$ is absent (i.e. n=0); or $(R^4)_n$ represents one halogen or methyl substituent];

or $R^1$ together with $(R^4)_n$ forms an aromatic 5- or 6-membered ring which is fused to the phenyl/pyridine ring; wherein said 5- or 6-membered ring contains one or two heteroatoms selected from nitrogen, wherein said fused 5- or 6-membered aromatic ring independently is optionally further mono- or di-substituted wherein the substituents are independently selected from $(C_{1-3})$alkyl (especially methyl, ethyl, isopropyl), $(C_{3-6})$cycloalkyl (especially cyclobutyl), $(C_1)$fluoroalkyl (especially trifluoromethyl), or cyano [in particular such aromatic 5- or 6-membered ring fused to the phenyl/pyridine ring forms, together with the phenyl/pyridine ring, a group selected from 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl-1H-benzoimidazol-6-yl, 1-methyl-1H-benzoimidazol-5-yl, 1-methyl-1H-benzoimidazol-6-yl, or quinolin-7-yl];

Y represents a ring carbon or a ring nitrogen atom; and $R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, isopropoxy); $(C_{3-6})$cycloalkyl-oxy (especially cyclopropyl-oxy); $(C_{1-3})$ fluoroalkyl (especially trifluoromethyl); $(C_{1-3})$fluoroalkoxy (especially difluoromethoxy, trifluoromethoxy, 2,2,2-trifluoroethoxy); halogen; or cyano;

and $(R^5)_m$ represents one or two optional substituents (i.e. m represents the integer 0, 1, or 2) independently selected from $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen; cyano; $(C_{1-3})$fluoroalkyl (especially difluoromethyl, trifluoromethyl); and $(C_{1-3})$fluoroalkoxy (especially trifluoromethoxy, 2,2,2-trifluoroethoxy); [especially $(R^5)_m$ is absent (i.e. m=0), or $(R^5)_m$ represents one halogen substituent; preferably $(R^5)_m$ is absent].

18) Another embodiment relates to compounds according to embodiment 1), wherein

X represents a ring carbon or a ring nitrogen atom;

$R^1$ represents

- $(C_{2-6})$alkyl [in particular isopropyl, tert.-butyl, or isobutyl];
- $(C_{2-4})$alkyl mono-substituted with cyano; [in particular such group is 1-cyano-1-methyl-ethyl];
- $(C_{1-4})$fluoroalkyl [in particular trifluoromethyl, 2,2,2-trifluoro-1,1-dimethyl-ethyl];
- $(C_{3-6})$cycloalkyl-$L_1$- wherein
    said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro; and
    the linker $L^1$ represents a direct bond, or $(C_{1-2})$alkylene;
    [in particular such group $(C_{3-6})$cycloalkyl-$L_1$- is cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-cyano-cyclopropyl, 1-hydroxy-cyclopropyl, 1-methoxy-cyclopropyl, or 3-hydroxy-oxetan-3-yl; or it is cyclopropyl-methyl];

5- or 6-membered heteroaryl, independently optionally mono-substituted with $(C_{1-3})$alkyl (especially methyl); [in particular oxadiazolyl, pyrazinyl, pyrimidinyl, or pyridinyl];

and $(R^4)_n$ represents one or two optional substituents (i.e. n represents the integer 0, 1, or 2) independently selected from $(C_{1-4})$alkyl (especially methyl, ethyl), $(C_{3-6})$cycloalkyl (especially cyclopropyl), $(C_{1-3})$fluoroalkyl (especially trifluoromethyl), halogen (especially fluoro), and cyano [especially $(R^4)_n$ is absent (i.e. n=0); or $(R^4)_n$ represents one halogen or methyl substituent];

or $R^1$ together with $(R^4)_n$ forms an aromatic 5- or 6-membered ring which is fused to the phenyl/pyridine ring to form a bicyclic aromatic ring system selected from indolyl, indazolyl and quinolinyl; wherein said fused 5- or 6-membered aromatic ring part of said aromatic bicyclic ring system independently is optionally further mono- or di-substituted wherein the substituents are independently selected from $(C_{1-3})$alkyl (especially methyl, ethyl, isopropyl), $(C_{3-6})$cycloalkyl (especially cyclobutyl), $(C_1)$fluoroalkyl (especially trifluoromethyl), or cyano [in particular such aromatic 5- or 6-membered ring fused to the phenyl/pyridine ring forms, together with the phenyl/pyridine ring, a group selected from 1H-indol-5-yl, 1H-indol-6-yl, 1-methyl-1H-indazol-5-yl, 1-methyl-1H-indazol-6-yl, 1-ethyl-1H-indazol-5-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, or quinolin-7-yl];

Y represents a ring carbon or a ring nitrogen atom; and
$R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, isopropoxy); $(C_{3-6})$cycloalkyl-oxy (especially cyclopropyl-oxy); $(C_{1-3})$fluoroalkyl (especially trifluoromethyl); $(C_{1-3})$fluoroalkoxy (especially difluoromethoxy, trifluoromethoxy, 2,2,2-trifluoroethoxy); halogen; or cyano;

and
$(R^5)_m$ represents one or two optional substituents (i.e. m represents the integer 0, 1, or 2) independently selected from $(C_{1-4})$alkyl (especially methyl, ethyl, isobutyl); $(C_{3-6})$cycloalkyl (especially cyclopropyl); $(C_{1-4})$alkoxy (especially methoxy, isopropoxy); halogen; cyano; $(C_{1-3})$fluoroalkyl (especially difluoromethyl, trifluoromethyl); and $(C_{1-3})$fluoroalkoxy (especially trifluoromethoxy, 2,2,2-trifluoroethoxy); [especially $(R^5)_m$ is absent (i.e. m=0), or $(R^5)_m$ represents one halogen substituent; preferably $(R^5)_m$ is absent].

19) Another embodiment relates to compounds according to any one of embodiments 17) or 18), wherein X represents a ring carbon atom.

20) Another embodiment relates to compounds according to any one of embodiments 17) or 18), wherein X represents a ring nitrogen atom.

21) Another embodiment relates to compounds according to any one of embodiments 1) to 4), 13) to 17), 19) or 20), wherein
$R^1$ represents $(C_{3-6})$cycloalkyl-$L^1$- wherein said $(C_{3-6})$cycloalkyl optionally contains one ring oxygen atom; wherein said $(C_{3-6})$cycloalkyl is unsubstituted, or mono-substituted with fluoro, $(C_{1-3})$alkyl (especially methyl), $(C_{1-3})$alkoxy (especially methoxy), hydroxy, cyano, or $(C_{1-3})$fluoroalkyl (especially trifluoromethyl), or di-substituted with fluoro; and the linker $L^1$ represents a direct bond, $(C_{1-2})$alkylene, or oxygen; [in particular such group $(C_{3-6})$cycloalkyl-$L_1$- is cyclopropyl, 3-fluoro-oxetan-3-yl, 3-methoxy-oxetan-3-yl, 3-methyl-oxetan-3-yl, 3,3-difluoro-cyclobutyl, 1-trifluoromethyl-cyclopropyl, 2-trifluoromethyl-cyclopropyl, 1-methyl-cyclopropyl, 1-cyano-cyclopropyl, 1-hydroxy-cyclopropyl, 1-methoxy-cyclopropyl, or 3-hydroxy-oxetan-3-yl; or it is cyclopropyl-methyl; or it is cyclopropyl-oxy, oxetan-3-yl-oxy, cyclobutyl-oxy, or 3,3-difluoro-cyclobutyl-oxy].

22) Another embodiment relates to compounds according to any one of embodiments 1) to 4) or 13) to 20), wherein
$R^1$ represents cyclopropyl wherein said cyclopropyl is unsubstituted, or mono-substituted with $(C_{1-3})$alkyl (especially methyl), $(C_{1-3})$alkoxy (especially methoxy), cyano, or $(C_{1-3})$fluoroalkyl (especially trifluoromethyl); [in particular cyclopropyl, 1-trifluoromethyl-cyclopropyl, 2-trifluoromethyl-cyclopropyl, 1-methyl-cyclopropyl, 1-cyano-cyclopropyl, or 1-methoxy-cyclopropyl].

23) Another embodiment relates to compounds according to any one of embodiments 1) to 4) or 13) to 20), wherein
$R^1$ together with $(R^4)_n$ forms an aromatic 5- or 6-membered ring which is fused to the phenyl/pyridine ring to form a bicyclic aromatic ring system selected from indolyl, indazolyl and quinolinyl; wherein said fused 5- or 6-membered aromatic ring part of said aromatic bicyclic ring system independently is optionally further mono- or di-substituted wherein the substituents are independently selected from $(C_{1-3})$alkyl (especially methyl, ethyl, isopropyl), $(C_{3-6})$cycloalkyl (especially cyclobutyl), $(C)$fluoroalkyl (especially trifluoromethyl), or cyano [in particular such aromatic 5- or 6-membered ring fused to the phenyl/pyridine ring forms, together with the phenyl/pyridine ring, a group selected from 1H-indol-5-yl, 1H-indol-6-yl, 1-methyl-1H-indazol-5-yl, 1-methyl-1H-indazol-6-yl, 1-ethyl-1H-indazol-5-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, or quinolin-7-yl].

24) Another embodiment relates to compounds according to any one of embodiments 1), 3), 4) or 13) to 16), wherein the fragment

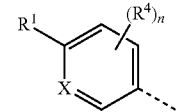

represents 4-(1-methoxy-cyclopropyl)-phenyl, 4-(1-cyano-cyclopropyl)-3-trifluoromethyl-phenyl, 4-(1-cyano-3,3-difluoro-cyclobutyl)-phenyl, 4-cyclopropylmethoxy-3-trifluoromethoxy-phenyl, 3-cyano-4-iso-butyl-phenyl, 3-methyl-4-trifluoromethoxy-phenyl, 3,5-dimethyl-4-(2,2,2-trifluoroethoxy)-phenyl, 3-ethyl-4-(2,2,2-trifluoroethoxy)-phenyl, 3-methyl-4-(3,3,3-trifluoropropoxy)-phenyl, 3-cyclopropyl-4-(2,2,2-trifluoroethoxy)-phenyl, 5-methyl-6-(2,2,2-trifluoroethoxy)-pyridin-3-yl, 3,3-dimethyl-2,3-dihydro-benzofuran-6-yl, or 3-methylchroman-7-yl.

25) Another embodiment relates to compounds according to any one of embodiments 1) to 12) or 17) to 24), wherein
Y represents a ring nitrogen atom;
$R^2$ represents $(C_{1-4})$alkyl (especially methyl, ethyl, isopropyl, isobutyl, tert.-butyl); $(C_{3-6})$cycloalkyl (especially cyclopropyl); $(C_{1-4})$alkoxy (especially methoxy, isopropoxy);

($C_{1-3}$)fluoroalkyl (especially trifluoromethyl); ($C_{1-3}$)fluoroalkoxy (especially difluoromethoxy, trifluoromethoxy, 2,2,2-trifluoroethoxy); halogen (especially fluoro); or cyano; and $(R^5)_m$ represents one optional substituent (i.e. m represents the integer 0, or 1) selected from the group consisting of ($C_{1-4}$)alkyl (especially methyl, ethyl, isobutyl); ($C_{3-6}$)cycloalkyl (especially cyclopropyl); ($C_{1-4}$)alkoxy (especially methoxy, isopropoxy); halogen (especially fluoro); cyano; ($C_{1-3}$)fluoroalkyl (especially difluoromethyl); and ($C_{1-3}$)fluoroalkoxy (especially trifluoromethoxy, 2,2,2-trifluoroethoxy); [especially $(R^5)_m$ is absent (i.e. m=0), or $(R^5)_m$ represents one halogen substituent, preferably $(R^5)_m$ is absent].

26) Another embodiment relates to compounds according to any one of embodiments 1) to 12) or 17) to 24), wherein Y represents a ring carbon atom;

$R^2$ represents ($C_{1-4}$)alkyl (especially methyl, ethyl, isopropyl, tert.-butyl); ($C_{3-6}$)cycloalkyl (especially cyclopropyl); ($C_{1-4}$)alkoxy (especially methoxy); ($C_{3-6}$)cycloalkyl-oxy (especially cyclopropyl-oxy); ($C_{1-3}$)fluoroalkyl (especially trifluoromethyl); ($C_{1-3}$)fluoroalkoxy (especially difluoromethoxy, trifluoromethoxy); halogen (especially fluoro); or cyano; and $(R^5)_m$ represents one or two optional substituents (i.e. m represents the integer 0, 1, or 2) independently selected from the group consisting of ($C_{1-4}$)alkyl (especially methyl); halogen (especially fluoro); cyano; ($C_{1-3}$)fluoroalkyl (especially trifluoromethyl); and ($C_{1-3}$)fluoroalkoxy (especially trifluoromethoxy); [especially $(R^5)_m$ is absent (i.e. m=0), or $(R^5)_m$ represents one halogen substituent, preferably $(R^5)_m$ is absent].

27) Another embodiment relates to compounds according to any one of embodiments 1) to 15) or 17) to 26), wherein $(R^5)_m$ is absent (i.e. m=0).

28) Another embodiment relates to compounds according to any one of embodiments 1) to 12) or 21) to 24), wherein the fragment

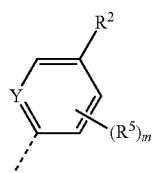

represents 5-cyano-3-fluoro-pyridin-2-yl, 4-cyano-5-fluoro-pyridin-2-yl, 5-cyano-6-difluoromethyl-pyridin-2-yl, 5-cyano-4-difluoromethyl-pyridin-2-yl, 5-(azetidin-1-yl)-pyridin-2-yl, 5-(pyrrolidin-1-yl)-pyridin-2-yl, or 5-(3,3-difluoro-pyrrolidin-1-yl)-pyridin-2-yl.

29) The invention, thus, relates to compounds of the formula (I) as defined in embodiment 1), or to such compounds further limited by the characteristics of any one of embodiments 2) to 28), under consideration of their respective dependencies; to pharmaceutically acceptable salts thereof; and to the use of such compounds as medicaments especially in the treatment of diseases or disorders where calcium T channels are involved as described herein below. For avoidance of any doubt, especially the following embodiments relating to the compounds of formula (I) are thus possible and intended and herewith specifically disclosed in individualized form:

1, 2+1, 3+1, 3+2+1, 4+1, 4+2+1, 5+2+1, 5+3+2+1, 5+4+2+1, 6+2+1, 6+3+2+1, 6+4+2+1, 7+2+1, 7+3+2+1, 7+4+2+1, 8+2+1, 8+3+2+1, 8+4+2+1, 9+2+1, 9+3+2+1, 9+4+2+1, 10+2+1, 10+3+2+1, 10+4+2+1, 11+2+1, 11+3+2+1, 11+4+2+1, 12+2+1, 12+3+2+1, 12+4+2+1, 13+1, 13+2+1, 13+3+1, 13+3+2+1, 13+4+1, 13+4+2+1, 13+5+2+1, 13+5+3+2+1, 13+5+4+2+1, 13+6+2+1, 13+6+3+2+1, 13+6+4+2+1, 13+7+2+1, 13+7+3+2+1, 13+7+4+2+1, 13+8+2+1, 13+8+3+2+1, 13+8+4+2+1, 13+9+2+1, 13+9+3+2+1, 13+9+4+2+1, 13+10+2+1, 13+10+3+2+1, 13+10+4+2+1, 13+11+2+1, 13+11+3+2+1, 13+11+4+2+1, 13+12+2+1, 13+12+3+2+1, 13+12+4+2+1, 14+1, 14+2+1, 14+3+1, 14+3+2+1, 14+4+1, 14+4+2+1, 14+5+2+1, 14+5+3+2+1, 14+5+4+2+1, 14+6+2+1, 14+6+3+2+1, 14+6+4+2+1, 14+7+2+1, 14+7+3+2+1, 14+7+4+2+1, 14+8+2+1, 14+8+3+2+1, 14+8+4+2+1, 14+9+2+1, 14+9+3+2+1, 14+9+4+2+1, 14+10+2+1, 14+10+3+2+1, 14+10+4+2+1, 14+11+2+1, 14+11+3+2+1, 14+11+4+2+1, 14+12+2+1, 14+12+3+2+1, 14+12+4+2+1, 15+1, 15+2+1, 15+3+1, 15+3+2+1, 15+4+1, 15+4+2+1, 15+5+2+1, 15+5+3+2+1, 15+5+4+2+1, 15+6+2+1, 15+6+3+2+1, 15+6+4+2+1, 15+7+2+1, 15+7+3+2+1, 15+7+4+2+1, 15+8+2+1, 15+8+3+2+1, 15+8+4+2+1, 15+9+2+1, 15+9+3+2+1, 15+9+4+2+1, 15+10+2+1, 15+10+3+2+1, 15+10+4+2+1, 15+11+2+1, 15+11+3+2+1, 15+11+4+2+1, 15+12+2+1, 15+12+3+2+1, 15+12+4+2+1, 16+1, 16+2+1, 16+3+1, 16+3+2+1, 16+4+1, 16+4+2+1, 16+5+2+1, 16+5+3+2+1, 16+5+4+2+1, 16+6+2+1, 16+6+3+2+1, 16+6+4+2+1, 16+7+2+1, 16+7+3+2+1, 16+7+4+2+1, 16+8+2+1, 16+8+3+2+1, 16+8+4+2+1, 16+9+2+1, 16+9+3+2+1, 16+9+4+2+1, 16+10+2+1, 16+10+3+2+1, 16+10+4+2+1, 16+11+2+1, 16+11+3+2+1, 16+11+4+2+1, 16+12+2+1, 16+12+3+2+1, 16+12+4+2+1, 17+1, 18+1, 19+17+1, 19+18+1, 20+17+1, 20+18+1, 21+1, 21+17+1, 21+19+17+1, 21+20+17+1, 22+1, 22+17+1, 22+18+1, 22+19+17+1, 22+19+18+1, 22+20+17+1, 22+20+18+1, 23+1, 23+17+1, 23+18+1, 23+19+171, 23+19+18+1, 23+20+17+1, 23+20+18+1, 24+1, 25+1, 25+17+1, 25+18+1, 25+19+17+1, 25+19+18+1, 25+20+17+1, 25+20+18+1, 25+21+1, 25+21+17+1, 25+21+19+17+1, 25+21+20+17+1, 25+22+1, 25+22+17+1, 25+22+18+1, 25+22+9+17+1, 25+22+19+18+1, 25+22+20+17+1, 25+22+20+18+1, 25+23+1, 25+23+17+1, 25+23+18+1, 25+23+19+17+1, 25+23+19+18+1, 25+23+20+17+1, 25+23+20+18+1, 25+24+1, 26+1, 26+17+1, 26+18+1, 26+19+17+1, 26+19+18+1, 26+20+17+1, 26+20+18+1, 26+21+1, 26+21+17+1, 26+21+19+17+1, 26+21+20+17+1, 26+22+1, 26+22+17+1, 26+22+18+1, 26+22+19+17+1, 26+22+19+18+1, 26+22+20+17+1, 26+22+20+18+1, 26+23+1, 26+23+17+1, 26+23+18+1, 26+23+1926+2317+20+126+23+1913+1, 2623+20+17+1, 26+23+20+18+1, 26+24+1, 27+1, 27+17+1, 27+18+1, 27+19+17+1, 27+19+18+1, 27+20+17+1, 27+20+18+1, 27+21+1, 27+21+17+1, 27+21+19+17+1, 27+21+20+17+1, 27+22+1, 27+22+17+1, 27+22+18+1, 27+22+19+17+1, 27+22+19+18+1, 27+22+20+17+1, 27+22+20+18+1, 27+23+1, 27+23+17+1, 27+23+18+1, 27+23+19+17+1, 27+23+19+18+1, 27+23+20+17+1, 27+23+20+18+1, 27+24+1, 27+25+1, 27+25+17+1, 27+25+18+1, 27+25+19+17+1, 27+25+19+18+1, 27+25+20+17+1, 27+25+20+18+1, 27+25+21+1, 27+25+21+17+1, 27+25+21+19+17+1 27+25+21+19+18+1, 27+25+21+20+17+1, 27+25+21+20+18+1, 27+25+22+1, 27+25+22+17+1, 27+25+22+18+1, 27+25+22+19+17+1, 27+25+22+19+18+1, 27+25+22+20+17+1, 27+25+22+20+18+1, 27+25+23+1, 27+25+23+17+1, 27+25+23+18+1, 27+25+23+19+17+1, 27+25+23+19+18+1, 27+25+23+20+17+1, 27+25+23+20+18+1, 27+25+24+1, 27+26+1, 27+26+17+1, 27+26+18+1, 27+26+19+17+1, 27+269+9+18+1, 27+26+20+17+1, 27+26+20+18+1, 27+26+21+1, 27+26+21+17+1, 27+26+21+19+17+1, 27+26+21+20+17+1, 27+26+22+1, 27+26+22+17+1, 27+26+22+18+1, 27+26+22+19+17+1, 27+26+

22+19+18+1, 27+26+22+20+17+1, 27+26+22+20+18+1, 27+26+23+1, 27+26+23+17+1, 27+26+23+18+1, 27+26+23+19+17+1, 27+26+23+19+18+1, 27+26+23+20+17+1 27+26+23+20+18+1, 27+26+24+1, 28+1, 28+21+1, 28+22+1, 28+23+1, 28+24+1; in the list above the numbers refer to the embodiments according to their numbering provided hereinabove whereas "+" indicates the dependency from another embodiment. The different individualized embodiments are separated by commas. In other words, "15+11+2+1" for example refers to embodiment 15) depending on embodiment 11), depending on embodiment 2), depending on embodiment 1), i.e. embodiment "15+11+2+1" corresponds to the compounds of formula (I) according to embodiment 1) further limited by all the features of the embodiments 2), 11), and 15).

30) A further embodiment relates to compounds of formula (I) which are selected from:

N-[1-(4-Chloro-benzyl)-1H-pyrazol-3-yl]-2-(4-isopropyl-phenyl)-acetamide;
N-[1-(4-Chloro-benzyl)-1H-pyrazol-3-yl]-2-(4-dimethylamino-phenyl)-acetamide;
2-(4-Dimethylamino-phenyl)-N-[1-(4-fluoro-benzyl)-1H-pyrazol-3-yl]-acetamide;
N-[1-(4-Chloro-benzyl)-1H-pyrazol-3-yl]-2-(6-dimethylamino-pyridin-3-yl)-acetamide;
N-[1-(4-Fluoro-benzyl)-1H-pyrazol-3-yl]-2-(4-isopropyl-phenyl)-acetamide;
2-(4-Isopropyl-phenyl)-N-[1-(4-methoxy-benzyl)-1H-pyrazol-3-yl]-acetamide;
2-(4-Dimethylamino-phenyl)-N-[1-(4-methoxy-benzyl)-1H-pyrazol-3-yl]-acetamide;
2-(4-Isopropyl-phenyl)-N-[1-(4-methyl-benzyl)-1H-pyrazol-3-yl]-acetamide;
2-(4-Dimethylamino-phenyl)-N-[1-(4-methyl-benzyl)-1H-pyrazol-3-yl]-acetamide;
N-[1-(4-Cyano-benzyl)-1H-pyrazol-3-yl]-2-(4-isopropyl-phenyl)-acetamide;
N-[1-(4-Cyano-benzyl)-1H-pyrazol-3-yl]-2-(4-dimethylamino-phenyl)-acetamide;
2-(4-Dimethylamino-phenyl)-N-[1-(4-ethyl-benzyl)-1H-pyrazol-3-yl]-acetamide;
2-(4-Dimethylamino-phenyl)-N-[1-(4-isopropyl-benzyl)-1H-pyrazol-3-yl]-acetamide;
N-[1-(4-tert-Butyl-benzyl)-1H-pyrazol-3-yl]-2-(4-dimethylamino-phenyl)-acetamide;
N-[1-(4-Difluoromethoxy-benzyl)-1H-pyrazol-3-yl]-2-(4-dimethylamino-phenyl)-acetamide;
2-(4-Dimethylamino-phenyl)-N-[1-(4-trifluoromethoxy-benzyl)-1H-pyrazol-3-yl]-acetamide;
N-[1-(3,4-Difluoro-benzyl)-1H-pyrazol-3-yl]-2-(4-dimethylamino-phenyl)-acetamide;
2-(4-Dimethylamino-phenyl)-N-[1-(4-fluoro-3-trifluoromethoxy-benzyl)-1H-pyrazol-3-yl]-acetamide;
2-(4-Dimethylamino-phenyl)-N-[1-(4-fluoro-3-trifluoromethyl-benzyl)-1H-pyrazol-3-yl]-acetamide;
2-(4-Dimethylamino-phenyl)-N-[1-(3,4,5-trifluoro-benzyl)-1H-pyrazol-3-yl]-acetamide;
2-(4-Dimethylamino-phenyl)-N-[1-(4-fluoro-3,5-dimethyl-benzyl)-1H-pyrazol-3-yl]-acetamide;
N-[1-(4-Chloro-3-fluoro-benzyl)-1H-pyrazol-3-yl]-2-(4-dimethylamino-phenyl)-acetamide;
N-[1-(4-Chloro-3-trifluoromethyl-benzyl)-1H-pyrazol-3-yl]-2-(4-dimethylamino-phenyl)-acetamide;
N-[1-(3,5-Difluoro-4-methoxy-benzyl)-1H-pyrazol-3-yl]-2-(4-dimethylamino-phenyl)-acetamide;
2-(4-Dimethylamino-phenyl)-N-[1-(4-methoxy-3-trifluoromethyl-benzyl)-1H-pyrazol-3-yl]-acetamide;
2-(4-Dimethylamino-phenyl)-N-[1-(4-fluoro-3-methyl-benzyl)-1H-pyrazol-3-yl]-acetamide;
N-[1-(3-Chloro-4-fluoro-benzyl)-1H-pyrazol-3-yl]-2-(4-dimethylamino-phenyl)-acetamide;
2-(4-Dimethylamino-phenyl)-N-[1-(3-fluoro-4-methyl-benzyl)-1H-pyrazol-3-yl]-acetamide;
2-(6-Dimethylamino-pyridin-3-yl)-N-[1-(4-ethyl-benzyl)-1H-pyrazol-3-yl]-acetamide;
2-(6-Dimethylamino-pyridin-3-yl)-N-[1-(4-trifluoromethoxy-benzyl)-1H-pyrazol-3-yl]-acetamide;
2-(6-Dimethylamino-pyridin-3-yl)-N-[1-(3-fluoro-4-methyl-benzyl)-1H-pyrazol-3-yl]-acetamide;
2-(6-Dimethylamino-pyridin-3-yl)-N-[1-(4-fluoro-3-methyl-benzyl)-1H-pyrazol-3-yl]-acetamide;
N-[1-(3-Chloro-4-fluoro-benzyl)-1H-pyrazol-3-yl]-2-(6-dimethylamino-pyridin-3-yl)-acetamide;
2-(6-Dimethylamino-pyridin-3-yl)-N-[1-(3,4,5-trifluoro-benzyl)-1H-pyrazol-3-yl]-acetamide;
N-[1-(4-Chloro-3-fluoro-benzyl)-1H-pyrazol-3-yl]-2-(6-dimethylamino-pyridin-3-yl)-acetamide;
N-[1-(4-Methoxy-benzyl)-1H-pyrazol-3-yl]-2-[4-(2,2,2-trifluoro-ethoxy)-phenyl]-acetamide;
N-[1-(4-Fluoro-benzyl)-1H-pyrazol-3-yl]-2-[4-(2,2,2-trifluoro-ethoxy)-phenyl]-acetamide;
N-[1-(4-Cyano-benzyl)-1H-pyrazol-3-yl]-2-[4-(2,2,2-trifluoro-ethoxy)-phenyl]-acetamide;
2-[4-(3,3-Difluoro-azetidin-1-yl)-phenyl]-N-[1-(4-fluoro-benzyl)-1H-pyrazol-3-yl]-acetamide;
N-[1-(4-Cyano-benzyl)-1H-pyrazol-3-yl]-2-[4-(3, 3-difluoro-azetidin-1-yl)-phenyl]-acetamide;
2-[4-(3,3-Difluoro-azetidin-1-yl)-phenyl]-N-[1-(4-methoxy-benzyl)-1H-pyrazol-3-yl]-acetamide;
2-[4-(3,3-Difluoro-azetidin-1-yl)-phenyl]-N-[1-(3,4-difluoro-benzyl)-1H-pyrazol-3-yl]-acetamide;
2-(4-Azetidin-1-yl-phenyl)-N-[1-(4-fluoro-benzyl)-1H-pyrazol-3-yl]-acetamide;
2-(4-Azetidin-1-yl-phenyl)-N-[1-(4-cyano-benzyl)-1H-pyrazol-3-yl]-acetamide;
2-(4-Azetidin-1-yl-phenyl)-N-[1-(4-methoxy-benzyl)-1H-pyrazol-3-yl]-acetamide;
N-[1-(3,4-Difluoro-benzyl)-1H-pyrazol-3-yl]-2-(6-dimethylamino-pyridin-3-yl)-acetamide;
N-[1-(4-Cyano-3-fluoro-benzyl)-1H-pyrazol-3-yl]-2-(4-dimethylamino-phenyl)-acetamide;
2-(4-Azetidin-1-yl-phenyl)-N-[1-(3,4-difluoro-benzyl)-1H-pyrazol-3-yl]-acetamide;
N-[1-(3,4-Difluoro-benzyl)-1H-pyrazol-3-yl]-2-[4-((S)-3-fluoro-pyrrolidin-1-yl)-phenyl]-acetamide;
N-[1-(3,4-Difluoro-benzyl)-1H-pyrazol-3-yl]-2-[4-(3-fluoro-azetidin-1-yl)-phenyl]-acetamide;
2-(4-Cyclopropoxy-phenyl)-N-[1-(4-fluoro-benzyl)-1H-pyrazol-3-yl]-acetamide;
2-(4-Cyclopropoxy-phenyl)-N-[1-(4-methoxy-benzyl)-1H-pyrazol-3-yl]-acetamide;
2-(4-Cyclopropoxy-phenyl)-N-[1-(3,4-difluoro-benzyl)-1H-pyrazol-3-yl]-acetamide;
N-[1-(3,4-Difluoro-benzyl)-1H-pyrazol-3-yl]-2-[4-(3,3-difluoro-pyrrolidin-1-yl)-phenyl]-acetamide;
N-[1-(3,4-Difluoro-benzyl)-1H-pyrazol-3-yl]-2-[4-((R)-3-fluoro-pyrrolidin-1-yl)-phenyl]-acetamide;
N-[1-(4-Cyano-benzyl)-1H-pyrazol-3-yl]-2-[4-((R)-3-fluoro-pyrrolidin-1-yl)-phenyl]-acetamide;
N-[1-(4-Fluoro-benzyl)-1H-pyrazol-3-yl]-2-[4-((R)-3-fluoro-pyrrolidin-1-yl)-phenyl]-acetamide;
N-[1-(5-Cyano-pyridin-2-ylmethyl)-1H-pyrazol-3-yl]-2-(4-isopropyl-phenyl)-acetamide;

N-[1-(4-Cyano-benzyl)-1H-pyrazol-3-yl]-2-[4-(3-fluoro-azetidin-1-yl)-phenyl]-acetamide;
2-[4-(3-Fluoro-azetidin-1-yl)-phenyl]-N-[1-(4-fluoro-benzyl)-1H-pyrazol-3-yl]-acetamide;
N-[1-(4-Cyano-benzyl)-1H-pyrazol-3-yl]-2-[4-((S)-3-fluoro-pyrrolidin-1-yl)-phenyl]-acetamide;
N-[1-(4-Fluoro-benzyl)-1H-pyrazol-3-yl]-2-[4-((S)-3-fluoro-pyrrolidin-1-yl)-phenyl]-acetamide;
N-[1-(4-Cyano-benzyl)-1H-pyrazol-3-yl]-2-[4-(3,3-difluoro-pyrrolidin-1-yl)-phenyl]-acetamide;
2-[4-(3,3-Difluoro-pyrrolidin-1-yl)-phenyl]-N-[1-(4-fluoro-benzyl)-1H-pyrazol-3-yl]-acetamide;
N-[1-(4-Fluoro-benzyl)-1H-pyrazol-3-yl]-2-(4-pyridin-2-yl-phenyl)-acetamide;
N-[1-(4-Fluoro-benzyl)-1H-pyrazol-3-yl]-2-(4-pyridin-3-yl-phenyl)-acetamide;
N-[1-(4-Fluoro-benzyl)-1H-pyrazol-3-yl]-2-(4-pyridin-4-yl-phenyl)-acetamide;
N-[1-(5-Cyano-pyridin-2-ylmethyl)-1H-pyrazol-3-yl]-2-[4-((R)-3-fluoro-pyrrolidin-1-yl)-phenyl]-acetamide;
N-[1-(5-Cyano-pyridin-2-ylmethyl)-1H-pyrazol-3-yl]-2-[4-(3,3-difluoro-pyrrolidin-1-yl)-phenyl]-acetamide;
N-[1-(4-Fluoro-benzyl)-1H-pyrazol-3-yl]-2-[4-(5-methyl-pyrimidin-4-yl)-phenyl]-acetamide;
2-(4-Isopropyl-phenyl)-N-{1-[5-(2,2,2-trifluoro-ethoxy)-pyridin-2-ylmethyl]-1H-pyrazol-3-yl}-acetamide;
N-[1-(5-Bromo-pyridin-2-ylmethyl)-1H-pyrazol-3-yl]-2-(4-isopropyl-phenyl)-acetamide;
N-[1-(5-Cyclopropyl-pyridin-2-ylmethyl)-1H-pyrazol-3-yl]-2-(4-isopropyl-phenyl)-acetamide;
2-(4-Isopropyl-phenyl)-N-[1-(5-methyl-pyridin-2-ylmethyl)-1H-pyrazol-3-yl]-acetamide;
N-[1-(5-Isobutyl-pyridin-2-ylmethyl)-1H-pyrazol-3-yl]-2-(4-isopropyl-phenyl)-acetamide;
2-(6-Azetidin-1-yl-pyridin-3-yl)-N-[1-(3,4-difluoro-benzyl)-1H-pyrazol-3-yl]-acetamide;
N-[1-(5-Ethyl-pyridin-2-ylmethyl)-1H-pyrazol-3-yl]-2-(4-isopropyl-phenyl)-acetamide;
N-[1-(5-Isopropoxy-pyridin-2-ylmethyl)-1H-pyrazol-3-yl]-2-(4-isopropyl-phenyl)-acetamide;
N-[1-(5-Fluoro-pyridin-2-ylmethyl)-1H-pyrazol-3-yl]-2-(4-isopropyl-phenyl)-acetamide;
2-(4-Isopropyl-phenyl)-N-[1-(5-trifluoromethyl-pyridin-2-ylmethyl)-1H-pyrazol-3-yl]-acetamide;
N-[1-(6-Chloro-5-cyano-pyridin-2-ylmethyl)-1H-pyrazol-3-yl]-2-(4-isopropyl-phenyl)-acetamide;
2-(4-Diethylamino-phenyl)-N-[1-(4-methoxy-benzyl)-1H-pyrazol-3-yl]-acetamide;
2-(4-Diethylamino-phenyl)-N-[1-(3,4-difluoro-benzyl)-1H-pyrazol-3-yl]-acetamide;
N-[1-(4-Cyano-benzyl)-1H-pyrazol-3-yl]-2-(4-diethylamino-phenyl)-acetamide;
N-[1-(5-Cyano-6-ethyl-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-[6-(3,3-difluoro-pyrrolidin-1-yl)-pyridin-3-yl]-acetamide;
N-[1-(4-Cyano-benzyl)-1H-pyrazol-3-yl]-2-[6-(3,3-difluoro-pyrrolidin-1-yl)-pyridin-3-yl]-acetamide;
2-[6-(3,3-Difluoro-pyrrolidin-1-yl)-pyridin-3-yl]-N-[1-(4-fluoro-benzyl)-1H-pyrazol-3-yl]-acetamide;
2-(6-Diethylamino-pyridin-3-yl)-N-[1-(3,4-difluoro-benzyl)-1H-pyrazol-3-yl]-acetamide;
N-[1-(4-Methoxy-benzyl)-1H-pyrazol-3-yl]-2-{4-[(2-methoxy-ethyl)-methyl-amino]-phenyl}-acetamide;
N-[1-(3,4-Difluoro-benzyl)-1H-pyrazol-3-yl]-2-{4-[(2-methoxy-ethyl)-methyl-amino]-phenyl}-acetamide;
N-[1-(4-Cyano-benzyl)-1H-pyrazol-3-yl]-2-{4-[(2-methoxy-ethyl)-methyl-amino]-phenyl}-acetamide;
N-[1-(4-Fluoro-benzyl)-1H-pyrazol-3-yl]-2-{4-[(2-methoxy-ethyl)-methyl-amino]-phenyl}-acetamide;
N-[1-(5-Cyano-6-methyl-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-[6-((R)-3-fluoro-pyrrolidin-1-yl)-pyridin-3-yl]-acetamide;
N-[1-(4-Fluoro-benzyl)-1H-pyrazol-3-yl]-2-[6-((R)-3-fluoro-pyrrolidin-1-yl)-pyridin-3-yl]-acetamide;
2-[6-(3,3-Difluoro-azetidin-1-yl)-pyridin-3-yl]-N-[1-(3,4-difluoro-benzyl)-1H-pyrazol-3-yl]-acetamide;
2-[6-(3,3-Difluoro-azetidin-1-yl)-pyridin-3-yl]-N-[1-(4-fluoro-benzyl)-1H-pyrazol-3-yl]-acetamide;
N-[1-(4-Fluoro-benzyl)-1H-pyrazol-3-yl]-2-(4-isobutyl-phenyl)-acetamide;
N-[1-(5-Cyano-6-fluoro-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-[6-((S)-3-fluoro-pyrrolidin-1-yl)-pyridin-3-yl]-acetamide;
N-[1-(4-Fluoro-benzyl)-1H-pyrazol-3-yl]-2-[6-((S)-3-fluoro-pyrrolidin-1-yl)-pyridin-3-yl]-acetamide;
N-[1-(4-Chloro-5-cyano-pyridin-2-ylmethyl)-1H-pyrazol-3-yl]-2-(4-isopropyl-phenyl)-acetamide;
2-(4-Cyclopropylmethyl-phenyl)-N-[1-(4-fluoro-benzyl)-1H-pyrazol-3-yl]-acetamide;
N-[1-(3,4-Difluoro-benzyl)-1H-pyrazol-3-yl]-2-[6-(3-fluoro-azetidin-1-yl)-pyridin-3-yl]-acetamide;
2-[6-(3-Fluoro-azetidin-1-yl)-pyridin-3-yl]-N-[1-(4-fluoro-benzyl)-1H-pyrazol-3-yl]-acetamide;
2-[6-(Cyclopropyl(methyl)amino)-pyridin-3-yl]-N-[1-(3,4-difluoro-benzyl)-1H-pyrazol-3-yl]-acetamide;
2-[6-(Cyclopropyl(methyl)amino)-pyridin-3-yl]-N-[1-(4-fluoro-benzyl)-1H-pyrazol-3-yl]-acetamide;
N-[1-(3,4-Difluoro-benzyl)-1H-pyrazol-3-yl]-2-[6-(ethyl-methyl-amino)-pyridin-3-yl]-acetamide;
N-[1-(3,4-Difluoro-benzyl)-1H-pyrazol-3-yl]-2-(6-pyrrolidin-1-yl-pyridin-3-yl)-acetamide;
N-[1-(4-Cyano-benzyl)-1H-pyrazol-3-yl]-2-(6-pyrrolidin-1-yl-pyridin-3-yl)-acetamide;
N-[1-(4-Fluoro-benzyl)-1H-pyrazol-3-yl]-2-(6-pyrrolidin-1-yl-pyridin-3-yl)-acetamide;
N-[1-(3,4-Difluoro-benzyl)-1H-pyrazol-3-yl]-2-{6-[(2-methoxy-ethyl)-methyl-amino]-pyridin-3-yl}-acetamide;
N-[1-(4-Fluoro-benzyl)-1H-pyrazol-3-yl]-2-{6-[(2-methoxy-ethyl)-methyl-amino]-pyridin-3-yl}-acetamide;
2-[6-(Cyclopropylmethyl-methyl-amino)-pyridin-3-yl]-N-[1-(3,4-difluoro-benzyl)-1H-pyrazol-3-yl]-acetamide;
N-[1-(4-Cyano-benzyl)-1H-pyrazol-3-yl]-2-[6-(cyclopropylmethyl-methyl-amino)-pyridin-3-yl]-acetamide;
2-[6-(Cyclopropylmethyl-methyl-amino)-pyridin-3-yl]-N-[1-(4-fluoro-benzyl)-1H-pyrazol-3-yl]-acetamide;
2-[6-(Cyclopropylmethyl-methyl-amino)-pyridin-3-yl]-N-[1-(4-methoxy-benzyl)-1H-pyrazol-3-yl]-acetamide;
2-(6-Diethylamino-pyridin-3-yl)-N-[1-(4-fluoro-benzyl)-1H-pyrazol-3-yl]-acetamide;
N-[1-(3-Chloro-4-fluoro-benzyl)-1H-pyrazol-3-yl]-2-(6-cyclopropyl-pyridin-3-yl)-acetamide;
N-[1-(4-Cyclopropoxy-benzyl)-1H-pyrazol-3-yl]-2-(4-isopropyl-phenyl)-acetamide;
N-[1-(4-Cyano-benzyl)-1H-pyrazol-3-yl]-2-(4-cyclobutoxy-phenyl)-acetamide;
2-(4-Cyclobutoxy-phenyl)-N-[1-(4-fluoro-benzyl)-1H-pyrazol-3-yl]-acetamide;
2-(4-Cyclobutoxy-phenyl)-N-[1-(4-methoxy-benzyl)-1H-pyrazol-3-yl]-acetamide;

2-(4-Cyclobutoxy-phenyl)-N-[1-(5-fluoro-pyridin-2-ylmethyl)-1H-pyrazol-3-yl]-acetamide;
N-[1-(4-Fluoro-benzyl)-1H-pyrazol-3-yl]-2-[4-(1-methoxy-ethyl)-phenyl]-acetamide;
N-[1-(3,4-Difluoro-benzyl)-1H-pyrazol-3-yl]-2-[4-(1-methoxy-ethyl)-phenyl]-acetamide;
N-[1-(3,4-Difluoro-benzyl)-1H-pyrazol-3-yl]-2-quinolin-7-yl-acetamide;
N-[1-(3,4-Difluoro-benzyl)-1H-pyrazol-3-yl]-2-(1H-indol-6-yl)-acetamide;
N-[1-(3,4-Difluoro-benzyl)-1H-pyrazol-3-yl]-2-(4-methyl-3-oxo-3,4-dihydro-2H-benzo[1,4]oxazin-7-yl)-acetamide;
N-[1-(6-Cyano-5-fluoro-pyridin-2-ylmethyl)-1H-pyrazol-3-yl]-2-(4-isopropyl-phenyl)-acetamide;
N-[1-(6-Chloro-5-fluoro-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-(1-methyl-1H-pyrrolo[2,3-b]pyridin-5-yl)-acetamide;
N-[1-(4-Fluoro-benzyl)-1H-pyrazol-3-yl]-2-(1-methyl-1H-pyrrolo[2,3-b]pyridin-5-yl)-acetamide;
N-[1-(3,4-Difluoro-benzyl)-1H-pyrazol-3-yl]-2-(3-methyl-2-oxo-2,3-dihydro-benzooxazol-6-yl)-acetamide;
N-[1-(3,4-Difluoro-benzyl)-1H-pyrazol-3-yl]-2-(1H-indol-5-yl)-acetamide;
N-[1-(3,4-Difluoro-benzyl)-1H-pyrazol-3-yl]-2-(1-methyl-1H-indol-5-yl)-acetamide;
N-[1-(3,4-Difluoro-benzyl)-1H-pyrazol-3-yl]-2-(1-methyl-1H-indol-6-yl)-acetamide;
N-[1-(3,4-Difluoro-benzyl)-1H-pyrazol-3-yl]-2-(1-methyl-1H-indazol-5-yl)-acetamide;
N-[1-(3,4-Difluoro-benzyl)-1H-pyrazol-3-yl]-2-(1-methyl-1H-indazol-6-yl)-acetamide;
N-[1-(3,4-Difluoro-benzyl)-1H-pyrazol-3-yl]-2-[4-(3-fluoro-oxetan-3-yl)-phenyl]-acetamide;
N-[1-(3,4-Difluoro-benzyl)-1H-pyrazol-3-yl]-2-[4-(3-hydroxy-oxetan-3-yl)-phenyl]-acetamide;
N-[1-(3,4-Difluoro-benzyl)-1H-pyrazol-3-yl]-2-[4-(3-methyl-oxetan-3-yl)-phenyl]-acetamide;
N-[1-(3,4-Difluoro-benzyl)-1H-pyrazol-3-yl]-2-(3,3-dimethyl-2-oxo-2,3-dihydro-1H-indol-5-yl)-acetamide;
N-[1-(3,4-Difluoro-benzyl)-1H-pyrazol-3-yl]-2-(1,3,3-trimethyl-2-oxo-2,3-dihydro-1H-indol-5-yl)-acetamide;
N-[1-(3,4-Difluoro-benzyl)-1H-pyrazol-3-yl]-2-[4-(3-methoxy-oxetan-3-yl)-phenyl]-acetamide;
N-[1-(3,4-Difluoro-benzyl)-1H-pyrazol-3-yl]-2-[4-((R)-1-methoxy-ethyl)-phenyl]-acetamide;
N-[1-(3,4-Difluoro-benzyl)-1H-pyrazol-3-yl]-2-[4-((S)-1-methoxy-ethyl)-phenyl]-acetamide;
N-[1-(3,4-Difluoro-benzyl)-1H-pyrazol-3-yl]-2-(4-isopropyl-phenyl)-acetamide;
N-[1-(3,4-Difluoro-benzyl)-1H-pyrazol-3-yl]-2-[4-(5-methyl-[1,2,4]oxadiazol-3-yl)-phenyl]-acetamide;
N-[1-(3,4-Difluoro-benzyl)-1H-pyrazol-3-yl]-2-(4-[1,2,4]oxadiazol-3-yl-phenyl)-acetamide;
N-[1-(3,4-Difluoro-benzyl)-1H-pyrazol-3-yl]-2-[4-(3,3-difluoro-cyclobutyl)-phenyl]-acetamide;
N-[1-(3,4-Difluoro-benzyl)-1H-pyrazol-3-yl]-2-[4-(oxetan-3-yloxy)-phenyl]-acetamide;
N-[1-(4-Bromo-benzyl)-1H-pyrazol-3-yl]-2-(4-dimethylamino-phenyl)-acetamide;
N-[1-(3,4-Difluoro-benzyl)-1H-pyrazol-3-yl]-2-[4-(3,3-difluoro-cyclobutoxy)-phenyl]-acetamide;
N-[1-(3,4-Difluoro-benzyl)-1H-pyrazol-3-yl]-2-[4-(3-methyl-oxetan-3-ylmethoxy)-phenyl]-acetamide;
N-[1-(3,4-Difluoro-benzyl)-1H-pyrazol-3-yl]-2-[4-(oxetan-3-ylmethoxy)-phenyl]-acetamide;
N-[1-(3,4-Difluoro-benzyl)-1H-pyrazol-3-yl]-2-[4-(3,3-difluoro-1-methyl-cyclobutylmethoxy)-phenyl]-acetamide;
N-[1-(3,4-Difluoro-benzyl)-1H-pyrazol-3-yl]-2-[4-(3,3-difluoro-cyclobutylmethoxy)-phenyl]-acetamide;
N-[1-(3,4-Difluoro-benzyl)-1H-pyrazol-3-yl]-2-[4-(3-fluoro-oxetan-3-ylmethoxy)-phenyl]-acetamide;
N-[1-(4-Cyano-benzyl)-1H-pyrazol-3-yl]-2-(1-methyl-1H-indazol-5-yl)-acetamide;
N-[1-(4-Cyano-3-fluoro-benzyl)-1H-pyrazol-3-yl]-2-[4-(3-fluoro-oxetan-3-yl)-phenyl]-acetamide;
N-[1-(4-Cyano-3-fluoro-benzyl)-1H-pyrazol-3-yl]-2-(1-methyl-1H-indazol-5-yl)-acetamide;
N-[1-(3,4-Difluoro-benzyl)-1H-pyrazol-3-yl]-2-(1,3-dimethyl-1H-indol-6-yl)-acetamide;
N-[1-(3,4-Difluoro-benzyl)-1H-pyrazol-3-yl]-2-(1,3-dimethyl-1H-indol-5-yl)-acetamide;
N-[1-(4-Cyano-3-fluoro-benzyl)-1H-pyrazol-3-yl]-2-[4-(3,3-difluoro-cyclobutoxy)-phenyl]-acetamide;
2-(4-tert-Butyl-phenyl)-N-[1-(4-cyano-3-fluoro-benzyl)-1H-pyrazol-3-yl]-acetamide;
N-[1-(4-Cyano-3-fluoro-benzyl)-1H-pyrazol-3-yl]-2-[4-(1-trifluoromethyl-cyclopropyl)-phenyl]-acetamide;
N-[1-(4-Cyano-3-fluoro-benzyl)-1H-pyrazol-3-yl]-2-(4-isopropyl-phenyl)-acetamide;
N-[1-(3-Cyano-4-fluoro-benzyl)-1H-pyrazol-3-yl]-2-(1-methyl-1H-indazol-5-yl)-acetamide;
N-[1-(3-Cyano-4-fluoro-benzyl)-1H-pyrazol-3-yl]-2-[4-(3-fluoro-oxetan-3-yl)-phenyl]-acetamide;
2-(4-tert-Butyl-phenyl)-N-[1-(4-cyano-benzyl)-1H-pyrazol-3-yl]-acetamide;
2-(4-tert-Butyl-phenyl)-N-[1-(5-cyano-pyridin-2-ylmethyl)-1H-pyrazol-3-yl]-acetamide;
N-[1-(4-Cyano-benzyl)-1H-pyrazol-3-yl]-2-[4-(3,3-difluoro-cyclobutoxy)-phenyl]-acetamide;
N-[1-(4-Cyano-3-fluoro-benzyl)-1H-pyrazol-3-yl]-2-(6-pyrrolidin-1-yl-pyridin-3-yl)-acetamide;
N-[1-(4-Cyano-benzyl)-1H-pyrazol-3-yl]-2-[4-(1-trifluoromethyl-cyclopropyl)-phenyl]-acetamide;
N-[1-(5-Cyano-pyridin-2-ylmethyl)-1H-pyrazol-3-yl]-2-[4-(1-trifluoromethyl-cyclopropyl)-phenyl]-acetamide;
N-[1-(3-Cyano-4-fluoro-benzyl)-1H-pyrazol-3-yl]-2-[4-(3,3-difluoro-cyclobutoxy)-phenyl]-acetamide;
N-[1-(3-Cyano-4-fluoro-benzyl)-1H-pyrazol-3-yl]-2-(4-isopropyl-phenyl)-acetamide;
2-(4-tert-Butyl-phenyl)-N-[1-(3-cyano-4-fluoro-benzyl)-1H-pyrazol-3-yl]-acetamide;
N-[1-(4-Cyano-3-fluoro-benzyl)-1H-pyrazol-3-yl]-2-[4-(3,3-difluoro-cyclobutyl)-phenyl]-acetamide;
N-[1-(4-Cyano-3-fluoro-benzyl)-1H-pyrazol-3-yl]-2-[4-(3,3-difluoro-cyclobutylmethoxy)-phenyl]-acetamide;
N-[1-(4-Cyano-3-fluoro-benzyl)-1H-pyrazol-3-yl]-2-[4-(3,3-difluoro-1-methyl-cyclobutylmethoxy)-phenyl]-acetamide;
N-[1-(4-Cyano-3-fluoro-benzyl)-1H-pyrazol-3-yl]-2-(1-methyl-1H-indol-5-yl)-acetamide;
N-[1-(4-Cyano-3-fluoro-benzyl)-1H-pyrazol-3-yl]-2-(1-methyl-1H-indol-6-yl)-acetamide;
N-[1-(4-Cyano-3-fluoro-benzyl)-1H-pyrazol-3-yl]-2-[6-(3,3-difluoro-pyrrolidin-1-yl)-pyridin-3-yl]-acetamide;
N-[1-(4-Cyano-benzyl)-1H-pyrazol-3-yl]-2-(1-methyl-1H-indol-5-yl)-acetamide;
N-[1-(4-Cyano-benzyl)-1H-pyrazol-3-yl]-2-(1-methyl-1H-indol-6-yl)-acetamide;
N-[1-(4-Cyano-benzyl)-1H-pyrazol-3-yl]-2-[4-(3,3-difluoro-1-methyl-cyclobutylmethoxy)-phenyl]-acetamide;
N-[1-(4-Cyano-benzyl)-1H-pyrazol-3-yl]-2-[4-(3,3-difluoro-cyclobutylmethoxy)-phenyl]-acetamide;

N-[1-(4-Cyano-benzyl)-1H-pyrazol-3-yl]-2-[4-(3,3-difluoro-cyclobutyl)-phenyl]-acetamide;
N-[1-(5-Cyano-pyridin-2-ylmethyl)-1H-pyrazol-3-yl]-2-(1-methyl-1H-indol-5-yl)-acetamide;
N-[1-(5-Cyano-pyridin-2-ylmethyl)-1H-pyrazol-3-yl]-2-(1-methyl-1H-indol-6-yl)-acetamide;
N-[1-(5-Cyano-pyridin-2-ylmethyl)-1H-pyrazol-3-yl]-2-[4-(3,3-difluoro-1-methyl-cyclobutylmethoxy)-phenyl]-acetamide;
N-[1-(5-Cyano-pyridin-2-ylmethyl)-1H-pyrazol-3-yl]-2-[4-(3,3-difluoro-cyclobutyl)-phenyl]-acetamide;
N-[1-(3-Cyano-4-fluoro-benzyl)-1H-pyrazol-3-yl]-2-[6-(3,3-difluoro-pyrrolidin-1-yl)-pyridin-3-yl]-acetamide;
N-[1-(3-Cyano-4-fluoro-benzyl)-1H-pyrazol-3-yl]-2-(6-pyrrolidin-1-yl-pyridin-3-yl)-acetamide;
N-[1-(3-Cyano-4-fluoro-benzyl)-1H-pyrazol-3-yl]-2-(1-methyl-1H-indol-6-yl)-acetamide;
N-[1-(3-Cyano-4-fluoro-benzyl)-1H-pyrazol-3-yl]-2-(1-methyl-1H-indol-5-yl)-acetamide;
N-[1-(3-Cyano-4-fluoro-benzyl)-1H-pyrazol-3-yl]-2-[4-(3,3-difluoro-cyclobutyl)-phenyl]-acetamide;
N-[1-(3-Cyano-4-fluoro-benzyl)-1H-pyrazol-3-yl]-2-[4-(3,3-difluoro-cyclobutylmethoxy)-phenyl]-acetamide;
N-[1-(3-Cyano-4-fluoro-benzyl)-1H-pyrazol-3-yl]-2-[4-(1-trifluoromethyl-cyclopropyl)-phenyl]-acetamide;
N-[1-(3-Cyano-4-fluoro-benzyl)-1H-pyrazol-3-yl]-2-[4-(3-methyl-oxetan-3-yl)-phenyl]-acetamide;
N-[1-(4-Cyano-benzyl)-1H-pyrazol-3-yl]-2-[4-(3-methyl-oxetan-3-yl)-phenyl]-acetamide;
N-[1-(3-Cyano-4-fluoro-benzyl)-1H-pyrazol-3-yl]-2-[4-(1-methoxy-ethyl)-phenyl]-acetamide;
N-[1-(3-Cyano-4-fluoro-benzyl)-1H-pyrazol-3-yl]-2-(1,3-dimethyl-1H-pyrrolo[2,3-b]pyridin-5-yl)-acetamide;
N-[1-(5-Cyano-pyridin-2-ylmethyl)-1H-pyrazol-3-yl]-2-(3-cyclobutyl-1-methyl-1H-indol-5-yl)-acetamide;
N-[1-(5-Cyano-pyridin-2-ylmethyl)-1H-pyrazol-3-yl]-2-(3-isopropyl-1-methyl-1H-indol-5-yl)-acetamide;
N-[1-(5-Cyano-pyridin-2-ylmethyl)-1H-pyrazol-3-yl]-2-(1-methyl-3-trifluoromethyl-1H-indol-5-yl)-acetamide;
N-[1-(3-Cyano-4-fluoro-benzyl)-1H-pyrazol-3-yl]-2-(3-cyclobutyl-1-methyl-1H-indol-5-yl)-acetamide;
N-[1-(3-Cyano-4-fluoro-benzyl)-1H-pyrazol-3-yl]-2-(3-isopropyl-1-methyl-1H-indol-5-yl)-acetamide;
N-[1-(3-Cyano-4-fluoro-benzyl)-1H-pyrazol-3-yl]-2-(1,3-dimethyl-1H-indol-6-yl)-acetamide;
N-[1-(5-Cyano-pyridin-2-ylmethyl)-1H-pyrazol-3-yl]-2-(1,3-dimethyl-1H-indol-6-yl)-acetamide;
N-(1-(3-cyano-4-fluorobenzyl)-1H-pyrazol-3-yl)-2-(4-(pentafluoro-λ⁶-sulfanyl)phenyl)acetamide;
2-[4-(Cyano-dimethyl-methyl)-phenyl]-N-[1-(3-cyano-4-fluoro-benzyl)-1H-pyrazol-3-yl]-acetamide;
N-(1-((5-cyanopyridin-2-yl)methyl)-1H-pyrazol-3-yl)-2-(4-(pentafluoro-λ⁶-sulfanyl)phenyl)acetamide;
N-[1-(5-Cyano-pyridin-2-ylmethyl)-1H-pyrazol-3-yl]-2-(4-trifluoromethyl-phenyl)-acetamide;
N-[1-(5-Cyano-pyridin-2-ylmethyl)-1H-pyrazol-3-yl]-2-[3-methyl-4-(2,2,2-trifluoro-ethoxy)-phenyl]-acetamide;
N-[1-(3-Cyano-4-fluoro-benzyl)-1H-pyrazol-3-yl]-2-(5-fluoro-6-pyrrolidin-1-yl-pyridin-3-yl)-acetamide;
N-[1-(5-Cyano-pyridin-2-ylmethyl)-1H-pyrazol-3-yl]-2-(5-fluoro-6-pyrrolidin-1-yl-pyridin-3-yl)-acetamide;
N-[1-(3-Cyano-4-fluoro-benzyl)-1H-pyrazol-3-yl]-2-(4-trifluoromethyl-phenyl)-acetamide;
N-[1-(3-Cyano-4-fluoro-benzyl)-1H-pyrazol-3-yl]-2-[3-methyl-4-(2,2,2-trifluoro-ethoxy)-phenyl]-acetamide;
N-[1-(4-Cyano-3,5-difluoro-benzyl)-1H-pyrazol-3-yl]-2-[4-(3,3-difluoro-cyclobutoxy)-phenyl]-acetamide;
N-[1-(4-Cyano-3,5-difluoro-benzyl)-1H-pyrazol-3-yl]-2-(1,3-dimethyl-1H-indazol-5-yl)-acetamide;
N-[1-(4-Cyano-3,5-difluoro-benzyl)-1H-pyrazol-3-yl]-2-[6-(3,3-difluoro-pyrrolidin-1-yl)-pyridin-3-yl]-acetamide;
N-[1-(4-Cyano-3,5-difluoro-benzyl)-1H-pyrazol-3-yl]-2-(6-pyrrolidin-1-yl-pyridin-3-yl)-acetamide;
2-(4-tert-Butyl-phenyl)-N-[1-(4-cyano-3,5-difluoro-benzyl)-1H-pyrazol-3-yl]-acetamide;
N-[1-(4-Cyano-3,5-difluoro-benzyl)-1H-pyrazol-3-yl]-2-(4-isopropyl-phenyl)-acetamide;
2-[4-(1-Cyano-cyclopropyl)-phenyl]-N-[1-(3-cyano-4-fluoro-benzyl)-1H-pyrazol-3-yl]-acetamide;
N-[1-(4-Cyano-3,5-difluoro-benzyl)-1H-pyrazol-3-yl]-2-(1-ethyl-1H-indazol-5-yl)-acetamide;
N-[1-(4-Cyano-3,5-difluoro-benzyl)-1H-pyrazol-3-yl]-2-(1,3-dimethyl-1H-indol-5-yl)-acetamide;
N-[1-(4-Cyano-3,5-difluoro-benzyl)-1H-pyrazol-3-yl]-2-[4-(3,3-difluoro-cyclobutylmethoxy)-phenyl]-acetamide;
N-[1-(6-Cyano-5-fluoro-pyridin-2-ylmethyl)-1H-pyrazol-3-yl]-2-[4-(1-trifluoromethyl-cyclopropyl)-phenyl]-acetamide;
N-[1-(6-Cyano-5-methyl-pyridin-2-ylmethyl)-1H-pyrazol-3-yl]-2-[3-methyl-4-(2,2,2-trifluoro-ethoxy)-phenyl]-acetamide;
2-(4-tert-Butyl-phenyl)-N-[1-(6-cyano-5-methyl-pyridin-2-ylmethyl)-1H-pyrazol-3-yl]-acetamide;
N-[1-(6-Cyano-5-methyl-pyridin-2-ylmethyl)-1H-pyrazol-3-yl]-2-[4-(1-trifluoromethyl-cyclopropyl)-phenyl]-acetamide;
N-[1-(5-Cyano-pyridin-2-ylmethyl)-1H-pyrazol-3-yl]-2-[4-(1-methyl-cyclopropyl)-phenyl]-acetamide;
N-[1-(5-Cyano-pyridin-2-ylmethyl)-1H-pyrazol-3-yl]-2-[4-(2,2,2-trifluoro-1,1-dimethyl-ethyl)-phenyl]-acetamide;
N-[1-(6-Cyano-5-methyl-pyridin-2-ylmethyl)-1H-pyrazol-3-yl]-2-[4-(1-methyl-cyclopropyl)-phenyl]-acetamide;
N-[1-(5-Cyano-pyridin-2-ylmethyl)-1H-pyrazol-3-yl]-2-[4-methyl-3-(2,2,2-trifluoro-ethoxy)-phenyl]-acetamide; and
N-[1-(5-Cyano-pyridin-2-ylmethyl)-1H-pyrazol-3-yl]-2-[4-((1S*,2S*)-2-trifluoromethyl-cyclopropyl)-phenyl]-acetamide.

31) A further embodiment relates to compounds of formula (I) which are selected from:
N-[1-(5-Cyano-pyridin-2-ylmethyl)-1H-pyrazol-3-yl]-2-[4-(1-methoxy-cyclopropyl)-phenyl]-acetamide;
N-[1-(5-Cyano-6-difluoromethyl-pyridin-2-ylmethyl)-1H-pyrazol-3-yl]-2-(4-isopropyl-phenyl)-acetamide;
N-[1-(5-cyano-4-difluoromethyl-pyridin-2-ylmethyl)-1H-pyrazol-3-yl]-2-(4-isopropyl-phenyl)-acetamide;
N-[1-(5-Cyano-pyridin-2-ylmethyl)-1H-pyrazol-3-yl]-2-(3,3-dimethyl-2,3-dihydro-benzofuran-6-yl)-acetamide;
N-[1-(5-Cyano-pyridin-2-ylmethyl)-1H-pyrazol-3-yl]-2-(3-methyl-chroman-7-yl)-acetamide;
N-[1-(5-Cyano-3-fluoro-pyridin-2-ylmethyl)-1H-pyrazol-3-yl]-2-[4-(1-trifluoromethyl-cyclopropyl)-phenyl]-acetamide;
2-[4-(1-Cyano-3,3-difluoro-cyclobutyl)-phenyl]-N-[1-(5-cyano-pyridin-2-ylmethyl)-1H-pyrazol-3-yl]-acetamide;
N-[1-(6-Cyano-5-fluoro-pyridin-2-ylmethyl)-1H-pyrazol-3-yl]-2-[3-methyl-4-(2,2,2-trifluoro-ethoxy)-phenyl]-acetamide;
2-(3-Cyano-4-isobutyl-phenyl)-N-[1-(5-cyano-pyridin-2-ylmethyl)-1H-pyrazol-3-yl]-acetamide;
2-(3-Cyano-4-isobutyl-phenyl)-N-[1-(3,4-difluoro-benzyl)-1H-pyrazol-3-yl]-acetamide;
N-[1-(5-Azetidin-1-yl-pyridin-2-ylmethyl)-1H-pyrazol-3-yl]-2-(4-isopropyl-phenyl)-acetamide;

2-(4-Isopropyl-phenyl)-N-[1-(5-pyrrolidin-1-yl-pyridin-2-ylmethyl)-1H-pyrazol-3-yl]-acetamide;

N-{1-[5-(3,3-Difluoro-pyrrolidin-1-yl)-pyridin-2-ylmethyl]-1H-pyrazol-3-yl}-2-(4-isopropyl-phenyl)-acetamide;

N-[1-(5-Cyano-pyridin-2-ylmethyl)-1H-pyrazol-3-yl]-2-(4-cyclopropylmethoxy-3-trifluoromethoxy-phenyl)-acetamide;

2-(4-Cyclopropylmethoxy-3-trifluoromethoxy-phenyl)-N-[1-(3,4-difluoro-benzyl)-1H-pyrazol-3-yl]-acetamide;

N-[1-(4-Cyano-5-fluoro-pyridin-2-ylmethyl)-1H-pyrazol-3-yl]-2-[3-methyl-4-(2,2,2-trifluoro-ethoxy)-phenyl]-acetamide;

2-(4-tert-Butyl-phenyl)-N-[1-(4-cyano-5-fluoro-pyridin-2-ylmethyl)-1H-pyrazol-3-yl]-acetamide;

N-[1-(4-Cyano-5-fluoro-pyridin-2-ylmethyl)-1H-pyrazol-3-yl]-2-(4-isopropyl-phenyl)-acetamide;

N-[1-(4-Cyano-5-fluoro-pyridin-2-ylmethyl)-1H-pyrazol-3-yl]-2-[4-(1-trifluoromethyl-cyclopropyl)-phenyl]-acetamide;

2-[4-(1-Cyano-cyclopropyl)-3-trifluoromethyl-phenyl]-N-[1-(5-cyano-pyridin-2-ylmethyl)-1H-pyrazol-3-yl]-acetamide;

2-[4-(1-Cyano-cyclopropyl)-3-trifluoromethyl-phenyl]-N-[1-(3,4-difluoro-benzyl)-1H-pyrazol-3-yl]-acetamide;

N-[1-(5-Cyano-pyridin-2-ylmethyl)-1H-pyrazol-3-yl]-2-[3-methyl-4-(3,3,3-trifluoro-propoxy)-phenyl]-acetamide;

N-[1-(5-Cyano-pyridin-2-ylmethyl)-1H-pyrazol-3-yl]-2-[3-cyclopropyl-4-(2,2,2-trifluoro-ethoxy)-phenyl]-acetamide;

N-[1-(5-Cyano-pyridin-2-ylmethyl)-1H-pyrazol-3-yl]-2-(3-methyl-4-trifluoromethoxy-phenyl)-acetamide;

N-[1-(6-Cyano-5-fluoro-pyridin-2-ylmethyl)-1H-pyrazol-3-yl]-2-[3-cyclopropyl-4-(2,2,2-trifluoro-ethoxy)-phenyl]-acetamide;

N-[1-(4-Cyano-5-fluoro-pyridin-2-ylmethyl)-1H-pyrazol-3-yl]-2-[3-cyclopropyl-4-(2,2,2-trifluoro-ethoxy)-phenyl]-acetamide;

N-[1-(6-Cyano-5-fluoro-pyridin-2-ylmethyl)-1H-pyrazol-3-yl]-2-(3-methyl-4-trifluoromethoxy-phenyl)-acetamide;

N-[1-(5-Cyano-pyridin-2-ylmethyl)-1H-pyrazol-3-yl]-2-[3-ethyl-4-(2,2,2-trifluoro-ethoxy)-phenyl]-acetamide;

N-[1-(6-Cyano-5-fluoro-pyridin-2-ylmethyl)-1H-pyrazol-3-yl]-2-[3-ethyl-4-(2,2,2-trifluoro-ethoxy)-phenyl]-acetamide;

N-[1-(4-Cyano-5-fluoro-pyridin-2-ylmethyl)-1H-pyrazol-3-yl]-2-[3-ethyl-4-(2,2,2-trifluoro-ethoxy)-phenyl]-acetamide;

N-[1-(5-Cyano-pyridin-2-ylmethyl)-1H-pyrazol-3-yl]-2-[3,5-dimethyl-4-(2,2,2-trifluoro-ethoxy)-phenyl]-acetamide;

N-[1-(6-Cyano-5-fluoro-pyridin-2-ylmethyl)-1H-pyrazol-3-yl]-2-[3,5-dimethyl-4-(2,2,2-trifluoro-ethoxy)-phenyl]-acetamide;

N-[1-(4-Cyano-5-fluoro-pyridin-2-ylmethyl)-1H-pyrazol-3-yl]-2-[3,5-dimethyl-4-(2,2,2-trifluoro-ethoxy)-phenyl]-acetamide;

N-[1-(5-Cyano-pyridin-2-ylmethyl)-1H-pyrazol-3-yl]-2-[5-methyl-6-(2,2,2-trifluoro-ethoxy)-pyridin-3-yl]-acetamide;

N-[1-(6-Cyano-5-fluoro-pyridin-2-ylmethyl)-1H-pyrazol-3-yl]-2-[5-methyl-6-(2,2,2-trifluoro-ethoxy)-pyridin-3-yl]-acetamide;

N-[1-(6-Cyano-5-fluoro-pyridin-2-ylmethyl)-1H-pyrazol-3-yl]-2-[3-methyl-4-(3,3,3-trifluoro-propoxy)-phenyl]-acetamide; and N-[1-(4-Cyano-5-fluoro-pyridin-2-ylmethyl)-1H-pyrazol-3-yl]-2-[3-methyl-4-(3,3,3-trifluoro-propoxy)-phenyl]-acetamide.

It is to be understood, that a stereogenic center in a compound disclosed above, which stereogenic center is not specifically assigned, may be in absolute (R)- or absolute (S)-configuration; for example a compound listed as N-[1-(5-cyano-pyridin-2-ylmethyl)-1H-pyrazol-3-yl]-2-(3-methyl-chroman-7-yl)-acetamide may be N-[1-(5-cyano-pyridin-2-ylmethyl)-1H-pyrazol-3-yl]-2-((R)-3-methyl-chroman-7-yl)-acetamide, N-[1-(5-cyano-pyridin-2-ylmethyl)-1H-pyrazol-3-yl]-2-((S)-3-methyl-chroman-7-yl)-acetamide or any mixture thereof.

The compounds of formula (I) according to embodiments 1) to 31) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) as defined in any one of embodiments 1) to 31).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively the term "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I) as defined in any one of embodiments 1) to 31) are useful for the prevention or treatment of diseases or disorders where calcium T channels are involved.

Such diseases or disorders where calcium T channels are involved may be defined as including especially:
- epilepsy (notably absence epilepsy, childhood absence and other forms of idiopathic generalized epilepsies, temporal lobe epilepsy);
- sleep disorders and sleep disturbances;
- pain (notably inflammatory pain, neuropathic pain, peripheral pain, chronic pain associated with peripheral axonal injury);
- neurological diseases and disorders (notably essential tremors, Parkinson's disease, schizophrenia, depression, anxiety, psychosis, neurodegenerative disorders, autism, drug addiction);
- cardiovascular diseases and disorders (notably hypertension, cardiac arrhythmias, atrial fibrillation, congenital heart failure, heart block);
- cancer;
- diabetes and diabetic neuropathy; and
- infertility and sexual dysfunction.

Notably such diseases or disorders where calcium T channels are involved refer to epilepsy, neurological disorders, and pain. Preferably such diseases or disorders refer to epilepsy and pain.

The term "epilepsy" describes recurrent unprovoked seizures wherein the term "seizure" refers to an excessive and/or hypersynchronous electrical neuronal activity. Different types of "epilepsy" are disclosed for example in [Berg et al., Epilepsia. 2010; 51(4): 676-685], which reference is herewith incorporated by reference. The term "epilepsy" as used herein preferably refers to absence epilepsy, childhood absence and other forms of idiopathic generalized epilepsies, temporal lobe epilepsy.

The term "pain" preferably refers to inflammatory pain, neuropathic pain, peripheral pain, and chronic pain associated with peripheral axonal injury.

The term "neurological diseases and disorders" preferably refers to essential tremors, Parkinson's disease, schizophrenia, depression, anxiety, psychosis, neurodegenerative disorders, autism, drug addiction.

The term "cardiovascular diseases and disorders" preferably refers to hypertension, cardiac arrhythmias, atrial fibrillation, congenital heart failure, heart block.

The compounds of formula (I) as defined in embodiments 1) to 31) are also useful in a method of reducing the concentration of calcium in a neuronal cell, and wherein said reduction in calcium is achieved by blocking the calcium T-channel present in such neuronal cell; said method comprising the administration of a compound of formula (I) as defined in embodiments 1) to 31).

The compounds of formula (I) as defined in embodiments 1) to 31) are also useful in a method of decreasing burst firing discharges in a neuronal cell and wherein said decrease of burst firing is achieved by blocking the calcium T-channel; said method comprising the administration of a compound of formula (I) as defined in embodiments 1) to 31).

Preparation of Compounds of Formula (I):

The compounds of formula (I) can be prepared by the methods given below, by the methods given in the experimental part below or by analogous methods. Optimum reaction conditions may vary with the particular reactants or solvents used, but such conditions can be determined by a person skilled in the art by routine optimisation procedures. In the schemes below, the generic groups X, Y, $R^1$, $R^2$, $(R^4)_n$, and $(R^5)_m$ are as defined for the compounds of formula (I). In some instances the generic groups $R^1$, $R^2$, $(R^4)_n$, and $(R^5)_m$ may be incompatible with the assembly illustrated in the schemes and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. The compounds obtained may also be converted into salts, especially pharmaceutically acceptable salts in a manner known per se.

Compounds of general formula (II) can be prepared via an amide coupling as final step (Scheme 1). Generally, the corresponding carboxylic acid (IV) can be activated to the corresponding acid chloride, typically with oxalyl chloride. Alternatively, the carboxylic acid (IV) can be directly coupled to the amine (III) using a coupling reagent, typically HATU or HBTU. In certain instances two coupling products can be formed and are separated by preparative HPLC.

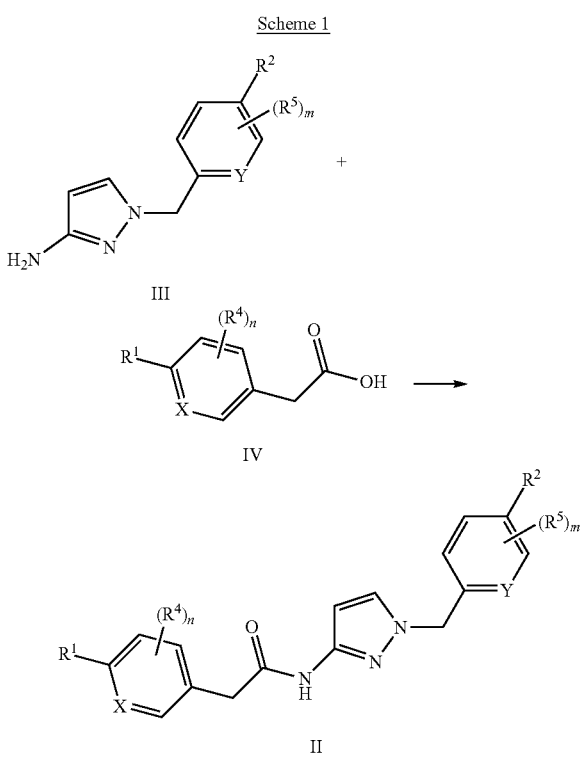

Scheme 1

The desired primary aminopyrazole (III) can be prepared from nitropyrazole (V) through an alkylation (compound of type (VI)) and a reduction step. For the reduction step, zinc, iron or palladium are preferentially used.

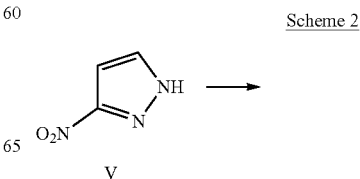

Scheme 2

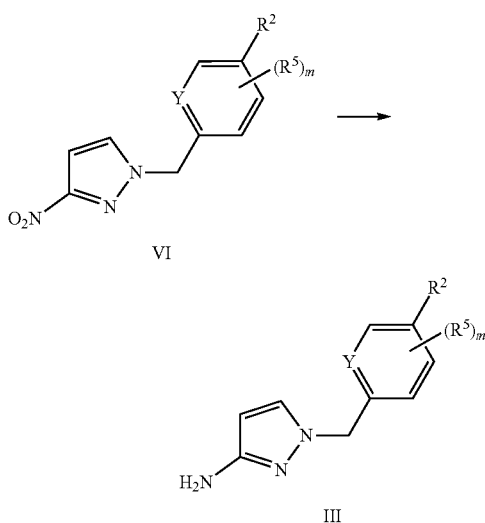

Aminopyrazoles of type (III) can be prepared via a Curtius rearrangement as well (Scheme 3). A suitable ester from the pyrazole-3-carboxylic acid (VIII) can be alkylated to compound (IX). Saponification leads to carboxylic acid (X), and subsequent Curtius rearrangement leads to the aminopyrazole (III).

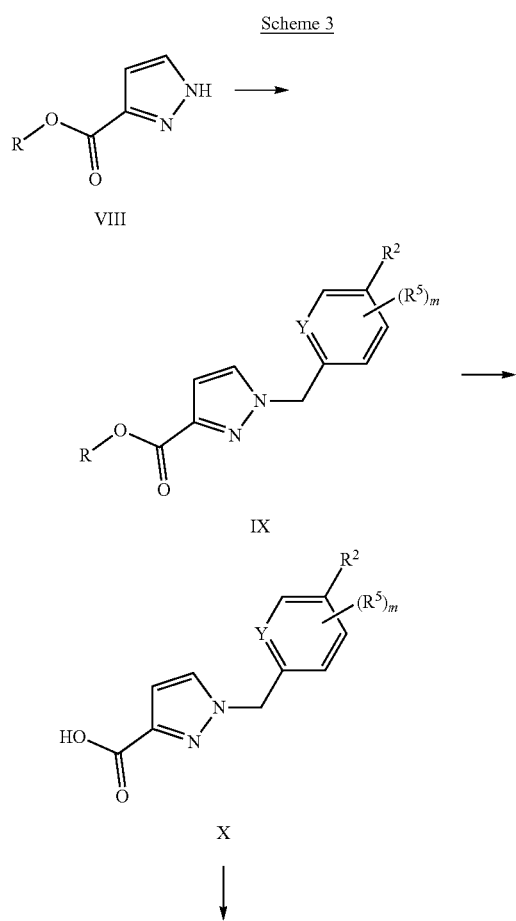

The corresponding benzyl chlorides, benzyl bromides, or benzyl mesylates necessary for the alkylation steps described in Schemes 2 (V→VI) and 3 (VIII→IX) can be prepared according to standard literature procedures or as described in the examples below.

The carboxylic acids of type (IV) can be prepared according to known procedures. In particular, a Negishi coupling (Scheme 4), or a similar carbon-carbon coupling between an (hetero)aryl bromide of type (XI) and (2-(tert-butoxy)-2-oxoethyl)zinc(II) bromide leads to the ester of type (XII): Hydrolysis, generally under acidic conditions, leads to the acid of type (IV). Bromide of type (XI) is either commercially available, or can be prepared according to known procedures (see experimental part).

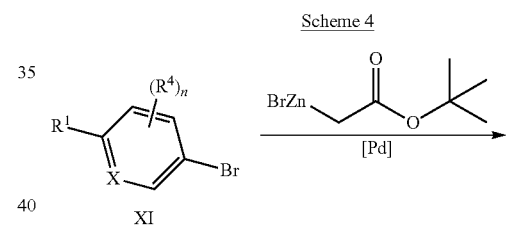

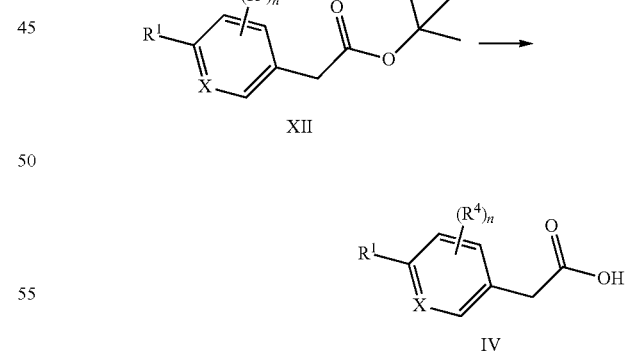

Alternatively, a benzoic acid of type (XIII) can be transformed into an acid of type (IV) via a Wolff rearrangement (Scheme 5). The acid of type (XIII) can be reduced to an alcohol of type (XIV). This alcohol can then be activated to a compound of type (XV), wherein LG represents a leaving group such as chloride, bromide, mesylate or tosylate, and homologated to nitrile of type (XVI): Hydrolysis would then lead to an acid of type (IV).

Scheme 5

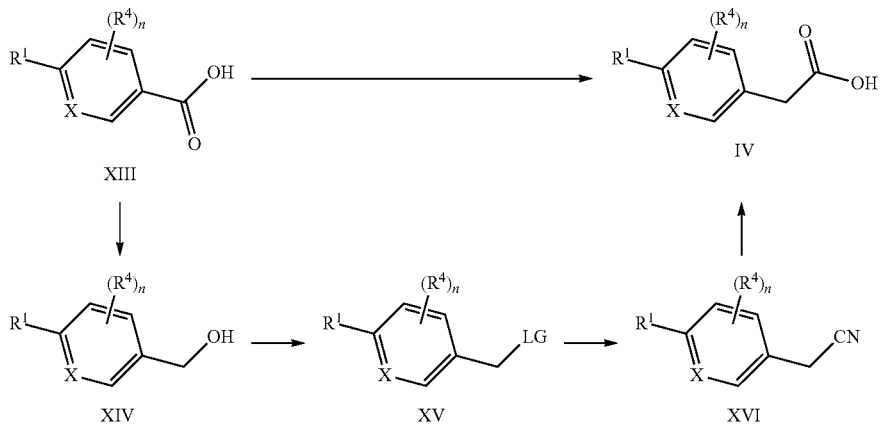

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm), IC (5 µm) or AD-H (5 µm) column. Typical conditions of chiral HPLC are an isocratic mixture of eluent A (EtOH, in presence or absence of an amine such as triethylamine or diethylamine) and eluent B (heptane), at a flow rate of 0.8 to 150 mL/min.

EXPERIMENTAL PART

The following examples illustrate the invention but do not at all limit the scope thereof.

Abbreviations: (as Used Herein and in the Description Above)

Ac Acetyl
aq. Aqueous
Bn Benzyl
Bu Butyl
CAS Chemical abstract system
comb. Combined
conc. Concentrated
DavePhos 2-Dicyclohexylphosphino-2'-(N,N-dimethylamino)biphenyl (CAS 213697-53-1)
dba Dibenzylideneacetone
DBU 1,8-Diazabicyclo[5.4.0]undec-7-ene
DIBAL Diisobutylaluminium hydride
DIPEA Diisopropylethylamine
Di-tBuXPhos 2-Di-tert-butylphosphino-2',4',6'-triisopropylbiphenyl (CAS 564483-19-8)
DMEM Dulbecco's modified eagle's medium
DMF N,N-Dimethylformamide
DMSO Dimethylsulfoxide
EDTA Ethylenediaminetetraacetic acid
eq. Equivalent
Et Ethyl
FC Flash chromatography
h Hour
HATU 1-[Bis(dimethylamino)methylene]-1H-1,2,3-triazolo[4,5-b]pyridinium 3-oxid hexafluorophosphate (CAS 148893-10-1)
HBTU O-Benzotriazole-N,N,N',N'-tetramethyl-uronium-hexafluoro-phosphate (CAS 94790-37-1)
HPLC High performance liquid chromatography
$^i$Bu iso-butyl
$^i$Pr iso-propyl
LC Liquid chromatography
Me Methyl
MH+ Mass of the protonated molecule
min Minute
MS Mass spectroscopy
NMR Nuclear magnetic resonance
org. Organic
PBS Phosphate Buffered Saline
PEPPSI-IPr 1,3-Bis(2,6-diisopropylphenyl)imidazolidene)-(3-chloropyridyl)palladium(I)dichloride (CAS 905459-27-0)
Ph Phenyl
Q-Phos 1,2,3,4,5-Pentaphenyl-1'-(di-tert-butylphosphino)ferrocene (CAS 312959-24-3)
rt Room temperature
RuPhos 2-Dicyclohexylphosphino-2',6'-diisopropoxybiphenyl (CAS 787618-22-8)
sat. saturated
sol Solution
TBDMS tert-Butyldimethylsilyl
tBu tert-Butyl
TEA Triethylamine
TFA Trifluoroacetic acid
THF tetrahydrofuran
TLC Thin layer chromatography
$t_R$ Retention time
Xantphos 4,5-Bis(diphenylphosphino)-9,9-dimethylxanthene (CAS 161265-03-8)
X-Phos 2-Dicyclohexylphosphino-2',4',6'-triisopropylbiphenyl (CAS 564483-18-7)
Preparation of Examples
General Procedures
General Procedure 1 for the Preparation of Acid Chlorides.
The desired carboxylic acid (1 eq.) is dissolved in toluene (5 mL/mmol). DMF (about 1 drop/mmol) and oxalyl chloride (1.5 eq.) are added, and the mixture is stirred at rt for 2 h. The solvents are removed under reduced pressure. The excess oxalyl chloride is removed azeotropically with toluene several times under reduced pressure. The residue is dried under high vacuum to yield the desired crude acid chloride.

General Procedure 2 for an Amide Coupling.

To a sol. of the desired amine (1 eq.) in dioxane (5 mL/mmol) is added the acid chloride (crude, 1.1 eq.) The mixture is heated to 60° C. to 90° C. for 1 h (or longer if the reaction is not complete). The mixture is allowed to cool to rt and the solvents are removed under reduced pressure. The residue is directly purified by automated FC, or by HPLC, to yield the desired product. Alternatively, the product can be isolated by crystallization.

General Procedure 3 for an Amide Coupling.

Unless indicated otherwise, a mixture of the desired carboxylic acid (1 eq.), the desired amine (1.5 eq), N-methylmorpholine (4 eq.) and HBTU (2 eq.) in DMF (around 20 mL/eq.) is stirred until the reaction is complete (a few hours to overnight). Other bases, coupling reagents and/or solvents can be used as well, see experimental details. The solvents are removed under reduced pressure. An aq. work-up (basic and/or acidic) is optionally realized. The residue is purified by automated FC, or by HPLC, to yield the desired product. Alternatively, the product can be isolated by crystallization.

General Procedure 4 for the N-Alkylation of 5-Nitro-1H-Pyrazole.

$K_2CO_3$ or NaH is added to a sol. of 5-nitro-1H-pyrazole in acetone or DMF or THF. The mixture is stirred for 15-30 min. The desired electrophile and $Bu_4NBr$ are added. The mixture is stirred efficiently at rt until the reaction is complete. The mixture is optionally filtered (if $K_2CO_3$ is used) or quenched with water (if NaH is used), and the filtrate is evaporated under reduced pressure. The residue is partitioned between water and EtOAc. The org. layer is dried over $MgSO_4$, filtered, and the solvents are removed under reduced pressure. Purification of the crude by automated FC or by HPLC yields the desired product.

General Procedure 5 for the Reduction of a Nitro Group.

Fe or Zn is added to a sol. of the starting material in EtOH or acetone with aq. sat. $NH_4Cl$. The mixture is heated to 75° C. and stirred at this temperature until the reaction is complete (about 1 h). The mixture is allowed to cool to rt and filtered through Celite®. The solvents were removed under reduced pressure to yield the desired crude product.

General Procedure 6 for a Negishi Coupling.

A sol. of bromoaryl/bromoheteroaryl, (2-(tert-butoxy)-2-oxoethyl)zinc(II) chloride (0.5M in $Et_2O$), palladium catalyst, and optionally a ligand in THF is stirred between rt and 90° C. until the starting materials are consumed. The mixture is allowed to cool to rt, and the solvents are removed under reduced pressure. Chromatographic purification yields the desired compound.

General Procedure 7 for the Hydrolysis of a Tert-Butyl Ester.

A sol. of the ester and an acid with optionally $CH_2Cl_2$ is prepared at 0° C. This mixture is stirred between at 0° C., optionally warming up to rt, until consumption of the starting material. The solvents are removed under reduced pressure to yield the crude desired compound.

General Procedure 9 for the N-Alkylation of a Pyridine.

A mixture of 2,5-dibromopyridine, an amine, and DBU in DMSO is stirred at 80° C. until the reaction is complete. The amine and DBU may have to be added several times. The mixture is allowed to cool to rt, and the solvents are removed under reduced pressure. Purification of the crude by FC yields the desired product.

Analytical Conditions for LC-MS

Unless notified otherwise, the following conditions were used for analytical LC-MS data:

Conditions 1: Ascentis Express C18 2.7 µm 2.1×30 mm, 5% $CH_3CN$/95% $H_2O$ with 0.05% $NH_4OH$→95% $CH_3CN$ over 2.0 min, 1.4 mL/min.

Conditions 2: Waters Atlantis T3 column, C18, 5 µm, 4.6×30 mm, 5% $CH_3CN$/95% $H_2O$ with 0.04% TFA→100% $CH_3CN$ over 1.0 min, 4.5 mL/min.

Conditions 3: Zorbax SB-Aq column, 3.5 µm, 4.6×50 mm, 5% $CH_3CN$/95% $H_2O$ with 0.04% TFA→100% $CH_3CN$ over 1.0 min, 4.5 mL/min.

Conditions 4: Waters XBridge C18, 2.5 µm, 4.6×30 mm, 5% $CH_3CN$/95% $H_2O$ with 0.04% TFA→100% $CH_3CN$ over 1.0 min, 4.5 mL/min.

Preparative HPLC

Reaction mixture can often be separated by preparative HPLC. A person skilled in the art will find suitable conditions for each separation.

Automated FC

Classical flash chromatography is often replaced by automated systems. This does not change the separation process per se. A person skilled in the art will be able to replace a classical FC process by an automated one, and vice versa. Typical automated systems can be used, as they are provided by Büchi, Isco (Combiflash), or Biotage for instance.

tert-Butyl 2-(6-(dimethylamino)pyridin-3-yl)acetate

According to general procedure 6, with 5-bromo-2-(dimethylamino)pyridine (600 mg, 3.00 mmol), 2-tert-butoxy-2-oxoethylzinc chloride (0.5M in $Et_2O$, 9.0 mL, 4.5 mmol), $Pd_2(dba)_3$ (275 mg, 0.300 mmol), and Q-Phos (215 mg, 0.30 mmol) in THF (6.00 mL). The reaction is complete after 4 h at 70° C. Purification of the crude by automated FC (Büchi, EtOAc/heptane 1:99→3:97→5:95→8:92→15:85, 20 g silicagel, flow 20 mL/min) yields the title compound. LC-MS: $t_R$=0.51 min, MH$^+$=237.09 (conditions 2).

2-(6-(Dimethylamino)pyridin-3-yl)acetic acid

According to general procedure 7 with tert-butyl 2-(6-(dimethylamino)pyridin-3-yl)acetate (570 mg, 2.41 mmol), HCl (4M in dioxane, 10 mL) and $CH_2Cl_2$ (10 mL) at 0° C. The mixture is stirred for 30 min at 0° C., and for 9 h at rt. Removal of the solvents under reduced pressure yields the crude title compound. LC-MS: $t_R$=0.27 min, MH$^+$=181.17 (conditions 2).

1-(4-Methoxybenzyl)-3-nitro-1H-pyrazole

Prepared according to general procedure 4 from $K_2CO_3$ (2.07 g, 15.0 mmol), 1-(chloromethyl)-4-methoxybenzene (0.405 mL, 3.00 mmol), 5-nitro-1H-pyrazole (339 mg, 3.00 mmol), and $Bu_4NBr$ (197 mg, 0.60 mmol) in acetone (15 mL). The reaction is complete after 3.5 h. Purification of the crude by automated FC (Büchi, EtOAc/heptane 1:99→5:95→10:90→15:85→25:75→35:65, 20 g silicagel, flow 20 mL/min) yields the title product. LC-MS: $t_R$=0.81 min (conditions 3).

1-(4-Methoxybenzyl)-1H-pyrazol-3-amine

Prepared according to general procedure 5 from Fe (powder, 592 mg, 10.7 mmol), 1-(3-methoxybenzyl)-3-nitro-1H-pyrazole (250 mg, 1.07 mmol), EtOH (10 mL), and aq. sat. $NH_4Cl$ (1 mL). The reaction is complete after 4 h. This yields the crude title compound. LC-MS: $t_R$=0.53 min, MH$^+$=204.47 (conditions 3).

1-(4-Methylbenzyl)-3-nitro-1H-pyrazole

Prepared according to general procedure 4 from $K_2CO_3$ (2.07 g, 15.0 mmol), 1-(chloromethyl)-4-methylbenzene (0.398 mL, 3.00 mmol), 5-nitro-1H-pyrazole (339 mg, 3.00 mmol), and Bu$_4$NBr (197 mg, 0.600 mmol) in acetone (15 mL). The reaction is complete after 3.5 h. Purification of the crude by automated FC (Büchi, EtOAc/heptane 1:99→5: 95→10:90→15:85→25:75→35:65, 20 g silicagel, flow 20 mL/min) yields the title product. LC-MS: $t_R$=0.85 min (conditions 3).

1-(4-Methylbenzyl)-1H-pyrazol-3-amine

Prepared according to general procedure 5 from Fe (powder, 592 mg, 10.7 mmol), 1-(4-methylbenzyl)-3-nitro-1H-pyrazole (233 mg, 1.07 mmol), EtOH (10 mL), and aq. sat. NH$_4$Cl (1 mL). The reaction is complete after 1 h. This yields the title compound. LC-MS: $t_R$=0.57 min, MH$^+$=188.48 (conditions 3).

4-((3-Nitro-1H-pyrazol-1-yl)methyl)benzonitrile

Prepared according to general procedure 4 from K$_2$CO$_3$ (2.07 g, 15.0 mmol), 4-(bromomethyl)benzonitrile (588 mg, 3.00 mmol), 5-nitro-1H-pyrazole (339 mg, 3.00 mmol), and Bu$_4$NBr (197 mg, 0.60 mmol) in acetone (15 mL). The reaction is complete after 3.5 h. Purification of the crude by automated FC (Büchi, EtOAc/heptane 1:99→5:95→10: 90→15:85→25:75→35:65, 20 g silicagel, flow 20 mL/min) yields the title product. LC-MS: $t_R$=0.77 min (conditions 3).

4-((3-Amino-1H-pyrazol-1-yl)methyl)benzonitrile

Prepared according to general procedure 5 from Fe (powder, 592 mg, 10.7 mmol), 4-((3-nitro-1H-pyrazol-1-yl)methyl)benzonitrile (245 mg, 1.07 mmol), EtOH (10 mL), and aq. sat. NH$_4$Cl (1 mL). The reaction is complete after 2.5 h. This yields the title compound. LC-MS: $t_R$=0.51 min, MH$^+$=199.46 (conditions 3).

1-(4-Ethylbenzyl)-3-nitro-1H-pyrazole

Prepared according to general procedure 4 with K$_2$CO$_3$ (4.47 g, 32.3 mmol), 4-ethylbenzyl chloride (0.962 mL, 6.47 mmol), 5-nitro-1H-pyrazole (731 mg, 6.47 mmol), and Bu$_4$NBr (425 mg, 1.29 mmol) in acetone (45 mL). The reaction is complete after 24 h. Purification of the crude by automated FC (Büchi, EtOAc/heptane 1:99→5:95→10: 90→15:85→25:75→35:65, 20 g silicagel, flow 20 mL/min) yields the title compound. LC-MS: $t_R$=0.89 min (conditions 3).

1-(4-Ethylbenzyl)-1H-pyrazol-3-amine

Prepared according to general procedure 5 with Fe (2.56 g, 46.3 mmol) and 1-(4-ethylbenzyl)-3-nitro-1H-pyrazole (1.07 g, 4.63 mmol) in EtOH (30 mL), and aq. sat. NH$_4$Cl (4 mL). The reaction is complete after 20 h and yields the crude title compound. LC-MS: $t_R$=0.63 min, MH$^+$=202.29 (conditions 3).

1-(4-Isopropylbenzyl)-3-nitro-1H-pyrazole

Prepared according to general procedure 4 with K$_2$CO$_3$ (4.47 g, 32.3 mmol), 4-isopropylbenzyl chloride (0.718 mL, 6.47 mmol), 5-nitro-1H-pyrazole (731 mg, 6.47 mmol), and Bu$_4$NBr (425 mg, 1.29 mmol) in acetone (45 mL). The reaction is complete after 24 h. Purification of the crude by automated FC (Büchi, EtOAc/heptane 1:99→5:95→10: 90→15:85→25:75→35:65, 20 g silicagel, flow 20 mL/min) yields the title compound. LC-MS: $t_R$=0.92 min (conditions 3).

1-(4-Isopropylbenzyl)-1H-pyrazol-3-amine

Prepared according to general procedure 5 with Fe (1.83 g, 33.0 mmol) and 1-(4-isopropylbenzyl)-3-nitro-1H-pyrazole (810 mg, 3.30 mmol) in EtOH (30 mL), and aq. sat. NH$_4$Cl (4 mL). The reaction is complete after 20 h and yields the crude title compound. LC-MS: $t_R$=0.67 min, MH$^+$=216.28 (conditions 3).

1-(4-(tert-Butyl)benzyl)-3-nitro-1H-pyrazole

Prepared according to general procedure 4 with K$_2$CO$_3$ (4.47 g, 32.3 mmol), 4-tert-butylbenzyl chloride (1.25 mL, 6.47 mmol), 5-nitro-1H-pyrazole (731 mg, 6.47 mmol), and Bu$_4$NBr (425 mg, 1.29 mmol) in acetone (45 mL). The reaction is complete after 24 h. Purification of the crude by automated FC (Büchi, EtOAc/heptane 1:99→5:95→10: 90→15:85→25:75→35:65, 20 g silicagel, flow 20 mL/min) yields the title compound. LC-MS: $t_R$=0.95 min (conditions 3).

1-(4-(tert-Butyl)benzyl)-1H-pyrazol-3-amine

Prepared according to general procedure 5 with Fe (2.67 g, 48.2 mmol) and 1-(4-(tert-butyl)benzyl)-3-nitro-1H-pyrazole (1.25 g, 4.82 mmol) in EtOH (40 mL), and aq. sat. NH$_4$Cl (5 mL). The reaction is complete after 20 h and yields the crude title compound. LC-MS: $t_R$=0.71 min, MH$^+$=230.21 (conditions 3).

1-(4-(Difluoromethoxy)benzyl)-3-nitro-1H-pyrazole

Prepared according to general procedure 4 with K$_2$CO$_3$ (4.47 g, 32.3 mmol), 4-difluoromethoxybenzyl chloride (1.25 mL, 6.47 mmol), 5-nitro-1H-pyrazole (731 mg, 6.47 mmol), and Bu$_4$NBr (425 mg, 1.29 mmol) in acetone (45 mL). The reaction is complete after 5 h at rt. Purification of the crude by automated FC (Büchi, EtOAc/heptane 1:99→5: 95→10:90→15:85→25:75→35:65, 20 g silicagel, flow 20 mL/min) yields the title compound. LC-MS: $t_R$=0.85 min (conditions 3).

1-(4-(Difluoromethoxy)benzyl)-1H-pyrazol-3-amine

Prepared according to general procedure 5 with Fe (2.77 g, 50.1 mmol) and 1-(4-(difluoromethoxy)benzyl)-3-nitro-1H-pyrazole (1.35 g, 5.01 mmol) in EtOH (40 mL), and aq. sat. NH$_4$Cl (5 mL). The reaction is complete after 45 min and yields the crude title compound. LC-MS: $t_R$=0.60 min, MH$^+$=240.09 (conditions 3).

3-Nitro-1-(4-(trifluoromethoxy)benzyl)-1H-pyrazole

Prepared according to general procedure 4 with K$_2$CO$_3$ (4.47 g, 32.3 mmol), 4-trifluoromethoxybenzyl chloride (1.36 g, 6.47 mmol), 5-nitro-1H-pyrazole (731 mg, 6.47 mmol), and Bu$_4$NBr (425 mg, 1.29 mmol) in acetone (45 mL). The reaction is complete after 24 h at rt. Purification of the crude by automated FC (Büchi, EtOAc/heptane 1:99→5: 95→10:90→15:85→25:75→35:65, 20 g silicagel, flow 20 mL/min) yields the title compound. LC-MS: $t_R$=0.90 min (conditions 3).

1-(4-(Trifluoromethoxy)benzyl)-1H-pyrazol-3-amine

Prepared according to general procedure 5 with Fe (2.25 g, 40.7 mmol) and 3-nitro-1-(4-(trifluoromethoxy)benzyl)-1H-pyrazole (1.17 g, 4.07 mmol) in EtOH (40 mL), and aq. sat. NH$_4$Cl (5 mL). The reaction is complete after 20 h at 75° C. and yields the crude title compound. LC-MS: $t_R$=0.67 min, MH$^+$=257.94 (conditions 3).

1-(3,4-Difluorobenzyl)-3-nitro-1H-pyrazole

Prepared according to general procedure 4 with K$_2$CO$_3$ (4.47 g, 32.3 mmol), 4-(chloromethyl)-1,2-difluorobenzene (1.05 g, 6.47 mmol), 5-nitro-1H-pyrazole (731 mg, 6.47 mmol), and Bu$_4$NBr (425 mg, 1.29 mmol) in acetone (45 mL). The reaction is complete after 3 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.83 min (conditions 3).

1-(3,4-Difluorobenzyl)-1H-pyrazol-3-amine

Prepared according to general procedure 5 with Fe (2.73 g, 49.3 mmol) and 1-(3,4-difluorobenzyl)-3-nitro-1H-pyrazole (1.18 g, 4.93 mmol) in EtOH (40 mL), and aq. sat. NH$_4$Cl (4 mL). The reaction is complete after 5 days at 75° C. and yields the crude title compound. LC-MS: $t_R$=0.56 min, MH$^+$=210.23 (conditions 3).

1-(3-Fluoro-4-(trifluoromethoxy)benzyl)-3-nitro-1H-pyrazole

Prepared according to general procedure 4 with K$_2$CO$_3$ (2.53 g, 18.3 mmol), 4-(bromomethyl)-2-fluoro-1-(trifluoromethoxy)benzene (1.00 g, 3.66 mmol), 5-nitro-1H-pyrazole (414 mg, 3.66 mmol), and Bu$_4$NBr (241 mg, 0.733 mmol) in acetone (45 mL). The reaction is complete after 5 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.90 min (conditions 3).

1-(3-Fluoro-4-(trifluoromethoxy)benzyl)-1H-pyrazol-3-amine

Prepared according to general procedure 5 with Fe (1.70 g, 30.8 mmol) and 1-(3-fluoro-4-(trifluoromethoxy)benzyl)-3-nitro-1H-pyrazole (940 mg, 3.08 mmol) in EtOH (40 mL), and aq. sat. NH$_4$Cl (4 mL). The reaction is complete after 4 h at 75° C. and yields the crude title compound. LC-MS: $t_R$=0.69 min, MH$^+$=276.13 (conditions 3).

1-(3-Fluoro-4-(trifluoromethyl)benzyl)-3-nitro-1H-pyrazole

Prepared according to general procedure 4 with K$_2$CO$_3$ (4.47 g, 32.4 mmol), 4-(chloromethyl)-2-fluoro-1-(trifluoromethyl)benzene (1.38 g, 6.47 mmol), 5-nitro-1H-pyrazole (732 mg, 6.47 mmol), and Bu$_4$NBr (426 mg, 1.29 mmol) in acetone (45 mL). The reaction is complete after 24 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.89 min (conditions 3).

1-(3-Fluoro-4-(trifluoromethyl)benzyl)-1H-pyrazol-3-amine

Prepared according to general procedure 5 with Fe (2.33 g, 42.2 mmol) and 1-(3-fluoro-4-(trifluoromethyl)benzyl)-3-nitro-1H-pyrazole (1.22 g, 4.22 mmol) in EtOH (40 mL), and aq. sat. NH$_4$Cl (4 mL). The reaction is complete after 6 h at 75° C. and yields the crude title compound. LC-MS: $t_R$=0.67 min, MH$^+$=260.11 (conditions 3).

3-Nitro-1-(3,4,5-trifluorobenzyl)-1H-pyrazole

Prepared according to general procedure 4 with K$_2$CO$_3$ (4.47 g, 32.4 mmol), 3,4,5-trifluorobenzyl chloride (1.17 g, 6.47 mmol), 5-nitro-1H-pyrazole (732 mg, 6.47 mmol), and Bu$_4$NBr (426 mg, 1.29 mmol) in acetone (45 mL). The reaction is complete after 24 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.85 min (conditions 3).

1-(3,4,5-Trifluorobenzyl)-1H-pyrazol-3-amine

Prepared according to general procedure 5 with Fe (2.45 g, 44.3 mmol) and 3-nitro-1-(3,4,5-trifluorobenzyl)-1H-pyrazole (1.14 g, 4.43 mmol) in EtOH (40 mL), and aq. sat. NH$_4$Cl (4 mL). The reaction is complete after 6 h at 75° C. and yields the crude title compound. LC-MS: $t_R$=0.60 min, MH$^+$=228.16 (conditions 3).

1-(4-Fluoro-3,5-dimethylbenzyl)-3-nitro-1H-pyrazole

Prepared according to general procedure 4 with K$_2$CO$_3$ (3.18 g, 23.0 mmol), 4-fluoro-3,5-dimethylbenzyl bromide (1.00 g, 4.61 mmol), 5-nitro-1H-pyrazole (521 mg, 4.61 mmol), and Bu$_4$NBr (303 mg, 0.921 mmol) in acetone (45 mL). The reaction is complete after 30 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.90 min (conditions 3).

1-(4-Fluoro-3,5-dimethylbenzyl)-1H-pyrazol-3-amine

Prepared according to general procedure 5 with Fe (2.44 g, 44.1 mmol) and 1-(4-fluoro-3,5-dimethylbenzyl)-3-nitro-1H-pyrazole (1.10 g, 4.41 mmol) in EtOH (40 mL), and aq. sat. NH$_4$Cl (4 mL). The reaction is complete after 30 h at 75° C. and yields the crude title compound. LC-MS: $t_R$=0.64 min, MH$^+$=220.24 (conditions 3).

1-(4-Chloro-3-fluorobenzyl)-3-nitro-1H-pyrazole

Prepared according to general procedure 4 with K$_2$CO$_3$ (1.55 g, 11.2 mmol), 4-chloro-3-fluorobenzyl bromide (500 mg, 2.24 mmol), 5-nitro-1H-pyrazole (253 mg, 2.24 mmol), and Bu$_4$NBr (147 mg, 0.447 mmol) in acetone (11 mL). The reaction is complete after 4 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.86 min (conditions 2).

1-(4-Chloro-3-fluorobenzyl)-1H-pyrazol-3-amine

Prepared according to general procedure 5 with Fe (876 mg, 15.8 mmol) and 1-(4-chloro-3-fluorobenzyl)-3-nitro- 1H-pyrazole (405 mg, 1.58 mmol) in EtOH (30 mL), and aq. sat. NH$_4$Cl (4 mL). The reaction is complete after 18 h at 75° C. and yields the crude title compound. LC-MS: $t_R$=0.61 min, MH$^+$=226.13 (conditions 3).

1-(4-Chloro-3-(trifluoromethoxy)benzyl)-3-nitro-1H-pyrazole

Prepared according to general procedure 4 with K$_2$CO$_3$ (1.55 g, 11.2 mmol), 4-chloro-3-trifluoromethoxybenzyl bromide (648 mg, 2.24 mmol), 5-nitro-1H-pyrazole (253 mg, 2.24 mmol), and Bu$_4$NBr (147 mg, 0.447 mmol) in acetone (11 mL). The reaction is complete after 4 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.95 min (conditions 2).

1-(4-Chloro-3-(trifluoromethoxy)benzyl)-1H-pyrazol-3-amine

Prepared according to general procedure 5 with Fe (1.01 g, 18.3 mmol) and 1-(4-chloro-3-(trifluoromethoxy)benzyl)-3-nitro-1H-pyrazole (587 mg, 1.83 mmol) in EtOH (30 mL), and aq. sat. NH$_4$Cl (4 mL). The reaction is complete after 18 h at 75° C. and yields the crude title compound. LC-MS: $t_R$=0.73 min, MH$^+$=292.16 (conditions 3).

1-(4-Chloro-3-(trifluoromethyl)benzyl)-3-nitro-1H-pyrazole

Prepared according to general procedure 4 with K$_2$CO$_3$ (1.55 g, 11.2 mmol), 4-chloro-3-trifluoromethylbenzyl bromide (612 mg, 2.24 mmol), 5-nitro-1H-pyrazole (253 mg, 2.24 mmol), and Bu$_4$NBr (147 mg, 0.447 mmol) in acetone (11 mL). The reaction is complete after 4 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.92 min (conditions 2).

1-(4-Chloro-3-(trifluoromethyl)benzyl)-1H-pyrazol-3-amine

Prepared according to general procedure 5 with Fe (1.24 g, 22.4 mmol) and 1-(4-chloro-3-(trifluoromethyl)benzyl)-3-nitro-1H-pyrazole (684 mg, 2.24 mmol) in EtOH (30 mL), and aq. sat. NH$_4$Cl (4 mL). The reaction is complete after 18 h at 75° C. and yields the crude title compound. LC-MS: $t_R$=0.71 min, MH$^+$=276.12 (conditions 3).

1-(3,5-Difluoro-4-methoxybenzyl)-3-nitro-1H-pyrazole

Prepared according to general procedure 4 with K$_2$CO$_3$ (1.55 g, 11.2 mmol), 3,5-difluoro-4-methoxybenzyl bromide (530 mg, 2.24 mmol), 5-nitro-1H-pyrazole (253 mg, 2.24 mmol), and Bu$_4$NBr (147 mg, 0.447 mmol) in acetone (11 mL). The reaction is complete after 4 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.83 min (conditions 2).

1-(3,5-Difluoro-4-methoxybenzyl)-1H-pyrazol-3-amine

Prepared according to general procedure 5 with Fe (980 mg, 17.7 mmol) and 1-(3,5-difluoro-4-methoxybenzyl)-3-nitro-1H-pyrazole (477 mg, 1.77 mmol) in EtOH (30 mL), and aq. sat. NH$_4$Cl (4 mL). The reaction is complete after 4 h at 75° C. and yields the crude title compound. LC-MS: $t_R$=0.59 min, MH$^+$=240.11 (conditions 3).

1-(4-Methoxy-3-(trifluoromethyl)benzyl)-3-nitro-1H-pyrazole

Prepared according to general procedure 4 with K$_2$CO$_3$ (1.55 g, 11.2 mmol), 4-methoxy-3-trifluorobenzyl bromide (530 mg, 2.24 mmol), 5-nitro-1H-pyrazole (253 mg, 2.24 mmol), and Bu$_4$NBr (147 mg, 0.447 mmol) in acetone (11 mL). The reaction is complete after 17 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.87 min (conditions 2).

1-(4-Methoxy-3-(trifluoromethyl)benzyl)-1H-pyrazol-3-amine

Prepared according to general procedure 5 with Fe (947 mg, 17.1 mmol) and 1-(4-methoxy-3-(trifluoromethyl)benzyl)-3-nitro-1H-pyrazole (516 mg, 1.71 mmol) in EtOH (30 mL), and aq. sat. NH$_4$Cl (4 mL). The reaction is complete after 1 h at 75° C. and yields the crude title compound. LC-MS: $t_R$=0.66 min, MH$^+$=272.16 (conditions 3).

1-(4-Fluoro-3-methylbenzyl)-3-nitro-1H-pyrazole

Prepared according to general procedure 4 with K$_2$CO$_3$ (3.51 g, 25.4 mmol), 4-fluoro-3-methylbenzyl bromide (1.03 g, 5.08 mmol), 5-nitro-1H-pyrazole (574 mg, 5.08 mmol), and Bu$_4$NBr (334 mg, 1.02 mmol) in acetone (45 mL). The reaction is complete after 8 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.86 min (conditions 3).

1-(4-Fluoro-3-methylbenzyl)-1H-pyrazol-3-amine

Prepared according to general procedure 5 with Fe (2.45 g, 44.2 mmol) and 1-(4-fluoro-3-methylbenzyl)-3-nitro-1H-pyrazole (1.04 g, 4.42 mmol) in EtOH (40 mL), and aq. sat. NH$_4$Cl (4 mL). The reaction is complete after 20 h at 75° C. and yields the crude title compound. LC-MS: $t_R$=0.59 min, MH$^+$=206.27 (conditions 3).

1-(3-Chloro-4-fluorobenzyl)-3-nitro-1H-pyrazole

Prepared according to general procedure 4 with K$_2$CO$_3$ (3.51 g, 25.4 mmol), 3-chloro-4-fluorobenzyl chloride (909 mg, 5.08 mmol), 5-nitro-1H-pyrazole (574 mg, 5.08 mmol), and Bu$_4$NBr (334 mg, 1.02 mmol) in acetone (45 mL). The reaction is complete after 8 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.86 min (conditions 3).

1-(3-Chloro-4-fluorobenzyl)-1H-pyrazol-3-amine

Prepared according to general procedure 5 with Fe (433 mg, 7.82 mmol) and 1-(3-chloro-4-fluorobenzyl)-3-nitro-1H-pyrazole (200 mg, 0.782 mmol) in EtOH (20 mL), and aq. sat. NH$_4$Cl (2 mL). The reaction is complete after 20 h at 75° C. and yields the crude title compound. LC-MS: $t_R$=0.61 min, MH$^+$=226.12 (conditions 3).

1-(3-Fluoro-4-methylbenzyl)-3-nitro-1H-pyrazole

Prepared according to general procedure 4 with K$_2$CO$_3$ (3.51 g, 25.4 mmol), 3-fluoro-4-methylbenzyl chloride (805 mg, 5.08 mmol), 5-nitro-1H-pyrazole (574 mg, 5.08 mmol), and Bu$_4$NBr (334 mg, 1.02 mmol) in acetone (45 mL). The reaction is complete after 3 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.86 min (conditions 3).

1-(3-Fluoro-4-methylbenzyl)-1H-pyrazol-3-amine

Prepared according to general procedure 5 with Fe (2.21 g, 40.0 mmol) and 1-(3-fluoro-4-methylbenzyl)-3-nitro-1H-pyrazole (940 mg, 4.00 mmol) in EtOH (40 mL), and aq. sat. NH$_4$Cl (4 mL). The reaction is complete after 2 h at 75° C. and yields the crude title compound. LC-MS: $t_R$=0.59 min, MH$^+$=206.26 (conditions 3).

6-((3-Nitro-1H-pyrazol-1-yl)methyl)nicotinonitrile

Prepared according to general procedure 4 with K$_2$CO$_3$ (3.51 g, 25.4 mmol), 6-(bromomethyl)nicotinonitrile (1000 mg, 5.08 mmol), 5-nitro-1H-pyrazole (574 mg, 5.08 mmol), and Bu$_4$NBr (334 mg, 1.02 mmol) in acetone (45 mL). The reaction is complete after 3 days at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.67 min (conditions 3).

6-((3-Amino-1H-pyrazol-1-yl)methyl)nicotinonitrile

Prepared according to general procedure 5 with Fe (1.05 g, 18.5 mmol) and 6-((3-nitro-1H-pyrazol-1-yl)methyl)nicotinonitrile (425 mg, 1.85 mmol) in EtOH (30 mL), and aq. sat. NH$_4$Cl (3 mL). The reaction is complete after 1 h at 75° C. and yields the crude title compound. LC-MS: $t_R$=0.40 min, MH$^+$=200.28 (conditions 3).

5-Methoxy-2-((3-nitro-1H-pyrazol-1-yl)methyl)pyridine

Prepared according to general procedure 4 with K$_2$CO$_3$ (4.39 g, 31.7 mmol), 2-(chloromethyl)-5-methoxypyridine (1000 mg, 6.35 mmol), 5-nitro-1H-pyrazole (717 mg, 6.35 mmol), and Bu$_4$NBr (417 mg, 1.27 mmol) in acetone (45 mL). The reaction is complete after 3 days at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.66 min (conditions 3).

1-((5-Methoxypyridin-2-yl)methyl)-1H-pyrazol-3-amine

Prepared according to general procedure 5 with Fe (1.36 g, 24.6 mmol) and 5-methoxy-2-((3-nitro-1H-pyrazol-1-yl)methyl)pyridine (575 mg, 2.46 mmol) in EtOH (20 mL), and aq. sat. NH$_4$Cl (3 mL). The reaction is complete after 18 h at 75° C. and yields the crude title compound. LC-MS: $t_R$=0.38 min, MH$^+$=205.28 (conditions 3).

The following examples were prepared according to general procedures 1 and 2, from the appropriate carboxylic acids and aminopyrazoles:

| Example No | Name | LC-MS ($t_R$; MH$^+$; conditions) |
|---|---|---|
| 1 | N-[1-(4-Chloro-benzyl)-1H-pyrazol-3-yl]-2-(4-isopropyl-phenyl)-acetamide | 1.42 min; 368.16; conditions 1 |
| 2 | N-[1-(4-Chloro-benzyl)-1H-pyrazol-3-yl]-2-(4-dimethylamino-phenyl)-acetamide | 1.22 min; 369.15; conditions 1 |
| 3 | 2-(4-Dimethylamino-phenyl)-N-[1-(4-fluoro-benzyl)-1H-pyrazol-3-yl]-acetamide | 1.13 min; 353.18; conditions 1 |
| 4 | 2-(6-Dimethylamino-pyridin-3-yl)-N-[1-(4-fluoro-benzyl)-1H-pyrazol-3-yl]-acetamide | 0.53 min; 354.18; conditions 2 |
| 5 | N-[1-(4-Chloro-benzyl)-1H-pyrazol-3-yl]-2-(6-dimethylamino-pyridin-3-yl)-acetamide | 0.57 min; 370.11; conditions 2 |
| 6 | N-[1-(4-Fluoro-benzyl)-1H-pyrazol-3-yl]-2-(4-isopropyl-phenyl)-acetamide | 1.33 min; 352.18; conditions 1 |
| 7 | 2-(4-Isopropyl-phenyl)-N-[1-(4-methoxy-benzyl)-1H-pyrazol-3-yl]-acetamide | 0.92 min; 364.30; conditions 3 |
| 8 | 2-(4-Dimethylamino-phenyl)-N-[1-(4-methoxy-benzyl)-1H-pyrazol-3-yl]-acetamide | 0.62 min; 365.25; conditions 3 |
| 9 | 2-(4-Isopropyl-phenyl)-N-[1-(4-methyl-benzyl)-1H-pyrazol-3-yl]-acetamide | 0.95 min; 348.30; conditions 3 |
| 10 | 2-(4-Dimethylamino-phenyl)-N-[1-(4-methyl-benzyl)-1H-pyrazol-3-yl]-acetamide | 0.65 min; 349.30; conditions 3 |
| 11 | N-[1-(4-Cyano-benzyl)-1H-pyrazol-3-yl]-2-(4-isopropyl-phenyl)-acetamide | 0.90 min; 359.26; conditions 3 |
| 12 | N-[1-(4-Cyano-benzyl)-1H-pyrazol-3-yl]-2-(4-dimethylamino-phenyl)-acetamide | 0.59 min; 360.31; conditions 3 |
| 13 | 2-(6-Dimethylamino-pyridin-3-yl)-N-[1-(4-methyl-benzyl)-1H-pyrazol-3-yl]-acetamide | 0.64 min; 350.26; conditions 3 |
| 14 | 2-(6-Dimethylamino-pyridin-3-yl)-N-[1-(4-methoxy-benzyl)-1H-pyrazol-3-yl]-acetamide | 0.61 min; 366.32; conditions 3 |
| 15 | N-[1-(4-Cyano-benzyl)-1H-pyrazol-3-yl]-2-(6-dimethylamino-pyridin-3-yl)-acetamide | 0.59 min; 361.28; conditions 3 |
| 16 | 2-(4-Dimethylamino-phenyl)-N-[1-(4-ethyl-benzyl)-1H-pyrazol-3-yl]-acetamide | 0.69 min; 363.19; conditions 3 |
| 17 | 2-(4-Dimethylamino-phenyl)-N-[1-(4-isopropyl-benzyl)-1H-pyrazol-3-yl]-acetamide | 0.72 min; 377.16; conditions 3 |

| Example No | Name | LC-MS ($t_R$; MH+; conditions) |
|---|---|---|
| 18 | N-[1-(4-tert-Butyl-benzyl)-1H-pyrazol-3-yl]-2-(4-dimethylamino-phenyl)-acetamide | 0.75 min; 391.21; conditions 3 |
| 19 | N-[1-(4-Difluoromethoxy-benzyl)-1H-pyrazol-3-yl]-2-(4-dimethylamino-phenyl)-acetamide | 0.67 min; 401.07; conditions 3 |
| 20 | 2-(4-Dimethylamino-phenyl)-N-[1-(4-trifluoromethoxy-benzyl)-1H-pyrazol-3-yl]-acetamide | 0.71 min; 419.18; conditions 3 |
| 21 | N-[1-(3,4-Difluoro-benzyl)-1H-pyrazol-3-yl]-2-(4-dimethylamino-phenyl)-acetamide | 0.64 min; 371.12; conditions 3 |
| 22 | 2-(4-Dimethylamino-phenyl)-N-[1-(4-fluoro-3-trifluoromethoxy-benzyl)-1H-pyrazol-3-yl]-acetamide | 0.72 min; 437.17; conditions 3 |
| 23 | 2-(4-Dimethylamino-phenyl)-N-[1-(4-fluoro-3-trifluoromethyl-benzyl)-1H-pyrazol-3-yl]-acetamide | 0.70 min; 421.17; conditions 3 |
| 24 | 2-(4-Dimethylamino-phenyl)-N-[1-(3,4,5-trifluoro-benzyl)-1H-pyrazol-3-yl]-acetamide | 0.66 min; 389.10; conditions 3 |
| 25 | 2-(4-Dimethylamino-phenyl)-N-[1-(4-fluoro-3,5-dimethyl-benzyl)-1H-pyrazol-3-yl]-acetamide | 0.70 min; 381.15; conditions 3 |
| 26 | N-[1-(4-Chloro-3-fluoro-benzyl)-1H-pyrazol-3-yl]-2-(4-dimethylamino-phenyl)-acetamide | 0.67 min; 387.04; conditions 3 |
| 27 | N-[1-(4-Chloro-3-trifluoromethyl-benzyl)-1H-pyrazol-3-yl]-2-(4-dimethylamino-phenyl)-acetamide | 0.72 min; 437.18; conditions 3 |
| 28 | N-[1-(3,5-Difluoro-4-methoxy-benzyl)-1H-pyrazol-3-yl]-2-(4-dimethylamino-phenyl)-acetamide | 0.65 min; 401.08; conditions 3 |
| 29 | 2-(4-Dimethylamino-phenyl)-N-[1-(4-methoxy-3-trifluoromethyl-benzyl)-1H-pyrazol-3-yl]-acetamide | 0.70 min; 433.16; conditions 3 |
| 30 | 2-(4-Dimethylamino-phenyl)-N-[1-(4-fluoro-3-methyl-benzyl)-1H-pyrazol-3-yl]-acetamide | 0.66 min; 367.1; conditions 3 |
| 31 | N-[1-(3-Chloro-4-fluoro-benzyl)-1H-pyrazol-3-yl]-2-(4-dimethylamino-phenyl)-acetamide | 0.67 min; 387.11; conditions 3 |
| 32 | 2-(4-Dimethylamino-phenyl)-N-[1-(3-fluoro-4-methyl-benzyl)-1H-pyrazol-3-yl]-acetamide | 0.66 min; 367.13; conditions 3 |
| 33 | N-[1-(5-Cyano-pyridin-2-ylmethyl)-1H-pyrazol-3-yl]-2-(4-dimethylamino-phenyl)-acetamide | 0.53 min; 361.07; conditions 3 |
| 34 | N-[1-(4-Chloro-3-trifluoromethoxy-benzyl)-1H-pyrazol-3-yl]-2-(4-dimethylamino-phenyl)-acetamide | 0.74 min; 453.17; conditions 3 |
| 35 | 2-(6-Dimethylamino-pyridin-3-yl)-N-[1-(4-ethyl-benzyl)-1H-pyrazol-3-yl]-acetamide | 0.68 min; 364.18; conditions 3 |
| 36 | N-[1-(4-Difluoromethoxy-benzyl)-1H-pyrazol-3-yl]-2-(6-dimethylamino-pyridin-3-yl)-acetamide | 0.66 min; 401.95; conditions 3 |
| 37 | 2-(6-Dimethylamino-pyridin-3-yl)-N-[1-(4-trifluoromethoxy-benzyl)-1H-pyrazol-3-yl]-acetamide | 0.70 min; 420.16; conditions 3 |
| 38 | 2-(6-Dimethylamino-pyridin-3-yl)-N-[1-(3-fluoro-4-methyl-benzyl)-1H-pyrazol-3-yl]-acetamide | 0.66 min; 368.13; conditions 3 |
| 39 | 2-(6-Dimethylamino-pyridin-3-yl)-N-[1-(4-fluoro-3-methyl-benzyl)-1H-pyrazol-3-yl]-acetamide | 0.65 min; 368.13; conditions 3 |
| 40 | N-[1-(3-Chloro-4-fluoro-benzyl)-1H-pyrazol-3-yl]-2-(6-dimethylamino-pyridin-3-yl)-acetamide | 0.66 min; 388.08; conditions 3 |
| 41 | 2-(6-Dimethylamino-pyridin-3-yl)-N-[1-(3,4,5-trifluoro-benzyl)-1H-pyrazol-3-yl]-acetamide | 0.65 min; 390.09; conditions 3 |
| 42 | N-[1-(4-Chloro-3-fluoro-benzyl)-1H-pyrazol-3-yl]-2-(6-dimethylamino-pyridin-3-yl)-acetamide | 0.66 min; 388.06; conditions 3 |
| 43 | N-[1-(3,5-Difluoro-4-methoxy-benzyl)-1H-pyrazol-3-yl]-2-(6-dimethylamino-pyridin-3-yl)-acetamide | 0.65 min; 401.91; conditions 3 |
| 44 | 2-(4-Dimethylamino-phenyl)-N-[1-(5-methoxy-pyridin-2-ylmethyl)-1H-pyrazol-3-yl]-acetamide | 0.51 min; 366.12; conditions 3 |
| 45 | N-[1-(4-Methoxy-benzyl)-1H-pyrazol-3-yl]-2-[4-(2,2,2-trifluoro-ethoxy)-phenyl]-acetamide | 0.90 min; 420.16; conditions 3 |
| 46 | N-[1-(4-Fluoro-benzyl)-1H-pyrazol-3-yl]-2-[4-(2,2,2-trifluoro-ethoxy)-phenyl]-acetamide | 0.90 min; 408.10; conditions 3 |
| 47 | N-[1-(4-Cyano-benzyl)-1H-pyrazol-3-yl]-2-[4-(2,2,2-trifluoro-ethoxy)-phenyl]-acetamide | 0.88 min; 415.15; conditions 3 |

2-(6-Bromopyridin-3-yl)acetic acid 2-(6-Bromopyridin-3-yl)acetonitrile (370 mg, 1.88 mmol) is diluted in conc. aq. HCl (2.8 mL), and the mixture was stirred at 100° C. for 90 min. The mixture is allowed to cool to rt and was thoroughly evaporated under reduced pressure. Water is added. The mixture is filtered to isolate the crude title product. LC-MS: $t_R$=0.54 min, MH+=214.96 (conditions 3).

2-(6-Bromopyridin-3-yl)-N-(1-(4-fluorobenzyl)-1H-pyrazol-3-yl)acetamide was prepared according to general procedure 3, starting from 2-(6-bromopyridin-3-yl)acetic acid (286 mg, 1.32 mmol) and 1-(4-fluorobenzyl)-1H-pyrazol-3-amine (253 mg, 1.32 mmol). LC-MS: $t_R$=0.80 min, MH+=388.96 (conditions 3).

Example 48, 2-[6-(Ethyl-methyl-amino)-pyridin-3-yl]-N-[1-(4-fluoro-benzyl)-1H-pyrazol-3-yl]-acetamide 2-(6-Bromopyridin-3-yl)-N-(1-(4-fluorobenzyl)-1H-pyrazol-3-yl)acetamide (50 mg, 0.13 mmol) is dissolved in toluene (3.0 mL), and the sol. is heated to 100° C. $Pd_2(dba)_3$ (2.4 mg, 0.0026 mmol), chloro(2-dicyclohexylphosphino-2', 6'-di-i-propoxy-1,1'-biphenyl) [2-(2-aminoethylphenyl)]palladium(II), methyl-t-butylether adduct (CAS 1028206-60-1, 37 mg, 0.051 mmol), NaO$^t$Bu (19 mg, 0.19 mmol) and a sol. of ethylmethylamine (9.1 mg, 0.15 mmol) in toluene (1.0 mL) are added. The mixture is stirred at 100° C. for 1.5 h, and is allowed to cool to rt. The solvents are removed under reduced pressure, and the residue is mixed with CH$_3$CN (1.0 mL), water (2 drops) and Et$_3$N (2 drops). The mixture is filtered, and the filtrate is purified by HPLC to yield Example 48. LC-MS: $t_R$=0.64 min, MH$^+$=368.01 (conditions 3).

Ethyl 2-(4-(3,3-difluoroazetidin-1-yl)phenyl)acetate

Xantphos (24 mg, 0.041 mmol), Pd(OAc)$_2$ (7 mg, 0.03 mmol) and Cs$_2$CO$_3$ (670 mg, 2.06 mmol) are added to a sol. of ethyl 4-bromophenylacetate (250 mg, 1.03 mmol) in toluene (8 mL). The mixture is heated rapidly to 100° C., and 3,3-difluoroazetidine hydrochloride (266 mg, 2.06 mmol) is added. The mixture is stirred for 18 h at 100° C., and is allowed to cool to rt. The mixture is filtered through Celite®, and the solvents are removed under reduced pressure. Purification of the crude by automated FC (Büchi, EtOAc/heptane 1:99→3:97→5:95→8:92→15:85, 20 g silicagel, flow 20 mL/min) yields the title compound. LC-MS: $t_R$=0.89 min, MH$^+$=297.22 (conditions 3).

2-(4-(3,3-Difluoroazetidin-1-yl)phenyl)acetic acid

A sol. of ethyl 2-(4-(3,3-difluoroazetidin-1-yl)phenyl)acetate (115 mg, 0.451 mmol) in EtOH (2 mL) and aq. 2.5M NaOH (2 mL) is stirred at rt for 18 h. The solvents are partially removed under reduced pressure, and the residue is suspended in CH$_2$Cl$_2$ (50 mL). This mixture is washed with aq. 1M HCl, and the phases are separated. The org. layer is dried over MgSO$_4$, filtered, and the solvents are removed under reduced pressure to yield the crude, title compound. LC-MS: $t_R$=0.72 min, MH$^+$=269.16 (conditions 3).

Ethyl 2-(4-(azetidin-1-yl)phenyl)acetate

Xantphos (48 mg, 0.082 mmol), Pd(OAc)$_2$ (14 mg, 0.062 mmol) and Cs$_2$CO$_3$ (1.34 g, 4.11 mmol) are added to a sol. of ethyl 4-bromophenylacetate (500 mg, 2.06 mmol) in toluene (8 mL). The mixture is heated rapidly to 100° C., and azetidine hydrochloride (0.28 mL, 4.11 mmol) is added. The mixture is stirred for 4 h at 100° C., and is allowed to cool to rt. The mixture is filtered through Celite®, and the solvents are removed under reduced pressure. Purification of the crude by automated FC (Büchi, EtOAc/heptane 1:99→3:97→5:95→8:92→15:85, 20 g silicagel, flow 20 mL/min) yields the title compound. LC-MS: $t_R$=0.60 min, MH$^+$=220.26 (conditions 3).

2-(4-(Azetidin-1-yl)phenyl)acetic acid

A sol. of ethyl 2-(4-(azetidin-1-yl)phenyl)acetate (150 mg, 0.684 mmol) in EtOH (1 mL) and aq. 2.5M NaOH (1 mL) is stirred at rt for 18 h. The solvents are partially removed under reduced pressure, and the residue is suspended in CH$_2$Cl$_2$ (50 mL). This mixture is washed with aq. 1M HCl, and the phases are separated. The org. layer is dried over MgSO$_4$, filtered, and the solvents are removed under reduced pressure to yield the crude, title compound. LC-MS: $t_R$=0.40 min (conditions 3).

2-Fluoro-4-((3-nitro

H-pyrazol-1-yl)methyl)benzonitrile. Prepared according to general procedure 4 with K$_2$CO$_3$ (3.23 g, 23.4 mmol), 4-cyano-3-fluorobenzylbromide (1000 mg, 4.67 mmol), 5-nitro-1H-pyrazole (528 mg, 4.67 mmol), and Bu$_4$NBr (301 mg, 0.934 mmol) in acetone (40 mL). The reaction is complete after 20 h at rt. Purification of the crude by automated FC (Büchi, EtOAc/heptane 1:99→5:95→10:90→15:85→25:75→35:65, 20 g silicagel, flow 20 mL/min) yields the title compound. LC-MS: $t_R$=0.79 min (conditions 3).

4-((3-Amino-1H-pyrazol-1-yl)methyl)-2-fluorobenzonitrile

Prepared according to general procedure 5 with Fe (2.00 g, 36.1 mmol) and 2-fluoro-4-((3-nitro-1H-pyrazol-1-yl)methyl)benzonitrile (890 mg, 3.61 mmol) in EtOH (40 mL), and aq. sat. NH$_4$Cl (8 mL). The reaction is complete after 1 h at 75° C. and yields the crude title compound. LC-MS: $t_R$=0.55 min, MH$^+$=217.24 (conditions 3).

2-(6-(2,2,2-Trifluoroethoxy)pyridin-3-yl)acetic acid

2-Chloropyridine-5-acetic acid (343 mg, 2.00 mmol) is added to a solution of NaH (65% in oil, 400 mg, about 10 mmol) in trifluoroethanol (4 mL). The mixture is stirred in a microwave oven at 160° C. for 7 h, and is allowed to cool to rt. The mixture is diluted with water and the pH is adjusted to 3. Removing the solvents under reduced pressure and drying the residue under high vacuum yields the crude title product. LC-MS: $t_R$=0.62 min, MH$^+$=236.18 (conditions 2).

(S)-Ethyl 2-(4-(3-fluoropyrrolidin-1-yl)phenyl)acetate

Xantphos (29 mg, 0.049 mmol), Pd(OAc)$_2$ (9 mg, 0.04 mmol) and Cs$_2$CO$_3$ (1.20 g, 3.7 mmol) are added to a sol. of ethyl 4-bromophenylacetate (300 mg, 1.23 mmol) in toluene (10 mL) at rt. The mixture is rapidly heated to 100° C., and (S)-3-fluoropyrrolidine (310 mg, 2.47 mmol) is added. The mixture is stirred for 3 h at 100° C., and is allowed to cool to rt. The mixture is filtered through Celite®, and the solvents are removed under reduced pressure. Purification of the residue by automated FC (Büchi, EtOAc/heptane 1:99→3:97→5:95→8:92→15:85, 20 g silicagel, flow 16 mL/min) yields the title compound. LC-MS: $t_R$=0.88 min, MH$^+$=252.14 (conditions 3).

(S)-2-(4-(3-Fluoropyrrolidin-1-yl)phenyl)acetic acid

A mixture of (S)-ethyl 2-(4-(3-fluoropyrrolidin-1-yl)phenyl)acetate (76 mg, 0.302 mmol) in EtOH (2.0 mL) and aq. 1M NaOH (1.0 mL) is stirred at rt for 2 h. The solvents are removed under reduced pressure, and the residue is diluted with CH$_2$Cl$_2$. The mixture is cooled to 0° C., and aq. 1M HCl is added to pH3. The phases are separated in a Separator® (Biotage) to yield the crude title product. LC-MS: $t_R$=0.70 min, MH$^+$=224.22 (conditions 3).

Ethyl 2-(4-(3-fluoroazetidin-1-yl)phenyl)acetate

Xantphos (29 mg, 0.049 mmol), Pd(OAc)$_2$ (9 mg, 0.04 mmol) and Cs$_2$CO$_3$ (1.20 g, 3.70 mmol) are added to a sol. of ethyl 4-bromophenylacetate (300 mg, 1.23 mmol) in toluene (10 mL) at rt. The mixture is rapidly heated to 100° C., and 3-fluoroazetidine hydrochloride (275 mg, 2.47 mmol) is added. The mixture is stirred for 24 h at 100° C., and is allowed to cool to rt. The mixture is filtered through Celite, and the solvents are removed under reduced pressure. Purification of the residue by automated FC (Büchi, EtOAc/heptane 1:99→3:97→5:95→8:92→15:85, 20 g silicagel, flow 16 mL/min) yields the title compound. LC-MS: $t_R$=0.84 min, MH$^+$=238.14 (conditions 3).

2-(4-(3-Fluoroazetidin-1-yl)phenyl)acetic acid

A mixture of ethyl 2-(4-(3-fluoroazetidin-1-yl)phenyl) acetate (130 mg, 0.548 mmol) in EtOH (2.0 mL) and aq. 1M NaOH (1.0 mL) is stirred at rt for 2 h. The solvents are removed under reduced pressure, and the residue is diluted with CH$_2$Cl$_2$. The mixture is cooled to 0° C., and aq. 1M HCl is added to pH3. The phases are separated in a Separator® (Biotage) to yield the crude title product. LC-MS: $t_R$=0.64 min, MH$^+$=210.32 (conditions 3).

Methyl 2-(4-(vinyloxy)phenyl)acetate

A mixture of methyl-4-hydroxyphenylacetate (1.66 g, 10 mmol), vinyl acetate (1.84 mL, 20.0 mmol), chloro(1,5-cyclooctadiene)iridium(I) dimer (133 mg, 0.20 mmol), and Na$_2$CO$_3$ (636 mg, 6.00 mmol) in toluene (10 mL) is stirred at 100° C. for 2.5 h. Subsequently, water is added, and the mixture is extracted with EtOAc. The combined org. layers are washed with brine, dried over MgSO$_4$, and concentrated under reduced pressure. Purification by automated FC (Biotage, 50 g silicagel, EtOAc/heptane 1:9-4:6, 50 mL/min) yields the title compound. LC-MS: $t_R$=0.83 min (conditions 3).

Methyl 2-(4-cyclopropoxyphenyl)acetate

At −5° C. Et$_2$Zn (1.0 M in hexanes, 4.8 mL, 4.8 mmol) is added to a sol. of methyl 2-(4-(vinyloxy)phenyl)acetate (384 mg, 2.00 mmol) and CH$_2$ClI (0.525 mL, 7.20 mmol) in CH$_2$Cl$_2$ (15.2 mL). The mixture is stirred between −5° C. and 0° C. for 4 h, and is quenched with aq. sat. NH$_4$Cl. The mixture is extracted with EtOAc. The combined org. layers are washed with brine, dried over MgSO$_4$, filtered, and the solvents are removed under reduced pressure. Purification of the crude by automated FC (Biotage, 25 g silicagel, EtOAc/heptane 1:19→4:6, 25 mL/min) yields the title compound. LC-MS: $t_R$=0.84 min (conditions 3).

2-(4-Cyclopropoxyphenyl)acetic acid

A sol. of methyl 2-(4-cyclopropoxyphenyl)acetate (364 mg, 1.76 mmol) and LiOH H$_2$O (111 mg, 2.65 mmol) in THF/MeOH/H$_2$O (3:1:1) (10 ml) is stirred at 0° C. for 3 h. The mixture is acidified with aq. 1 M HCl to pH 3 and extracted with EtOAc. The combined org. layers are washed with brine, dried over MgSO$_4$, and filtered. Removing the solvents under reduced pressure yields the crude title compound. LC-MS: $t_R$=0.71 min (conditions 3).

Ethyl 2-(4-(3,3-difluoropyrrolidin-1-yl)phenyl)acetate

Xantphos (29 mg, 0.049 mmol), Pd(OAc)$_2$ (9 mg, 0.04 mmol) and Cs$_2$CO$_3$ (1.20 g, 3.70 mmol) are added to a sol. of ethyl 4-bromophenylacetate (300 mg, 1.23 mmol) in toluene (10 mL) at rt. The mixture is rapidly heated to 100° C., and 3,3-difluoropyrrolidine (354 mg, 2.47 mmol) is added. The mixture is stirred for 48 h at 100° C., and is allowed to cool to rt. The mixture is filtered through Celite®, and the solvents are removed under reduced pressure. Purification of the residue by automated FC (Büchi, EtOAc/heptane 1:99→3:97→5:95→8:92→15:85, 20 g silicagel, flow 16 mL/min) yields the title compound. LC-MS: $t_R$=0.92 min, MH$^+$=270.20 (conditions 3).

2-(4-(3,3-Difluoropyrrolidin-1-yl)phenyl)acetic acid

A mixture of ethyl 2-(4-(3,3-difluoropyrrolidin-1-yl)phenyl)acetate (68 mg, 0.25 mmol) in EtOH (2.0 mL) and aq. 1M NaOH (1.0 mL) is stirred at rt for 1 h. The solvents are removed under reduced pressure, and the residue is diluted with CH$_2$Cl$_2$. The mixture is cooled to 0° C., and aq. 1M HCl is added to pH3. The phases are separated in a Separator® (Biotage) to yield the crude title product. LC-MS: $t_R$=0.77 min, MH$^+$=241.92 (conditions 3).

(R)-Ethyl 2-(4-(3-fluoropyrrolidin-1-yl)phenyl)acetate

Xantphos (29 mg, 0.049 mmol), Pd(OAc)$_2$ (9 mg, 0.04 mmol) and Cs$_2$CO$_3$ (1.20 g, 3.70 mmol) are added to a sol. of ethyl 4-bromophenylacetate (300 mg, 1.23 mmol) in toluene (10 mL) at rt. The mixture is rapidly heated to 100° C., and (R)-3-fluoropyrrolidine (310 mg, 2.47 mmol) is added. The mixture is stirred for 18 h at 100° C., and is allowed to cool to rt. The mixture is filtered through Celite®, and the solvents are removed under reduced pressure. Purification of the residue by automated FC (Büchi, EtOAc/heptane 1:99→3:97→5:95→8:92→15:85, 20 g silicagel, flow 16 mL/min) yields the title compound. LC-MS: $t_R$=0.88 min, MH$^+$=252.18 (conditions 3).

(R)-2-(4-(3-Fluoropyrrolidin-1-yl)phenyl)acetic acid

A mixture of (R)-ethyl 2-(4-(3-fluoropyrrolidin-1-yl)phenyl)acetate (250 mg, 1.00 mmol) in EtOH (2.0 mL) and aq. 1M NaOH (1.0 mL) is stirred at rt for 2 h. The solvents are removed under reduced pressure, and the residue is diluted with CH$_2$Cl$_2$. The mixture is cooled to 0° C., and aq. 1M HCl is added to pH3. The phases are separated in a Separator® (Biotage) to yield the crude title product. LC-MS: $t_R$=0.70 min, MH$^+$=224.25 (conditions 3).

The following examples were prepared according to general procedure 3, from the appropriate carboxylic acids and aminopyrazoles:

| Example No | Name | LC-MS ($t_R$; MH$^+$; conditions) |
| --- | --- | --- |
| 49 | 2-[4-(3,3-Difluoro-azetidin-1-yl)-phenyl]-N-[1-(4-fluoro-benzyl)-1H-pyrazol-3-yl]-acetamide | 0.88 min; 401.05; conditions 3 |
| 50 | N-[1-(4-Cyano-benzyl)-1H-pyrazol-3-yl]-2-[4-(3,3-difluoro-azetidin-1-yl)-phenyl]-acetamide | 0.86 min; 408.16; conditions 3 |
| 51 | 2-[4-(3,3-Difluoro-azetidin-1-yl)-phenyl]-N-[1-(4-methoxy-benzyl)-1H-pyrazol-3-yl]-acetamide | 0.88 min; 413.18; conditions 3 |
| 52 | 2-[4-(3,3-Difluoro-azetidin-1-yl)-phenyl]-N-[1-(3,4-difluoro-benzyl)-1H-pyrazol-3-yl]-acetamide | 0.90 min; 419.17; conditions 3 |

-continued

| Example No | Name | LC-MS ($t_R$; MH+; conditions) |
|---|---|---|
| 53 | 2-(4-Azetidin-1-yl-phenyl)-N-[1-(4-fluoro-benzyl)-1H-pyrazol-3-yl]-acetamide | 0.67 min; 365.15; conditions 3 |
| 54 | 2-(4-Azetidin-1-yl-phenyl)-N-[1-(4-cyano-benzyl)-1H-pyrazol-3-yl]-acetamide | 0.64 min; 372.12; conditions 3 |
| 55 | 2-(4-Azetidin-1-yl-phenyl)-N-[1-(4-methoxy-benzyl)-1H-pyrazol-3-yl]-acetamide | 0.67 min; 377.05; conditions 3 |
| 56 | N-[1-(3,4-Difluoro-benzyl)-1H-pyrazol-3-yl]-2-(6-dimethylamino-pyridin-3-yl)-acetamide | 0.63 min; 372.09; conditions 3 |
| 57 | N-[1-(4-Cyano-3-fluoro-benzyl)-1H-pyrazol-3-yl]-2-(4-dimethylamino-phenyl)-acetamide | 0.62 min; 378.11; conditions 3 |
| 58 | N-[1-(4-Cyano-3-fluoro-benzyl)-1H-pyrazol-3-yl]-2-(6-dimethylamino-pyridin-3-yl)-acetamide | 0.61 min; 379.07; conditions 3 |
| 59 | N-[1-(3,4-Difluoro-benzyl)-1H-pyrazol-3-yl]-2-[6-(2,2,2-trifluoro-ethoxy)-pyridin-3-yl]-acetamide | 0.81 min; 427.09; conditions 2 |
| 60 | 2-(4-Azetidin-1-yl-phenyl)-N-[1-(3,4-difluoro-benzyl)-1H-pyrazol-3-yl]-acetamide | 0.69 min; 383.07; conditions 3 |
| 61 | N-[1-(3,4-Difluoro-benzyl)-1H-pyrazol-3-yl]-2-[4-((S)-3-fluoro-pyrrolidin-1-yl)-phenyl]-acetamide | 0.89 min; 415.16; conditions 3 |
| 62 | N-[1-(3,4-Difluoro-benzyl)-1H-pyrazol-3-yl]-2-[4-(3-fluoro-azetidin-1-yl)-phenyl]-acetamide | 0.86 min; 401.03; conditions 3 |
| 63 | 2-(4-Cyclopropoxy-phenyl)-N-[1-(4-fluoro-benzyl)-1H-pyrazol-3-yl]-acetamide | 0.79 min; 366.31; conditions 2 |
| 64 | N-[1-(4-Cyano-benzyl)-1H-pyrazol-3-yl]-2-(4-cyclopropoxy-phenyl)-acetamide | 0.75 min; 373.34; conditions 2 |
| 65 | 2-(4-Cyclopropoxy-phenyl)-N-[1-(4-methoxy-benzyl)-1H-pyrazol-3-yl]-acetamide | 0.78 min; 378.35; conditions 2 |
| 66 | 2-(4-Cyclopropoxy-phenyl)-N-[1-(3,4-difluoro-benzyl)-1H-pyrazol-3-yl]-acetamide | 0.81 min; 384.32; conditions 2 |
| 67 | N-[1-(3,4-Difluoro-benzyl)-1H-pyrazol-3-yl]-2-[4-(3,3-difluoro-pyrrolidin-1-yl)-phenyl]-acetamide | 0.92 min; 433.06; conditions 3 |
| 68 | N-[1-(3,4-Difluoro-benzyl)-1H-pyrazol-3-yl]-2-[4-((R)-3-fluoro-pyrrolidin-1-yl)-phenyl]-acetamide | 0.89 min; 415.16; conditions 3 |
| 69 | N-[1-(4-Cyano-benzyl)-1H-pyrazol-3-yl]-2-[4-((R)-3-fluoro-pyrrolidin-1-yl)-phenyl]-acetamide | 0.85 min; 404.16; conditions 3 |
| 70 | N-[1-(4-Fluoro-benzyl)-1H-pyrazol-3-yl]-2-[4-((R)-3-fluoro-pyrrolidin-1-yl)-phenyl]-acetamide | 0.88 min; 397.12; conditions 3 |
| 71 | N-[1-(5-Cyano-pyridin-2-ylmethyl)-1H-pyrazol-3-yl]-2-(4-isopropyl-phenyl)-acetamide | 0.83 min; 360.04; conditions 2 |
| 72 | N-[1-(4-Cyano-benzyl)-1H-pyrazol-3-yl]-2-[4-(3-fluoro-azetidin-1-yl)-phenyl]-acetamide | 0.82 min; 389.86; conditions 3 |
| 73 | 2-[4-(3-Fluoro-azetidin-1-yl)-phenyl]-N-[1-(4-fluoro-benzyl)-1H-pyrazol-3-yl]-acetamide | 0.85 min; 383.13; conditions 3 |
| 74 | N-[1-(4-Cyano-benzyl)-1H-pyrazol-3-yl]-2-[4-((S)-3-fluoro-pyrrolidin-1-yl)-phenyl]-acetamide | 0.86 min; 403.98; conditions 3 |
| 75 | N-[1-(4-Fluoro-benzyl)-1H-pyrazol-3-yl]-2-[4-((S)-3-fluoro-pyrrolidin-1-yl)-phenyl]-acetamide | 0.88 min; 397.26; conditions 3 |
| 76 | N-[1-(4-Cyano-benzyl)-1H-pyrazol-3-yl]-2-[4-(3,3-difluoro-pyrrolidin-1-yl)-phenyl]-acetamide | 0.89 min; 421.99; conditions 3 |
| 77 | 2-[4-(3,3-Difluoro-pyrrolidin-1-yl)-phenyl]-N-[1-(4-fluoro-benzyl)-1H-pyrazol-3-yl]-acetamide | 0.91 min; 414.84; conditions 3 |

2-(4-Cyclopropylphenyl)acetyl chloride

Prepared according to general procedure 1 from 2-(4-cyclopropylphenyl)acetic acid (Reger, T. S.; Yang, Z.-Q.; Schlegel, K.-A. S.; Shu, Y.; Mattern, C.; Cube, R.; Rittle, K. E.; McGaughey, G. B.; Hartman, G. D.; T., Cuyue; et al., *Bioorg. Med. Chem. Lett.*, 2011, 21, 1692; 260 mg, 1.48 mmol) and oxalyl chloride (0.192 mL, 2.21 mmol) to yield to the crude, title compound.

Example 78: N-[1-(5-Cyano-pyridin-2-ylmethyl)-1H-pyrazol-3-yl]-2-(4-cyclopropyl-phenyl)-acetamide Prepared according to general procedure 2 from 2-(4-cyclopropylphenyl)acetyl chloride (41 mg, 0.21 mmol) and 6-((3-amino-1H-pyrazol-1-yl)methyl)nicotinonitrile (35 mg, 0.18 mmol). The reaction is complete after 17 h. Purification by HPLC yields example 78. LC-MS: $t_R$=0.79 min, MH+=358.07 (conditions 3).

2-(6-Chloropyridin-3-yl)-N-(1-(3,4-difluorobenzyl)-1H-pyrazol-3-yl)acetamide

Prepared according to general procedure 3 from 2-(6-chloropyridin-3-yl)acetic acid (257 mg, 1.50 mmol), 1-(3,4-difluorobenzyl)-1H-pyrazol-3-amine (314 mg, 1.50 mmol), HATU (856 mg, 2.25 mmol), and DIPEA (1.28 mL, 7.50 mmol) in DMF (5 mL). The reaction is complete after 1 h. The mixture is partitioned between EtOAc and aq. sat. NaHCO$_3$. The combined org. layers are washed with brine, dried over MgSO$_4$, filtered and evaporated. The crude is purified by automated FC (Biotage, CH$_2$Cl$_2$/0.5% Et$_3$N in MeOH, 50 g silicagel). Another purification by HPLC yields the title compound. LC-MS: $t_R$=0.70 min, MH+=363.07 (conditions 4).

Example 79: 2-(6-Cyclopropyl-pyridin-3-yl)-N-[1-(3, 4-difluoro-benzyl)-1H-pyrazol-3-yl]-acetamide A mixture of 2-(6-chloropyridin-3-yl)-N-(1-(3,4-difluorobenzyl)-1H-pyrazol-3-yl)acetamide (100 mg, 0.273 mmol), cyclopropylboronic acid (117 mg, 1.36 mmol), PEPPSI-IPr (27.9 mg, 0.0409 mmol) and K$_3$PO$_4$ (290 mg, 1.36 mmol) is prepared in toluene (3.4 ml). The mixture is purged and filled with Ar 3×. Then the mixture is stirred at 100° C. overnight. The mixture is filtered and evaporated. The residue is directly purified by HPLC to yield example 79. LC-MS: t$_R$=0.54 min, MH$^+$=369.07 (conditions 4).

N-(1-(4-fluorobenzyl)-1H-pyrazol-3-yl)-2-(4-(4,4,5,5-tetramethyl-1,3,2-dioxaborolan-2-yl)phenyl)acetamide 1-(4-Fluoro-benzyl)-1H-pyrazol-3-ylamine (300 mg, 1.57 mmol) is dissolved in DMF (3.00 mL). 2-(4-(4,4,5,5-tetramethyl-1,3,2-dioxaborolan-2-yl)phenyl)acetic acid (411 mg, 1.57 mmol), EDC HCl (361 mg, 1.88 mmol), HOBt (256 mg, 1.88 mmol) and DIPEA (1.05 ml, 6.12 mmol) are successively added. The mixture is stirred for 3 h at rt, and the solvents are removed under reduced pressure. Purification of the crude by automated FC (Combiflash RF200, column 20 g silicagel, flow rate 35 mL/min, EtOAc/heptane 0:100→5:95→10:90) yields the title product. LC-MS: t$_R$=0.94 min, MH$^+$=436.18 (conditions 2).

Example 80: N-[1-(4-Fluoro-benzyl)-1H-pyrazol-3-yl]-2-[4-(3-methyl-pyrazin-2-yl)-phenyl]-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 2-Chloro-3-methylpyrazine (31.9 mg, 0.248 mmol), tricyclohexylphosphine (1.45 mg, 0.00517 mmol), Pd$_2$(dba)$_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over MgSO$_4$, filtered, the solvents are removed under reduced pressure. Purification of the crude by HPLC yields example 80. LC-MS: t$_R$=0.74 min, MH$^+$=401.97 (conditions 2).

Example 81: N-[1-(4-Fluoro-benzyl)-1H-pyrazol-3-yl]-2-(4-pyrazin-2-yl-phenyl)-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 2-Chloropyrazine (23.7 mg, 0.248 mmol), tricyclohexylphosphine (1.45 mg, 0.00517 mmol), Pd$_2$(dba)$_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over MgSO$_4$, filtered, the solvents are removed under reduced pressure. Purification of the crude by HPLC yields example 81. LC-MS: t$_R$=0.76 min, MH$^+$=387.87 (conditions 2).

Example 82: N-[1-(4-Fluoro-benzyl)-1H-pyrazol-3-yl]-2-(4-pyridin-2-yl-phenyl)-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 2-Chloropyridine (23.5 mg, 0.248 mmol), tricyclohexylphosphine (1.45 mg, 0.00517 mmol), Pd$_2$(dba)$_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over MgSO$_4$, filtered, the solvents are removed under reduced pressure. Purification of the crude by HPLC yields example 82. LC-MS: t$_R$=0.60 min, MH$^+$=386.86 (conditions 2).

Example 83: N-[1-(4-Fluoro-benzyl)-1H-pyrazol-3-yl]-2-(4-pyridin-3-yl-phenyl)-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 3-Chloropyridine (23.5 mg, 0.248 mmol), tricyclohexylphosphine (1.45 mg, 0.00517 mmol), Pd$_2$(dba)$_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over MgSO$_4$, filtered, the solvents are removed under reduced pressure. Purification of the crude by HPLC yields example 83. LC-MS: t$_R$=0.58 min, MH$^+$=386.92 (conditions 2).

Example 84: N-[1-(4-Fluoro-benzyl)-1H-pyrazol-3-yl]-2-(4-pyridin-4-yl-phenyl)-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 4-Chloropyridine (23.5 mg, 0.248 mmol), tricyclohexylphosphine (1.45 mg, 0.00517 mmol), Pd$_2$(dba)$_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over MgSO$_4$, filtered, the solvents are removed under reduced pressure. Purification of the crude by HPLC yields example 84. LC-MS: t$_R$=0.57 min, MH$^+$=386.92 (conditions 2).

Example 85: N-[1-(4-Fluoro-benzyl)-1H-pyrazol-3-yl]-2-(4-pyrimidin-2-yl-phenyl)-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 2-Chloropyrimidine (23.7 mg, 0.248 mmol), tricyclohexylphosphine (1.45 mg, 0.00517 mmol), Pd$_2$(dba)$_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over MgSO$_4$, filtered, the solvents are removed under reduced pressure. Purification of the crude by HPLC yields example 85. LC-MS: t$_R$=0.71 min, MH$^+$=387.87 (conditions 2).

Example 86: N-[1-(4-Fluoro-benzyl)-1H-pyrazol-3-yl]-2-(4-pyrimidin-5-yl-phenyl)-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 5-Bromopyrimidine (32.9 mg, 0.248 mmol), tricyclohexylphosphine (1.45 mg, 0.00517 mmol), $Pd_2(dba)_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over $MgSO_4$, filtered, the solvents are removed under reduced pressure. Purification of the crude by HPLC yields example 86. LC-MS: $t_R$=0.71 min, $MH^+$=387.94 (conditions 2).

Example 87: N-[1-(4-Fluoro-benzyl)-1H-pyrazol-3-yl]-2-(4-pyrimidin-4-yl-phenyl)-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 4-Chloropyrimidine (23.7 mg, 0.248 mmol), tricyclohexylphosphine (1.45 mg, 0.00517 mmol), $Pd_2(dba)_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over $MgSO_4$, filtered, the solvents are removed under reduced pressure. Purification of the crude by HPLC yields example 87. LC-MS: $t_R$=0.72 min, $MH^+$=387.96 (conditions 2).

Example 88: N-[1-(3, 4-Difluoro-benzyl)-1H-pyrazol-3-yl]-2-(6-isopropyl-pyridin-3-yl)-acetamide A mixture of 2-(6-chloropyridin-3-yl)-N-(1-(3,4-difluorobenzyl)-1H-pyrazol-3-yl)acetamide (95.6 mg, 0.261 mmol), iron(III) acetylacetonate (5 mg, 0.0142 mmol), 1-methyl-2-pyrrolidone (0.174 mL) in toluene (0.9 mL) and THF (0.9 mL) is stirred for 5 min under Ar. $^iPrMgCl$ (2M in THF, 0.52 ml, 1.04 mmol) is added dropwise at rt. The mixture is stirred for further 1 h. $^iPrMgCl$ (2M in THF, 0.26 ml, 0.52 mmol) is added again, and the mixture is stirred for 40 min. $^iPrMgCl$ (2M in THF, 0.26 ml, 0.52 mmol) is added again, and the mixture is stirred overnight. The mixture is quenched with aq. 1M HCl, and the pH is adjusted to 8. The aq. layer is extracted with EtOAc (3×). The combined org. layers are washed with brine, dried over $MgSO_4$, filtered and evaporated under reduced pressure. Purification of the crude by HPLC yields the title compound. LC-MS: $t_R$=0.56 min, $MH^+$=371.13; conditions 4.

The following examples were prepared according to general procedure 3, from the appropriate carboxylic acids and aminopyrazoles:

| Example No | Name | LC-MS ($t_R$; $MH^+$; conditions) |
| --- | --- | --- |
| 89 | N-[1-(5-Cyano-pyridin-2-ylmethyl)-1H-pyrazol-3-yl]-2-[4-((R)-3-fluoro-pyrrolidin-1-yl)-phenyl]-acetamide | 0.80 min; 404.92; conditions 3 |
| 90 | N-[1-(5-Cyano-pyridin-2-ylmethyl)-1H-pyrazol-3-yl]-2-[4-((S)-3-fluoro-pyrrolidin-1-yl)-phenyl]-acetamide | 0.80 min; 404.92; conditions 3 |
| 91 | N-[1-(5-Cyano-pyridin-2-ylmethyl)-1H-pyrazol-3-yl]-2-[4-(3,3-difluoro-pyrrolidin-1-yl)-phenyl]-acetamide | 0.84 min; 422.91; conditions 3 |

Example 92: N-[1-(4-Fluoro-benzyl)-1H-pyrazol-3-yl]-2-[4-(5-methyl-pyrimidin-4-yl)-phenyl]-acetamide N-(1-(4-Fluorobenzyl)-1H-pyrazol-3-yl)-2-(4-(4,4,5,5-tetramethyl-1,3,2-dioxaborolan-2-yl)phenyl)acetamide (90 mg, 0.207 mmol) is dissolved in dioxane (0.55 mL). 4-Chloro-5-methylpyrimidine (31.7 mg, 0.248 mmol), tricyclohexylphosphine (1.45 mg, 0.00517 mmol), $Pd_2(dba)_3$ (1.89 mg, 0.00207 mmol) and aq. 1.7M potassium phosphate (0.28 ml, 0.48 mmol) are added. The resulting mixture is degassed for 10 min, and is heated in a microwave oven at 150° C. for 30 min. The mixture is allowed to cool to rt. EtOAc is added, and the mixture is washed with brine. The org. layer is dried over $MgSO_4$, filtered, the solvents are removed under reduced pressure. Purification of the crude by HPLC yields example 92. LC-MS: $t_R$=0.79 min, $MH^+$=401.98 (conditions 2).

Methyl 5-((tert-butyldimethylsilyl)oxy)picolinate

At 0° C., tert-butyldimethylsilyl chloride (2.71 g, 18.0 mmol) is added to a sol. of methyl 5-hydroxypyridine-2-carboxylate (2.30 g, 15.0 mmol) and imidazole (1.53 g, 22.5 mmol) in DMF (30 mL). The mixture is allowed to warm to rt, and is stirred overnight. More imidazole (11.3 mmol) and TBDMS-Cl (9.00 mmol) are added, and the mixture is stirred at rt for 2 h. The mixture is quenched with aq. sat. $NaHCO_3$, and is extracted with EtOAc. The comb. org. layers are washed with brine, dried over $MgSO_4$, filtered, and the solvents are removed under reduced pressure. Purification of the crude by FC (EtOAc/heptane 10:90→60:40) yields the title compound. LC-MS: $t_R$=0.96 min, $MH^+$=268.34 (conditions 3).

(5-((tert-Butyldimethylsilyl)oxy)pyridin-2-yl)methanol

At 0° C., DIBAL (20 wt % solution in toluene, 1.2 M, 28.6 mL, 34.1 mmol) is slowly added to a sol. of methyl 5-((tert-butyldimethylsilyl)oxy)picolinate (3.65 g, 13.6 mmol) in $CH_2Cl_2$ (68 mL). The mixture is stirred at 0° C. for 2 h. More DIBAL (11.4 mL) is added and the mixture is stirred at 0° C. for an additional hour. More DIBAL (5.7 mL) is added and the mixture is stirred at 0° C. for an additional hour. Water (2.24 mL), followed by aq. 15% NaOH (2.24 mL) and water (5.6 mL) are added, along some THF, and the mixture is stirred at rt for 30 min. $MgSO_4$ was added, the mixture is stirred for 20 min, filtrated, and the filtrate is concentrated under reduced pressure to yield the crude title product. LC-MS: $t_R$=0.68 min, $MH^+$=240.35 (conditions 3).

(5-((tert-Butyldimethylsilyl)oxy)pyridin-2-yl)methyl methanesulfonate

At 0° C., $Et_3N$ (0.835 mL, 6.00 mmol) and methansulfonyl chloride (0.341 mL, 4.40 mmol) are added to a sol. of (5-((tert-butyldimethylsilyl)oxy)pyridin-2-yl)methanol (958 mg, 4.00 mmol) in $CH_2Cl_2$ (20 mL). The mixture is stirred at 0° C. for 20 min. Aq. sat. $NaHCO_3$ is added, and the mixture is extracted with EtOAc. The comb. org. layers are washed with brine, dried over $MgSO_4$, filtered, and solvents are removed under reduced pressure to yield the crude title compound.

5-((tert-Butyldimethylsilyl)oxy)-2-((3-nitro-1H-pyrazol-1-yl)methyl)pyridine Prepared according to general procedure 4 with NaH (60% in oil, 76.5 mg, 3.19 mmol), (5-(((tert-butyldimethylsilyl)oxy)pyridin-2-yl)methyl methanesulfonate (1.06 g, 3.34 mmol), and 5-nitro-1H-pyrazole (343 mg, 3.03 mmol) in DMF (15 mL). The reaction is complete after 3 h at rt. Purification of the crude by FC (EtOAc/heptane 20:80→80:20) yields the title compound. LC-MS: $t_R$=0.97 min, MH$^+$=337.24 (conditions 3).

1-((5-((tert-Butyldimethylsilyl)oxy)pyridin-2-yl)methyl)-1H-pyrazol-3-amine

Prepared according to general procedure 5 with Zn (163 mg, 2.50 mmol) and 5-((tert-butyldimethylsilyl)oxy)-2-((3-nitro-1H-pyrazol-1-yl)methyl)pyridine (83.6 mg, 0.25 mmol) in acetone (2.5 mL) and aq. sat. NH$_4$Cl (0.5 mL). The reaction is complete after 20 min at rt and yields the crude title compound. LC-MS: $t_R$=0.75 min, MH$^+$=305.24 (conditions 3).

N-(1-((5-((tert-Butyldimethylsilyl)oxy)pyridin-2-yl)methyl)-1H-pyrazol-3-yl)-2-(4-isopropylphenyl)acetamide Prepared according to general procedure 3, starting from 2-(4-isopropylphenyl)acetic acid (234 mg, 1.31 mmol) and 1-((5-((tert-butyldimethylsilyl)oxy)pyridin-2-yl)methyl)-1H-pyrazol-3-amine (400 mg, 1.31 mmol). LC-MS: $t_R$=1.02 min, MH$^+$=465.25 (conditions 3).

N-(1-((5-Hydroxypyridin-2-yl)methyl)-1H-pyrazol-3-yl)-2-(4-isopropylphenyl)acetamide At 0° C., a sol. of TBAF (1 M in THF, 0.545 mL, 0.545 mmol) is added to a sol. of N-(1-((5-((tert-butyldimethylsilyl)oxy)pyridin-2-yl)methyl)-1H-pyrazol-3-yl)-2-(4-isopropylphenyl)acetamide (211 mg, 0.454 mmol) in THF (4.5 mL). The mixture is stirred at 0° C. for 20 min, quenched with aq. sat. NaHCO$_3$ and extracted with EtOAc. The combined org. layers are washed with brine, dried over MgSO$_4$, filtered, and the solvents are removed under reduced pressure. Purification of the crude by FC (MeOH/CH$_2$Cl$_2$ 2:98→5:95) yields the title compound. LC-MS: $t_R$=0.71 min, MH$^+$=351.32 (conditions 3).

Example 93: 2-(4-Isopropyl-phenyl)-N-{1-[5-(2,2,2-trifluoro-ethoxy)-pyridin-2-ylmethyl]-1H-pyrazol-3-yl}-acetamide A mixture of N-(1-((5-hydroxypyridin-2-yl)methyl)-1H-pyrazol-3-yl)-2-(4-isopropylphenyl)acetamide (28 mg, 0.08 mmol), Cs$_2$CO$_3$ (39.1 mg, 0.12 mmol) and 1,1,1-trifluoro-2-iodoethane (0.00946 mL, 0.096 mmol) in CH$_3$CN (1 mL) is stirred at 70° C., and for 20 min at 100° C. in a microwave oven. The solvents are removed under reduced pressure. Purification of the residue by HPLC yields example 93. LC-MS: $t_R$=0.91 min, MH$^+$=333.20 (conditions 3).

(5-Bromopyridin-2-yl)methyl methanesulfonate

To a sol. of 5-bromo-2-(hydroxymethyl)pyridine (2.50 g, 13.3 mmol) and Et$_3$N (2.78 mL, 19.9 mmol) in CH$_2$Cl$_2$ (67 mL) is added at 0° C. methansulfonyl chloride (1.14 mL, 14.6 mmol). The mixture is stirred at 0° C. for 15 min. Aq. sat. NaHCO$_3$ is added, and the phases are separated. The org. layer is washed with brine, dried over Na$_2$SO$_4$, filtered, and the solvents are evaporated under reduced pressure. Purification of the crude was purified by automated FC (Biotage, 100 g KP column, EtOAc/heptane 0→30%) yields the title product. LC-MS: $t_R$=0.57 min, MH$^+$=268.15 (conditions 4).

5-Bromo-2-((3-nitro-1H-pyrazol-1-yl)methyl)pyridine

Prepared according to general procedure 4 with NaH (60% in oil, 378 mg, 9.45 mmol), (5-bromopyridin-2-yl)methyl methanesulfonate (2.90 g, 10.8 mmol), and 5-nitro-1H-pyrazole (1.07 g, 9.00 mmol) in DMF (25 mL). The reaction is complete after 2 h at rt. Purification of the crude by FC (EtOAc/heptane 0:100→50:50) yields the title compound. LC-MS: $t_R$=0.66 min, MH$^+$=285.02 (conditions 4).

1-((5-Bromopyridin-2-yl)methyl)-1H-pyrazol-3-amine

Prepared according to general procedure 5 with Fe (2.42 g, 43.8 mmol) and 5-bromo-2-((3-nitro-1H-pyrazol-1-yl)methyl)pyridine (1.24 g, 4.38 mmol) in EtOH (50 mL), and aq. sat. NH$_4$Cl (6.0 mL). The reaction is complete overnight at 70° C., and yields the crude title compound. LC-MS: $t_R$=0.39 min, MH$^+$=253.09 (conditions 4).

Example 94: N-[1-(5-Bromo-pyridin-2-ylmethyl)-1H-pyrazol-3-yl]-2-(4-isopropyl-phenyl)-acetamide Prepared according to general procedure 3, starting from 2-(4-isopropylphenyl)acetic acid (232 mg, 1.30 mmol) and 1-((5-bromopyridin-2-yl)methyl)-1H-pyrazol-3-amine (329 mg, 1.30 mmol). LC-MS: $t_R$=0.83 min, MH$^+$=413.08 (conditions 4).

tert-Butyl 2-(5,6-difluoropyridin-3-yl)acetate

According to general procedure 6, from 5-bromo-2,3-difluoropyridine (1.16 g, 6.00 mmol), 2-tert-butoxy-2-oxoethylzinc chloride (0.5M in Et$_2$O, 14.4 mL, 7.20 mmol), Q-Phos (432 mg, 0.60 mmol), and Pd$_2$(dba)$_3$ (173 mg, 0.30 mmol) in THF (18 mL). Purification of the crude by automated FC (Biotage, EtOAc/heptane 20→40:60), and subsequent purification by HPLC, yields the title product. LC-MS: $t_R$=0.81 min (conditions 4).

2-(5-Fluoro-6-(2,2,2-trifluoroethoxy)pyridin-3-yl)acetic acid

NaH (60% in oil, 69.1 mg, 1.73 mmol) is added to 2,2,2-trifluoroethanol (8 mL) at 0° C., and the mixture is stirred for 15 min at rt. tert-Butyl 2-(5,6-difluoropyridin-3-yl)acetate (200 mg, 0.864 mmol) is added, and the mixture is stirred at 120° C. for 3 h, and at 140° C. (microwave) for 1 h. The mixture was allowed to cool to rt, and LiOH H$_2$O (18.1 mg, 0.432 mmol) and water (2 mL) were added. The mixture is stirred at rt for 1 h, and water is added. The mixture is washed with CH$_2$Cl$_2$. The water layer is adjust to pH 1-3 with aq. HCl, and is extracted 3× with CH$_2$Cl$_2$. The combined org. layers are dried over Na$_2$SO$_4$, filtered, and the solvents are removed under reduced pressure. The crude is purified by prep. HPLC, and the combined product-containing fractions are partitioned between water and CH$_2$Cl$_2$. The combined org. layers are dried over Na$_2$SO$_4$, filtered and evaporated under reduced pressure to yield the title compound. LC-MS: $t_R$=0.67 min, MH$^+$=254.08 (conditions 3).

Example 95: N-[1-(3,4-Difluoro-benzyl)-1H-pyrazol-3-yl]-2-[5-fluoro-6-(2,2,2-trifluoro-ethoxy)-pyridin-3-yl]-acetamide Prepared according to general procedure 3, starting from 2-(5,6-difluoropyridin-3-yl)acetic acid (50.6 mg, 0.20 mmol) and 1-(3,4-difluorobenzyl)-1H-pyrazol-3-amine (41.8 mg, 0.20 mmol). LC-MS: $t_R$=0.84 min, MH$^+$=445.11 (conditions 4).

Example 96: N-[1-(5-Cyclopropyl-pyridin-2-ylmethyl)-1H-pyrazol-3-yl]-2-(4-isopropyl-phenyl)-acetamide A mixture of example 94 (104 mg, 0.25 mmol), cyclopropylboronic acid (64.4 mg, 0.75 mmol), K$_2$CO$_3$ (51.8 mg, 0.375 mmol) and Pd(PPh$_3$)$_4$ (28.9 mg, 0.025 mmol) in dioxane (1 mL) is degased and is stirred in a closed vial at 110° C. overnight. The mixture is allowed to cool to rt, and is diluted with water and extracted with EtOAc. The org. layer is washed with brine, dried over MgSO$_4$, filtered, and the solvents are evaporated under reduced pressure. The crude was purified by prep. HPLC to yield example 96. LC-MS: $t_R$=0.72 min, MH$^+$=375.18 (conditions 4).

Example 97: 2-(4-Isopropyl-phenyl)-N-[1-(5-methyl-pyridin-2-ylmethyl)-1H-pyrazol-3-yl]-acetamide A mixture of example 94 (104 mg, 0.25 mmol), trimethylboroxine (31.4 mg, 0.25 mmol), K$_2$CO$_3$ (51.8 mg, 0.375 mmol) and Pd(PPh$_3$)$_4$ (28.9 mg, 0.025 mmol) in dioxane (1 mL) is degased and is stirred in a closed vial at 110° C. overnight. The mixture is allowed to cool to rt, and is diluted with water and extracted with EtOAc. The org. layer is washed with brine, dried over MgSO$_4$, filtered, and the solvents are evaporated under reduced pressure. The crude was purified by prep. HPLC to yield example 97. LC-MS: $t_R$=0.67 min, MH$^+$=349.15 (conditions 4).

Example 98: N-[1-(5-Isobutyl-pyridin-2-ylmethyl)-1H-pyrazol-3-yl]-2-(4-isopropyl-phenyl)-acetamide A mixture of example 94 (60 mg, 0.144 mmol), (2-methylpropyl)boronic acid (44 mg, 0.431 mmol), K$_2$CO$_3$ (30 mg, 0.22 mmol) and Pd(PPh$_3$)$_4$ (16.6 mg, 0.0144 mmol) in dioxane (0.8 mL) is degased and is stirred in a closed vial at 110° C. overnight. The mixture is allowed to cool to rt, and is diluted with water and extracted with EtOAc. The org. layer is washed with brine, dried over MgSO$_4$, filtered, and the solvents are evaporated under reduced pressure. The crude was purified by prep. HPLC to yield example 98. LC-MS: $t_R$=0.80 min, MH$^+$=391.38 (conditions 4).

tert-Butyl 2-(6-(azetidin-1-yl)pyridin-3-yl)acetate

According to general procedure 6, from 2-(azetidin-1-yl)-5-bromopyridine (WO 2010139731, 545 mg, 1.56 mmol), 2-tert-butoxy-2-oxoethylzinc chloride (0.5M in diethyl ether, 5.62 ml, 2.81 mmol), Pd$_2$(dba)$_3$ (117 mg, 0.13 mmol) and Q-PHOS (182 mg, 0.26 mmol) in THF (10.0 mL). The reaction is complete after 1 h at 80° C. Purification of the crude by automated FC (Combiflash, column 20 g, flow rate 35 mL/min, EtOAc/heptane 0/100→10:90→30→70) yields the title product. LC-MS: $t_R$=0.60 min, MH$^+$=249.10 (conditions 3).

2-(6-(Azetidin-1-yl)pyridin-3-yl)acetic acid

According to general procedure 7, from tert-butyl 2-(6-(azetidin-1-yl)pyridin-3-yl)acetate (480 mg, 1.93 mmol) and HCl (4M in dioxane, 15 mL) in CH$_2$Cl$_2$ (10 mL). The reaction is complete after 2 days at rt to yield the crude title product.

Example 99: 2-(6-Azetidin-1-yl-pyridin-3-yl)-N-[1-(3,4-difluoro-benzyl)-1H-pyrazol-3-yl]-acetamide Prepared according to general procedure 3, starting from 2-(6-(azetidin-1-yl)pyridin-3-yl)acetic acid (371 mg, 1.93 mmol) and 1-(3,4-difluorobenzyl)-1H-pyrazol-3-amine (474 mg, 2.03 mmol). LC-MS: $t_R$=0.64 min, MH$^+$=383.95 (conditions 3).

Example 100: N-[1-(5-Ethyl-pyridin-2-ylmethyl)-1H-pyrazol-3-yl]-2-(4-isopropyl-phenyl)-acetamide A mixture of example 94 (60 mg, 0.144 mmol), ethylboronic acid (31.9 mg, 0.431 mmol), K$_2$CO$_3$ (30 mg, 0.22 mmol) and Pd(PPh$_3$)$_4$ (16.6 mg, 0.0144 mmol) in dioxane (0.8 mL) is degased and is stirred in a closed vial at 110° C. overnight. Ethylboronic acid (31.9 mg, 0.431 mmol), K$_2$CO$_3$ (29.8 mg, 0.216 mmol) and Pd(PPh$_3$)$_4$ (16.6 mg, 0.0144 mmol) are added again, and the mixture is stirred at 110° C. for 7 h. The mixture is allowed to cool to rt, and is diluted with water and extracted with EtOAc. The org. layer is washed with brine, dried over MgSO$_4$, filtered, and the solvents are evaporated under reduced pressure. The crude was purified by prep. HPLC to yield example 100. LC-MS: $t_R$=0.71 min, MH$^+$=363.35 (conditions 4).

The following examples were prepared according to general procedure 3, from the appropriate carboxylic acids and aminopyrazoles:

| Example No | Name | LC-MS ($t_R$; MH$^+$; conditions) |
| --- | --- | --- |
| 101 | 2-(6-Azetidin-1-yl-pyridin-3-yl)-N-[1-(4-methoxy-benzyl)-1H-pyrazol-3-yl]-acetamide | 0.61 min; 377.85; conditions 3 |
| 102 | 2-(6-Azetidin-1-yl-pyridin-3-yl)-N-[1-(5-cyano-pyridin-2-ylmethyl)-1H-pyrazol-3-yl]-acetamide | 0.53 min; 373.99; conditions 3 |
| 103 | 2-(6-Azetidin-1-yl-pyridin-3-yl)-N-[1-(4-fluoro-benzyl)-1H-pyrazol-3-yl]-acetamide | 0.62 min; 365.98; conditions 3 |

Example 104: 2-(4-Isopropyl-phenyl)-N-{1-[5-(2-methoxy-ethoxy)-pyridin-2-ylmethyl]-1H-pyrazol-3-yl}-acetamide A mixture of N-(1-((5-hydroxypyridin-2-yl)methyl)-1H-pyrazol-3-yl)-2-(4-isopropylphenyl)acetamide (35 mg, 0.10 mmol), 2-methoxyethanol (0.0118 mL, 0.15 mmol), and PPh$_3$ (39.3 mg, 0.15 mmol) in THF (2 mL) at 0° C. is treated with diisopropyl azodicarboxylate (0.0295 mL, 0.15 mmol). The mixture is allowed to warm to rt and is stirred overnight. The mixture is conc. and purified by prep. HPLC to yield example 104. LC-MS: $t_R$=0.72 min, MH$^+$=409.34 (conditions 4).

Example 105: N-[1-(5-Isopropoxy-pyridin-2-ylmethyl)-1H-pyrazol-3-yl]-2-(4-isopropyl-phenyl)-acetamide A mixture of N-(1-((5-hydroxypyridin-2-yl)methyl)-1H-pyrazol-3-yl)-2-(4-isopropylphenyl)acetamide (35 mg, 0.10 mmol), 2-propanol (0.0115 mL, 0.15 mmol), and PPh$_3$ (39.3 mg, 0.15 mmol) in THF (2 mL) at 0° C. is treated with diisopropyl azodicarboxylate (0.0295 mL, 0.15 mmol). The mixture is allowed to warm to rt and is stirred overnight. The mixture is conc. and purified by prep. HPLC to yield example 105. LC-MS: $t_R$=0.79 min, MH$^+$=393.36 (conditions 4).

(5-Fluoropyridin-2-yl)methyl methanesulfonate

To a sol. of (5-fluoropyridin-2-yl)methanol (339 mg, 2.64 mmol) and Et$_3$N (0.551 mL, 3.96 mmol) in CH$_2$Cl$_2$ (13 mL) is added at 0° C. methansulfonyl chloride (225 µl, 2.9 mmol). The mixture is stirred at 0° C. for 10 min. Aq. sat. NaHCO$_3$ is added, and the phases are separated. The aq. layer is extracted with CH$_2$Cl$_2$ several times. The combined org. layers are washed with brine, dried over Na$_2$SO$_4$, filtered and evaporated under reduced pressure to yield the example 106. LC-MS: $t_R$=0.45 min, MH$^+$=206.22 (conditions 4).

5-Fluoro-2-((3-nitro-1H-pyrazol-1-yl)methyl)pyridine

Prepared according to general procedure 4 with NaH (60% in oil, 100 mg, 2.51 mmol), (5-fluoropyridin-2-yl)methyl methanesulfonate (589 mg, 2.87 mmol), and 5-nitro-1H-pyrazole (285 mg, 2.39 mmol) in DMF (6.4 mL). The reaction is complete after 2 h. Purification of the crude by automated FC (Biotage, EtOAc/heptane 0:100→50:50, 100 g silicagel) yields the title compound. LC-MS: $t_R$=0.56 min, MH$^+$=223.20 (conditions 4).

1-((5-Fluoropyridin-2-yl)methyl)-1H-pyrazol-3-amine

Prepared according to general procedure 5 with Fe (1.32 g, 23.9 mmol) and 5-fluoro-2-((3-nitro-1H-pyrazol-1-yl)methyl)pyridine (531 mg, 2.39 mmol) in EtOH (27 mL), and aq. sat. NH$_4$Cl (3.3 mL). The reaction is complete after 5 h at 75° C., and yields the crude title compound. LC-MS: $t_R$=0.29 min, MH$^+$=193.32 (conditions 4).

Example 106: N-[1-(5-Fluoro-pyridin-2-ylmethyl)-1H-pyrazol-3-yl]-2-(4-isopropyl-phenyl)-acetamide Prepared according to general procedures 1 and 2, starting from 2-(4-isopropylphenyl)acetic acid (154 mg, 0.84 mmol) and 1-((5-fluoropyridin-2-yl)methyl)-1H-pyrazol-3-amine (145 mg, 0.747 mmol). LC-MS: $t_R$=0.86 min, MH$^+$=353.02 (conditions 3).

Example 107: N-[1-(5-Dimethylamino-pyridin-2-ylmethyl)-1H-pyrazol-3-yl]-2-(4-isopropyl-phenyl)-acetamide To a degased mixture of Example 94 (62.6 mg, 0.15 mmol), Pd$_2$(dba)$_3$ (6.87 mg, 0.0075 mmol), RuPhos (7 mg, 0.015 mmol), $^t$BuONa (28.8 mg, 0.3 mmol), and molecular sieve (4 Å powder, a spatula) in toluene (2 mL) is added Me$_2$NH (2M in THF, 0.375 ml, 0.75 mmol). The mixture is stirred in a closed vial at 110° C. overnight. The mixture is cooled to rt. The mixture is partitioned between EtOAc and aq. sat. NaHCO$_3$, and the org. layer is washed with brine, dried over MgSO$_4$, filtered, and the solvents are removed under reduced pressure. Purification of the crude by HPLC yields example 107. LC-MS: $t_R$=0.65 min, MH$^+$=378.20 (conditions 4).

Example 108: N-{1-[5-((S)-3-Fluoro-pyrrolidin-1-yl)-pyridin-2-ylmethyl]-1H-pyrazol-3-yl}-2-(4-isopropyl-phenyl)-acetamide To a degased mixture of Example 94 (62.6 mg, 0.15 mmol), Pd$_2$(dba)$_3$ (6.87 mg, 0.0075 mmol), RuPhos (7 mg, 0.015 mmol), $^t$BuONa (28.8 mg, 0.3 mmol), and molecular sieve (4 Å powder, a spatula) in toluene (2 mL) is added (S)-3-fluoropyrrolidine (48.5 mg, 0.375 mmol). The mixture is stirred in a closed vial at 110° C. overnight. The mixture is cooled to rt. The mixture is partitioned between EtOAc and aq. sat. NaHCO$_3$, and the org. layer is washed with brine, dried over MgSO$_4$, filtered, and the solvents are removed under reduced pressure. Purification of the crude by HPLC yields example 108. LC-MS: $t_R$=0.68 min, MH$^+$=422.22 (conditions 4).

(5-(Trifluoromethyl)pyridin-2-yl)methyl methanesulfonate

To a sol. of (5-(trifluoromethyl)pyridin-2-yl)methanol (480 mg, 2.71 mmol) and Et$_3$N (0.566 mL, 4.06 mmol) in CH$_2$Cl$_2$ (13 mL) is added at 0° C. methansulfonyl chloride (231 µL, 2.98 mmol). The mixture is stirred at 0° C. for 10 min. Aq. sat. NaHCO$_3$ is added, and the phases are separated. The aq. layer is extracted with CH$_2$Cl$_2$ several times. The combined org. layers are washed with brine, dried over Na$_2$SO$_4$, filtered and evaporated under reduced pressure to yield the title crude product. LC-MS: $t_R$=0.63 min, MH$^+$=256.08 (conditions 4).

2-((3-Nitro-1H-pyrazol-1-yl)methyl)-5-(trifluoromethyl)pyridine

Prepared according to general procedure 4 with NaH (60% in oil, 94.6 mg, 2.36 mmol), (5-(trifluoromethyl)pyridin-2-yl)methyl methanesulfonate (690 mg, 2.70 mmol), and 5-nitro-1H-pyrazole (268 mg, 2.25 mmol) in DMF (6.0 mL). The reaction is complete after 2 h. Purification of the crude by automated FC (Biotage, EtOAc/heptane 0:100→50:50, 100 g silicagel) yields the title compound. LC-MS: $t_R$=0.70 min, MH$^+$=273.10 (conditions 4).

1-((5-(Trifluoromethyl)pyridin-2-yl)methyl)-1H-pyrazol-3-amine

Prepared according to general procedure 5 with Fe (1.10 g, 20.0 mmol) and 2-((3-nitro-1H-pyrazol-1-yl)methyl)-5-(trifluoromethyl)pyridine (544 mg, 2.00 mmol) in EtOH (23 mL), and aq. sat. NH$_4$Cl (2.8 mL). The reaction is complete overnight at 75° C., and yields the crude title compound. LC-MS: $t_R$=0.44 min, MH$^+$=243.12 (conditions 4).

Example 109: 2-(4-Isopropyl-phenyl)-N-[1-(5-trifluoromethyl-pyridin-2-ylmethyl)-1H-pyrazol-3-yl]-acetamide Prepared according to general procedures 1 and 2, starting from 2-(4-isopropylphenyl)acetic acid (35.6 mg, 0.20 mmol) and 1-((5-(trifluoromethyl)pyridin-2-yl)methyl)-1H-pyrazol-3-amine (48.4 mg, 0.20 mmol). LC-MS: $t_R$=0.86 min, MH$^+$=403.14 (conditions 4). 2-Chloro-6-(hydroxymethyl) nicotinonitrile. Conc. H$_2$SO$_4$ (3 drops) is added to a sol. of 2-chloro-3-cyano-6-methylpyridine 1-oxide (Kiss, L. E.; Ferreira, H. S.; Torrao, L.; Bonifacio, M. J.; Palma, P. N.; Soares-da-Silva, P.; Learmonth, D. A., *J. Med. Chem.*, 2010, 53, 3396, 512 g, 30.4 mmol) in Ac$_2$O (59.7 mL, 626 mmol) at rt. The mixture is stirred at 110° C. for 1 h and is allowed to cool to rt. The mixture is poured slowly on ice water and stirred with aq. sat. NaHCO$_3$ for 15 min. The aq. layer is extracted with EtOAc (3×), and the combined org. layers are washed with brine, dried over Na$_2$SO$_4$, filtered, and the solvents are removed under reduced pressure. The crude is taken up in MeOH (75 mL), water (38 mL), and K$_2$CO$_3$ (13.8 g, 100 mmol) is added. The mixture is stirred at rt for 30 min. The solvents are removed under reduced pressure. The residue is diluted with CH$_2$Cl$_2$ (400 mL) and dried over Na$_2$SO$_4$ under stirring for 60 min. The mixture is filtered, washed with MeOH, and the solvents are removed under reduced pressure. Purification of the crude by automated FC (Biotage, 100 g KP column, MeOH/CH$_2$Cl$_2$ 1:99→3:97) yields the title product. LC-MS: $t_R$=0.42 min, MH$^+$=199.00 (conditions 4).

(6-Chloro-5-cyanopyridin-2-yl)methyl methanesulfonate

To a sol. of 2-chloro-6-(hydroxymethyl)nicotinonitrile (1.95 g, 11.5 mmol) and Et$_3$N (2.41 mL, 17.3 mmol) in CH$_2$Cl$_2$ (60 mL) is added at 0° C. methansulfonyl chloride (0.986 mL, 12.7 mmol). The mixture is stirred at 0° C. for 10 min. Aq. sat. NaHCO$_3$ is added, and the phases are separated. The aq. layer is extracted with CH$_2$Cl$_2$ several times. The combined org. layers are washed with brine, dried over Na$_2$SO$_4$, filtered and evaporated under reduced pressure to yield the title crude product. LC-MS: $t_R$=0.58 min (conditions 4).

2-Chloro-6-((3-nitro

H-pyrazol-1-yl)methyl)nicotinonitrile. Prepared according to general procedure 4 with NaH (60% in oil, 402 mg, 10.1 mmol), (6-chloro-5-cyanopyridin-2-yl)methyl methanesulfonate (2.84 g, 11.5 mmol), and 5-nitro-1H-pyrazole (1.08 g, 9.58 mmol) in DMF (25 mL). The reaction is complete after 2 h. Purification of the crude by automated FC (Biotage, EtOAc/heptane 5:95→80:20, 100 g silicagel) yields the title compound. LC-MS: $t_R$=0.66 min (conditions 4).

6-((3-Amino-1H-pyrazol-1-yl)methyl)-2-chloronicotinonitrile

Prepared according to general procedure 5 with Fe (3.96 g, 71.6 mmol) and 2-chloro-6-((3-nitro-1H-pyrazol-1-yl)methyl)nicotinonitrile (1.89 g, 7.16 mmol) in EtOH (82 mL), and aq. sat. NH$_4$Cl (10 mL). The reaction is complete overnight at 75° C., and yields the crude title compound. LC-MS: $t_R$=0.41 min, MH$^+$=234.16 (conditions 4).

Example 110: N-[1-(6-Chloro-5-cyano-pyridin-2-ylmethyl)-1H-pyrazol-3-yl]-2-(4-isopropyl-phenyl)-acetamide Prepared according to general procedures 1 and 2, starting from 2-(4-isopropylphenyl)acetic acid (831 mg, 4.66 mmol) and 6-((3-amino-1H-pyrazol-1-yl)methyl)-2-chloronicotinonitrile (1.09 g, 4.66 mmol). LC-MS: $t_R$=0.83 min, MH$^+$=394.08 (conditions 3).

Ethyl 2-(4-(diethylamino)phenyl)acetate

A mixture of ethyl 4-bromophenylacetate (500 mg, 2.06 mmol) Et$_2$NH (181 mg, 2.47 mmol), DavePhos (64.8 mg, 0.165 mmol), K$_3$PO$_4$ (611 mg, 2.88 mmol) and Pd$_2$(dba)$_3$ (94.2 mg, 0.103 mmol) in 1,2-dimethoxyethane (3 mL) is heated to 120° C. for 20 min in a microwave oven. The mixture is allowed to cool to rt, and Et$_2$NH (181 mg, 2.47 mmol), DavePhos (64.8 mg, 0.165 mmol), K$_3$PO$_4$ (611 mg, 2.88 mmol) and Pd$_2$(dba)$_3$ (94.2 mg, 0.103 mmol) are added again. The mixture is stirred at 120° C. for 54 h, and is allowed to cool to rt. The suspension is filtered through Celite®, and the precipitate is washed with CH$_2$Cl$_2$. The solvents are removed under reduced pressure. Purification of the crude by HPLC yields the title product. LC-MS: $t_R$=0.54 min, MH$^+$=236.34 (conditions 3).

2-(4-(Diethylamino)phenyl)acetic acid

Aq. 2.5M NaOH (0.5 mL) is added to a sol. of ethyl 2-(4-(diethylamino)phenyl)acetate (73 mg, 0.31 mmol) in EtOH (1 mL). The mixture is stirred for 1 h at rt, and the solvents are partially removed under reduced pressure. The residue is diluted in CH$_2$Cl$_2$, and aq. 1M HCl is added to adjust the pH to 3. Separation of the phases with a Separator® (Biotage), and removing the solvents under reduced pressure yields to title product. LC-MS: $t_R$=0.42 min, MH$^+$=208.15 (conditions 3).

The following examples were prepared according to general procedure 3, from the appropriate carboxylic acids and aminopyrazoles:

| Example No | Name | LC-MS ($t_R$; MH$^+$; conditions) |
|---|---|---|
| 111 | 2-(6-Azetidin-1-yl-pyridin-3-yl)-N-[1-(4-cyano-benzyl)-1H-pyrazol-3-yl]-acetamide | 0.60 min; 373.01; conditions 3 |
| 112 | 2-(4-Diethylamino-phenyl)-N-[1-(4-methoxy-benzyl)-1H-pyrazol-3-yl]-acetamide | 0.64 min; 392.89; conditions 3 |
| 113 | 2-(4-Diethylamino-phenyl)-N-[1-(3,4-difluoro-benzyl)-1H-pyrazol-3-yl]-acetamide | 0.66 min; 398.98; conditions 3 |
| 114 | N-[1-(4-Cyano-benzyl)-1H-pyrazol-3-yl]-2-(4-diethylamino-phenyl)-acetamide | 0.62 min; 388.00; conditions 3 |

Example 115: N-[1-(5-Cyano-6-ethyl-pyridin-2-ylmethyl)-1H-pyrazol-3-yl]-2-(4-isopropyl-phenyl)-acetamide Example 110 (80 mg, 0.203 mmol) is mixed with ethylboronic acid (45 mg, 0.61 mmol), K$_2$CO$_3$ (42.1 mg, 0.305 mmol) and Pd(PPh$_3$)$_4$ (23.5 mg, 0.0203 mmol) in dioxane (1 mL), and the mixture is degased. The mixture is stirred in a closed vial at 110° C. overnight, and is allowed to cool to rt. The mixture is diluted with water and extracted with EtOAc. The org. layer is washed with brine, dried over MgSO$_4$, filtered, and the solvents are removed under reduced pressure. The crude is mixed again with ethylboronic acid (45 mg, 0.609 mmol), K$_2$CO$_3$ (42.1 mg, 0.305 mmol), and Pd(PPh$_3$)$_4$ (23.5 mg, 0.0203 mmol) in dioxane (1 mL), and the mixture is degased. The mixture is stirred in a closed vial at 110° C. overnight, and is allowed to cool to rt. The mixture is diluted with water and extracted with EtOAc. The org. layer is washed with brine, dried over MgSO$_4$, filtered,

Example 116: N-[1-(5-Cyano-6-methoxy-pyridin-2-ylmethyl)-1H-pyrazol-3-yl]-2-(4-isopropyl-phenyl)-acetamide To a suspension of NaH (60% in oil, 11.6 mg, 0.289 mmol) in MeOH (1.5 mL) at 0° C. is added Example 110 (80 mg, 0.19 mmol). The mixture is stirred for 3 h at 0° C., and is warmed to 50° C. The mixture is stirred at 50° C. overnight. The mixture is partitioned between water and EtOAc, and the org. layer is washed with brine, dried over MgSO$_4$, filtered and evaporated under reduced pressure. Purification of the crude by HPLC yields example 116. LC-MS: $t_R$=0.84 min, MH$^+$=390.13 (conditions 4).

Example 117: N-{1-[5-Cyano-6-(2,2,2-trifluoro-ethoxy)-pyridin-2-ylmethyl]-1H-pyrazol-3-yl}-2-(4-isopropyl-phenyl)-acetamide To a suspension of NaH (60% in oil, 11.6 mg, 0.289 mmol) in CF$_3$CH$_2$OH (1.5 mL) at 0° C. is added Example 110 (80 mg, 0.193 mmol). The mixture is stirred for 3 h at 0° C., and is warmed to 50° C. The mixture is stirred at 50° C. overnight. The mixture is partitioned between water and EtOAc, and the org. layer is washed with brine, dried over MgSO$_4$, filtered and evaporated under reduced pressure. Purification of the crude by HPLC yields example 117. LC-MS: $t_R$=0.89 min, MH$^+$=458.13 (conditions 4).

Example 118: N-[1-(5-Cyano-6-isopropoxy-pyridin-2-ylmethyl)-1H-pyrazol-3-yl]-2-(4-isopropyl-phenyl)-acetamide To a suspension of NaH (60% in oil, 11.6 mg, 0.289 mmol) in $^i$PrOH (1.5 mL) at 0° C. is added Example 110 (80 mg, 0.193 mmol). The mixture is stirred for 3 h at 0° C., and is warmed to 50° C. The mixture is stirred at 50° C. overnight. The mixture is partitioned between water and EtOAc, and the org. layer is washed with brine, dried over MgSO$_4$, filtered and evaporated under reduced pressure. Purification of the crude by HPLC yields example 118. LC-MS: $t_R$=0.90 min, MH$^+$=417.93 (conditions 4).

5-Bromo-2-(3,3-difluoropyrrolidin-1-yl)pyridine

A mixture of 2,5-dibromopyridine (1.00 g, 4.22 mmol), 3,3-difluoropyrrolidine hydrochloride (1.33 g, 9.04 mmol) and DBU (2.70 mL, 18.1 mmol) in DMSO (30 mL) is stirred at 80° C. for 72 h. The mixture is allowed to cool to rt, and the solvents are removed under reduced pressure. Purification of the crude by automated FC (Büchi, 20 g silicagel, EtOAc/heptane 2:98→3:97→5:95→10:90→15:85) yields the title product. LC-MS: $t_R$=0.78 min, MH$^+$=264.91 (conditions 3).

tert-Butyl 2-(6-(3,3-difluoropyrrolidin-1-yl)pyridin-3-yl)acetate

According to general procedure 6, from 5-bromo-2-(3,3-difluoropyrrolidin-1-yl)pyridine (300 mg, 1.14 mmol), 2-tert-butoxy-2-oxoethylzinc chloride (0.5M in diethyl ether, 3.1 mL, 1.25 mmol), Pd$_2$(dba)$_3$ (52.2 mg, 0.057 mmol) and Q-PHOS (81 mg, 0.114 mmol) in THF (3 mL). The reaction is complete after 3 h at 90° C. Purification of the crude by automated FC (Büchi, 10 g silicagel, flow 10 mL/min, EtOAc/heptane 2:98→5:95→10:90) yields the title product. LC-MS: $t_R$=0.65 min, MH$^+$=299.17 (conditions 3).

2-(6-(3,3-Difluoropyrrolidin-1-yl)pyridin-3-yl)acetic acid

According to general procedure 7, tert-butyl 2-(6-(3,3-difluoropyrrolidin-1-yl)pyridin-3-yl)acetate (50 mg, 0.168 mmol) and HCl (4M in dioxane, 1 mL) in CH$_2$Cl$_2$ (1 mL). The reaction is complete after 50 h at rt. Removing the solvents under reduced pressure leads to the title crude product. LC-MS: $t_R$=0.42 min, MH$^+$=242.90 (conditions 3).

5-Bromo-N,N-diethylpyridin-2-amine

A mixture of 2,5-dibromopyridine (1.00 g, 4.22 mmol), diethylamine (0.469 mL, 4.52 mmol) and DBU (0.674 mL, 4.52 mmol) in DMSO (30 mL) is stirred at 80° C. for 2 weeks, whereas diethylamine (0.469 mL, 4.52 mmol) and DBU (0.674 mL, 4.52 mmol) are added every 2 days. The mixture is allowed to cool to rt, and the solvents are removed under reduced pressure. Purification of the crude by automated FC (Büchi, 20 g silicagel, EtOAc/heptane 2:98→3:97→5:95→10:90→15:85→20:80) yields the title product. LC-MS: $t_R$=0.53 min, MH$^+$=231.00 (conditions 3).

tert-Butyl 2-(6-(diethylamino)pyridin-3-yl)acetate

According to general procedure 6 from 5-bromo-N,N-diethylpyridin-2-amine (178 mg, 0.726 mmol), 2-tert-butoxy-2-oxoethylzinc chloride (0.5M in diethyl ether, 3.1 mL, 1.25 mmol), Pd$_2$(dba)$_3$ (33.2 mg, 0.0363 mmol) and Q-PHOS (51.6 mg, 0.726 mmol) in THF (3 mL). The reaction is complete after 90 min at 75° C. Purification of the crude by automated FC (Büchi, 10 g silicagel, flow 10 mL/min, EtOAc/heptane 2:98→5:95→10:90→20:80) yields the title product. LC-MS: $t_R$=0.66 min, MH$^+$=265.17 (conditions 3).

2-(6-(Diethylamino)pyridin-3-yl)acetic acid

According to general procedure 7, from tert-butyl 2-(6-(diethylamino)pyridin-3-yl)acetate (53.3 mg, 0.179 mmol) and HCl (4M in dioxane, 3 mL) in CH$_2$Cl$_2$ (2 mL). The reaction is complete after 40 h at rt. Removing the solvents under reduced pressure leads to the title crude product.

Ethyl 2-(4-((2-methoxyethyl)(methyl)amino)phenyl)acetate

A mixture of ethyl-4-bromophenylacetate (500 mg, 2.06 mmol), N-(2-methoxyethyl)methylamine (0.45 mL, 4.11 mmol) and K$_3$PO$_4$ (1.75 g, 8.23 mmol) in 1,2-dimethoxy-ethane (4 mL) is degased with nitrogen. DavePhos (130 mg, 0.329 mmol) and Pd$_2$(dba)$_3$ (188 mg, 0.206 mmol) are added, and the mixture is heated to 120° C. The mixture is stirred at 120° C. for 48 h, and is allowed to cool to rt. The mixture is filtered through Celite®, and the filtrate is evaporated under reduced pressure. Purification of the crude by HPLC yields the title product. LC-MS: $t_R$=0.57 min, MH$^+$=252.07 (conditions 3).

2-(4-((2-Methoxyethyl)(methyl)amino)phenyl)acetic acid

A mixture of ethyl 2-(4-((2-methoxyethyl)(methyl) amino)phenyl)acetate (215 mg, 0.855 mmol) in EtOH (1 ml) and aq. 2.5M NaOH (0.5 mL) is stirred at rt for 1 h. The solvents are removed under reduced pressure and the residue is diluted with $CH_2Cl_2$. Aq. 1M HCl is added to adjust pH to 3, and phases are separated in a Separator® (Biotage). The org. layer is dried over $MgSO_4$, filtered, and the solvents are removed under reduced pressure to yield the crude title product. LC-MS: $t_R$=0.41 min, $MH^+$=242.76 (conditions 3).

Ethyl 2-(4-(ethyl(methyl)amino)phenyl)acetate

A mixture of ethyl 4-bromophenylacetate (500 mg, 2.06 mmol), methylethylamine (0.358 mL, 4.11 mmol), 2-dicyclohexylphosphino-2'-(N,N-dimethylamino)biphenyl (130 mg, 0.33 mmol) $K_3PO_4$ (1.75 g, 8.23 mmol) and $Pd_2(dba)_3$ (188 mg, 0.206 mmol) in 1,2-dimethoxyethane (4 mL) is heated at 120° C. for 2 days, and is allowed to cool to rt. The mixture is filtered through Celite®, and the cake is washed with $CH_2Cl_2$. The filtrate is evaporated under reduced pressure. Purification of the crude by HPLC yields the title compound. LC-MS: $t_R$=0.53 min, $MH^+$=222.22 (conditions 3).

2-(4-(Ethyl(methyl)amino)phenyl)acetic acid

A mixture of ethyl 2-(6-(ethyl(methyl)amino)pyridin-3-yl)acetate (49 mg, 0.22 mmol) in EtOH (1 mL) and aq. 2.5M NaOH (0.5 mL) is stirred at rt for 1 h. The solvents are partially removed under reduced pressure, and the residue is cooled to 0° C. $CH_2Cl_2$ is added, and the mixture is acidified to pH 3 with aq. 1M HCl. The phases are separated in a Separator® (Biotage) to yield the crude title product. LC-MS: $t_R$=0.39 min, $MH^+$=194.12 (conditions 3).

The following examples were prepared according to general procedure 3, from the appropriate carboxylic acids and aminopyrazoles:

Example 132: N-[1-(5-Cyano-6-methyl-pyridin-2-ylmethyl)-1H-pyrazol-3-yl]-2-(4-isopropyl-phenyl)-acetamide A mixture of Example 110 (100 mg, 0.254 mmol), trimethylboroxine (32 mg, 0.25 mmol), $K_2CO_3$ (53 mg, 0.38 mmol), and $Pd(PPh_3)_4$ (29 mg, 0.025 mmol) in dioxane (1 mL) is stirred at 110° C. overnight. The mixture is allowed to cool to rt, and is diluted with water. The phases are separated, and the aq. layer is extracted with EtOAc. The combined org. layers are washed with brine, dried over $MgSO_4$, filtered, and the solvents are removed under reduced pressure. Purification of the crude by HPLC yields example 132. LC-MS: $t_R$=0.80 min, $MH^+$=374.12 (conditions 4).

Example 133: N-[1-(5-Cyano-6-cyclopropyl-pyridin-2-ylmethyl)-1H-pyrazol-3-yl]-2-(4-isopropyl-phenyl)-acetamide A mixture of Example 110 (80 mg, 0.20 mmol), cyclopropylboronic acid (52 mg, 0.60 mmol), $K_2CO_3$ (42 mg, 0.30 mmol), and $Pd(PPh_3)_4$ (24 mg, 0.020 mmol) in dioxane (1 mL) is stirred at 110° C. overnight. The mixture is allowed to cool to rt, and is diluted with water. The phases are separated, and the aq. layer is extracted with EtOAc. The combined org. layers are washed with brine, dried over $MgSO_4$, filtered, and the solvents are removed under reduced pressure. Purification of the crude by HPLC yields example 133. LC-MS: $t_R$=0.89 min, $MH^+$=400.16 (conditions 4).

Example 134: N-[1-(5-Cyano-6-isobutyl-pyridin-2-ylmethyl)-1H-pyrazol-3-yl]-2-(4-isopropyl-phenyl)-acetamide A mixture of Example 110 (80 mg, 0.20 mmol), 2-methylpropyl boronic acid (62 mg, 0.60 mmol), $K_2CO_3$ (42 mg, 0.30 mmol), and $Pd(PPh_3)_4$ (24 mg, 0.020 mmol) in dioxane (1 mL) is stirred at 110° C. overnight. The mixture is

| Example No | Name | LC-MS ($t_R$; $MH^+$; conditions) |
|---|---|---|
| 119 | N-[1-(5-Cyano-pyridin-2-ylmethyl)-1H-pyrazol-3-yl]-2-[6-(3,3-difluoro-pyrrolidin-1-yl)-pyridin-3-yl]-acetamide | 0.57 min; 423.97; conditions 3 |
| 120 | N-[1-(3,4-Difluoro-benzyl)-1H-pyrazol-3-yl]-2-[6-(3,3-difluoro-pyrrolidin-1-yl)-pyridin-3-yl]-acetamide | 0.68 min; 433.71; conditions 3 |
| 121 | N-[1-(4-Cyano-benzyl)-1H-pyrazol-3-yl]-2-[6-(3,3-difluoro-pyrrolidin-1-yl)-pyridin-3-yl]-acetamide | 0.64 min; 422.94; conditions 3 |
| 122 | 2-[6-(3,3-Difluoro-pyrrolidin-1-yl)-pyridin-3-yl]-N-[1-(4-fluoro-benzyl)-1H-pyrazol-3-yl]-acetamide | 0.66 min; 416.22; conditions 3 |
| 123 | N-[1-(5-Cyano-pyridin-2-ylmethyl)-1H-pyrazol-3-yl]-2-(6-diethylamino-pyridin-3-yl)-acetamide | 0.58 min; 390.02; conditions 3 |
| 124 | 2-(6-Diethylamino-pyridin-3-yl)-N-[1-(3,4-difluoro-benzyl)-1H-pyrazol-3-yl]-acetamide | 0.68 min; 400.07; conditions 3 |
| 125 | N-[1-(4-Methoxy-benzyl)-1H-pyrazol-3-yl]-2-{4-[(2-methoxy-ethyl)-methyl-amino]-phenyl}-acetamide | 0.65 min; 409.05; conditions 3 |
| 126 | N-[1-(3,4-Difluoro-benzyl)-1H-pyrazol-3-yl]-2-{4-[(2-methoxy-ethyl)-methyl-amino]-phenyl}-acetamide | 0.68 min; 415.00; conditions 3 |
| 127 | N-[1-(4-Cyano-benzyl)-1H-pyrazol-3-yl]-2-{4-[(2-methoxy-ethyl)-methyl-amino]-phenyl}-acetamide | 0.63 min; 403.96; conditions 3 |
| 128 | N-[1-(4-Fluoro-benzyl)-1H-pyrazol-3-yl]-2-{4-[(2-methoxy-ethyl)-methyl-amino]-phenyl}-acetamide | 0.66 min; 397.04; conditions 3 |
| 129 | 2-[4-(Ethyl-methyl-amino)-phenyl]-N-[1-(4-methoxy-benzyl)-1H-pyrazol-3-yl]-acetamide | 0.62 min; 379.02; conditions 3 |
| 130 | N-[1-(3,4-Difluoro-benzyl)-1H-pyrazol-3-yl]-2-[4-(ethyl-methyl-amino)-phenyl]-acetamide | 0.64 min; 384.92; conditions 3 |
| 131 | 2-(4-Isopropyl-phenyl)-N-[1-(5-methoxy-pyridin-2-ylmethyl)-1H-pyrazol-3-yl]-acetamide | 0.72 min; 365.09; conditions 4 | allowed to cool to rt, and is diluted with water. The phases are separated, and the aq. layer is extracted with EtOAc. The combined org. layers are washed with brine, dried over MgSO$_4$, filtered, and the solvents are removed under reduced pressure. Purification of the crude by HPLC yields example 134. LC-MS: $t_R$=0.91 min, MH$^+$=416.18 (conditions 4).

(R)-5-Bromo-2-(3-fluoropyrrolidin-1-yl)pyridine

Prepared according to general procedure 9 from 2,5-dibromopyridine (350 mg, 1.48 mmol), (R)-3-fluoropyrrolidine hydrochloride (199 mg, 1.58 mmol), and DBU (0.472 mL, 3.16 mmol) in DMSO (20 mL). After the same amounts of (R)-3-fluoropyrrolidine hydrochloride and DBU are added again, and the reaction is complete after 72 h. Purification of the crude by automated FC (Büchi, EtOAc/heptane 2:98→3:97→5:95→10:90→15:85, 20 g silicagel, flow 13 mL/min) yields the title product. LC-MS: $t_R$=0.52 min, MH$^+$=244.96 (conditions 3).

(R)-tert-Butyl 2-(6-(3-fluoropyrrolidin-1-yl)pyridin-3-yl)acetate

Prepared according to general procedure 6 from (R)-5-bromo-2-(3-fluoropyrrolidin-1-yl)pyridine (110 mg, 0.449 mmol), (2-(tert-butoxy)-2-oxoethyl)zinc(II) chloride (0.5M in Et$_2$O, 1.00 mL, 0.50 mmol), Pd$_2$(dba)$_3$ (21 mg, 0.024 mmol) and Q-Phos (32 mg, 0.045 mmol) in THF (3 mL). The reaction is complete overnight. Purification of the crude by automated FC (Büchi, EtOAc/heptane 2:98→5:95→10:90, 10 g silicagel, flow 10 mL/min) yields the title product. LC-MS: $t_R$=0.61 min, MH$^+$=281.16 (conditions 3).

(R)-2-(6-(3-Fluoropyrrolidin-1-yl)pyridin-3-yl)acetic acid

Prepared according to general procedure 7 from (R)-tert-butyl 2-(6-(3-fluoropyrrolidin-1-yl)pyridin-3-yl)acetate (54 mg, 0.193 mmol) and HCl (4M in dioxane, 3 mL) in CH$_2$Cl$_2$ (2 mL). The reaction is complete after 2 days. Removing the solvents under reduced pressure yields the crude title product.

5-Bromo-2-(3,3-difluoroazetidin-1-yl)pyridine

Prepared according to general procedure 9 from 2,5-dibromopyridine (1.00 g, 4.22 mmol), 3,3-difluoroazetidine hydrochloride (485 mg, 4.52 mmol), and DBU (1.35 mL, 9.03 mmol) in DMSO (30 mL). The same amounts of 3,3-difluoroazetidine hydrochloride, and DBU are added again each day, and the reaction is complete after 3 days. Purification of the crude by automated FC (Büchi, EtOAc/heptane 2:98→3:97→5:95→10:90→15:85, 20 g silicagel, flow 13 mL/min) yields the title product. LC-MS: $t_R$=0.78 min, MH$^+$=250.88 (conditions 3).

tert-Butyl 2-(6-(3,3-difluoroazetidin-1-yl)pyridin-3-yl)acetate

Prepared according to general procedure 6 from 5-bromo-2-(3,3-difluoroazetidin-1-yl)pyridine (473 mg, 1.90 mmol), (2-(tert-butoxy)-2-oxoethyl)zinc(III) chloride (0.5M in Et$_2$O, 4.20 mL, 2.10 mmol), Pd$_2$(dba)$_3$ (87 mg, 0.095 mmol) and Q-Phos (135 mg, 0.190 mmol) in THF (3 mL). The reaction is complete after 2 h. Purification of the crude by automated FC (Büchi, EtOAc/heptane 2:98→5:95→10:90, 10 g silicagel, flow 10 mL/min) yields the title product. LC-MS: $t_R$=0.64 min, MH$^+$=285.18 (conditions 3).

2-(6-(3,3-Difluoroazetidin-1-yl)pyridin-3-yl)acetic acid

Prepared according to general procedure 7 from tert-butyl 2-(6-(3,3-difluoroazetidin-1-yl)pyridin-3-yl)acetate (300 mg, 1.06 mmol) and HCl (4M in dioxane, 12 mL) in CH$_2$Cl$_2$ (10 mL). The reaction is complete overnight. Removing the solvents under reduced pressure yields the crude title product.

The following examples were prepared according to general procedure 3, from the appropriate carboxylic acids and aminopyrazoles:

| Example No | Name | LC-MS ($t_R$; MH$^+$; conditions) |
| --- | --- | --- |
| 135 | N-[1-(3,4-Difluoro-benzyl)-1H-pyrazol-3-yl]-2-(2-methyl-3H-benzoimidazol-5-yl)-acetamide | 0.62 min; 381.99; conditions 3 |
| 136 | N-[1-(4-Cyano-benzyl)-1H-pyrazol-3-yl]-2-(2-methyl-3H-benzoimidazol-5-yl)-acetamide | 0.58 min; 370.77; conditions 3 |
| 137 | N-[1-(4-Fluoro-benzyl)-1H-pyrazol-3-yl]-2-(2-methyl-3H-benzoimidazol-5-yl)-acetamide | 0.61 min; 363.93; conditions 3 |
| 138 | N-[1-(5-Cyano-pyridin-2-ylmethyl)-1H-pyrazol-3-yl]-2-[6-((R)-3-fluoro-pyrrolidin-1-yl)-pyridin-3-yl]-acetamide | 0.60 min; 406.00; conditions 3 |
| 139 | N-[1-(3,4-Difluoro-benzyl)-1H-pyrazol-3-yl]-2-[6-((R)-3-fluoro-pyrrolidin-1-yl)-pyridin-3-yl]-acetamide | 0.65 min; 416.04; conditions 3 |
| 140 | N-[1-(4-Cyano-benzyl)-1H-pyrazol-3-yl]-2-[6-((R)-3-fluoro-pyrrolidin-1-yl)-pyridin-3-yl]-acetamide | 0.61 min; 405.01; conditions 3 |
| 141 | N-[1-(4-Fluoro-benzyl)-1H-pyrazol-3-yl]-2-[6-((R)-3-fluoro-pyrrolidin-1-yl)-pyridin-3-yl]-acetamide | 0.64 min; 397.90; conditions 3 |
| 142 | N-[1-(5-Cyano-pyridin-2-ylmethyl)-1H-pyrazol-3-yl]-2-[6-(3,3-difluoro-azetidin-1-yl)-pyridin-3-yl]-acetamide | 0.56 min; 409.99; conditions 3 |
| 143 | 2-[6-(3,3-Difluoro-azetidin-1-yl)-pyridin-3-yl]-N-[1-(3,4-difluoro-benzyl)-1H-pyrazol-3-yl]-acetamide | 0.68 min; 420.01; conditions 3 |
| 144 | N-[1-(4-Cyano-benzyl)-1H-pyrazol-3-yl]-2-[6-(3,3-difluoro-azetidin-1-yl)-pyridin-3-yl]-acetamide | 0.63 min; 409.03; conditions 3 |
| 145 | 2-[6-(3,3-Difluoro-azetidin-1-yl)-pyridin-3-yl]-N-[1-(4-fluoro-benzyl)-1H-pyrazol-3-yl]-acetamide | 0.66 min; 401.69; conditions 3 |
| 146 | 2-[6-(3,3-Difluoro-azetidin-1-yl)-pyridin-3-yl]-N-[1-(4-methoxy-benzyl)-1H-pyrazol-3-yl]-acetamide | 0.65 min; 414.04; conditions 3 |

2-(4-Bromophenyl)-N-(1-(4-fluorobenzyl)-1H-pyrazol-3-yl)acetamide

Prepared according to general procedure 3 from 2-(4-bromophenyl)acetic acid (1.20 g, 5.58 mmol), 1-(4-fluorobenzyl)-1H-pyrazol-3-amine (1.07 g, 5.58 mmol), HATU (3.18 g, 8.37 mmol), and DIPEA (4.78 mL, 27.9 mmol) in DMF (15 mL). The reaction is complete overnight. The mixture is partitioned between aq. sat. $NaHCO_3$ and EtOAc. The org. layer is washed with brine, dried over $MgSO_4$, filtered, and the solvents are removed under reduced pressure. Purification of the crude by automated FC (Biotage, 50 g silicagel, EtOAc/heptane 0:100→90:10) yields the title product. LC-MS: $t_R$=0.81 min, $MH^+$=387.98 (conditions 4).

Example 147. N-[1-(4-Fluoro-benzyl)-1H-pyrazol-3-yl]-2-(4-isobutyl-phenyl)-acetamide A mixture of 2-(4-bromophenyl)-N-(1-(4-fluorobenzyl)-1H-pyrazol-3-yl)acetamide (60 mg, 0.15 mmol), (2-methylpropyl)boronic acid (47 mg, 0.46 mmol), $K_2CO_3$ (32 mg, 0.23 mmol) and $Pd(PPh_3)_4$ (18 mg, 0.016 mmol) in dioxane (1.0 mL) is stirred in a closed vial at 110° C. overnight. The mixture is allowed to cool to rt, and is diluted with water and extracted with EtOAc. The org. layer is washed with brine, dried over $MgSO_4$, filtered, and the solvents are evaporated under reduced pressure. Purification of the crude by HPLC yields example 147. LC-MS: $t_R$=0.92 min, $MH^+$=366.09 (conditions 4).

Example 148: N-[1-(5-Cyano-6-fluoro-pyridin-2-ylmethyl)-1H-pyrazol-3-yl]-2-(4-isopropyl-phenyl)-acetamide A mixture of Example 110 (30 mg, 0.075 mmol), KF (13 mg, 0.23 mmol), and 4,7,13,16,21,24-hexaoxa-1,10-diazabicyclo[8.8.8]-hexacosane (42 mg, 0.11 mmol) in DMSO (1 mL) is stirred at 60° C. for 2 h. The mixture is diluted with $H_2O$, and is extracted with EtOAc. The comb. org. layers are dried over $MgSO_4$, filtered, and the solvents are removed under reduced pressure. Purification of the crude by HPLC yields example 148. LC-MS: $t_R$=0.82 min, $MH^+$=378.31 (conditions 4).

5-Bromo-N-(2,2-difluoroethyl)-N-methylpyridin-2-amine

Prepared according to general procedure 9 from 2,5-dibromopyridine (1.00 g, 4.22 mmol), (2,2-difluoroethyl)(methyl)amine hydrochloride (2.78 g, 21.1 mmol), and DBU (6.30 mL, 42.2 mmol) in DMSO (30 mL). The reaction is complete after 6 days. Purification of the crude by automated FC (Büchi, EtOAc/heptane 2:98→3:97→5:95→10:90→15:85, 20 g silicagel, flow 13 mL/min) yields the title product. LC-MS: $t_R$=0.38 min (conditions 3).

tert-Butyl 2-(6-((2,2-difluoroethyl)(methyl)amino)pyridin-3-yl)acetate

Prepared according to general procedure 6 from 5-bromo-N-(2,2-difluoroethyl)-N-methylpyridin-2-amine (255 mg, 1.02 mmol), (2-(tert-butoxy)-2-oxoethyl)zinc(II) chloride (0.5M in $Et_2O$, 2.24 mL, 1.12 mmol), $Pd_2(dba)_3$ (47 mg, 0.051 mmol) and Q-Phos (72 mg, 0.102 mmol) in THF (3 mL). The reaction is complete after 7 days. Purification of the crude by automated FC (Büchi, EtOAc/heptane 2:98→5:95→10:90, 10 g silicagel, flow 10 mL/min) yields the title product. LC-MS: $t_R$=0.64 min, $MH^+$=287.06 (conditions 3).

2-(6-((2,2-Difluoroethyl)(methyl)amino)pyridin-3-yl)acetic acid

Prepared according to general procedure 7 from tert-butyl 2-(6-((2,2-difluoroethyl)(methyl)amino)pyridin-3-yl)acetate (40 mg, 0.14 mmol) and HCl (4M in dioxane, 3 mL) in $CH_2Cl_2$ (3 mL). The reaction is complete overnight. Removing the solvents under reduced pressure yields the crude title product.

(S)-5-Bromo-2-(3-fluoropyrrolidin-1-yl)pyridine

Prepared according to general procedure 9 from 2,5-dibromopyridine (1.00 g, 4.22 mmol), (S)-3-fluoropyrrolidine hydrochloride (567 mg, 4.52 mmol), and DBU (1.35 mL, 9.03 mmol) in DMSO (30 mL). The same amounts of (S)-3-fluoropyrrolidine hydrochloride, and DBU are added again after 24 h, and the reaction is complete after 6 days. Purification of the crude by automated FC (Büchi, EtOAc/heptane 2:98→3:97→5:95→10:90→15:85, 20 g silicagel, flow 13 mL/min) yields the title product. LC-MS: $t_R$=0.52 min, $MH^+$=244.96 (conditions 3).

(S)-tert-Butyl 2-(6-(3-fluoropyrrolidin-1-yl)pyridin-3-yl)acetate

Prepared according to general procedure 6 from (S)-5-bromo-2-(3-fluoropyrrolidin-1-yl)pyridine (110 mg, 0.449 mmol), (2-(tert-butoxy)-2-oxoethyl)zinc(II) chloride (0.5M in $Et_2O$, 1.00 mL, 0.50 mmol), $Pd_2(dba)_3$ (21 mg, 0.024 mmol) and Q-Phos (32 mg, 0.045 mmol) in THF (3 mL). The reaction is complete overnight h. Purification of the crude by automated FC (Büchi, EtOAc/heptane 2:98→5:95→10:90, 10 g silicagel, flow 10 mL/min) yields the title product. LC-MS: $t_R$=0.61 min, $MH^+$=281.16 (conditions 3).

(S)-2-(6-(3-Fluoropyrrolidin-1-yl)pyridin-3-yl)acetic acid

Prepared according to general procedure 7 from (R)-tert-butyl 2-(6-(3-fluoropyrrolidin-1-yl)pyridin-3-yl)acetate (54 mg, 0.193 mmol) and HCl (4M in dioxane, 3 mL) in $CH_2Cl_2$ (2 mL). The reaction is complete after 2 days. Removing the solvents under reduced pressure yields the crude title product.

The following examples were prepared according to general procedure 3, from the appropriate carboxylic acids and aminopyrazoles:

| Example No | Name | LC-MS ($t_R$; $MH^+$; conditions) |
| --- | --- | --- |
| 149 | 2-(4-Dimethylamino-phenyl)-N-[1-(5-fluoro-pyridin-2-ylmethyl)-1H-pyrazol-3-yl]-acetamide | 0.42 min; 353.84; conditions 3 |
| 150 | 2-(6-Dimethylamino-pyridin-3-yl)-N-[1-(5-fluoro-pyridin-2-ylmethyl)-1H-pyrazol-3-yl]-acetamide | 0.41 min; 355.03; conditions 3 |
| 151 | N-[1-(5-Cyano-pyridin-2-ylmethyl)-1H-pyrazol-3-yl]-2-{6-[(2,2-difluoro-ethyl)-methyl-amino]-pyridin-3-yl}-acetamide | 0.56 min; 412.07; conditions 3 |
| 152 | N-[1-(5-Cyano-pyridin-2-ylmethyl)-1H-pyrazol-3-yl]-2-[6-((S)-3-fluoro-pyrrolidin-1-yl)-pyridin-3-yl]-acetamide | 0.60 min; 406.00; conditions 3 |

-continued

| Example No | Name | LC-MS ($t_R$; MH+; conditions) |
|---|---|---|
| 153 | N-[1-(3,4-Difluoro-benzyl)-1H-pyrazol-3-yl]-2-[6-((S)-3-fluoro-pyrrolidin-1-yl)-pyridin-3-yl]-acetamide | 0.65 min; 416.04; conditions 3 |
| 154 | N-[1-(4-Cyano-benzyl)-1H-pyrazol-3-yl]-2-[6-((S)-3-fluoro-pyrrolidin-1-yl)-pyridin-3-yl]-acetamide | 0.61 min; 405.01; conditions 3 |
| 155 | N-[1-(4-Fluoro-benzyl)-1H-pyrazol-3-yl]-2-[6-((S)-3-fluoro-pyrrolidin-1-yl)-pyridin-3-yl]-acetamide | 0.64 min; 397.90; conditions 3 |
| 156 | 2-[6-((S)-3-Fluoro-pyrrolidin-1-yl)-pyridin-3-yl]-N-[1-(4-methoxy-benzyl)-1H-pyrazol-3-yl]-acetamide | 0.64 min; 409.99; conditions 3 |

4-Chloro-6-methylnicotinonitrile

A suspension of 4-chloro-6-methylnicotinamide (29.7 g, 195 mmol) in POCl$_3$ (80.2 mL, 860 mmol) is heated at 110° C. for 15 min (gas development). The mixture is allowed to cool to rt, and is treated with PCl$_5$ (57.0 g, 274 mmol) over 20 min. The mixture is heated again at 110° C. for 1 h. The mixture is allowed to cool to rt, and is evaporated under reduced pressure. The residue is diluted with EtOAc, and cooled to 0° C. Aq. 10% Na$_2$CO$_3$ is added. The mixture is extracted with EtOAc (3×). The combined org. layers are washed with brine, dried over Na$_2$SO$_4$, filtered, and the solvents are removed under reduced pressure. Purification of the crude by automated FC (Biotage, EtOAc/heptane 2:98→30:70) yields the title compound. LC-MS: $t_R$=0.55 min, MH+=194.15 (conditions 4).

4-Chloro-5-cyano-2-methylpyridine 1-oxide

To a sol. of 4-chloro-6-methylnicotinonitrile (10.0 g, 65.5 mmol) and H$_2$O$_2$.H$_2$NCONH$_2$ (18.5 g, 197 mmol) in CH$_2$Cl$_2$ (80 mL) at 0° C. is added trifluoroacetic acid anhydride (27.9 mL, 197 mmol) dropwise. The mixture is stirred at rt for 3.5 h. Aq. 10% KI (800 mL) is carefully added. The phases are separated, and the aq. Layer is extracted with CH$_2$Cl$_2$. The combined org. layers are washed with aq. sat. Na$_2$S$_2$O$_3$ and brine. The org. layer is dried over Na$_2$SO$_4$, filtered, and the solvents are removed under reduced pressure to yield the crude title compound. LC-MS: $t_R$=0.34 min, MH+=210.22 (conditions 4).

4-Chloro-6-(hydroxymethyl)nicotinonitrile

4-Chloro-5-cyano-2-methylpyridine 1-oxide (11.3 g, 66.9 mmol) is dissolved in Ac$_2$O (132 mL), and conc. H$_2$SO$_4$ (3 drops) is added at rt. The mixture is heated to 110° C. and stirred at this temperature for 1 h. The mixture is poured slowly onto ice/water, and aq. sat. NaHCO$_3$ is added. The resulting mixture is stirred for 15 min. The phases are separated, and the aq. layer is extracted with EtOAc (2×). The combined org. layers are washed with brine, dried over Na$_2$SO$_4$, filtered, and the solvents are removed under reduced pressure. The crude is diluted with MeOH (162 mL). Water (82 mL) and K$_2$CO$_3$ (30.5 g, 221 mmol) are added. The mixture is stirred at rt for 30 min. The solvents are partially removed under reduced pressure. Purification of the residue by automated FC (Biotage, MeOH/CH$_2$Cl$_2$ 1:99→3:97, 340 g silicagel, then a second time with EtOAc/heptane 1:99→45:55, 100 g silicagel) yields the title product. LC-MS: $t_R$=0.41 min, MH+=168.95 (conditions 4).

(4-Chloro-5-cyanopyridin-2-yl)methyl methanesulfonate

Methansulfonyl chloride (0.527 mL, 6.79 mmol) is added to a solution of 4-chloro-6-(hydroxymethyl)nicotinonitrile (1.10 g, 6.17 mmol) and Et$_3$N (1.29 mL, 9.26 mmol) in CH$_2$Cl$_2$ (32 mL) at 0° C., and the mixture is stirred for 15 min. Aq. sat. NaHCO$_3$ is added, and the phases are separated. The org. layer is extracted with CH$_2$Cl$_2$, and the combined org. layers are washed with brine, dried over Na$_2$SO$_4$, filtered, and the solvents are removed under reduced pressure to yield the crude title compound. LC-MS: $t_R$=0.56 min, MH+=247.19 (conditions 4).

4-Chloro-6-((3-nitro-1H-pyrazol-1-yl)methyl)nicotinonitrile

Prepared according to general procedure 4 with NaH (55% suspension in oil, 215 mg, about 5.37 mmol), (4-chloro-5-cyanopyridin-2-yl)methyl methanesulfonate (1.52 g, 6.14 mmol), 5-methyl-3-nitro-1H-pyrazole (609 mg, 5.12 mmol) in DMF (15 mL). The reaction is complete after 2 h at rt. Purification of the crude by automated FC (Biotage, EtOAc/heptane 5:95→20:80, 50 g silicagel) yields the title compound. LC-MS: $t_R$=0.63 min (conditions 4).

6-((3-Amino-1H-pyrazol-1-yl)methyl)-4-chloronicotinonitrile

Prepared according to general procedure 5 with Fe (2.32 g, 42.1 mmol) and 4-chloro-6-((3-nitro-1H-pyrazol-1-yl)methyl)nicotinonitrile (1.11 g, 4.21 mmol) in EtOH (48 mL), and aq. sat. NH$_4$Cl (7 mL). The reaction is complete after 2 days at 75° C. and yields the crude title compound. LC-MS: $t_R$=0.38 min, MH+=234.14 (conditions 4).

N-(1-((4-((3H-[1,2,3]Triazolo[4,5-b]pyridin-3-yl)oxy)-5-cyanopyridin-2-yl)methyl)-1H-pyrazol-3-yl)-2-(4-isopropylphenyl)acetamide Prepared according to general procedure 3 from 2-(4-isopropylphenyl)acetic acid (407 mg, 2.29 mmol), 6-((3-amino-1H-pyrazol-1-yl)methyl)-4-chloronicotinonitrile (534 mg, 2.29 mmol), HATU (1.30 g, 3.43 mmol), and DIPEA (1.96 mL, 11.4 mmol) in DMF (5 mL). The reaction is complete overnight. Purification by HPLC yields the title compound. LC-MS: $t_R$=0.82 min, MH+=494.18 (conditions 4).

Example 157. N-[1-(4-Chloro-5-cyano-pyridin-2-ylmethyl)-1H-pyrazol-3-yl]-2-(4-isopropyl-phenyl)-acetamide A solution of N-(1-((4-((3H-[1,2,3]triazolo[4,5-b]pyridin-3-yl)oxy)-5-cyanopyridin-2-yl)methyl)-1H-pyrazol-3-yl)-2-(4-isopropylphenyl)acetamide (162 mg, 0.328 mmol) in POCl$_3$ (0.65 mL) is stirred at rt for 10 min. The mixture is quenched with aq. sat. NaHCO$_3$, the phases are separated, and the org. layer is extracted with EtOAc. The comb. org. layers are washed with brine, dried over MgSO$_4$, filtered, and the solvents are removed under reduced pressure. Purification of the crude by HPLC yields example 157. LC-MS: $t_R$=0.90 min, MH+=394.26 (conditions 4).

2-(4-Allylphenyl)-N-(1-(4-fluorobenzyl)-1H-pyrazol-3-yl)acetamide

A mixture of 2-(4-bromophenyl)-N-(1-(4-fluorobenzyl)-1H-pyrazol-3-yl)acetamide (252 mg, 0.65 mmol), allylboronic acid pinacol ester (0.366 mL, 1.95 mmol), $K_2CO_3$ (135 mg, 0.975 mmol) and $Pd(PPh_3)_4$ (75.1 mg, 0.065 mmol) in dioxane (6.5 mL) is stirred at 110° C. for 4 h. The mixture is stirred further at rt overnight. The mixture is filtrated, and the filtrate is diluted with EtOAc and washed with brine. The org. layer is dried over $MgSO_4$, filtered, and the solvents are removed under reduced pressure. Purification of the crude by automated FC (Biotage, 25 g silicagel, EtOAc/heptane 30:70→100:0) yields the title product. LC-MS: $t_R$=0.91 min, $MH^+$=350.26 (conditions 3).

Example 158: 2-(4-Cyclopropylmethyl-phenyl)-N-[1-(4-fluoro-benzyl)-1H-pyrazol-3-yl]-acetamide A solution of 2-(4-allylphenyl)-N-(1-(4-fluorobenzyl)-1H-pyrazol-3-yl)acetamide (63 mg, 0.18 mmol) and $CH_2ClI$ (0.0472 mL, 0.648 mmol) in $CH_2Cl_2$ (1.8 mL) is treated at 0° C. with $Et_2Zn$ (1.0 M in hexanes, 0.43 mL, 0.432 mmol). The mixture is stirred at 0° C. for 1 h, and is allowed to warm to rt, and stirred for 2 h. The mixture is again cooled to 0° C., and $CH_2ClI$ (0.0944 mL, 1.296 mmol), followed by $Et_2Zn$ (1.0 M in hexanes, 0.86 mL, 0.864 mmol) are added. The mixture is stirred at 0° C. for 30 min. Aq. sat. $NH_4Cl$ is added, and the mixture was extracted with EtOAc. The combined org. layers are washed with brine, dried over $MgSO_4$, filtered, and the solvents are removed under reduced pressure. Purification of the crude by automated FC (Biotage, 10 g silicagel, EtOAc/heptane 20:80→65:35) and subsequently by HPLC yields example 158. LC-MS: $t_R$=0.94 min, $MH^+$=364.30 (conditions 3).

5-Bromo-2-(3-fluoroazetidin-1-yl)pyridine

Prepared according to general procedure 9 from 2,5-dibromopyridine (1.00 g, 4.22 mmol), 3-fluoroazetidine hydrochloride (504 mg, 4.52 mmol), and DBU (1.35 mL, 9.03 mmol) in DMSO (30 mL). The same amounts of 3-fluoroazetidine hydrochloride, and DBU are added again after 24 h, and the reaction is complete after 4 days. Purification of the crude by automated FC (Büchi, EtOAc/heptane 2:98→3:97→5:95→10:90→15:85, 20 g silicagel, flow 13 mL/min) yields the title product.

tert-Butyl 2-(6-(3-fluoroazetidin-1-yl)pyridin-3-yl)acetate

Prepared according to general procedure 6 from 5-bromo-2-(3-fluoroazetidin-1-yl)pyridine (546 mg, 2.36 mmol), (2-(tert-butoxy)-2-oxoethyl)zinc(II) chloride (0.5M in $Et_2O$, 5.20 mL, 2.60 mmol), $Pd_2(dba)_3$ (108 mg, 0.118 mmol) and Q-Phos (168 mg, 0.236 mmol) in THF (3 mL). The reaction is complete after 3 h. Purification of the crude by automated FC (Büchi, EtOAc/heptane 2:98→5:95→10:90, 20 g silicagel, flow 18 mL/min) yields the title product. LC-MS: $t_R$=0.59 min, $MH^+$=267.08 (conditions 3).

2-(6-(3-Fluoroazetidin-1-yl)pyridin-3-yl)acetic acid

Prepared according to general procedure 7 from tert-butyl 2-(6-(3-fluoroazetidin-1-yl)pyridin-3-yl)acetate (370 mg, 1.39 mmol) and HCl (4M in dioxane, 12 mL) in $CH_2Cl_2$ (12 mL). The reaction is complete after 20 h. Removing the solvents under reduced pressure yields the crude title product.

5-Bromo-N-cyclopropyl-N-methylpyridin-2-amine

Prepared according to general procedure 9 from 2,5-dibromopyridine (1.00 g, 4.22 mmol), N-cyclopropyl methylamine hydrochloride (486 mg, 4.52 mmol), and DBU (1.35 mL, 9.03 mmol) in DMSO (30 mL). The same amounts of N-cyclopropyl methylamine hydrochloride, and DBU are added again after 24 h, and the reaction is complete after 7 days. Purification of the crude by automated FC (Büchi, EtOAc/heptane 2:98→3:97→5:95→10:90→15:85, 20 g silicagel, flow 13 mL/min) yields the title product.

tert-Butyl 2-(6-(cyclopropyl(methyl)amino)pyridin-3-yl)acetate

Prepared according to general procedure 6 from 5-bromo-N-cyclopropyl-N-methylpyridin-2-amine (148 mg, 0.652 mmol), (2-(tert-butoxy)-2-oxoethyl)zinc(II) chloride (0.5M in $Et_2O$, 1.24 mL, 0.62 mmol), $Pd_2(dba)_3$ (30 mg, 0.033 mmol) and Q-Phos (46 mg, 0.065 mmol) in THF (3 mL). The reaction is complete after 20 h. Purification of the crude by automated FC (Büchi, EtOAc/heptane 2:98→5:95→10:90, 10 g silicagel, flow 10 mL/min) yields the title product.

2-(6-(Cyclopropyl(methyl)amino)pyridin-3-yl)acetic acid

Prepared according to general procedure 7 from tert-butyl 2-(6-(cyclopropyl(methyl)amino)pyridin-3-yl)acetate (459 mg, 1.55 mmol) and HCl (4M in dioxane, 15 mL) in $CH_2Cl_2$ (15 mL). The reaction is complete after 20 h. Removing the solvents under reduced pressure yields the crude title product.

The following examples were prepared according to general procedure 3, from the appropriate carboxylic acids and aminopyrazoles:

| Example No | Name | LC-MS ($t_R$; $MH^+$; conditions) |
|---|---|---|
| 159 | N-[1-(5-Cyano-pyridin-2-ylmethyl)-1H-pyrazol-3-yl]-2-[6-(3-fluoro-azetidin-1-yl)-pyridin-3-yl]-acetamide | 0.53 min; 392.30; conditions 3 |
| 160 | N-[1-(3,4-Difluoro-benzyl)-1H-pyrazol-3-yl]-2-[6-(3-fluoro-azetidin-1-yl)-pyridin-3-yl]-acetamide | 0.59 min; 401.73; conditions 3 |
| 161 | N-[1-(4-Cyano-benzyl)-1H-pyrazol-3-yl]-2-[6-(3-fluoro-azetidin-1-yl)-pyridin-3-yl]-acetamide | 0.59 min; 391.18; conditions 3 |
| 162 | 2-[6-(3-Fluoro-azetidin-1-yl)-pyridin-3-yl]-N-[1-(4-fluoro-benzyl)-1H-pyrazol-3-yl]-acetamide | 0.62 min; 383.79; conditions 3 |
| 163 | 2-[6-(3-Fluoro-azetidin-1-yl)-pyridin-3-yl]-N-[1-(4-methoxy-benzyl)-1H-pyrazol-3-yl]-acetamide | 0.62 min; 396.01; conditions 3 |
| 164 | N-[1-(5-Cyano-pyridin-2-ylmethyl)-1H-pyrazol-3-yl]-2-[6-(cyclopropyl(methyl)amino)-pyridin-3-yl]-acetamide | 0.56 min; 387.75; conditions 3 |
| 165 | 2-[6-(Cyclopropyl(methyl)amino)-pyridin-3-yl]-N-[1-(3,4-difluoro-benzyl)-1H-pyrazol-3-yl]-acetamide | 0.66 min; 397.99; conditions 3 |

-continued

| Example No | Name | LC-MS ($t_R$; MH+; conditions) |
|---|---|---|
| 166 | N-[1-(4-Cyano-benzyl)-1H-pyrazol-3-yl]-2-[6-(cyclopropyl(methyl)amino)-pyridin-3-yl]-acetamide | 0.62 min; 386.84; conditions 3 |
| 167 | 2-[6-(Cyclopropyl(methyl)amino)-pyridin-3-yl]-N-[1-(4-fluoro-benzyl)-1H-pyrazol-3-yl]-acetamide | 0.64 min; 380.02; conditions 3 |
| 168 | 2-[6-(Cyclopropyl(methyl)amino)-pyridin-3-yl]-N-[1-(4-methoxy-benzyl)-1H-pyrazol-3-yl]-acetamide | 0.64 min; 392.02; conditions 3 |

Example 169. N-[1-(5-Cyano-4-methyl-pyridin-2-ylmethyl)-1H-pyrazol-3-yl]-2-(4-isopropyl-phenyl)-acetamide A mixture of Example 157 (30 mg, 0.0762 mmol), trimethylboroxine (9.56 mg, 0.0762 mmol), $K_2CO_3$ (15.8 mg, 0.114 mmol) and Pd(PPh$_3$)$_4$ (8.8 mg, 0.00762 mmol) in dioxane (0.5 mL) is degased, and is stirred in a closed vial at 110° C. overnight. The mixture is allowed to cool to rt, is diluted with water, and is extracted with EtOAc. The org. layer is washed with brine, dried over MgSO$_4$, filtered, and the solvents are removed under reduced pressure. Purification of the crude by HPLC yields example 169. LC-MS: $t_R$=0.79 min, MH+=374.31 (conditions 4).

Example 170. N-[1-(5-Cyano-4-cyclopropyl-pyridin-2-ylmethyl)-1H-pyrazol-3-yl]-2-(4-isopropyl-phenyl)-acetamide A mixture of Example 157 (30 mg, 0.0762 mmol), cyclopropylboronic acid (19.6 mg, 0.228 mmol), $K_2CO_3$ (15.8 mg, 0.114 mmol) and Pd(PPh$_3$)$_4$ (8.8 mg, 0.00762 mmol) in dioxane (0.5 mL) is degased, and is stirred in a closed vial at 110° C. overnight. The mixture is allowed to cool to rt, is diluted with water, and is extracted with EtOAc. The org. layer is washed with brine, dried over MgSO$_4$, filtered, and the solvents are removed under reduced pressure. Purification of the crude by HPLC yields example 170. LC-MS: $t_R$=0.83 min, MH+=400.32 (conditions 4).

5-Bromo-2-(pyrrolidin-1-yl)pyridine

A mixture of 2,5-dibromopyridine (2.00 g, 8.44 mmol), pyrrolidine (0.698 mL, 8.44 mmol) and DBU (1.35 mL, 9.03 mmol) in DMSO (30 mL) is stirred at 80° C. for 4 days. The mixture is allowed to cool to rt, and the solvents are removed under reduced pressure. Purification of the crude by automated FC (Büchi, 20 g silicagel, EtOAc/heptane 2:98→3:97→5:95→10:90→15:85) yields the title product. LC-MS: $t_R$=0.48 min, MH+=229.01 (conditions 3).

tert-Butyl 2-(6-(pyrrolidin-1-yl)pyridin-3-yl)acetate

According to general procedure 6, from 5-bromo-2-(pyrrolidin-1-yl)pyridine (1.63 g, 7.18 mmol), 2-tert-butoxy-2-oxoethylzinc chloride (0.5M in diethyl ether, 15.8 mL, 7.90 mmol), Pd$_2$(dba)$_3$ (329 mg, 0.359 mmol) and Q-PHOS (510 mg, 0.718 mmol) in THF (3 mL). After 3 h at 90° C. the reaction is complete. Purification of the crude by automated FC (Büchi, 10 g silicagel, flow 10 mL/min, EtOAc/heptane 2:98→5:95→10:90) yields the title product. LC-MS: $t_R$=0.63 min, MH+=263.14 (conditions 3).

2-(6-(Pyrrolidin-1-yl)pyridin-3-yl)acetic acid

According to general procedure 7, from tert-butyl 2-(6-(pyrrolidin-1-yl)pyridin-3-yl)acetate (410 mg, 1.56 mmol) and HCl (4M in dioxane, 15 mL) in $CH_2Cl_2$ (15 mL). After 21 h at rt the reaction is complete. Removing the solvents under reduced pressure leads to the title crude product. LC-MS: $t_R$=0.42 min, MH+=207.22 (conditions 3).

5-Bromo-N-(2-methoxyethyl)-N-methylpyridin-2-amine

A mixture of 2,5-dibromopyridine (2.00 g, 8.44 mmol), N-(2-methoxyethyl)methylamine (0.97 mL, 9.03 mmol) and DBU (1.35 mL, 9.03 mmol) in DMSO (30 mL) is stirred at 80° C. for 5 days. The mixture is allowed to cool to rt, and the solvents are removed under reduced pressure. Purification of the crude by automated FC (Büchi, 20 g silicagel, EtOAc/heptane 2:98→3:97→5:95→10:90→15:85) yields the title product. LC-MS: $t_R$=0.50 min, MH+=244.95 (conditions 3).

tert-Butyl 2-(6-((2-methoxyethyl)(methyl)amino)pyridin-3-yl)acetate

According to general procedure 6, from 5-bromo-N-(2-methoxyethyl)-N-methylpyridin-2-amine (1.47 g, 6.00 mmol), 2-tert-butoxy-2-oxoethylzinc chloride (0.5M in diethyl ether, 13.2 mL, 6.60 mmol), Pd$_2$(dba)$_3$ (275 mg, 0.300 mmol) and Q-PHOS (426 mg, 0.600 mmol) in THF (3 mL). The reaction is complete after 4 days at 90° C. Purification of the crude by automated FC (Büchi, 10 g silicagel, flow 10 mL/min, EtOAc/heptane 2:98→5:95→10:90) yields the title product. LC-MS: $t_R$=0.60 min, MH+=281.14 (conditions 3).

2-(6-((2-Methoxyethyl)(methyl)amino)pyridin-3-yl)acetic acid

According to general procedure 7, from tert-butyl 2-(6-((2-methoxyethyl)(methyl)amino)pyridin-3-yl)acetate (197 mg, 0.703 mmol) and HCl (4M in dioxane, 7 mL) in $CH_2Cl_2$ (7 mL). The reaction is complete overnight at rt. Removing the solvents under reduced pressure leads to the title crude product. LC-MS: $t_R$=0.39 min, MH+=225.13 (conditions 3).

5-Bromo-N-(cyclopropylmethyl)-N-methylpyridin-2-amine

A mixture of 2,5-dibromopyridine (2.00 g, 8.44 mmol), (cyclopropylmethyl)methylamine hydrochloride (1.10, 9.03 mmol) and DBU (2.70 mL, 18.1 mmol) in DMSO (30 mL) is stirred at 80° C. for 2 days. The mixture is allowed to cool to rt, and the solvents are removed under reduced pressure. Purification of the crude by automated FC (Büchi, 20 g silicagel, EtOAc/heptane 2:98→3:97→5:95→10:90→15:85) yields the title product. LC-MS: $t_R$=0.59 min, MH+=240.96 (conditions 3).

tert-Butyl 2-(6-((cyclopropylmethyl)(methyl)amino)pyridin-3-yl)acetate

A mixture of 5-bromo-N-(cyclopropylmethyl)-N-methyl-pyridin-2-amine (1.50 g, 6.20 mmol), Pd$_2$(dba)$_3$ (284 mg, 0.31 mmol) and Q-PHOS (440 mg, 0.620 mmol) in THF (3 mL) is heated to 90° C., and 2-tert-butoxy-2-oxoethylzinc chloride (0.5M in diethyl ether, 13.6 mL, 6.80 mmol) is added. The mixture is stirred at 90° C. for 5 days. Pd$_2$(dba)$_3$ (284 mg, 0.31 mmol), Q-PHOS (440 mg, 0.620 mmol) and 2-tert-butoxy-2-oxoethylzinc chloride (0.5M in diethyl ether, 13.6 mL, 6.80 mmol) are added again, and the mixture is stirred for 6 days at 80° C. The mixture is allowed to cool to rt. The mixture is filtered, and the filtrate is evaporated under reduced pressure. Purification of the crude by automated FC (Büchi, 10 g silicagel, flow 10 mL/min, EtOAc/heptane 2:98→5:95→10:90→15:85→20:80→25:75) yields the title product.

2-(6-(((Cyclopropylmethyl)(methyl)amino)pyridin-3-yl)acetic acid

According to general procedure 7, from tert-butyl 2-(6-((cyclopropylmethyl)(methyl)amino)pyridin-3-yl)acetate (115 mg, 0.416 mmol) and HCl (4M in dioxane, 6 mL) in CH$_2$Cl$_2$ (6 mL). The reaction is complete overnight at rt. Removing the solvents under reduced pressure leads to the title crude product.

The following examples were prepared according to general procedure 3, from the appropriate carboxylic acids and aminopyrazoles:

| Example No | Name | LC-MS (t$_R$; MH$^+$; conditions) |
|---|---|---|
| 171 | N-[1-(5-Cyano-pyridin-2-ylmethyl)-1H-pyrazol-3-yl]-2-[6-(ethyl-methyl-amino)-pyridin-3-yl]-acetamide | 0.55 min; 375.97; conditions 3 |
| 172 | N-[1-(3,4-Difluoro-benzyl)-1H-pyrazol-3-yl]-2-[6-(ethyl-methyl-amino)-pyridin-3-yl]-acetamide | 0.65 min; 386.01; conditions 3 |
| 173 | N-[1-(4-Cyano-benzyl)-1H-pyrazol-3-yl]-2-[6-(ethyl-methyl-amino)-pyridin-3-yl]-acetamide | 0.61 min; 375.04; conditions 3 |
| 174 | 2-[6-(Ethyl-methyl-amino)-pyridin-3-yl]-N-[1-(4-methoxy-benzyl)-1H-pyrazol-3-yl]-acetamide | 0.63 min; 380.02; conditions 3 |
| 175 | N-[1-(3,4-Difluoro-benzyl)-1H-pyrazol-3-yl]-2-(6-pyrrolidin-1-yl-pyridin-3-yl)-acetamide | 0.66 min; 398.00; conditions 3 |
| 176 | N-[1-(4-Cyano-benzyl)-1H-pyrazol-3-yl]-2-(6-pyrrolidin-1-yl-pyridin-3-yl)-acetamide | 0.62 min; 387.00; conditions 3 |
| 177 | N-[1-(4-Fluoro-benzyl)-1H-pyrazol-3-yl]-2-(6-pyrrolidin-1-yl-pyridin-3-yl)-acetamide | 0.65 min; 380.02; conditions 3 |
| 178 | N-[1-(4-Methoxy-benzyl)-1H-pyrazol-3-yl]-2-(6-pyrrolidin-1-yl-pyridin-3-yl)-acetamide | 0.64 min; 392.01; conditions 3 |
| 179 | N-[1-(5-Cyano-pyridin-2-ylmethyl)-1H-pyrazol-3-yl]-2-{6-[(2-methoxy-ethyl)-methyl-amino]-pyridin-3-yl}-acetamide | 0.54 min; 405.99; conditions 3 |
| 180 | N-[1-(3,4-Difluoro-benzyl)-1H-pyrazol-3-yl]-2-{6-[(2-methoxy-ethyl)-methyl-amino]-pyridin-3-yl}-acetamide | 0.65 min; 415.98; conditions 3 |
| 181 | N-[1-(4-Cyano-benzyl)-1H-pyrazol-3-yl]-2-{6-[(2-methoxy-ethyl)-methyl-amino]-pyridin-3-yl}-acetamide | 0.61 min; 404.98; conditions 3 |
| 182 | N-[1-(4-Fluoro-benzyl)-1H-pyrazol-3-yl]-2-{6-[(2-methoxy-ethyl)-methyl-amino]-pyridin-3-yl}-acetamide | 0.64 min; 398.01; conditions 3 |
| 183 | N-[1-(4-Methoxy-benzyl)-1H-pyrazol-3-yl]-2-{6-[(2-methoxy-ethyl)-methyl-amino]-pyridin-3-yl}-acetamide | 0.63 min; 410.00; conditions 3 |
| 184 | N-[1-(5-Cyano-pyridin-2-ylmethyl)-1H-pyrazol-3-yl]-2-[6-(cyclopropylmethyl-methyl-amino)-pyridin-3-yl]-acetamide | 0.60 min; 402.02; conditions 3 |
| 185 | 2-[6-(Cyclopropylmethyl-methyl-amino)-pyridin-3-yl]-N-[1-(3,4-difluoro-benzyl)-1H-pyrazol-3-yl]-acetamide | 0.70 min; 412.00; conditions 3 |
| 186 | N-[1-(4-Cyano-benzyl)-1H-pyrazol-3-yl]-2-[6-(cyclopropylmethyl-methyl-amino)-pyridin-3-yl]-acetamide | 0.66 min; 401.01; conditions 3 |
| 187 | 2-[6-(Cyclopropylmethyl-methyl-amino)-pyridin-3-yl]-N-[1-(4-fluoro-benzyl)-1H-pyrazol-3-yl]-acetamide | 0.68 min; 394.01; conditions 3 |
| 188 | 2-[6-(Cyclopropylmethyl-methyl-amino)-pyridin-3-yl]-N-[1-(4-methoxy-benzyl)-1H-pyrazol-3-yl]-acetamide | 0.68 min; 406.00; conditions 3 |
| 189 | N-[1-(4-Cyano-benzyl)-1H-pyrazol-3-yl]-2-(6-diethylamino-pyridin-3-yl)-acetamide | 0.64 min; 388.94; conditions 3 |
| 190 | 2-(6-Diethylamino-pyridin-3-yl)-N-[1-(4-fluoro-benzyl)-1H-pyrazol-3-yl]-acetamide | 0.66 min; 382.00; conditions 3 |
| 191 | 2-(6-Diethylamino-pyridin-3-yl)-N-[1-(4-methoxy-benzyl)-1H-pyrazol-3-yl]-acetamide | 0.66 min; 394.00; conditions 3 |

N-(1-(4-Bromobenzyl)-1H-pyrazol-3-yl)-2-(4-isopropylphenyl)acetamide

According to general procedure 3, from 1-(4-bromobenzyl)-1H-pyrazol-3-amine and 2-(4-isopropylphenyl)acetic acid. LC-MS: t$_R$=0.92 min, MH$^+$=412.21 (conditions 4).

Example 192: N-[1-(4-Cyclopropyl-benzyl)-1H-pyrazol-3-yl]-2-(4-isopropyl-phenyl)-acetamide A mixture of N-(1-(4-bromobenzyl)-1H-pyrazol-3-yl)-2-(4-isopropylphenyl)acetamide (109 mg, 0.25 mmol), cyclopropylboronic acid (64.4 mg, 0.75 mmol), K$_2$CO$_3$ (51.8 mg, 0.375 mmol) and Pd(Ph$_3$)$_4$ (28.9 mg, 0.025 mmol) in dioxane (1 ml) is degased, and is stirred in a closed vial at 110° C. overnight. The mixture is diluted with water and extracted with EtOAc. The org. layer is washed with brine, dried over MgSO$_4$, filtered and the solvents are removed under reduced pressure. Purification of the crude by HPLC yields example 192. LC-MS: t$_R$=0.94 min, MH$^+$=374.35 (conditions 4).

tert-Butyl 2-(6-chloropyridin-3-yl)acetate $BF_3OEt_2$ (0.2 mL) is added to a mixture of 2-chloropyridine-5-acetic acid (1.72 g, 10 mmol) and tert-butyl 2,2,2-trichloroacetimidate (3.58 mL, 20 mmol) in THF (20 mL), and the mixture is stirred overnight. The mixture is quenched with aq. sat. $NaHCO_3$ and extracted with EtOAc. The comb. org. layers are washed with brine, dried over $MgSO_4$, and concentrated under reduced pressure. Purification of the crude by FC (EtOAc/heptane 5:95→40:60) yields the title product. LC-MS: $t_R$=0.85 min, $MH^+$=228.29 (conditions 3).

tert-Butyl 2-(6-cyclopropylpyridin-3-yl)acetate

A mixture of tert-butyl 2-(6-chloropyridin-3-yl)acetate (250 mg, 1.1 mmol), cyclopropylboronic acid (283 mg, 3.29 mmol), $K_2CO_3$ (228 mg, 1.65 mmol) and $Pd(PPh_3)_4$ (127 mg, 0.11 mmol) in dioxane (11 mL) is degased. The mixture is stirred in a closed vial at 110° C. overnight. The mixture is extracted between EtOAc and brine, and the org. layer is dried over $MgSO_4$, filtered, and the solvents are removed under reduced pressure. Purification of the crude by automated FC (Biotage, 50 g silicagel, EtOAc/heptane 2:98→90:10) yields the title product. LC-MS: $t_R$=0.50 min, $MH^+$=234.37 (conditions 4).

2-(6-Cyclopropylpyridin-3-yl)acetic acid

A mixture of tert-butyl 2-(6-cyclopropylpyridin-3-yl)acetate (148 mg, 0.634 mmol) in HCl (4M in dioxane, 10 mL) is stirred at rt for 7 h. The solvents are removed under reduced pressure to yield the crude title product. LC-MS: $t_R$=0.22 min, $MH^+$=178.44 (conditions 4).

The following examples were prepared according to general procedure 3, from the appropriate carboxylic acids and aminopyrazoles:

| Example No | Name | LC-MS (to $MH^+$; conditions) |
|---|---|---|
| 193 | N-[1-(4-Chloro-3-fluoro-benzyl)-1H-pyrazol-3-yl]-2-(6-cyclopropyl-pyridin-3-yl)-acetamide | 0.59 min; 385.00; conditions 4 |
| 194 | N-[1-(3-Chloro-4-fluoro-benzyl)-1H-pyrazol-3-yl]-2-(6-cyclopropyl-pyridin-3-yl)-acetamide | 0.59 min; 385.17; conditions 4 |

1-(4-Bromobenzyl)-3-nitro-1H-pyrazole

According to general procedure 4 from $K_2CO_3$ (3.46 g, 25.0 mmol), 4-bromobenzyl bromide (2.50 g, 10.0 mmol), 5-nitro-1H-pyrazole (1.13 g, 10.0 mmol), and $Bu_4NBr$ (658 mg 2.00 mmol) in acetone (50 mL). The reaction is complete overnight. Purification of the crude by automated FC (Biotage, 100 g silicagel, EtOAc/heptane 20:80→80:20) yields the desired product. LC-MS: $t_R$=0.86 min, (conditions 3).

4-((3-Nitro-1H-pyrazol-1-yl)methyl)phenol

A degassed mixture of 1-(4-bromobenzyl)-3-nitro-1H-pyrazole (564 mg, 2 mmol), $Pd_2(dba)_3$ (91.6 mg, 0.1 mmol), tetramethyl di-tBuXPhos (96.2 mg, 0.2 mmol) and KOH (673 mg, 12 mmol) in dioxane (2 mL) and $H_2O$ (4 mL) is stirred at 100° C. for 1 h. The mixture is quenched with aq. 1 M HCl and extracted with EtOAc. The combined org. layers are washed with brine, dried over $MgSO_4$, filtered, and the solvents are removed under reduced pressure. Purification by automated FC (Biotage, 50 g silicagel, MeOH/$CH_2Cl_2$ 2:998→15:985), followed by HPLC yields the title product. LC-MS: $t_R$=0.69 min, (conditions 3).

3-Nitro-1-(4-(vinyloxy)benzyl)

H-pyrazole. A mixture of 4-((3-nitro-1H-pyrazol-1-yl)methyl)phenol (304 mg, 1.39 mmol), vinyl acetate (0.256 mL, 2.77 mmol), chloro(1,5-cyclooctadiene)iridium(I) dimer (18.5 mg, 0.0277 mmol) and $Na_2CO_3$ (88.2 mg, 0.832 mmol) in toluene (2 mL) is stirred at 105° C. for 4 h. The mixture is allowed to cool to rt, and is diluted with $H_2O$. The mixture is extracted with EtOAc. The combined org. layers is washed with brine, and the solvents are removed under reduced pressure. Purification of the crude by automated FC (Biotage, 25 g silicagel, EtOAc/heptane 2:8→8:2) yields the title compound. LC-MS: $t_R$=0.86 min, (conditions 3).

1-(4-(Vinyloxy)benzyl)-1H-pyrazol-3-amine

Prepared according to general procedure 5 from Zn (powder, 140 mg, 2.14 mmol), 3-nitro-1-(4-(vinyloxy)benzyl)-1H-pyrazole (105 mg, 0.428 mmol) in acetone (4 mL), and aq. sat. $NH_4Cl$ (1 mL). The title product is obtained. LC-MS: $t_R$=0.60 min, $MH^+$=316.31 (conditions 3).

2-(4-Isopropylphenyl)-N-(1-(4-(vinyloxy)benzyl)-1H-pyrazol-3-yl)acetamide

Prepared according to general procedure 3 from 2-(4-isopropylphenyl)acetic acid (79 mg, 0.44 mmol), 1-(4-(vinyloxy)benzyl)-1H-pyrazol-3-amine (95 mg, 0.44 mmol), HATU (252 mg, 0.662 mmol), and DIPEA (0.227 mL, 1.32 mmol) in DMF (4 mL). The reaction is complete after 1 h. Purification by HPLC yields the title compound. LC-MS: $t_R$=0.96 min, $MH^+$=376.33 (conditions 4).

Example 195. N-[1-(4-Cyclopropoxy-benzyl)-1H-pyrazol-3-yl]-2-(4-isopropyl-phenyl)-acetamide A soln. of 2-(4-isopropylphenyl)-N-(1-(4-(vinyloxy)benzyl)-1H-pyrazol-3-yl)acetamide (65 mg, 0.173 mmol) in $CH_2Cl_2$ (1.7 mL) is treated at 0° C. with $CH_2ClI$ (0.0454 mL, 0.623 mmol) and $Et_2Zn$ (1.0 M in hexanes, 0.415 mL, 0.415 mmol). The mixture is stirred at 0° C. for 1 h. Then, more $CH_2ClI$ (0.0908 mL, 1.246 mmol) and $Et_2Zn$ (1.0 M in hexanes, 0.830 mL, 0.830 mmol, 4.8 eq) are added. The mixture is allowed to warm to RT and stirred for 30 min. Aq. sat. $NH_4Cl$ is added, and the mixture is extracted with EtOAc. The combined org. layers are washed with brine, dried over $MgSO_4$, filtered, and the solvents are removed under reduced pressure. Purification by HPLC yields example 195. LC-MS: $t_R$=0.97 min, $MH^+$=390.33 (conditions 4).

(rac.)-1-Bromo-4-(1-methoxyethyl)benzene

NaH (55% in oil, 197 mg, about 4.51 mmol) is added to a sol. of (rac.)-1-(4-bromophenyl)ethanol (605 mg, 3.01 mmol) in THF (10 mL) at 0° C. The mixture is stirred for 30 min at 0° C., and MeI (0.94 mL, 15 mmol) is added. The mixture is allowed to warm up to rt, and is stirred for 4 h. A little water is added, and the solvents are removed under reduced pressure. The residue is diluted with $CH_2Cl_2$, and is dried over $MgSO_4$. The mixture is filtered, and the solvents are removed under reduced pressure. Purification of the residue by automated FC (Büchi, EtOAc/heptane 1:99→3:97→5:95→8:92, 20 g silicagel, flow 18 mL/min) yields the title product.

(rac.)-tert-butyl 2-(4-(1-methoxyethyl)phenyl)acetate

According to general procedure 6, from (rac.)-1-bromo-4-(1-methoxyethyl)benzene (470 mg, 2.19 mmol), 2-tert-butoxy-2-oxoethylzinc chloride (0.5M in Et$_2$O, 5.0 mL, 2.5 mmol), Pd$_2$(dba)$_3$ (100 mg, 0.109 mmol), and Q-Phos (158 mg, 0.219 mmol) in THF (5 mL). The reaction is complete after 30 min at 90° C. Purification of the residue by automated FC (Büchi, EtOAc/heptane 2:98→4:96-10:90, 20 g silicagel, flow 18 mL/min) yields the title product. LC-MS: $t_R$=0.93 min, (conditions 3).

(rac.)-2-(4-(1-Methoxyethyl)phenyl)acetic acid

According to general procedure 7, from (rac.)-tert-butyl 2-(4-(1-methoxyethyl)phenyl)acetate (240 mg, 0.959 mmol) and HCl (4M in dioxane, 5 mL) in CH$_2$Cl$_2$ (10 mL). The reaction is complete overnight at rt. The solvents are removed under reduced pressure to yield the crude title compound that is used without further purification. LC-MS: $t_R$=0.65 min (conditions 3).

Methyl 2-(4-methyl-3-oxo-3,4-dihydro-2H-benzo[b][1,4]oxazin-6-yl)acetate

NaH (55% in oil, 12 mg, 0.27 mmol) in added to a sol. of methyl (3,4-dihydro-3-oxo-2H-1,4-benzoxazin-6-yl)acetate (50 mg, 0.22 mmol) in THF (2 mL) at 0° C. The mixture is stirred for 15 min, and MeI (0.030 mL, 0.34 mmol) is added. The mixture is stirred for 30 min at 0° C., and the solvents are removed under reduced pressure. Purification by HPLC yields the title product. LC-MS: $t_R$=0.71 min, MH$^+$=277.12 (conditions 3).

2-(4-Methyl-3-oxo-3,4-dihydro-2H-benzo[b][1,4]oxazin-6-yl)acetic acid

A mixture of methyl 2-(4-methyl-3-oxo-3,4-dihydro-2H-benzo[b][1,4]oxazin-6-yl)acetate (7.0 mg, 0.030 mmol) in aq. 2.5 M NaOH (0.5 mL) and MeOH (1.5 mL) is stirred at rt for 30 min. The solvents are partially removed under reduced pressure, and the pH is adjusted to 3 with aq. 1M HCl. The mixture is extracted with CH$_2$Cl$_2$. The combined org. layers are dried over MgSO$_4$, filtered, and the solvents are removed under reduced pressure to yield the title crude product. LC-MS: $t_R$=0.59 min, MH$^+$=263.00 (conditions 3).

The following examples were prepared according to general procedure 3, from the appropriate carboxylic acids and aminopyrazoles:

| Example No | Name | LC-MS ($t_R$; MH$^+$; conditions) |
| --- | --- | --- |
| 196[1] | N-[1-(5-Cyano-pyridin-2-ylmethyl)-1H-pyrazol-3-yl]-2-(4-cyclobutoxy-phenyl)-acetamide | 0.84 min; 387.73; conditions 3 |
| 197[1] | N-[1-(4-Cyano-benzyl)-1H-pyrazol-3-yl]-2-(4-cyclobutoxy-phenyl)-acetamide | 0.89 min; 386.71; conditions 3 |
| 198[1] | 2-(4-Cyclobutoxy-phenyl)-N-[1-(4-fluoro-benzyl)-1H-pyrazol-3-yl]-acetamide | 0.92 min; 380.01; conditions 3 |
| 199[1] | 2-(4-Cyclobutoxy-phenyl)-N-[1-(4-methoxy-benzyl)-1H-pyrazol-3-yl]-acetamide | 0.91 min; 392.04; conditions 3 |
| 200[1] | 2-(4-Cyclobutoxy-phenyl)-N-[1-(5-fluoro-pyridin-2-ylmethyl)-1H-pyrazol-3-yl]-acetamide | 0.84 min; 380.87; conditions 3 |
| 201 | rac-N-[1-(4-Fluoro-benzyl)-1H-pyrazol-3-yl]-2-[4-(1-methoxy-ethyl)-phenyl]-acetamide | 0.85 min; 368.02; conditions 3 |
| 202 | rac-N-[1-(3,4-Difluoro-benzyl)-1H-pyrazol-3-yl]-2-[4-(1-methoxy-ethyl)-phenyl]-acetamide | 0.87 min; 385.87; conditions 3 |
| 203 | rac-N-[1-(5-Cyano-pyridin-2-ylmethyl)-1H-pyrazol-3-yl]-2-[4-(1-methoxy-ethyl)-phenyl]-acetamide | 0.76 min; 376.03; conditions 3 |
| 204 | N-[1-(4-Fluoro-benzyl)-1H-pyrazol-3-yl]-2-[4-(2-oxo-pyrrolidin-1-yl)-phenyl]-acetamide | 0.78 min; 392.99; conditions 3 |
| 205 | N-[1-(3,4-Difluoro-benzyl)-1H-pyrazol-3-yl]-2-quinoxalin-6-yl-acetamide | 0.80 min; 379.95; conditions 3 |
| 206 | N-[1-(3,4-Difluoro-benzyl)-1H-pyrazol-3-yl]-2-quinolin-7-yl-acetamide | 0.64 min; 378.95; conditions 3 |
| 207 | N-[1-(3,4-Difluoro-benzyl)-1H-pyrazol-3-yl]-2-(1H-indol-6-yl)-acetamide | 0.84 min; 367.25; conditions 3 |
| 208 | N-[1-(3,4-Difluoro-benzyl)-1H-pyrazol-3-yl]-2-(3-oxo-3,4-dihydro-2H-benzo[1,4]oxazin-7-yl)-acetamide | 0.76 min; 398.97; conditions 3 |
| 209 | N-[1-(3,4-Difluoro-benzyl)-1H-pyrazol-3-yl]-2-(4-methyl-3-oxo-3,4-dihydro-2H-benzo[1,4]oxazin-7-yl)-acetamide | 0.81 min; 412.99; conditions 3 |

[1]For the preparation of the carboxylic acid, see: Page, D.; Balaux, E.; Boisvert, L; Liu, Z.; Milburn, C.; Tremblay, M.; Wei, Zhongyong; W., Simon; L., Xuehong; Cheng, Y; et al., Bioorg. Med. Chem. Lett., 2008, 18, 3695.

5-Fluoro-2-((3-(2-(4-isopropylphenyl)acetamido)-1H-pyrazol-1-yl)methyl)pyridine 1-oxide To a solution of Example 106 (350 mg, 0.993 mmol,) in CH$_2$Cl$_2$ (3.5 mL) is added 3-chloroperbenzoic acid (343 mg, 1.99 mmol). The mixture is stirred overnight at rt. The mixture is diluted with EtOAc, and the org. layer is washed with aq. sat. Na$_2$S$_2$O$_3$, aq. sat. NaHCO$_3$, and brine. The org. layer is dried over MgSO$_4$, filtered and the solvents are removed under reduced pressure. Purification of the crude by automated FC (Biotage, 50 g silicagel, MeOH/CH$_2$Cl$_2$

Example 210: N-[1-(6-Cyano-5-fluoro-pyridin-2-ylmethyl)-1H-pyrazol-3-yl]-2-(4-isopropyl-phenyl)-acetamide To a sol. of 5-fluoro-2-((3-(2-(4-isopropylphenyl)acetamido)-1H-pyrazol-1-yl)methyl)pyridine 1-oxide (175 mg, 0.475 mmol) in $CH_3CN$ (10 mL) is added $Me_3SiCN$ (0.119 ml, 0.95 mmol) at rt. The mixture is stirred for 5 min, and diethylcarbamyl chloride (0.0903 ml, 0.713 mmol) is added dropwise. The mixture is stirred at 85° C. overnight. The mixture is partitioned between aq. sat. $NaHCO_3$ and EtOAc. The combined org. layers are washed with brine, dried over $MgSO_4$, filtered, and the solvents are removed under reduced pressure. Purification of the crude by HPLC yields example 210. LC-MS: $t_R$=0.82 min, $MH^+$=378.31 (conditions 4).

Example 211: N-[1-(6-Chloro-5-fluoro-pyridin-2-ylmethyl)-1H-pyrazol-3-yl]-2-(4-isopropyl-phenyl)-acetamide 5-Fluoro-2-((3-(2-(4-isopropylphenyl)acetamido)-1H-pyrazol-1-yl)methyl)pyridine 1-oxide (37.7 mg, 0.102 mmol) is added to $POCl_3$ (1 mL) at 0° C., and the mixture is stirred for 10 min at 0° C., and then for 2.5 h at rt. The mixture is heated to 60° C., and stirred at this temperature for 2 h. The mixture is dropped slowly on aq. sat. $NaHCO_3$ at 0° C. The mixture is extracted with EtOAc, and the combined org. layers are washed with brine, dried over $MgSO_4$, filtered and the solvents are removed under reduced pressure. Purification by HPLC yields example 211. LC-MS: $t_R$=0.86 min, $MH^+$=387.26 (conditions 4).

5-Bromo-1-methyl-1H-pyrrolo[2,3-b]pyridine

NaH (55% suspension in oil, 95 mg, about 213 mmol) is added to a sol. of 5-bromo-1H-pyrrolo[2,3-b]pyridine (350 mg, 1.78 mmol) in THF (2 mL) at 0° C. The mixture is stirred for 15 min, and MeI (0.17 mL, 2.7 mmol) is added. The mixture is stirred for 30 min at 0° C., and little water was added. The solvents were removed under reduced pressure. Purification of the residue by automated FC (Büchi, EtOAc/heptane 1:99→3:97→5:95→8:92, 20 g silicagel, flow 18 mL/min) yields the title product. LC-MS: $t_R$=0.81 min, $MH^+$=211.02 (conditions 3).

tert-Butyl 2-(1-methyl-1H-pyrrolo[2,3-b]pyridin-5-yl)acetate

Prepared according to general procedure 6 from 5-bromo-1-methyl-1H-pyrrolo[2,3-b]pyridine (100 mg, 0.474 mmol), (2-(tert-butoxy)-2-oxoethyl)zinc(II) chloride (0.5M in $Et_2O$, 1.90 mL, 0.95 mmol), $Pd_2(dba)_3$ (22 mg, 0.024 mmol) and Q-Phos (34 mg, 0.048 mmol) in THF (1 mL). The reaction is complete after 90 min. Purification of the crude by automated FC (Büchi, EtOAc/heptane 1:99→3:97→5:95→8:92, 20 g silicagel, flow 16 mL/min) yields the title product. LC-MS: $t_R$=0.78 min, $MH^+$=247.15 (conditions 3).

2-(1-Methyl-1H-pyrrolo[2,3-b]pyridin-5-yl)acetic acid

Prepared according to general procedure 7 from tert-butyl 2-(1-methyl-1H-pyrrolo[2,3-b]pyridin-5-yl)acetate (235 mg, 0.954 mmol) and HCl (4M in dioxane, 10 mL) in $CH_2Cl_2$ (10 mL). The reaction is complete overnight. Removing the solvents under reduced pressure yields the crude title product.

tert-Butyl 2-(3-methyl-2-oxo-2,3-dihydrobenzo[d]oxazol-6-yl)acetate

Prepared according to general procedure 6 from 6-bromo-3-methylbenzo[d]oxazol-2(3H)-one (230 mg, 1.01 mmol), (2-(tert-butoxy)-2-oxoethyl)zinc(II) chloride (0.5M in $Et_2O$, 4.00 mL, 2.00 mmol), $Pd_2(dba)_3$ (46 mg, 0.051 mmol) and Q-Phos (73 mg, 0.10 mmol) in dioxane (5 mL). The reaction is complete after 1 h at 90° C. Purification of the crude by automated FC (Büchi, EtOAc/heptane 1:99→3:97→5:95→8:92→15:85, 10 g silicagel, flow 10 mL/min) yields the title product. LC-MS: $t_R$=0.85 min, $MH^+$=305.12 (conditions 3).

2-(3-Methyl-2-oxo-2,3-dihydrobenzo[d]oxazol-6-yl)acetic acid

Prepared according to general procedure 7 from tert-butyl 2-(3-methyl-2-oxo-2,3-dihydrobenzo[d]oxazol-6-yl)acetate (198 mg, 0.752 mmol) and HCl (4M in dioxane, 4 mL) in $CH_2Cl_2$ (4 mL). The reaction is complete overnight. Removing the solvents under reduced pressure yields the crude title product. LC-MS: $t_R$=0.57 min (conditions 3).

tert-Butyl 2-(2-oxo-2,3-dihydrobenzo[d]oxazol-6-yl)acetate

Prepared according to general procedure 6 from 6-bromobenzo[d]oxazol-2(3H)-one (216 mg, 1.01 mmol), (2-(tert-butoxy)-2-oxoethyl)zinc(II) chloride (0.5M in $Et_2O$, 4.00 mL, 2.00 mmol), $Pd_2(dba)_3$ (46 mg, 0.051 mmol) and Q-Phos (73 mg, 0.10 mmol) in dioxane (5 mL). The reaction is complete after 1 h at 90° C. Purification of the crude by automated FC (Büchi, EtOAc/heptane 1:99→3:97→5:95→8:92→15:85, 10 g silicagel, flow 10 mL/min) yields the title product. LC-MS: $t_R$=0.78 min, $MH^+$=291.18 (conditions 3).

2-(2-Oxo-2,3-dihydrobenzo[d]oxazol-6-yl)acetic acid

Prepared according to general procedure 7 from tert-butyl 2-(2-oxo-2,3-dihydrobenzo[d]oxazol-6-yl)acetate (100 mg, 0.401 mmol) and HCl (4M in dioxane, 3 mL) in $CH_2Cl_2$ (3 mL). The reaction is complete overnight. Removing the solvents under reduced pressure yields the crude title product. LC-MS: $t_R$=0.50 min (conditions 3).

tert-Butyl 2-(1H-indol-5-yl)acetate

Prepared according to general procedure 6 from 5-bromoindole (300 mg, 1.53 mmol), (2-(tert-butoxy)-2-oxoethyl)zinc(II) chloride (0.5M in $Et_2O$, 6.00 mL, 3.00 mmol), $Pd_2(dba)_3$ (70 mg, 0.077 mmol) and Q-Phos (110 mg, 0.15 mmol) in dioxane (5 mL). The reaction is complete after 1 h at 90° C. Purification of the crude by automated FC (Büchi, EtOAc/heptane 1:99→3:97→5:95→8:92→15:85, 10 g silicagel, flow 10 mL/min) yields the title product. LC-MS: $t_R$=0.89 min, $MH^+$=232.19 (conditions 3).

2-(1H-Indol-5-yl)acetic acid

A mixture of tert-butyl 2-(1H-indol-5-yl)acetate (50 mg, 0.22 mmol) and NaOH (11 mg, 0.26 mmol) in MeOH (4 mL) is heated to 55° C. and stirred at this temperature for 2 h. The mixture is allowed to cool to rt, and the solvents are removed under reduced pressure. The residue is diluted with $CH_2Cl_2$, and aq. 1M HCl is added to pH 2-3. The phases are separated, and the org. layer is dried over $MgSO_4$, and filtered. The solvents are removed under reduced pressure to yield the crude title compound. LC-MS: $t_R$=0.89 min (conditions 3).

tert-Butyl 2-(1-methyl-1H-indol-5-yl)acetate

Prepared according to general procedure 6 from 5-bromo-1-methylindole (321 mg, 1.53 mmol), (2-(tert-butoxy)-2-oxoethyl)zinc(II) chloride (0.5M in $Et_2O$, 6.00 mL, 3.00 mmol), $Pd_2(dba)_3$ (70 mg, 0.077 mmol) and Q-Phos (110 mg, 0.15 mmol) in dioxane (5 mL). The reaction is complete after 1 h at 90° C. Purification of the crude by automated FC (Büchi, EtOAc/heptane 1:99→3:97→5:95→8:92→15:85, 10 g silicagel, flow 10 mL/min) yields the title product. LC-MS: $t_R$=0.94 min, $MH^+$=246.28 (conditions 3).

2-(1-Methyl-1H-indol-5-yl)acetic acid

A mixture of tert-butyl 2-(1H-indol-5-yl)acetate (53 mg, 0.22 mmol) and NaOH (11 mg, 0.26 mmol) in MeOH (4 mL) is heated to 55° C. and stirred at this temperature for 2 h. The mixture is allowed to cool to rt, and the solvents are removed under reduced pressure. The residue is diluted with $CH_2Cl_2$, and aq. 1M HCl is added to pH 2-3. The phases are separated, and the org. layer is dried over $MgSO_4$, and filtered. The solvents are removed under reduced pressure to yield the crude title compound. LC-MS: $t_R$=0.69 min (conditions 3).

tert-Butyl 2-(1-methyl-1H-indol-6-yl)acetate

Prepared according to general procedure 6 from 6-bromo-1-methylindole (321 mg, 1.53 mmol), (2-(tert-butoxy)-2-oxoethyl)zinc(II) chloride (0.5M in $Et_2O$, 6.00 mL, 3.00 mmol), $Pd_2(dba)_3$ (70 mg, 0.077 mmol) and Q-Phos (110 mg, 0.15 mmol) in dioxane (5 mL). The reaction is complete after 1 h at 90° C. Purification of the crude by automated FC (Büchi, EtOAc/heptane 1:99→3:97→5:95→8:92→15:85, 10 g silicagel, flow 10 mL/min) yields the title product. LC-MS: $t_R$=0.95 min, $MH^+$=246.25 (conditions 3).

2-(1-Methyl-1H-indol-6-yl)acetic acid

A mixture of tert-butyl 2-(1H-indol-6-yl)acetate (53 mg, 0.22 mmol) and NaOH (11 mg, 0.26 mmol) in MeOH (4 mL) is heated to 55° C. and stirred at this temperature for 2 h. The mixture is allowed to cool to rt, and the solvents are removed under reduced pressure. The residue is diluted with $CH_2Cl_2$, and aq. 1M HCl is added to pH 2-3. The phases are separated, and the org. layer is dried over $MgSO_4$, and filtered. The solvents are removed under reduced pressure to yield the crude title compound. LC-MS: $t_R$=0.69 min (conditions 3).

tert-Butyl 2-(1-methyl-1H-benzo[d]imidazol-6-yl)acetate

Prepared according to general procedure 6 from 6-bromo-1-methyl-1H-benzo[d]imidazole (490 mg, 2.32 mmol), (2-(tert-butoxy)-2-oxoethyl)zinc(II) chloride (0.5M in $Et_2O$, 5.10 mL, 2.55 mmol), $Pd_2(dba)_3$ (106 mg, 0.116 mmol) and Q-Phos (167 mg, 0.232 mmol) in dioxane (4 mL). The reaction is complete after 1 h at rt. Purification of the crude by automated FC (Büchi, EtOAc/heptane 1:99→3:97→5:95→8:92→15:85, 10 g silicagel, flow 10 mL/min) yields the title product. LC-MS: $t_R$=0.59 min, $MH^+$=247.11 (conditions 3).

2-(1-Methyl-1H-benzo[d]imidazol-6-yl)acetic acid

Prepared according to general procedure 7 from tert-butyl 2-(1-methyl-1H-benzo[d]imidazol-6-yl)acetate (50 mg, 0.203 mmol) and HCl (4M in dioxane, 2 mL) in $CH_2Cl_2$ (4 mL). The reaction is complete after 90 min. Removing the solvents under reduced pressure yields the crude title product. LC-MS: $t_R$=0.36 min (conditions 3).

tert-Butyl 2-(1-methyl-1H-indazol-5-yl)acetate

Prepared according to general procedure 6 from 5-bromo-1-methyl-1H-indazole (490 mg, 2.32 mmol), (2-(tert-butoxy)-2-oxoethyl)zinc(II) chloride (0.5M in $Et_2O$, 5.10 mL, 2.55 mmol), $Pd_2(dba)_3$ (106 mg, 0.116 mmol) and Q-Phos (167 mg, 0.232 mmol) in dioxane (4 mL). The reaction is complete after 1 h at rt. Purification of the crude by automated FC (Büchi, EtOAc/heptane 1:99→3:97→5:95→8:92→15:85, 10 g silicagel, flow 10 mL/min) yields the title product. LC-MS: $t_R$=0.88 min, $MH^+$=247.14 (conditions 3).

2-(1-Methyl-1H-indazol-5-yl)acetic acid

Prepared according to general procedure 7 from tert-butyl 2-(1-methyl-1H-indazol-5-yl)acetate (50 mg, 0.20 mmol) and HCl (4M in dioxane, 2 mL) in $CH_2Cl_2$ (4 mL). The reaction is complete after 4.5 h. Removing the solvents under reduced pressure yields the crude title product. LC-MS: $t_R$=0.60 min (conditions 3).

tert-Butyl 2-(1-methyl-1H-indazol-6-yl)acetate

Prepared according to general procedure 6 from 6-bromo-1-methyl-1H-indazole (490 mg, 2.32 mmol), (2-(tert-butoxy)-2-oxoethyl)zinc(II) chloride (0.5M in $Et_2O$, 5.10 mL, 2.55 mmol), $Pd_2(dba)_3$ (106 mg, 0.116 mmol) and Q-Phos (167 mg, 0.232 mmol) in dioxane (4 mL). The reaction is complete after 1 h at rt. Purification of the crude by automated FC (Büchi, EtOAc/heptane 1:99→3:97→5:95→8:92→15:85, 10 g silicagel, flow 10 mL/min) yields the title product. LC-MS: $t_R$=0.88 min, $MH^+$=247.14 (conditions 3).

2-(1-Methyl-1H-indazol-6-yl)acetic acid

Prepared according to general procedure 7 from tert-butyl 2-(1-methyl-1H-indazol-6-yl)acetate (50 mg, 0.20 mmol) and HCl (4M in dioxane, 2 mL) in $CH_2Cl_2$ (4 mL). The reaction is complete after 6.5 h. Removing the solvents under reduced pressure yields the crude title product. LC-MS: $t_R$=0.60 min (conditions 3).

tert-Butyl 2-(4-(3-fluorooxetan-3-yl)phenyl)acetate

Prepared according to general procedure 6 from 3-(4-bromophenyl)-3-fluorooxetane (WO2008156726, 150 mg, 0.649 mmol), (2-(tert-butoxy)-2-oxoethyl)zinc(II) chloride (0.5M in $Et_2O$, 1.43 mL, 0.714 mmol), $Pd_2(dba)_3$ (29.7 mg, 0.033 mmol) and Q-Phos (46 mg, 0.065 mmol) in THF (4 mL). The reaction is complete after 2 h at 85° C. Purification of the crude by automated FC (Büchi, EtOAc/heptane 10:90→30:70→50:50→75:25) yields the title product. LC-MS: $t_R$=0.90 min (conditions 3).

2-(4-(3-Fluorooxetan-3-yl)phenyl)acetic acid

A mixture of tert-butyl 2-(4-(3-fluorooxetan-3-yl)phenyl)acetate (10 mg, 0.038 mmol) in HCOOH (1 mL) is stirred at rt for 1 h. The solvents are removed under reduced pressure. The residue is dissolved in $CH_2Cl_2$, and the mixture is washed with aq. 0.01M HCl. After partitioning the layers in a Separator® (Biotage), the org. layer is concentrated under reduced pressure to yield the crude title product. LC-MS: $t_R$=0.63 min (conditions 3).

tert-Butyl 2-(4-(3-hydroxyoxetan-3-yl)phenyl)acetate

Prepared according to general procedure 6 from 3-(4-bromophenyl)oxetan-3-ol (WO2008156726, 200 mg, 0.873 mmol), (2-(tert-butoxy)-2-oxoethyl)zinc(II) chloride (0.5M in $Et_2O$, 3.66 mL, 1.83 mmol), $Pd_2(dba)_3$ (40 mg, 0.044 mmol) and Q-Phos (62 mg, 0.087 mmol) in THF (4 mL). The reaction is complete after 2 h at 85° C. Purification of the crude by automated FC (Büchi, EtOAc/heptane 10:90→30:70→50:50→75:25) yields the title product. LC-MS: $t_R$=0.76 min (conditions 3).

2-(4-(3-Hydroxyoxetan-3-yl)phenyl)acetic acid

Prepared according to general procedure 7 from tert-butyl 2-(4-(3-hydroxyoxetan-3-yl)phenyl)acetate (20 mg, 0.076 mmol) in HCOOH (1 mL). The reaction is complete after 1 h at rt. Removing the solvents under reduced pressure yields the crude title product. LC-MS: $t_R$=0.48 min (conditions 3).

tert-butyl 2-(4-(3-Methyloxetan-3-yl)phenyl)acetate

Prepared according to general procedure 6 from 3-(4-bromophenyl)-3-methyloxetane (105 mg, 0.462 mmol), (2-(tert-butoxy)-2-oxoethyl)zinc(II) chloride (0.5M in $Et_2O$, 1.02 mL, 0.509 mmol), $Pd_2(dba)_3$ (21 mg, 0.023 mmol) and Q-Phos (33 mg, 0.046 mmol) in THF (2.5 mL). The reaction is complete after 1.5 h at 85° C. Purification of the crude by automated FC (Büchi, EtOAc/heptane 10:90→30:70→50:50→75:25) yields the title product. LC-MS: $t_R$=0.91 min (conditions 3).

2-(4-(3-Methyloxetan-3-yl)phenyl)acetic acid

Prepared according to general procedure 7 from tert-butyl 2-(4-(3-methyloxetan-3-yl)phenyl)acetate (25 mg, 0.095 mmol) in HCOOH (1 mL). The reaction is complete after 1 h at rt. Removing the solvents under reduced pressure yields the crude title product. LC-MS: $t_R$=0.64 min (conditions 3).

tert-Butyl 2-(3,3-dimethyl-2-oxoindolin-5-yl)acetate

Prepared according to general procedure 6 from 5-bromo-3,3-dimethylindolin-2-one (367 mg, 1.53 mmol), (2-(tert-butoxy)-2-oxoethyl)zinc(II) chloride (0.5M in $Et_2O$, 6.0 mL, 3.0 mmol), $Pd_2(dba)_3$ (70 mg, 0.077 mmol) and Q-Phos (110 mg, 0.153 mmol) in dioxane (5 mL). The reaction is complete after 1.5 h at 90° C. Purification of the crude by automated FC (Büchi, EtOAc/heptane 1:99→3:97→5: 95→10:90→25:75→50:50) yields the title product. LC-MS: $t_R$=0.83 min, $MH^+$=276.28 (conditions 3).

2-(3,3-Dimethyl-2-oxoindolin-5-yl)acetic acid

Prepared according to general procedure 7 from tert-butyl 2-(3,3-dimethyl-2-oxoindolin-5-yl)acetate (56 mg, 0.20 mmol) in HCl (4M in dioxane, 2 mL) and $CH_2Cl_2$ (4 mL). The reaction is complete overnight at rt. Removing the solvents under reduced pressure yields the crude title product.

tert-Butyl 2-(1,3,3-trimethyl-2-oxoindolin-5-yl)acetate

Prepared according to general procedure 6 from 5-bromo-1,3,3-trimethylindolin-2-one (170 mg, 0.669 mmol), (2-(tert-butoxy)-2-oxoethyl)zinc(II) chloride (0.5M in $Et_2O$, 2.6 mL, 1.3 mmol), $Pd_2(dba)_3$ (31 mg, 0.033 mmol) and Q-Phos (48 mg, 0.077 mmol) in dioxane (4 mL). The reaction is complete after 20 min at 90° C. Purification of the crude by automated FC (Büchi, EtOAc/heptane 1:99→3: 97→5:95→10:90→25:75→50:50) yields the title product. LC-MS: $t_R$=0.89 min, $MH^+$=290.01 (conditions 3).

2-(1,3,3-Trimethyl-2-oxoindolin-5-yl)acetic acid

Prepared according to general procedure 7 from tert-butyl 2-(1,3,3-trimethyl-2-oxoindolin-5-yl)acetate (90 mg, 0.31 mmol) in HCl (4M in dioxane, 2 mL) and $CH_2Cl_2$ (4 mL). The reaction is complete overnight at rt. Removing the solvents under reduced pressure yields the crude title product. LC-MS: $t_R$=0.63 min, $MH^+$=275.23 (conditions 3).

tert-Butyl 2-(1-methyl-1H-benzo[d]imidazol-5-yl)acetate

Prepared according to general procedure 6 from 5-bromo-1-methyl-1H-benzo[d]imidazole (490 mg, 2.32 mmol), (2-(tert-butoxy)-2-oxoethyl)zinc(II) chloride (0.5M in $Et_2O$, 5.1 mL, 2.55 mmol), $Pd_2(dba)_3$ (106 mg, 0.116 mmol) and Q-Phos (167 mg, 0.232 mmol) in dioxane (4 mL). The reaction is complete after 2 h at 90° C. Purification of the crude by automated FC (Büchi, EtOAc/heptane 1:99→3: 97→5:95→10:90→25:75→50:50) yields the title product. LC-MS: $t_R$=0.60 min, $MH^+$=246.99 (conditions 3).

2-(1-Methyl-1H-benzo[d]imidazol-5-yl)acetic acid

Prepared according to general procedure 7 from tert-butyl 2-(1-methyl-1H-benzo[d]imidazol-5-yl)acetate (44 mg, 0.17 mmol) in HCl (4M in dioxane, 2 mL) and $CH_2Cl_2$ (4 mL). The reaction is complete after 3 h at rt. Removing the solvents under reduced pressure yields the crude title product. LC-MS: $t_R$=0.37 min, $MH^+$=191.16 (conditions 3).

3-(4-Bromophenyl)-3-methoxyoxetane 3-(4-Bromophenyl)oxetan-3-ol (WO2008156726, 150 mg, 0.65 mmol) is dissolved in DMF (2.00 mL). The mixture is cooled to 0° C., and NaH (29 mg, 0.72 mmol) is added. The mixture is stirred for 1 h at 0° C., and MeI (0.05 ml, 0.79 mmol) is added. The mixture is stirred at rt over 3 days. Water is added. The mixture is extracted with ether. The combined org. extracts are dried over $MgSO_4$, filtered, and the solvents are removed under reduced pressure under reduced pressure. Purification of the crude by automated FC (Combiflash, column 24 g, flow rate 35 mL/min, EtOAc/heptane 0:100→10:90→30:70) yields the title product. LC-MS: $t_R$=0.80 min, MH+=205.30 (conditions 3).

tert-Butyl 2-(4-(3-methoxyoxetan-3-yl)phenyl)acetate

Prepared according to general procedure 6 from 3-(4-bromophenyl)-3-methoxyoxetane (100 mg, 0.41 mmol), (2-(tert-butoxy)-2-oxoethyl)zinc(II) chloride (0.5M in Et$_2$O, 0.9 mL, 0.45 mmol), Pd$_2$(dba)$_3$ (19 mg, 0.021 mmol) and Q-Phos (29 mg, 0.041 mmol) in dioxane (3 mL). The reaction is complete after 2 h at 90° C. Purification of the crude by automated FC (Büchi, EtOAc/heptane 1:99→3:97→5:95→10:90→25:75→50:50) yields the title product. LC-MS: $t_R$=0.87 min, (conditions 3).

2-(4-(3-Methoxyoxetan-3-yl)phenyl)acetic acid

Prepared according to general procedure 7 from tert-butyl 2-(4-(3-methoxyoxetan-3-yl)phenyl)acetate (40 mg, 0.14 mmol) in HCOOH (1 mL). The reaction is complete after 1 h at rt. Removing the solvents under reduced pressure yields the crude title product. LC-MS: $t_R$=0.59 min (conditions 3).

The following examples were prepared according to general procedure 3, from the appropriate carboxylic acids and aminopyrazoles:

Examples 232 and 233: N-[1-(3,4-Difluoro-benzyl)-1H-pyrazol-3-yl]-2-[4-((R)-1-methoxy-ethyl)-phenyl]-acetamide and N-[1-(3,4-Difluoro-benzyl)-1H-pyrazol-3-yl]-2-[4-((S)-1-methoxy-ethyl)-phenyl]-acetamide Separation of the enantiomers from Example 202 by chiral HPLC yields examples 232 and 233. Absolute configuration of each enantiomer was attributed arbitrarily.

4-Cyanophenethyl acetate

Pyridine (1.1 mL, 13.6 mmol) and Ac$_2$O (0.51 mL, 5.44 mmol) are added to a sol. of 4-(2-hydroxyethyl)benzonitrile (200 mg, 1.36 mmol) in CH$_2$Cl$_2$ (3 mL). The mixture is stirred at rt overnight. The solvents are removed under reduced pressure, and the residue is partitioned between Et$_2$O and aq. 1M HCl. The org. layer is washed with aq. 1M HCl, aq. 10% Na$_2$CO$_3$, and brine. The org. layer is dried over MgSO$_4$, filtered, and the solvents are removed under reduced pressure to yield the crude title product. LC-MS: $t_R$=0.77 min (conditions 3).

4-(N-Hydroxycarbamimidoyl)phenethyl acetate

H$_2$NOH HCl (97.2 mg, 1.4 mmol) is added to a sol. of 4-cyanophenethyl acetate (241 mg, 1.27 mmol) in MeOH (4.2 mL). The sol. is stirred at 45° C. for 45 h, and is allowed

| Example No | Name | LC-MS ($t_R$; MH+; conditions) |
|---|---|---|
| 212 | N-[1-(3,4-Difluoro-benzyl)-1H-pyrazol-3-yl]-2-(1-methyl-1H-pyrrolo[2,3-b]pyridin-5-yl)-acetamide | 0.75 min; 382.26; conditions 3 |
| 213 | N-[1-(4-Fluoro-benzyl)-1H-pyrazol-3-yl]-2-(1-methyl-1H-pyrrolo[2,3-b]pyridin-5-yl)-acetamide | 0.73 min; 364.22; conditions 3 |
| 214 | N-[1-(4-Cyano-benzyl)-1H-pyrazol-3-yl]-2-(1-methyl-1H-pyrrolo[2,3-b]pyridin-5-yl)-acetamide | 0.70 min; 371.25; conditions 3 |
| 215 | N-[1-(4-Methoxy-benzyl)-1H-pyrazol-3-yl]-2-(1-methyl-1H-pyrrolo[2,3-b]pyridin-5-yl)-acetamide | 0.73 min; 376.29; conditions 3 |
| 216 | N-[1-(4-Cyano-3-fluoro-benzyl)-1H-pyrazol-3-yl]-2-(6-cyclopropyl-pyridin-3-yl)-acetamide | 0.51 min; 376.33; conditions 4 |
| 217 | N-[1-(3,4-Difluoro-benzyl)-1H-pyrazol-3-yl]-2-(3-methyl-2-oxo-2,3-dihydro-benzooxazol-6-yl)-acetamide | 0.80 min; 399.25; conditions 3 |
| 218 | N-[1-(3,4-Difluoro-benzyl)-1H-pyrazol-3-yl]-2-(2-oxo-2,3-dihydro-benzooxazol-6-yl)-acetamide | 0.75 min; 385.18; conditions 3 |
| 219 | N-[1-(3,4-Difluoro-benzyl)-1H-pyrazol-3-yl]-2-(1H-indol-5-yl)-acetamide | 0.83 min; 367.23; conditions 3 |
| 220 | N-[1-(3,4-Difluoro-benzyl)-1H-pyrazol-3-yl]-2-(1-methyl-1H-indol-5-yl)-acetamide | 0.88 min; 381.29; conditions 3 |
| 221 | N-[1-(3,4-Difluoro-benzyl)-1H-pyrazol-3-yl]-2-(1-methyl-1H-indol-6-yl)-acetamide | 0.88 min; 381.27; conditions 3 |
| 222 | N-[1-(3,4-Difluoro-benzyl)-1H-pyrazol-3-yl]-2-(3-methyl-3H-benzoimidazol-5-yl)-acetamide | 0.62 min; 382.29; conditions 3 |
| 223 | N-[1-(3,4-Difluoro-benzyl)-1H-pyrazol-3-yl]-2-(1-methyl-1H-indazol-5-yl)-acetamide | 0.83 min; 382.30; conditions 3 |
| 224 | N-[1-(3,4-Difluoro-benzyl)-1H-pyrazol-3-yl]-2-(1-methyl-1H-indazol-6-yl)-acetamide | 0.83 min; 382.28; conditions 3 |
| 225 | N-[1-(3,4-Difluoro-benzyl)-1H-pyrazol-3-yl]-2-[4-(3-fluoro-oxetan-3-yl)-phenyl]-acetamide | 0.85 min; 402.82; conditions 3 |
| 226 | N-[1-(3,4-Difluoro-benzyl)-1H-pyrazol-3-yl]-2-[4-(3-hydroxy-oxetan-3-yl)-phenyl]-acetamide | 0.73 min; 400.11; conditions 3 |
| 227 | N-[1-(3,4-Difluoro-benzyl)-1H-pyrazol-3-yl]-2-[4-(3-methyl-oxetan-3-yl)-phenyl]-acetamide | 0.85 min; 398.02; conditions 3 |
| 228 | N-[1-(3,4-Difluoro-benzyl)-1H-pyrazol-3-yl]-2-(3,3-dimethyl-2-oxo-2,3-dihydro-1H-indol-5-yl)-acetamide | 0.78 min; 411.29; conditions 3 |
| 229 | N-[1-(3,4-Difluoro-benzyl)-1H-pyrazol-3-yl]-2-(1,3,3-trimethyl-2-oxo-2,3-dihydro-1H-indol-5-yl)-acetamide | 0.83 min; 425.27; conditions 3 |
| 230 | N-[1-(3,4-Difluoro-benzyl)-1H-pyrazol-3-yl]-2-(1-methyl-1H-benzoimidazol-5-yl)-acetamide | 0.62 min; 382.29; conditions 3 |
| 231 | N-[1-(3,4-Difluoro-benzyl)-1H-pyrazol-3-yl]-2-[4-(3-methoxy-oxetan-3-yl)-phenyl]-acetamide | 0.82 min; 414.28; conditions 3 | to cool to rt. The solvents are removed under reduced pressure. Purification of the crude by automated FC (Combiflash, 24 g silicagel, MeOH/CH$_2$Cl$_2$ 0:100→5:95) yields the title product. LC-MS: $t_R$=0.45 min, MH$^+$=223.08 (conditions 3).

4-(5-Methyl-1,2,4-oxadiazol-3-yl)phenethyl acetate

A mixture of 4-(N-hydroxycarbamimidoyl)phenethyl acetate (50 mg, 0.225 mmol) in Ac$_2$O (0.225 mL) is stirred at 100° C. for 2 h. The mixture is allowed to cool to rt, and the solvents are removed under reduced pressure. The residue is dried in a Kugelrohr oven. Purification of the crude by automated FC (Combiflash, 4 g silicagel, MeOH/CH2Cl2 0:100→0.5:99.5) yields the title product. LC-MS: $t_R$=0.81 min, MH$^+$=247.22 (conditions 3).

2-(4-(5-Methyl-1,2,4-oxadiazol-3-yl)phenyl)ethan-1-ol

A mixture of 4-(5-methyl-1,2,4-oxadiazol-3-yl)phenethyl acetate (38.5 mg, 0.156 mmol), K$_2$CO$_3$ (216 mg, 1.56 mmol), in MeOH (1.35 mL) and water (0.15 mL) is stirred at rt overnight. The mixture is taken up in EtOAc and washed twice with water. The org. layer is dried over Na$_2$SO$_4$, filtered, and the solvents are removed under reduced pressure. LC-MS: $t_R$=0.65 min (conditions 3).

2-(4-(5-Methyl-1,2,4-oxadiazol-3-yl)phenyl)acetic acid

CrO$_3$ 2M in H$_2$SO$_4$, 0.288 mL, 0.575 mmol) is added at rt to a sol. of 2-(4-(5-methyl-1,2,4-oxadiazol-3-yl)phenyl)ethan-1-ol (23.5 mg, 0.115 mmol) in acetone (1.5 mL). The resulting mixture is stirred at rt for 6 min, and water is added. The mixture is extracted with CH$_2$Cl$_2$ (5×). The combined org. layers are dried over Na$_2$SO$_4$, filtered, and the solvents are removed under reduced pressure. LC-MS: $t_R$=0.65 min, MH$^+$=260.23 (conditions 3).

4-(1,2,4-Oxadiazol-3-yl)phenethyl acetate

A mixture of 4-(N-hydroxycarbamimidoyl)phenethyl acetate (50 mg, 0.225 mmol) in HC(OEt)$_3$ (0.225 mL) is stirred at 100° C. for 5 h. The mixture is allowed to cool to rt, and the solvents are removed under reduced pressure. The residue is dried in a Kugelrohr oven to yield the crude title product. LC-MS: $t_R$=0.80 min (conditions 3).

2-(4-(1,2,4-Oxadiazol-3-yl)phenyl)ethan-1-ol

A mixture of 4-(1,2,4-oxadiazol-3-yl)phenethyl acetate (52.2 mg, 0.225 mmol), K$_2$CO$_3$ (311 mg, 2.25 mmol), in MeOH (1.94 mL) and water (0.22 mL) is stirred at rt overnight. The mixture is taken up in EtOAc and washed twice with water. The org. layer is dried over Na$_2$SO$_4$, filtered, and the solvents are removed under reduced pressure. LC-MS: $t_R$=0.59 min (conditions 3).

2-(4-(1,2,4-Oxadiazol-3-yl)phenyl)acetic acid

CrO$_3$ 2M in H$_2$SO$_4$, 0.585 mL, 1.17 mmol) is added at rt to a sol. of 2-(4-(1,2,4-oxadiazol-3-yl)phenyl)ethan-1-ol (44.5 mg, 0.234 mmol) in acetone (3 mL). The resulting mixture is stirred at rt for 20 min, and water is added. The mixture is extracted with CH$_2$Cl$_2$ (5×). The combined org. layers are dried over Na$_2$SO$_4$, filtered, and the solvents are removed under reduced pressure. LC-MS: $t_R$=0.62 min (conditions 3).

tert-Butyl 2-(4-(3,3-difluorocyclobutyl)phenyl)acetate

Prepared according to general procedure 6 from 1-bromo-4-(3,3-difluorocyclobutyl)benzene (US 20100197591, 22 mg, 0.089 mmol), (2-(tert-butoxy)-2-oxoethyl)zinc(II) chloride (0.5M in Et$_2$O, 0.2 mL, 0.1 mmol), Pd$_2$(dba)$_3$ (4.1 mg, 0.045 mmol) and Q-Phos (6.3 mg, 0.089 mmol) in dioxane (1 mL). The reaction is complete after 3 h at 60° C. Purification of the crude by automated FC (Combiflash, EtOAc/heptane 0:100 80:20) yields the title product. LC-MS: $t_R$=1.00 min, (conditions 3).

2-(4-(3,3-Difluorocyclobutyl)phenyl)acetic acid

Prepared according to general procedure 7 from tert-butyl 2-(4-(3,3-difluorocyclobutyl)phenyl)acetate (12 mg, 0.050 mmol) in HCOOH (0.55 mL). The reaction is complete after 2 h at rt. Removing the solvents under reduced pressure yields the crude title product. LC-MS: $t_R$=0.78 min (conditions 3).

tert-Butyl 2-(4-(oxetan-3-yloxy)phenyl)acetate

Prepared according to general procedure 6 from 3-(4-bromophenoxy)oxetane (WO 2012120397, 68 mg, 0.30 mmol), (2-(tert-butoxy)-2-oxoethyl)zinc(II) chloride (0.5M in Et$_2$O, 0.70 mL, 0.35 mmol), Pd$_2$(dba)$_3$ (14 mg, 0.015 mmol) and X-Phos (7.1 mg, 0.015 mmol) in THF (1.85 mL). The reaction is complete overnight at 50° C. Purification of the crude by automated FC (Combiflash, MeOH/CH$_2$Cl$_2$ 0:100 2:98) yields the title product. LC-MS: $t_R$=0.88 min, (conditions 3).

2-(4-(Oxetan-3-yloxy)phenyl)acetic acid

Prepared according to general procedure 7 from tert-butyl 2-(4-(oxetan-3-yloxy)phenyl)acetate (40 mg, 0.15 mmol) in HCOOH (1.5 mL). The reaction is complete after 2.5 h at rt. Removing the solvents under reduced pressure yields the crude title product. LC-MS: $t_R$=0.60 min (conditions 3).

1-Bromo-4-(3,3-difluorocyclobutoxy)benzene

PPh$_3$ (267 mg, 1.02 mmol) is dissolved in dry toluene (2 mL) and cooled to 0° C. Dropwise, diethyl azodicarboxylate (0.165 mL, 1.02 mmol) is added and the light yellow sol. is stirred at 0° C. for 10 min. A sol. of 3,3-difluorocyclobutanol (100 mg, 0.925 mmol) in toluene (0.8 ml) is added. After stirring for another 10 min at rt, 4-bromophenol (160 mg, 0.925 mmol) is added, and the sol. is stirred at 100° C. overnight. The mixture is allowed to cool to rt, and the solvents are removed under reduced pressure. Purification of the crude by automated FC (Combiflash, 40 g silicagel, EtOAc/heptane 0:100→5:95) yields the title product. LC-MS: $t_R$=0.94 min (conditions 3).

tert-Butyl 2-(4-(3,3-difluorocyclobutoxy)phenyl)acetate

Prepared according to general procedure 6 from 1-bromo-4-(3,3-difluorocyclobutoxy)benzene (78 mg, 0.30 mmol), (2-(tert-butoxy)-2-oxoethyl)zinc(II) chloride (0.5M in Et$_2$O, 0.74 mL, 0.37 mmol), Pd$_2$(dba)$_3$ (14 mg, 0.015 mmol) and X-Phos (7.1 mg, 0.015 mmol) in THF (1.85 mL). The reaction is complete overnight at 50° C. Purification of the crude by automated FC (Combiflash, MeOH/CH$_2$Cl$_2$ 0:100 2:98) yields the title product. LC-MS: $t_R$=0.98 min, (conditions 3).

2-(4-(3,3-Difluorocyclobutoxy)phenyl)acetic acid

Prepared according to general procedure 7 from tert-butyl 2-(4-(3,3-difluorocyclobutoxy)phenyl)acetate (66 mg, 0.22 mmol) in HCOOH (2.2 mL). The reaction is complete after 40 min at rt. Removing the solvents under reduced pressure yields the crude title product. LC-MS: $t_R$=0.77 min (conditions 3).

(3-Methyloxetan-3-yl)methyl 4-methylbenzenesulfonate p-Toluenesulfonyl chloride (2.17 g, 11.4 mmol) is dissolved in CH$_2$Cl$_2$ (9.5 mL) at rt. Pyridine (1.53 mL, 19 mmol) is added, followed by 3-methyl-3-oxetanemethanol (0.977 mL, 9.5 mmol). The sol. is stirred at rt for 4 h. The sol. is diluted with CH$_2$Cl$_2$ and washed with aq. 0.1M HCl and with aq. sat. NaHCO$_3$. The org. layer is dried over Na$_2$SO$_4$, filtered, and the solvents are removed under reduced pressure. Purification of the crude by automated FC (Combiflash, EtOAc/heptane 0:100→60:40) yields the title product. LC-MS: $t_R$=0.80 min, MH$^+$=257.17 (conditions 3).

3-((4-Bromophenoxy)methyl)-3-methyloxetane

A mixture of (3-methyloxetan-3-yl)methyl 4-methylbenzenesulfonate (500 mg, 1.95 mmol), 4-bromphenol (371 mg, 2.15 mmol), KI (139 mg, 0.839 mmol) and K$_2$CO$_3$ (539 mg, 3.9 mmol) in DMF (2.8 mL) is stirred at 130° C. for 1.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g cartridge, EtOAc/heptane 0:100→30:70) yields the title product. LC-MS: $t_R$=0.87 min (conditions 3).

tert-Butyl 2-(4-((3-methyloxetan-3-yl)methoxy)phenyl)acetate

Prepared according to general procedure 6 from 3-((4-bromophenoxy)methyl)-3-methyloxetane (200 mg, 0.778 mmol), (2-(tert-butoxy)-2-oxoethyl)zinc(II) chloride (0.5M in Et$_2$O, 2.34 mL, 1.17 mmol), Pd$_2$(dba)$_3$ (36 mg, 0.039 mmol) and X-Phos (19 mg, 0.039 mmol) in THF (4.9 mL). The reaction is complete after 1.5 h at rt. Purification of the crude by automated FC (Combiflash, MeOH/CH$_2$Cl$_2$ 0:100 2:98) yields the title product. LC-MS: $t_R$=0.93 min, (conditions 3).

2-(4-((3-methyloxetan-3-yl)methoxy)phenyl)acetic acid

Prepared according to general procedure 7 from tert-butyl 2-(4-((3-methyloxetan-3-yl)methoxy)phenyl)acetate (105 mg, 0.36 mmol) in HCOOH (3.4 mL). The reaction is complete after 1.5 h at rt. Removing the solvents under reduced pressure yields the crude title product. LC-MS: $t_R$=0.68 min (conditions 3).

Oxetan-3-ylmethyl 4-methylbenzenesulfonate p-Toluenesulfonyl chloride (370 mg, 1.94 mmol) is dissolved in pyridine (1.62 mL, 20 mmol). 3-Oxetanemethanol (150 mg, 1.62 mmol) is added. The sol. is stirred at rt for 3 h. The sol. is diluted with EtOAc, and washed with aq. 0.1M HCl and with aq. sat. NaHCO$_3$. The org. layer is dried over Na$_2$SO$_4$, filtered, and the solvents are removed under reduced pressure. Purification of the crude by automated FC (Combiflash, EtOAc/heptane 0:100→50:50) yields the title product. LC-MS: $t_R$=0.75 min, MH$^+$=243.12 (conditions 3).

3-((4-Bromophenoxy)methyl)-3-oxetane

A mixture of oxetan-3-ylmethyl 4-methylbenzenesulfonate (300 mg, 1.24 mmol), 4-bromphenol (236 mg, 1.36 mmol), KI (88 mg, 0.43 mmol) and K$_2$CO$_3$ (342 mg, 2.48 mmol) in DMF (1.8 mL) is stirred at 130° C. for 1.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=0.82 min (conditions 3).

tert-Butyl 2-(4-(oxetan-3-ylmethoxy)phenyl)acetate

Prepared according to general procedure 6 from 3-((4-bromophenoxy)methyl)-3-oxetane (182 mg, 0.749 mmol), (2-(tert-butoxy)-2-oxoethyl)zinc(II) chloride (0.5M in Et$_2$O, 2.2 mL, 1.1 mmol), Pd$_2$(dba)$_3$ (34 mg, 0.037 mmol) and X-Phos (18 mg, 0.037 mmol) in THF (4.7 mL). The reaction is complete after 2.5 h at rt. Purification of the crude by automated FC (Combiflash, MeOH/CH$_2$Cl$_2$ 0:100 2:98) yields the title product. LC-MS: $t_R$=0.89 min, (conditions 3).

2-(4-(Oxetan-3-ylmethoxy)phenyl)acetic acid

Prepared according to general procedure 7 from tert-butyl 2-(4-(oxetan-3-ylmethoxy)phenyl)acetate (95 mg, 0.34 mmol) in HCOOH (1.3 mL). The reaction is complete after 2 h at rt. Removing the solvents under reduced pressure yields the crude title product. LC-MS: $t_R$=0.62 min (conditions 3).

(3,3-Difluoro-1-methylcyclobutyl)methyl 4-methylbenzenesulfonate p-Toluenesulfonyl chloride (252 mg, 1.32 mmol) is dissolved in pyridine (1.1 mL). (3,3-Difluoro-1-methylcyclobutyl)methanol (150 mg, 1.10 mmol) is added. The sol. is stirred at rt overnight. The sol. is diluted with EtOAc, and washed with aq. 0.1M HCl and with aq. sat. NaHCO$_3$. The org. layer is dried over Na$_2$SO$_4$, filtered, and the solvents are removed under reduced pressure to yield the crude title product. LC-MS: $t_R$=0.93 min, MH$^+$=243.12 (conditions 3).

1-Bromo-4-((3,3-difluoro-1-methylcyclobutyl)methoxy)benzene

A mixture of (3,3-difluoro-1-methylcyclobutyl)methyl 4-methylbenzenesulfonate (232 mg, 0.799 mmol), 4-bromphenol (152 mg, 0.879 mmol), KI (57 mg, 0.34 mmol) and K$_2$CO$_3$ (221 mg, 1.60 mmol) in DMF (1.2 mL) is stirred at 130° C. for 2.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=1.01 min (conditions 3).

tert-Butyl 2-(4-((3,3-difluoro-1-methylcyclobutyl) methoxy)phenyl)acetate

Prepared according to general procedure 6 from 1-bromo-4-((3,3-difluoro-1-methylcyclobutyl)methoxy)benzene (152 mg, 0.522 mmol), (2-(tert-butoxy)-2-oxoethyl)zinc(II) chloride (0.5M in Et$_2$O, 1.57 mL, 0.78 mmol), Pd$_2$(dba)$_3$ (24 mg, 0.026 mmol) and X-Phos (12.4 mg, 0.026 mmol) in THF (3.3 mL). The reaction is complete after 2.5 h at rt. Purification of the crude by automated FC (Combiflash, MeOH/CH$_2$Cl$_2$ 0:100 2:98) yields the title product. LC-MS: $t_R$=1.04 min, (conditions 3).

2-(4-((3,3-Difluoro-1-methylcyclobutyl)methoxy) phenyl)acetic acid

Prepared according to general procedure 7 from tert-butyl 2-(4-((3,3-difluoro-1-methylcyclobutyl)methoxy)phenyl) acetate (100 mg, 0.306 mmol) in HCOOH (1.2 mL). The reaction is complete after 2 h at rt. Removing the solvents under reduced pressure yields the crude title product. LC-MS: $t_R$=0.85 min (conditions 3).

(3,3-Difluorocyclobutyl)methyl 4-methylbenzenesulfonate p-Toluenesulfonyl chloride (281 mg, 1.47 mmol) is dissolved in pyridine (1.23 mL). (3,3-Difluorocyclobutyl) methanol (150 mg, 1.23 mmol) is added. The sol. is stirred at rt overnight. The sol. is diluted with EtOAc, and washed with aq. 0.1M HCl and with aq. sat. NaHCO$_3$. The org. layer is dried over Na$_2$SO$_4$, filtered, and the solvents are removed under reduced pressure to yield the crude title product. LC-MS: $t_R$=0.90 min (conditions 3).

1-Bromo-4-((3,3-difluorocyclobutyl)methoxy)benzene

A mixture of (3,3-difluorocyclobutyl)methyl 4-methylbenzenesulfonate (227 mg, 0.822 mmol), 4-bromphenol (156 mg, 0.904 mmol), KI (59 mg, 0.35 mmol) and K$_2$CO$_3$ (227 mg, 1.64 mmol) in DMF (1.2 mL) is stirred at 130° C. for 2.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=0.97 min (conditions 3).

tert-butyl 2-(4-((3,3-difluorocyclobutyl)methoxy) phenyl)acetate

Prepared according to general procedure 6 from 1-bromo-4-((3,3-difluorocyclobutyl)methoxy)benzene (102 mg, 0.368 mmol), (2-(tert-butoxy)-2-oxoethyl)zinc(II) chloride (0.5M in Et$_2$O, 1.52 mL, 0.76 mmol), Pd$_2$(dba)$_3$ (17 mg, 0.018 mmol) and X-Phos (8.8 mg, 0.018 mmol) in THF (2.3 mL). The reaction is complete after 2.5 h at rt. Purification of the crude by automated FC (Combiflash, EtOAc/heptane 0:100 10:90) yields the title product. LC-MS: $t_R$=1.00 min, (conditions 3).

2-(4-((3,3-Difluorocyclobutyl)methoxy)phenyl)acetic acid

Prepared according to general procedure 7 from tert-butyl 2-(4-((3,3-difluorocyclobutyl)methoxy)phenyl)acetate (72 mg, 0.231 mmol) in HCOOH (0.87 mL). The reaction is complete after 2 h at rt. Removing the solvents under reduced pressure yields the crude title product. LC-MS: $t_R$=0.80 min (conditions 3).

(3-Fluorooxetan-3-yl)methyl 4-methylbenzenesulfonate p-Toluenesulfonyl chloride (216 mg, 1.13 mmol) is dissolved in CH$_2$Cl$_2$ (0.95 mL). Pyridine (0.152 mL, 1.89 mmol) and (3-fluorooxetan-3-yl)methanol (WO 2011084402, 100 mg, 0.943 mmol) is added. The sol. is stirred at rt for 6 h. The sol. is diluted with CH$_2$Cl$_2$, and washed with aq. 0.1M HCl and with aq. sat. NaHCO$_3$. The org. layer is dried over Na$_2$SO$_4$, filtered, and the solvents are removed under reduced pressure to yield the crude title product. LC-MS: $t_R$=0.80 min, MH$^+$=261.13 (conditions 3).

3-((4-Bromophenoxy)methyl)-3-fluorooxetane

A mixture of (3-fluorooxetan-3-yl)methyl 4-methylbenzenesulfonate (138 mg, 0.530 mmol), 4-bromphenol (101 mg, 0.583 mmol), KI (38 mg, 0.23 mmol) and K$_2$CO$_3$ (147 mg, 1.06 mmol) in DMF (0.75 mL) is stirred at 130° C. for 1.5 h. The mixture is allowed to cool to rt, and is partitioned between EtOAc and water. The org. layer is washed with water (3×), dried over Na$_2$SO$_4$, filtered, and the solvents are removed under reduced pressure. Purification of the crude by FC (Combiflash, 12 g silicagel, EtOAc/heptane 0:100→30:70) yields the title product. LC-MS: $t_R$=0.84 min (conditions 3).

tert-Butyl 2-(4-((3-fluorooxetan-3-yl)methoxy)phenyl)acetate

Prepared according to general procedure 6 from 3-((4-bromophenoxy)methyl)-3-fluorooxetane (84 mg, 0.32 mmol), (2-(tert-butoxy)-2-oxoethyl)zinc(II) chloride (0.5M in Et$_2$O, 1.28 mL, 0.64 mmol), Pd$_2$(dba)$_3$ (15 mg, 0.016 mmol) and X-Phos (7.6 mg, 0.016 mmol) in THF (2.0 mL). The reaction is complete after 3 h at rt. Purification of the crude by automated FC (Combiflash, MeOH/CH$_2$Cl$_2$ 0:100→2:98) yields the title product. LC-MS: $t_R$=0.91 min, (conditions 3).

2-(4-((3-Fluorooxetan-3-yl)methoxy)phenyl)acetic acid

Prepared according to general procedure 7 from tert-butyl 2-(4-((3-fluorooxetan-3-yl)methoxy)phenyl)acetate (63 mg, 0.21 mmol) in HCOOH (0.80 mL). The reaction is complete after 3 h at rt. Removing the solvents under reduced pressure yields the crude title product. LC-MS: $t_R$=0.65 min (conditions 3).

5-Bromo-2-(3-methoxyoxetan-3-yl)pyridine

To an ice-cooled solution of 3-(5-bromopyridin-2-yl)oxetan-3-ol (U.S. Ser. No. 14/018,993, 1.34 g, 5.82 mmol) in DMF (30 mL), NaH (60% in oil, 303 mg, 7.57 mmol) is added, and the mixture is stirred at 0° C. for 30 min. MeI (0.44 mL, 6.99 mmol) is added, and the mixture is stirred at rt overnight. The mixture is diluted with water (100 mL) and EtOAc (100 mL). The layers are separated. The aq. phase is extracted with EtOAc (2×50 mL). The combined org. layers are washed with water and brine, dried over MgSO$_4$, filtered, and the solvents are removed under reduced pressure. Purification of the crude by automated FC (Flash master, column 100 g, flow: 45 mL/min, EtOAc/heptane 0:100→50:50) yields the title product. LC-MS: $t_R$=0.66 min, MH$^+$=244.06 (conditions 3).

tert-Butyl 2-(6-(3-methoxyoxetan-3-yl)pyridin-3-yl) acetate

Prepared according to general procedure 6 from 5-bromo-2-(3-methoxyoxetan-3-yl)pyridine (366 mg, 1.50 mmol), (2-(tert-butoxy)-2-oxoethyl)zinc(II) chloride (0.5M in Et$_2$O, 6.0 mL, 3.0 mmol), Pd$_2$(dba)$_3$ (69 mg, 0.075 mmol) and X-Phos (37 mg, 0.075 mmol) in THF (20 mL). The reaction is complete overnight at 45° C. Purification of the crude by HPLC yields the title product. LC-MS: $t_R$=0.71 min, MH$^+$=280.29 (conditions 3).

2-(6-(3-Methoxyoxetan-3-yl)pyridin-3-yl)acetic acid

Prepared according to general procedure 7 from tert-butyl 2-(6-(3-methoxyoxetan-3-yl)pyridin-3-yl)acetate (50 mg, 0.18 mmol) in HCOOH (2.0 mL). The reaction is complete overnight at rt. Removing the solvents under reduced pressure yields the crude title product. LC-MS: $t_R$=0.40 min, MH$^+$=224.20 (conditions 3).

6-Bromo-1,3-dimethyl-1H-indole

To an ice-cooled solution of 6-bromo-3-methylindole (1.00 g, 4.76 mmol) in DMF (20 mL), NaH (60% in oil, 381 mg, 9.52 mmol) is added, and the mixture is stirred at 0° C. for 30 min. MeI (0.449 mL, 7.14 mmol) is added, and the mixture is stirred at rt for 2 h. The mixture is diluted with water (100 mL) and EtOAc (100 mL). The layers are separated. The aq. phase is extracted with EtOAc (2×50 mL). The comb. org. layers are washed with water and brine, dried over MgSO$_4$, filtered, and the solvents are removed under reduced pressure to yield the crude title product. LC-MS: $t_R$=0.95 min (conditions 3).

tert-Butyl 2-(1,3-dimethyl-1H-indol-6-yl)acetate

Prepared according to general procedure 6 from 6-bromo-1,3-dimethyl-1H-indole (300 mg, 1.34 mmol), (2-(tert-butoxy)-2-oxoethyl)zinc(II) chloride (0.5M in Et$_2$O, 5.4 mL, 2.7 mmol), Pd$_2$(dba)$_3$ (61 mg, 0.067 mmol) and X-Phos (33 mg, 0.067 mmol) in THF (20 mL). The reaction is complete overnight at 45° C. Purification of the crude by HPLC yields the title product. LC-MS: $t_R$=0.98 min, MH$^+$=260.29 (conditions 3).

2-(1,3-Dimethyl-1H-indol-6-yl)acetic acid

Prepared according to general procedure 7 from tert-butyl 2-(1,3-dimethyl-1H-indol-6-yl)acetate (50 mg, 0.19 mmol) in HCOOH (2.0 mL). The reaction is complete after 3 h at rt. Removing the solvents under reduced pressure yields the crude title product. LC-MS: $t_R$=0.75 min, MH$^+$=204.28 (conditions 3).

tert-Butyl 2-(1,3-dimethyl-1H-indol-5-yl)acetate

Prepared according to general procedure 6 from 5-bromo-1,3-dimethyl-1H-indole (Repka, L. M.; Ni, J.; Reisman, S. E. J. Am. Chem. Soc., 2010, 132, 14418, 300 mg, 1.34 mmol), (2-(tert-butoxy)-2-oxoethyl)zinc(II) chloride (0.5M in Et$_2$O, 5.4 mL, 2.7 mmol), Pd$_2$(dba)$_3$ (61 mg, 0.067 mmol) and X-Phos (33 mg, 0.067 mmol) in THF (20 mL). The reaction is complete overnight at 45° C. Purification of the crude by HPLC yields the title product. LC-MS: $t_R$=0.98 min, MH$^+$=260.30 (conditions 3).

2-(1,3-Dimethyl-1H-indol-5-yl)acetic acid

Prepared according to general procedure 7 from tert-butyl 2-(1,3-dimethyl-1H-indol-5-yl)acetate (50 mg, 0.19 mmol) in HCOOH (2.0 mL). The reaction is complete after 3 h at rt. Removing the solvents under reduced pressure yields the crude title product. LC-MS: $t_R$=0.75 min, MH$^+$=204.30 (conditions 3).

tert-Butyl 2-(4-(1-(trifluoromethyl)cyclopropyl)phenyl)acetate

Prepared according to general procedure 6 from 1-bromo-4-(1-(trifluoromethyl)cyclopropyl)benzene (1.00 g, 3.77 mmol), (2-(tert-butoxy)-2-oxoethyl)zinc(II) chloride (0.5M in Et$_2$O, 10.6 mL, 5.3 mmol), Pd$_2$(dba)$_3$ (69 mg, 0.076 mmol) and X-Phos (37 mg, 0.076 mmol) in THF (20 mL). The reaction is complete overnight at rt. Purification of the crude by automated FC (Combiflash, EtOAc/heptane 0:100 to 45:55) yields the title product. LC-MS: $t_R$=1.02 min, (conditions 3).

2-(4-(1-(Trifluoromethyl)cyclopropyl)phenyl)acetic acid

Prepared according to general procedure 7 from tert-butyl 2-(4-(1-(trifluoromethyl)cyclopropyl)phenyl)acetate (100 mg, 0.33 mmol) in HCOOH (2.3 mL). The reaction is complete after 2.5 h at rt. Removing the solvents under reduced pressure yields the crude title product. LC-MS: $t_R$=0.82 min (conditions 3).

5-Bromo-2-(3-fluorooxetan-3-yl)pyridine

To a sol. of 3-(5-bromopyridin-2-yl)oxetan-3-ol (2.50 g, 10.9 mmol) in CH$_2$Cl$_2$ (60 mL) cooled at −78° C. is added (diethylamino)sulfur trifluoride (1.72 mL, 13 mmol) dropwise. The resulting mixture is stirred at −78° C. for 90 min, further at 0° C. for 20 min. The mixture is carefully quenched with aq. sat. NaHCO$_3$ (100 mL). The layers are separated and the aq. phase is extracted with CH$_2$Cl$_2$ (2×100 mL). The comb. org. layers are washed with brine (1×100 mL), dried over MgSO$_4$, filtered, and the solvents are removed under reduced pressure. Purification of the residue by automated FC (Flash master, column 100 g, flow 45 mL/min, EtOAc/heptane 0:100→25:75) yields the title product. LC-MS: $t_R$=0.72 min, MH$^+$=232.04 (conditions 3).

tert-Butyl 2-(6-(3-fluorooxetan-3-yl)pyridin-3-yl) acetate

Prepared according to general procedure 6 from 5-bromo-2-(3-fluorooxetan-3-yl)pyridine (600 mg, 2.59 mmol), (2-(tert-butoxy)-2-oxoethyl)zinc(II) chloride (0.5M in Et$_2$O, 10.4 mL, 5.2 mmol), Pd$_2$(dba)$_3$ (118 mg, 0.129 mmol) and X-Phos (64 mg, 0.129 mmol) in THF (20 mL). The reaction is complete overnight at 45° C. Purification of the crude by automated FC (Combiflash, EtOAc/heptane 0:100 20:80) yields the title product. LC-MS: $t_R$=0.80 min, MH$^+$=268.20 (conditions 3).

2-(6-(3-Fluorooxetan-3-yl)pyridin-3-yl)acetic acid

Prepared according to general procedure 7 from tert-butyl 2-(6-(3-fluorooxetan-3-yl)pyridin-3-yl)acetate (200 mg, 0.748 mmol) in HCOOH (5.0 mL). The reaction is complete overnight at rt. Removing the solvents under reduced pressure yields the crude title product. LC-MS: $t_R$=0.50 min, MH$^+$=212.12 (conditions 3).

5-Bromo-1,3-dimethyl-1H-pyrrolo[2,3-b]pyridine

NaH (60 in oil, 284 mg, 7.11 mmol) is added to an ice-cooled sol. of 5-bromo-3-methyl-7-azaindole (1.0 g, 4.74 mmol) in THF (12 mL). The mixture is stirred at rt for 15 min, then cooled again to 0° C. MeI (1.19 mL, 19 mmol) is added, and the resulting mixture is stirred at 0° C. for 10 min, then at rt overnight. Water is slowly added, followed by MgSO$_4$. The mixture is filtered, and the solvents are removed under reduced pressure. Purification of the residue by automated FC (Combiflash, column 40 g, flow 40 mL/min, EtOAc/heptane 0:100→20:80) yields the title product. LC-MS: $t_R$=0.87 min, MH$^+$=226.94 (conditions 3).

tert-Butyl 2-(1,3-dimethyl-1H-pyrrolo[2,3-b]pyridin-5-yl)acetate

Prepared according to general procedure 6 from 5-bromo-1,3-dimethyl-1H-pyrrolo[2,3-b]pyridine (450 mg, 1.98 mmol), (2-(tert-butoxy)-2-oxoethyl)zinc(II) chloride (0.5M in Et$_2$O, 8.00 mL, 4.00 mmol), Pd$_2$(dba)$_3$ (91 mg, 0.099 mmol) and X-Phos (49 mg, 0.099 mmol) in THF (30 mL). The reaction is complete overnight at 75° C. Purification of the crude by automated FC (Combiflash, EtOAc/heptane 0:100 30:70) yields the title product. LC-MS: $t_R$=0.76 min, MH$^+$=261.16 (conditions 3).

2-(1,3-Dimethyl-1H-pyrrolo[2,3-b]pyridin-5-yl)acetic acid

Prepared according to general procedure 7 from tert-butyl 2-(1,3-dimethyl-1H-pyrrolo[2,3-b]pyridin-5-yl)acetate (375 mg, 1.41 mmol) in HCOOH (9.3 mL). The reaction is complete overnight at rt. Removing the solvents under reduced pressure yields the crude title product. LC-MS: $t_R$=0.50 min, MH$^+$=205.18 (conditions 3).

5-Bromo-3-cyclobutyl-1H-indole

To a sol. of Et$_3$SiH (2.45 mL, 15 mmol) and trichloroacetic acid (0.75 mL, 7.36 mmol) in toluene (5 mL), is added dropwise at 70° C. a sol. of 5-bromoindole (990 mg, 5 mmol) and cyclobutanone (0.374 mL, 5 mmol) in toluene (2.5 mL). The resulting mixture is stirred at that temperature overnight. The mixture is allowed to cool to rt, and aq. 10% Na$_2$CO$_3$ is added. Et$_2$O is added, and the layers are separated. The aq. layer is extracted with Et$_2$O (2×) and the combined org. layers are dried over MgSO$_4$, filtered, and the solvents are removed under reduced pressure. Purification of the crude by automated FC (Combiflash, column 24 g, flow 35 mL/min, EtOAc/heptane 0:100→20:80) yields the title product. LC-MS: $t_R$=0.96 min, MH$^+$=250.07 (conditions 3).

5-Bromo-3-cyclobutyl-1-methyl-1H-indole

NaH (60% in oil, 175 mg, 4.38 mmol) is added to an ice-cooled sol. of 5-bromo-3-cyclobutyl-1H-indole (820 mg, 2.92 mmol) in THF (7.1 mL). The reaction mixture is stirred at rt for 15 min, and is cooled again to 0° C. MeI (0.734 mL, 11.7 mmol) is added, and the resulting mixture is stirred at 0° C. for 10 min, then at rt overnight. Water is slowly added, followed by EtOAc. The layers are separated, and the aq. layer is extracted with EtOAc (2×). The combined org. layers are washed with brine, dried over MgSO$_4$, filtered, and the solvents are removed under reduced pressure. Purification of the residue by FC (Combiflash, column 24 g, flow 35 mL/min, EtOAc/heptane 0:100→15:85) yields the title product. LC-MS: $t_R$=1.02 min, MH$^+$=264.08 (conditions 3).

tert-Butyl 2-(3-cyclobutyl-1-methyl-1H-indol-5-yl)acetate

Prepared according to general procedure 6 from 5-bromo-3-cyclobutyl-1-methyl-1H-indole (790 mg, 2.39 mmol), (2-(tert-butoxy)-2-oxoethyl)zinc(II) chloride (0.5M in Et$_2$O, 9.7 mL, 4.85 mmol), Pd$_2$(dba)$_3$ (94 mg, 0.102 mmol) and X-Phos (59 mg, 0.119 mmol) in THF (36 mL). The reaction is complete overnight at 45° C. Purification of the crude by automated FC (Combiflash, EtOAc/heptane 0:100 15:85) yields the title product. LC-MS: $t_R$=1.04 min, MH$^+$=300.14 (conditions 3).

2-(3-cyclobutyl-1-methyl-1H-indol-5-yl)acetic acid

Prepared according to general procedure 7 from tert-butyl 2-(3-cyclobutyl-1-methyl-1H-indol-5-yl)acetate (538 mg, 1.41 mmol) in HCOOH (9.3 mL). The reaction is complete after 3 h at rt. Removing the solvents under reduced pressure yields the crude title product. LC-MS: $t_R$=0.84 min, MH$^+$=244.21 (conditions 3).

5-Bromo-3-isopropyl-1H-indole

To a sol. of Et$_3$SiH (2.45 mL, 15 mmol) and trichloroacetic acid (0.75 mL, 7.36 mmol) in toluene (5 mL), is added dropwise at 70° C. a sol. of 5-bromoindole (990 mg, 5 mmol) and acetone (0.532 mL, 7.25 mmol) in toluene (2.5 mL). The resulting mixture is stirred at that temperature overnight. The mixture is allowed to cool to rt, and aq. 10% Na$_2$CO$_3$ is added. Et$_2$O is added, and the layers are separated. The aq. layer is extracted with Et$_2$O (2×) and the combined org. layers are dried over MgSO$_4$, filtered, and the solvents are removed under reduced pressure. Purification of the crude by automated FC (Combiflash, column 24 g, flow 35 mL/min, EtOAc/heptane 0:100→35:65) yields the title product. LC-MS: $t_R$=0.94 min, MH$^+$=238.11 (conditions 3).

5-Bromo-3-isopropyl-1-methyl-1H-indole

NaH (60% in oil, 782 mg, 7.06 mmol) is added to an ice-cooled sol. of 5-bromo-3-isopropyl-1H-indole (1.12 g, 4.70 mmol) in THF (11.5 mL). The reaction mixture is stirred at rt for 15 min, and is cooled again to 0° C. MeI (1.18 mL, 18.8 mmol) is added, and the resulting mixture is stirred at 0° C. for 10 min, then at rt overnight. Water is slowly added, followed by EtOAc. The layers are separated, and the aq. layer is extracted with EtOAc (2×). The combined org. layers are washed with brine, dried over MgSO$_4$, filtered, and the solvents are removed under reduced pressure. Purification of the residue by FC (Combiflash, column 24 g, flow 35 mL/min, EtOAc/heptane 0:100→30:70) yields the title product. LC-MS: $t_R$=1.00 min, MH$^+$=252.14 (conditions 3).

tert-Butyl 2-(3-isopropyl-1-methyl-1H-indol-5-yl) acetate

Prepared according to general procedure 6 from 5-bromo-3-isopropyl-1-methyl-1H-indole (570 mg, 2.05 mmol), (2-(tert-butoxy)-2-oxoethyl)zinc(III) chloride (0.5M in Et$_2$O, 8.3 mL, 4.15 mmol), Pd$_2$(dba)$_3$ (94 mg, 0.102 mmol) and X-Phos (59 mg, 0.119 mmol) in THF (31 mL). The reaction is complete overnight at 45° C. Purification of the crude by automated FC (Combiflash, EtOAc/heptane 0:100 to 20:80) yields the title product. LC-MS: $t_R$=1.02 min, MH$^+$=288.20 (conditions 3).

2-(3-Isopropyl-1-methyl-1H-indol-5-yl)acetic acid

Prepared according to general procedure 7 from tert-butyl 2-(3-isopropyl-1-methyl-1H-indol-5-yl)acetate (423 mg, 1.41 mmol) in HCOOH (9.3 mL). The reaction is complete after 3 h at rt. Removing the solvents under reduced pressure yields the crude title product. LC-MS: $t_R$=0.82 min, MH$^+$=232.23 (conditions 3).

5-Bromo-1-methyl-1H-indole-3-carbonitrile

NaH (60% in oil, 600 mg, 15 mmol) is added to an ice-cooled sol. of 5-bromo-1H-indole-3-carbonitrile (2.26 g, 10.0 mmol) in THF (24 mL). The reaction mixture is stirred at rt for 15 min, and is cooled again to 0° C. MeI (2.52 mL, 40.0 mmol) is added, and the resulting mixture is stirred at 0° C. for 10 min, then at rt overnight. Water is slowly added, followed by EtOAc. The layers are separated, and the aq. layer is extracted with EtOAc (2×). The combined org. layers are washed with brine, dried over MgSO$_4$, filtered, and the solvents are removed under reduced pressure. Purification of the residue by FC (Combiflash, column 24 g, flow 35 mL/min, EtOAc/heptane 0:100→40:60) yields the title product. LC-MS: $t_R$=0.86 min, MH$^+$=276.06 (conditions 3).

tert-Butyl 2-(3-cyano-1-methyl-1H-indol-5-yl)acetate

Prepared according to general procedure 6 from 5-bromo-1-methyl-1H-indole-3-carbonitrile (2.13 g, 8.87 mmol), (2-(tert-butoxy)-2-oxoethyl)zinc(II) chloride (0.5M in Et$_2$O, 36 mL, 18 mmol), Pd$_2$(dba)$_3$ (218 mg, 0.443 mmol) and X-Phos (406 mg, 0.443 mmol) in THF (104 mL). The reaction is complete overnight at 45° C. Purification of the crude by automated FC (Combiflash, EtOAc/heptane 0:100 35:65) yields the title product. LC-MS: $t_R$=0.91 min, MH$^+$=271.19 (conditions 3).

2-(3-Cyano-1-methyl-1H-indol-5-yl)acetic acid

Prepared according to general procedure 7 from tert-butyl 2-(3-cyano-1-methyl-1H-indol-5-yl)acetate (200 mg, 0.654 mmol) in TFA (0.75 mL) and CH$_2$Cl$_2$ (0.77 mL). The reaction is complete after 1 h at rt. Purification by HPLC yields title product. LC-MS: $t_R$=0.67 min, MH$^+$=215.19 (conditions 3).

(rac.)-5-Bromo-3-hydroxy-1-methyl-3-(trifluoromethyl)indolin-2-one

To a sol. of 5-bromo-1-methyl-1H-indole-2,3-dione (3.60 g, 15.0 mmol) in THF (100 mL) are added sequentially at rt trifluoromethyl)trimethylsilane (4.43 mL, 30.0 mmol) and CsF (91.1 mg, 0.60 mmol). The resulting sol. is stirred at rt overnight. The mixture is quenched with cold water (100 mL). The mixture is extracted with EtOAc (3×100 mL). The comb. org. layers are washed with brine (100 mL), dried over MgSO$_4$, filtered, and the solvents are removed under reduced pressure. Purification of the residue by automated FC (Combiflash, column 80 g, flow 60 mL/min, EtOAc/heptane 0:100→20:80) yields the trimethylsilyl-protected product. To a sol. of this isolated compound in MeOH (50 mL) is added aq. 2M HCl (40 mL). The resulting sol. is stirred at rt for 2 h. The reaction is diluted with CH$_2$Cl$_2$ (100 mL). The layers are separated and the aq. phase is extracted with CH$_2$Cl$_2$ (2×50 mL). The comb. org. layers are washed with brine (1×50 mL), dried over MgSO$_4$, filtered, and the solvents are removed under reduced pressure to yield the crude title product. LC-MS: $t_R$=0.79 min (conditions 3).

(rac.)-5-Bromo-1-methyl-3-(trifluoromethyl)indolin-3-ol

To an ice-cooled sol. of (rac.)-5-bromo-3-hydroxy-1-methyl-3-(trifluoromethyl)indolin-2-one (2.42 g, 7.80 mmol) in THF (100 mL) is added dropwise BH$_3$ (1M in THF, 24 mL, 24 mmol). The sol. is allowed to warm to rt overnight. Aq. 2M HCl (40 mL) is carefully added dropwise at 0° C. The biphasic system is stirred at t. for 5 min. Aq. 2M NaOH (40 mL) is added dropwise at 0° C. The resulting mixture is diluted with EtOAc (100 mL). The layers are separated, and the aq. layer is extracted with EtOAc (2×50 mL). The comb. org. layers are washed with aq. sat. NaHCO3 (1×100 mL), brine (1×100 mL), dried over MgSO$_4$, filtered, and the solvents are removed under reduced pressure to yield the crude title product. LC-MS: $t_R$=0.85 min (conditions 3).

5-Bromo-1-methyl-3-(trifluoromethyl)-1H-indole

To an ice-cooled solution of (rac.)-5-bromo-1-methyl-3-(trifluoromethyl)indolin-3-ol (3.32 g, 11.2 mmol) in pyridine (40 mL) is added dropwise SOCl$_2$ (1.22 mL, 16.8 mmol, 1.5 eq). The sol. is allowed to warm up to rt overnight. Aq. 2M HCl (40 mL) is carefully added at 0° C. The biphasic system is stirred at rt for 5 min. The resulting mixture is diluted with EtOAc (100 mL). The layers are separated, and the aq. layer is extracted with EtOAc (2×50 mL). The comb. org. layers are washed with aq. sat. NaHCO$_3$ (1×100 mL), brine (1×100 mL), dried over MgSO$_4$, filtered, and the solvents are removed under reduced pressure. Purification of the residue by automated FC (Combiflash, column 80 g, flow 60 mL/min, EtOAc/heptane 0:100→20:80) yields the title product. LC-MS: $t_R$=0.96 min (conditions 3).

tert-Butyl 2-(1-methyl-3-(trifluoromethyl)-1H-indol-5-yl)acetate

Prepared according to general procedure 6 from 5-bromo-1-methyl-3-(trifluoromethyl)-1H-indole (850 mg, 3.06 mmol), (2-(tert-butoxy)-2-oxoethyl)zinc(II) chloride (0.5M in Et$_2$O, 6.0 mL, 3.0 mmol), Pd$_2$(dba)$_3$ (140 mg, 0.153 mmol) and X-Phos (75.1 mg, 0.153 mmol) in THF (50 mL). The reaction is complete overnight at 45° C. Purification of the crude by automated FC (Combiflash, EtOAc/heptane 0:100 to 25:75) yields the title product. LC-MS: $t_R$=0.99 min (conditions 3).

2-(1-Methyl-3-(trifluoromethyl)-1H-indol-5-yl)acetic acid

Prepared according to general procedure 7 from tert-butyl 2-(1-methyl-3-(trifluoromethyl)-1H-indol-5-yl)acetate (200 tert-Butyl 2-(4-fluoro-2-(2,2,2-trifluoroethoxy)phenyl)acetate

Prepared according to general procedure 6 from 1-bromo-4-fluoro-2-(2,2,2-trifluoroethoxy)benzene (2.40 g, 8.79 mmol), (2-(tert-butoxy)-2-oxoethyl)zinc(II) chloride (0.5M in Et$_2$O, 35.2 mL, 17.6 mmol), Pd$_2$(dba)$_3$ (402 mg, 0.44 mmol) and X-Phos (216 mg, 0.44 mmol) in THF (110 mL). The reaction is complete overnight at 45° C. Purification of the crude by automated FC (Combiflash, EtOAc/heptane 0:100 to 25:75) yields the title product. LC-MS: $t_R$=0.98 min (conditions 3).

2-(4-fluoro-2-(2,2,2-trifluoroethoxy)phenyl)acetic acid

Prepared according to general procedure 7 from tert-butyl 2-(4-fluoro-2-(2,2,2-trifluoroethoxy)phenyl)acetate (2.60 g, 8.43 mmol) in HCl (4M in dioxane, 15 mL). The reaction is complete overnight at rt. Purification by HPLC yields title product. LC-MS: $t_R$=0.76 min (conditions 3).

tert-Butyl 2-(4-(pentafluoro-λ$^6$-sulfanyl)phenyl)acetate

Prepared according to general procedure 6 from pentafluoro(4-iodophenyl)-λ$^6$-sulfane (660 mg, 2.00 mmol), (2-(tert-butoxy)-2-oxoethyl)zinc(II) chloride (0.5M in Et$_2$O, 8.0 mL, 4.0 mmol), Pd$_2$(dba)$_3$ (92 mg, 0.10 mmol) and X-Phos (49 mg, 0.10 mmol) in THF (30 mL). The reaction is complete overnight at 45° C. Purification of the crude by HPLC yields the title product. LC-MS: $t_R$=0.89 min (conditions 3).

2-(4-(Pentafluoro-λ$^6$-sulfanyl)phenyl)acetic acid

Prepared according to general procedure 7 from tert-butyl 2-(4-(pentafluoro-λ$^6$-sulfanyl)phenyl)acetate (103 mg, 0.30 mmol) in HCOOH (3.0 mL). The reaction is complete after 30 min at rt. Removing the solvents under reduced pressure yields the crude title product. LC-MS: $t_R$=0.79 min (conditions 3).

tert-Butyl 2-(4-(2-cyanopropan-2-yl)phenyl)acetate

Prepared according to general procedure 6 from 2-(4-bromophenyl)-2-methylpropanenitrile (462 mg, 2.00 mmol), (2-(tert-butoxy)-2-oxoethyl)zinc(II) chloride (0.5M in Et$_2$O, 8.0 mL, 4.0 mmol), Pd$_2$(dba)$_3$ (92 mg, 0.10 mmol) and X-Phos (49 mg, 0.10 mmol) in THF (30 mL). The reaction is complete overnight at 45° C. Purification of the crude by HPLC yields the title product. LC-MS: $t_R$=0.94 min, MH$^+$=260.25 (conditions 3).

2-(4-(2-Cyanopropan-2-yl)phenyl)acetic acid

Prepared according to general procedure 7 from tert-butyl 2-(4-(2-cyanopropan-2-yl)phenyl)acetate (77.8 mg, 0.30 mmol) in TFA (0.34 mL) and CH$_2$Cl$_2$ (0.35 mL). The reaction is complete overnight at rt. Removing the solvents under reduced pressure yields the crude title product. LC-MS: $t_R$=0.70 min (conditions 3).

Methyl 2-(3-methyl-4-(2,2,2-trifluoroethoxy)phenyl)acetate

To an ice-cooled sol. of methyl 4-hydroxy-3-methylphenylacetate (0.33 mL, 2 mmol) and Cs$_2$CO$_3$ (1.30 g, 4.00 mmol) in DMF (5.3 mL), is added dropwise 2,2,2-trifluoroethyl trifluoromethanesulfonate (0.46 mL, 3.0 mmol). The mixture is stirred at rt over 3 days while warming up to rt. The mixture is partitioned between water (10 mL) and EtOAc (10 mL). The layers are separated. The aq. layer is extracted with EtOAc (2×5 mL). The comb. org. layers are washed with water (2×10 mL) and with brine (1×10 mL), dried over MgSO$_4$, filtered, and the solvents are removed under reduced pressure to yield the crude title product. LC-MS: $t_R$=0.90 min (conditions 3).

2-(3-Methyl-4-(2,2,2-trifluoroethoxy)phenyl)acetic acid

To a sol. of methyl 2-(3-methyl-4-(2,2,2-trifluoroethoxy)phenyl)acetate (710 mg, 2.59 mmol) in THF (8.2 mL) and MeOH (2 mL), is added aq. 1M NaOH (2.8 mL). The sol. is stirred at rt for 1 h. The solvents are removed under reduced pressure. The residue is diluted with water and washed with EtOAc (1×). The aq. phase is acidified with aq. 1M HCl. The mixture is extracted with CH$_2$Cl$_2$ (3×). The comb. org. layers are dried over MgSO$_4$, filtered and the solvents are removed under reduced pressure to yield the crude title product. LC-MS: $t_R$=0.80 min (conditions 3).

5-Bromo-3-fluoro-2-(pyrrolidin-1-yl)pyridine

To a sol. of 5-bromo-2,3-difluoropyridine (680 mg, 3.51 mmol) in DMSO (20 mL), are added pyrrolidine (0.307 mL, 3.68 mmol) and then DBU (1.10 mL, 7.36 mmol). The mixture is heated to 80° C. and stirred at this temperature for one day. The mixture is allowed to cool down to rt. The mixture is diluted with aq. sat. NaHCO$_3$ (200 mL) and EtOAc (200 mL). The layers are separated, and the aq. layer is extracted with EtOAc (1×100 mL). The comb. org. layers are washed with aq. sat. NaHCO$_3$ (2×200 mL), and brine (1×100 mL), are dried over MgSO$_4$, filtered, and the solvents are removed under reduced pressure to yield the crude title product. LC-MS: $t_R$=0.85 min, MH$^+$=245.09 (conditions 3).

tert-Butyl 2-(5-fluoro-6-(pyrrolidin-1-yl)pyridin-3-yl)acetate

Prepared according to general procedure 6 from 5-bromo-3-fluoro-2-(pyrrolidin-1-yl)pyridine (504 mg, 2.06 mmol), (2-(tert-butoxy)-2-oxoethyl)zinc(II) chloride (0.5M in Et$_2$O, 8.22 mL, 4.11 mmol), Pd$_2$(dba)$_3$ (94 mg, 0.10 mmol) and X-Phos (50 mg, 0.10 mmol) in THF (20 mL). The reaction is complete after 1 h at 50° C. Purification of the crude by HPLC yields the title product. LC-MS: $t_R$=0.66 min, MH$^+$=281.22 (conditions 3).

2-(5-Fluoro-6-(pyrrolidin-1-yl)pyridin-3-yl)acetic acid

Prepared according to general procedure 7 from tert-butyl 2-(5-fluoro-6-(pyrrolidin-1-yl)pyridin-3-yl)acetate (200 mg, 0.713 mmol) in HCl (4M in dioxane, 10 mL). The reaction is complete overnight at rt. Purification by HPLC yields title product. LC-MS: $t_R$=0.44 min, MH$^+$=225.16 (conditions 3).

4-Bromomethyl-2,6-difluorobenzonitrile 2,6-Difluoro-4-(hydroxymethyl)benzonitrile (WO 2003101423, 2.97 g, 17.6 mmol) is dissolved in THF (80 mL). PPh$_3$ (5.07 g, 19.3 mmol) is added and the mixture is cooled to 0° C. CBr$_4$ (7.28 g, 22.0 mmol) is added in portions. The mixture is stirred for 20 h while warming up to rt. The mixture is filtered, and the filtrate is partitioned between EtOAc and aq. sat. NH$_4$Cl. The org. layer is dried over MgSO4, filtered, and the solvents are removed under reduced pressure. Purification of the residue by automated FC (Büchi, 50 g silicagel, flow 26 mL/min, EtOAc/heptane 1:99→3:97→8:92→15:85) yields the title product. LC-MS: $t_R$=0.85 min (conditions 3).

2,6-Difluoro-4-((3-nitro-1H-pyrazol-1-yl)methyl)benzonitrile

Prepared according to general procedure 4 from K$_2$CO$_3$ (2.13 g, 15.4 mmol), 4-bromomethyl-2,6-difluorobenzonitrile (716 mg, 3.09 mmol), 5-nitro-1H-pyrazole (349 mg, 3.09 mmol), and Bu$_4$NBr (114 mg, 0.309 mmol) in acetone (7 mL). The reaction is complete after 1 h. Purification of the crude by automated FC (Büchi, EtOAc/heptane 1:99→10:90→20:80→50:50→80:20, 24 g silicagel, flow 35 mL/min) yields the title product. LC-MS: $t_R$=0.81 min, MH$^+$=242.22 (conditions 3).

4-((3-Amino-1H-pyrazol-1-yl)methyl)-2,6-difluorobenzonitrile

Prepared according to general procedure 5 from Fe (powder, 358 mg, 6.42 mmol), 2,6-difluoro-4-((3-nitro-1H-pyrazol-1-yl)methyl)benzonitrile (565 mg, 2.14 mmol) and NH$_4$Cl (572 mg, 10.7 mmol) in a 2:1-mixture of EtOH and water (21 mL). The reaction is complete after 45 min at 85° C. This yields the crude title compound. LC-MS: $t_R$=0.60 min, MH$^+$=276.16 (conditions 3).

tert-Butyl 2-(4-(1-cyanocyclopropyl)phenyl)acetate

Prepared according to general procedure 6 from 1-(4-bromophenyl)cyclopropane-1-carbonitrile (227 mg, 1.00 mmol), (2-(tert-butoxy)-2-oxoethyl)zinc(III) chloride (0.5M in Et$_2$O, 4.00 mL, 2.00 mmol), Pd$_2$(dba)$_3$ (46 mg, 0.05 mmol) and X-Phos (25 mg, 0.05 mmol) in THF (15 mL). The reaction is complete after 2 days at 45° C. Purification of the crude by HPLC yields the title product. LC-MS: $t_R$=0.92 min, MH$^+$=258.14 (conditions 3).

2-(4-(1-Cyanocyclopropyl)phenyl)acetic acid

Prepared according to general procedure 7 from tert-butyl 2-(4-(1-cyanocyclopropyl)phenyl)acetate (77.4 mg, 0.030 mmol) in TFA (0.34 mL) and CH$_2$Cl$_2$ (0.35 mL). The reaction is complete after 2.5 h at 0° C. Purification by HPLC yields title product. LC-MS: $t_R$=0.68 min (conditions 3).

tert-Butyl 2-(4-(1-((tert-butyldimethylsilyl)oxy)cyclopropyl)phenyl)acetate

Prepared according to general procedure 6 from (1-(4-bromophenyl)cyclopropoxy)(tert-butyl)dimethylsilane (Isabel, E.; Bateman, K. P.; Chauret, N.; Cromlish, W.; Desmarais, S.; Duong, Le T.; Falgueyret, J.-P.; Gauthier, J. Y.; Lamontagne, S.; Lau, C. K.; et al., *Bioorg. Med. Chem. Lett.*, 2010, 20, 887, 200 mg, 0.601 mmol), (2-(tert-butoxy)-2-oxoethyl)zinc(II) chloride (0.5M in Et$_2$O, 2.40 mL, 1.20 mmol), Pd$_2$(dba)$_3$ (28 mg, 0.030 mmol) and X-Phos (15 mg, 0.030 mmol) in THF (15 mL). The reaction is complete after 2 days at 45° C. Purification of the crude by HPLC yields the title product. LC-MS: $t_R$=1.13 min, (conditions 3).

tert-Butyl 2-(4-(1-hydroxycyclopropyl)phenyl)acetate

To an ice-cooled sol. of tert-butyl 2-(4-(1-((tert-butyldimethylsilyl)oxy)cyclopropyl)phenyl)acetate (200 mg, 0.534 mmol) in THF (12 mL) is added tetrabutylammonium fluoride (1.0 M in THF, 1.7 mL, 1.7 mmol). The resulting sol. is stirred at 0° C. for 30 min. The sol. is diluted with EtOAc (10 mL), and aq. sat. NH4Cl (25 mL) is added. The mixture is extracted with EtOAc (3×30 mL). The comb. org. layers are dried over MgSO$_4$, filtered, and the solvents are removed under reduced pressure. Purification of the residue by automated FC (Flash Master, 25 g silicagel, flow 30 mL/min, EtOAc/heptane 0:100→20:80) yields the title product. LC-MS: $t_R$=0.83 min, (conditions 3).

2-(4-(1-Hydroxycyclopropyl)phenyl)acetic acid

Prepared according to general procedure 7 from tert-butyl 2-(4-(1-hydroxycyclopropyl)phenyl)acetate (75 mg, 0.030 mmol) in TFA (0.34 mL) and CH$_2$Cl$_2$ (0.35 mL). The reaction is complete after 2.5 h at 0° C. Purification by HPLC yields title product. LC-MS: $t_R$=0.55 min (conditions 3).

(6-Cyano-5-methylpyridin-2-yl)methyl acetate

To Ac$_2$O (8.08 mL, 84.7 mmol) at 120° C. is added 2-cyano-3,6-dimethylpyridine 1-oxide (WO 2006066968, 2.27 g, 14.9 mmol). The resulting sol. is stirred at 120° C. for 5 min, and is heated to reflux for 1 h. The mixture is allowed to cool to rt, and is poured into ice (63 g). The mixture is then neutralized with NaHCO$_3$. Et$_2$O (70 mL) is added, and the layers are separated. The aq. phase is extracted with Et$_2$O (2×35 mL), and the combined org. layers are washed with brine, dried over MgSO$_4$, filtered, and the solvents are removed under reduced pressure. Purification of the residue by automated FC by (Flash Master, column 100 g, flow 45 mL/min, EtOAc/heptane 0:100→40:60) yields the title product. LC-MS: $t_R$=0.69 min, MH$^+$=191.95 (conditions 3).

6-(Hydroxymethyl)-3-methylpicolinonitrile

K$_2$CO$_3$ (41.7 mg, 0.302 mmol) is added to a sol. of (6-cyano-5-methylpyridin-2-yl)methyl acetate (1.79 g, 9.37 mmol) in MeOH (12.6 mL). The resulting mixture is stirred at rt overnight. Water (25 mL) is added, and the mixture is neutralized with aq. 5% AcOH. CH$_2$Cl$_2$ is added, and the phases are separated. The aq. layer is extracted with CH$_2$Cl$_2$ (2×). The combined org. layers are washed with brine, dried over MgSO$_4$, filtered, and the solvents are removed under reduced pressure to yield to crude title compound. LC-MS: $t_R$=0.51 min, MH$^+$=149.18 (conditions 3).

6-(Chloromethyl)-3-methylpicolinonitrile

A sol. of 6-(hydroxymethyl)-3-methylpicolinonitrile (1.49 g, 9.35 mmol) and SOCl$_2$ (1.61 mL, 9.35 mmol) in CH$_2$Cl$_2$ (35.2 mL) is stirred at rt for 6 h. The solvents are removed under reduced pressure. Toluene (20 mL) is added, and the solvents are removed under reduced pressure to yield the crude title product. LC-MS: $t_R$=0.74 min, MH$^+$=167.09 (conditions 3).

3-Methyl-6-((3-nitro-1H-pyrazol-1-yl)methyl)picolinonitrile

Prepared according to general procedure 4 from K$_2$CO$_3$ (1.26 g, 9.13 mmol), 6-(chloromethyl)-3-methylpicolinonitrile (1.64 g, 9.19 mmol), 5-nitro-1H-pyrazole (859 mg, 7.60 mmol) in DMF (6 mL). The reaction is complete overnight. Purification of the crude by automated FC (Combiflash, EtOAc/heptane 0:100→40:60, 40 g silicagel, flow 40 mL/min) yields the title product. LC-MS: $t_R$=0.75 min, MH$^+$=244.18 (conditions 3).

6-((3-Amino-1H-pyrazol-1-yl)methyl)-3-methylpicolinonitrile

Prepared according to general procedure 5 from Fe (powder, 1.03 g, 18.3 mmol), 3-methyl-6-((3-nitro-1H-pyrazol-1-yl)methyl)picolinonitrile (1.90 g, 6.09 mmol) and NH$_4$Cl (1.23 g, 30.4 mmol) in a 2:1-mixture of EtOH and water (43 mL). The reaction is complete overnight at 100° C. This yields the crude title compound.

tert-Butyl 2-(4-(1-methylcyclopropyl)phenyl)acetate

Prepared according to general procedure 6 from 1-bromo-4-(1-methylcyclopropyl)benzene (500 mg, 2.37 mmol), (2-(tert-butoxy)-2-oxoethyl)zinc(II) chloride (0.5M in Et$_2$O, 9.50 mL, 4.75 mmol), Pd$_2$(dba)$_3$ (108 mg, 0.118 mmol) and X-Phos (58 mg, 0.12 mmol) in THF (20 mL). The reaction is complete after 2 h at 50° C. Purification of the crude by HPLC yields the title product. LC-MS: $t_R$=1.01 (conditions 3).

2-(4-(1-Methylcyclopropyl)phenyl)acetic acid

Prepared according to general procedure 7 from tert-butyl 2-(4-(1-methylcyclopropyl)phenyl)acetate (500 mg, 2.03 mmol) in HCOOH (17 mL). The reaction is complete after 2.5 h at 0° C. Purification by HPLC yields title product. LC-MS: $t_R$=0.79 min (conditions 3).

tert-Butyl 2-(4-(1,1,1-trifluoro-2-methylpropan-2-yl)phenyl)acetate

Prepared according to general procedure 6 from 1-bromo-4-(1,1,1-trifluoro-2-methylpropan-2-yl)benzene (WO 2013011033, 575 mg, 2.11 mmol), (2-(tert-butoxy)-2-oxoethyl)zinc(II) chloride (0.5M in Et$_2$O, 8.40 mL, 4.20 mmol), Pd$_2$(dba)$_3$ (97 mg, 0.105 mmol) and X-Phos (52 mg, 0.105 mmol) in THF (32 mL). The reaction is complete overnight at 45° C. Purification of the crude by HPLC yields the title product. LC-MS: $t_R$=1.02 (conditions 3).

2-(4-(1,1,1-Trifluoro-2-methylpropan-2-yl)phenyl)acetic acid

Prepared according to general procedure 7 from tert-butyl 2-(4-(1,1,1-trifluoro-2-methylpropan-2-yl)phenyl)acetate (63 mg, 0.20 mmol) in TFA (0.23 mL) and CH$_2$Cl$_2$ (0.23 mL). The reaction is complete after 2.5 h at 0° C. Purification by HPLC yields title product. LC-MS: $t_R$=0.82 min (conditions 3).

tert-Butyl 2-(2,2-dimethyl-2,3-dihydrobenzofuran-5-yl)acetate

Prepared according to general procedure 6 from 5-bromo-2,2-dimethyl-2,3-dihydrobenzofuran (468 mg, 2.06 mmol), (2-(tert-butoxy)-2-oxoethyl)zinc(II) chloride (0.5M in Et$_2$O, 8.24 mL, 4.12 mmol), Pd$_2$(dba)$_3$ (94 mg, 0.103 mmol) and X-Phos (51 mg, 0.103 mmol) in THF (20 mL). The reaction is complete overnight at 50° C. Purification of the crude by HPLC yields the title product. LC-MS: $t_R$=0.96, MH$^+$=263.28 (conditions 3).

2-(2,2-Dimethyl-2,3-dihydrobenzofuran-5-yl)acetic acid

Prepared according to general procedure 7 from tert-butyl 2-(2,2-dimethyl-2,3-dihydrobenzofuran-5-yl)acetate (300 mg, 1.14 mmol) in HCl (4M in dioxane, 5.0 mL). The reaction is complete overnight at rt. Purification by HPLC yields title product. LC-MS: $t_R$=0.71 min, MH$^+$=207.20 (conditions 3).

tert-Butyl 2-(3,3-dimethyl-2,3-dihydrobenzofuran-5-yl)acetate

Prepared according to general procedure 6 from 5-bromo-3,3-dimethyl-2,3-dihydrobenzofuran (468 mg, 2.06 mmol), (2-(tert-butoxy)-2-oxoethyl)zinc(II) chloride (0.5M in Et$_2$O, 8.24 mL, 4.12 mmol), Pd$_2$(dba)$_3$ (94 mg, 0.103 mmol) and X-Phos (51 mg, 0.103 mmol) in THF (20 mL). The reaction is complete overnight at 50° C. Purification of the crude by HPLC yields the title product. LC-MS: $t_R$=0.96 (conditions 3).

2-(3,3-Dimethyl-2,3-dihydrobenzofuran-5-yl)acetic acid

Prepared according to general procedure 7 from tert-butyl 2-(3,3-dimethyl-2,3-dihydrobenzofuran-5-yl)acetate (300 mg, 1.14 mmol) in HCl (4M in dioxane, 5.0 mL). The reaction is complete overnight at rt. Purification by HPLC yields title product. LC-MS: $t_R$=0.72 min, MH$^+$=207.20 (conditions 3).

tert-Butyl 2-(2,2-dimethyl-2,3-dihydrobenzofuran-6-yl)acetate

Prepared according to general procedure 6 from 6-bromo-2,2-dimethyl-2,3-dihydrobenzofuran (Wang, X.; Lu, Y.; Dai, H.-X.; Yu, J.-Q., J. Am. Chem. Soc., 2010, 132, 12203, 480 mg, 2.11 mmol), (2-(tert-butoxy)-2-oxoethyl)zinc(II) chloride (0.5M in Et$_2$O, 8.46 mL, 4.23 mmol), Pd$_2$(dba)$_3$ (97 mg, 0.106 mmol) and X-Phos (52 mg, 0.106 mmol) in THF (30 mL). The reaction is complete after 2 h at 50° C. Purification of the crude by HPLC yields the title product. LC-MS: $t_R$=0.96 (conditions 3).

2-(2,2-Dimethyl-2,3-dihydrobenzofuran-6-yl)acetic acid

Prepared according to general procedure 7 from tert-butyl 2-(2,2-dimethyl-2,3-dihydrobenzofuran-6-yl)acetate (300 mg, 1.14 mmol) in HCl (4M in dioxane, 5.0 mL). The reaction is complete overnight at rt. Purification by HPLC yields title product. LC-MS: $t_R$=0.72 min, MH$^+$=207.19 (conditions 3).

4-Bromo-1-methyl-2-(2,2,2-trifluoroethoxy)benzene

To an ice-cooled sol. of 5-bromo-2-methylphenol (1.87 g, 10 mmol) and $Cs_2CO_3$ (4.23 g, 13 mmol) in DMF (20 mL) is added dropwise 2,2,2-trifluoroethyl trifluoromethanesulfonate (1.67 mL, 11 mmol). The mixture is stirred overnight while warming up to rt. The mixture is partitioned between water (100 mL) and EtOAc (100 mL). The layers are separated. The aq. phase is extracted with EtOAc (2×50 mL). The comb. org. layers are washed with water (3×100 mL) and brine (1×100 mL), dried over $MgSO_4$, filtered, and the solvents are removed under reduced pressure to yield the crude title product. LC-MS: $t_R$=0.96 min (conditions 3).

tert-Butyl 2-(4-methyl-3-(2,2,2-trifluoroethoxy)phenyl)acetate

Prepared according to general procedure 6 from 4-bromo-1-methyl-2-(2,2,2-trifluoroethoxy)benzene (800 mg, 2.97 mmol), (2-(tert-butoxy)-2-oxoethyl)zinc(II) chloride (0.5M in $Et_2O$, 12.0 mL, 6.00 mmol), $Pd_2(dba)_3$ (136 mg, 0.150 mmol) and X-Phos (73 mg, 0.150 mmol) in THF (20 mL). The reaction is complete after 2 h at 50° C. Purification of the crude by HPLC yields the title product. LC-MS: $t_R$=1.00 (conditions 3).

2-(4-methyl-3-(2,2,2-trifluoroethoxy)phenyl)acetic acid

Prepared according to general procedure 7 from tert-butyl 2-(4-methyl-3-(2,2,2-trifluoroethoxy)phenyl)acetate (300 mg, 0.986 mmol) in HCl (4M in dioxane, 5.0 mL). The reaction is complete overnight at rt. LC-MS: $t_R$=0.81 min (conditions 3).

Ethyl 2-(3-fluoro-4-(2,2,2-trifluoroethoxy)phenyl)acetate

To an ice-cooled sol. of ethyl 2-(3-fluoro-4-hydroxyphenyl)acetate (Cho, Y.; Kim, M. S.; Kim, Ho S.; Ann, J.; Lee, J.; Pearce, L. V.; Pavlyukovets, V. A.; Morgan, M. A.; Blumberg, P. M.; Lee, J., *Bioorg. Med. Chem. Lett.*, 2012, 22, 5227, 2.87 g, 14.5 mmol) and $Cs_2CO_3$ (6.13 g, 18.8 mmol) in DMF (20 mL) is added dropwise 2,2,2-trifluoroethyl trifluoromethanesulfonate (2.42 mL, 15.9 mmol). The mixture is stirred overnight while warming up to rt. The mixture is partitioned between water (100 mL) and EtOAc (100 mL). The layers are separated. The aq. phase is extracted with EtOAc (2×50 mL). The comb. org. layers are washed with water (3×100 mL) and brine (1×100 mL), dried over $MgSO_4$, filtered, the solvents are removed under reduced pressure to yield the crude title product. LC-MS: $t_R$=0.91 min (conditions 3).

2-(3-Fluoro-4-(2,2,2-trifluoroethoxy)phenyl)acetic acid

To a sol. of ethyl 2-(3-fluoro-4-(2,2,2-trifluoroethoxy)phenyl)acetate (2.00 g, 7.14 mmol) in THF (50 mL) and MeOH (10 mL) is added aq. 1M NaOH (10 mL). The sol. is stirred at rt for 1 h. The solvents are removed under reduced pressure. The residue is diluted with water and washed with EtOAc (1×). The aq. phase is acidified with aq. 2M HCl. The mixture is extracted with $CH_2Cl_2$ (3×). The comb. org. layers are washed with brine, dried over $MgSO_4$, filtered, and the solvents are removed under reduced pressure to yield the crude title product. LC-MS: $t_R$=0.77 min (conditions 3).

rac-tert-Butyl 2-(4-((1R*,2R*)-2-(trifluoromethyl)cyclopropyl)phenyl)acetate Prepared according to general procedure 6 from rac-1-bromo-4-((1R*,2R*)-2-(trifluoromethyl)cyclopropyl)benzene (0.156 mL, 0.896 mmol), (2-(tert-butoxy)-2-oxoethyl)zinc(II) chloride (0.5M in $Et_2O$, 3.20 mL, 1.60 mmol), and bis(tri-tert-butylphosphine)palladium(0) (45.8 mg, 0.0896 mmol) in dioxane (7.7 mL). The reaction is complete overnight at rt. Purification of the crude by HPLC yields the title product. LC-MS: $t_R$=1.01 (conditions 3).

rac-2-(4-((1R*,2R*)-2-(trifluoromethyl)cyclopropyl)phenyl)acetic acid

Prepared according to general procedure 7 from rac-tert-butyl 2-(4-((1R*,2R*)-2-(trifluoromethyl)cyclopropyl)phenyl)acetate (61 mg, 0.20 mmol) in TFA (0.23 mL) and $CH_2Cl_2$ (0.23 mL) The reaction is complete after 3 h at 0° C. LC-MS: $t_R$=0.82 min (conditions 3).

General Procedure 10 for the Preparation of Arylacetic Acid Derivatives.

A sol. of bromoaryl/bromoheteroaryl (1 eq.), (2-(tert-butoxy)-2-oxoethyl)zinc(II) chloride (0.5M in $Et_2O$, 1.2 eq.)), $Pd_2(dba)_3$ (0.05 eq.) and Q-Phos or X-Phos (0.1 eq.) in dioxane (0.5M) is stirred between rt and 90° C. until the starting materials are consumed (0.33-18 h). The mixture is allowed to cool to rt, and the solvents are removed under reduced pressure. Chromatographic purification yields the tert-butyl arylacetate.

A sol. of the tert-butyl arylacetate in an acid (HCl/dioxane, or HCOOH) with optionally $CH_2Cl_2$ is prepared at 0° C. This mixture is stirred at 0° C., optionally warming up to rt, until consumption of the starting material. The solvents are removed under reduced pressure to yield the crude desired arylacetic acid derivative.

Following general procedure 10, the following examples have been prepared

| Product name | LC-MS tert-butyl arylacetate $t_R$ (min.), MH+, conditions | LC-MS final product $t_R$ (min.), MH+, conditions | Acid used for ester hydrolysis |
|---|---|---|---|
| 2-(1-ethyl-1H-indazol-5-yl)acetic acid | 0.90, —, cond. 3 | 0.64, 205.21, cond. 3 | 4M HCl/dioxane |
| 2-(1,3-dimethyl-1H-indazol-5-yl)acetic acid | 0.90, 261.23, cond. 3 | 0.63, 205.20, cond. 3 | 4M HCl/dioxane |
| 2-(3-cyclopropyl-1H-indazol-5-yl)acetic acid | 0.87, 273.32, cond. 3 | 0.64, 217.13, cond. 1 | 4M HCl/dioxane |
| 2-(1-butyl-1H-indazol-5-yl)acetic acid | 0.89, 289.26, cond. 3 | 0.82, 233.15, cond. 1 | 4M HCl/dioxane |
| 2-(2-methyl-1H-indol-5-yl)acetic acid | 0.91, 246.19, cond. 3 | — | 4M HCl/dioxane |
| 2-(3-butyl-1H-indazol-5-yl)acetic acid | 0.93, 289.26, cond. 3 | — | 4M HCl/dioxane |

-continued

| Product name | LC-MS tert-butyl arylacetate $t_R$ (min.), MH$^+$, conditions | LC-MS final product $t_R$ (min.), MH$^+$, conditions | Acid used for ester hydrolysis |
|---|---|---|---|
| 2-(1-isopropyl-1H-indazol-5-yl)acetic acid | 0.94, 275.30, cond. 3 | — | 4M HCl/dioxane |
| 2-(1-propyl-1H-indazol-5-yl)acetic acid | 0.94, 275.14, cond. 3 | — | 4M HCl/dioxane |
| 2-(3-cyclopropyl-1-methyl-1H-indazol-5-yl)acetic acid | 0.93, 287.18, cond. 3 | — | 4M HCl/dioxane |
| 2-(benzofuran-5-yl)acetic acid | 0.94, —, cond. 3 | — | 4M HCl/dioxane |
| 2-(benzo[b]thiophen-5-yl)acetic acid | 0.97, —, cond. 3 | — | 4M HCl/dioxane |
| 2-(1-methyl-1H-pyrazolo[3,4-b]pyridin-5-yl)acetic acid | 0.83, 248.28, cond. 3 | — | 4M HCl/dioxane |
| 2-(3-(trifluoromethyl)-1H-indazol-5-yl)acetic acid | — | — | 4M HCl/dioxane | tert-Butyl 2-(4-(1-methoxycyclopropyl)phenyl)acetate

Prepared according to general procedure 6 from 1-bromo-4-(1-methoxycyclopropyl)benzene (790 mg, 2.92 mmol), (2-(tert-butoxy)-2-oxoethyl)zinc(II) chloride (0.5M in Et$_2$O, 11.7 mL, 5.80 mmol), Pd$_2$(dba)$_3$ (133 mg, 0.146 mmol), and X-Phos (72 mg, 0.15 mmol) in THF (44 mL). The reaction is complete after 2.5 h at 45° C. Purification of the crude by automated FC (Combiflash, acetone/heptane 0:100→85:15, 40 g silicagel, flow 40 mL/min) yields the title product. LC-MS: $t_R$=0.94 min, MH$^+$=263.25 (conditions 3).

2-(4-(1-Methoxycyclopropyl)phenyl)acetic acid

Prepared according to general procedure 7 from tert-butyl 2-(4-(1-methoxycyclopropyl)phenyl)acetate (84 mg, 0.30 mmol) in TFA (0.34 mL) and CH$_2$Cl$_2$ (0.35 mL). The reaction is complete after 2.5 h at 0° C. LC-MS: $t_R$=0.70 min (conditions 3).

The following examples were prepared according to general procedure 3, from the appropriate carboxylic acids and aminopyrazoles:

| Example No | Name | LC-MS ($t_R$; MH$^+$; conditions) |
|---|---|---|
| 234 | N-[1-(3,4-Difluoro-benzyl)-1H-pyrazol-3-yl]-2-(4-isopropyl-phenyl)-acetamide | 0.94 min; 370.33; conditions 3 |
| 235 | N-[1-(3,4-Difluoro-benzyl)-1H-pyrazol-3-yl]-2-[4-(5-methyl-[1,2,4]oxadiazol-3-yl)-phenyl]-acetamide | 0.85 min; 410.21; conditions 3 |
| 236 | N-[1-(3,4-Difluoro-benzyl)-1H-pyrazol-3-yl]-2-(4-[1,2,4]oxadiazol-3-yl-phenyl)-acetamide | 0.83 min; 396.09; conditions 3 |
| 237 | N-[1-(3,4-Difluoro-benzyl)-1H-pyrazol-3-yl]-2-[4-(3,3-difluoro-cyclobutyl)-phenyl]-acetamide | 0.93 min; 418.00; conditions 3 |
| 238 | N-[1-(3,4-Difluoro-benzyl)-1H-pyrazol-3-yl]-2-[4-(oxetan-3-yloxy)-phenyl]-acetamide | 0.82 min; 400.18; conditions 3 |
| 239 | N-[1-(4-Bromo-benzyl)-1H-pyrazol-3-yl]-2-(4-dimethylamino-phenyl)-acetamide | 0.66 min; 413.11; conditions 3 |
| 240 | N-[1-(3,4-Difluoro-benzyl)-1H-pyrazol-3-yl]-2-[4-(3,3-difluoro-cyclobutoxy)-phenyl]-acetamide | 0.92 min; 434.05; conditions 3 |
| 241 | N-[1-(3,4-Difluoro-benzyl)-1H-pyrazol-3-yl]-2-[4-(3-methyl-oxetan-3-ylmethoxy)-phenyl]-acetamide | 0.86 min; 428.16; conditions 3 |
| 242 | N-[1-(3,4-Difluoro-benzyl)-1H-pyrazol-3-yl]-2-[4-(oxetan-3-ylmethoxy)-phenyl]-acetamide | 0.83 min; 414.18; conditions 3 |
| 243 | N-[1-(3,4-Difluoro-benzyl)-1H-pyrazol-3-yl]-2-[4-(3,3-difluoro-1-methyl-cyclobutylmethoxy)-phenyl]-acetamide | 0.97 min; 462.08; conditions 3 |
| 244 | N-[1-(3,4-Difluoro-benzyl)-1H-pyrazol-3-yl]-2-[4-(3,3-difluoro-cyclobutylmethoxy)-phenyl]-acetamide | 0.94 min; 448.01; conditions 3 |
| 245 | N-[1-(3,4-Difluoro-benzyl)-1H-pyrazol-3-yl]-2-[4-(3-fluoro-oxetan-3-ylmethoxy)-phenyl]-acetamide | 0.85 min; 432.07; conditions 3 |
| 246 | N-[1-(5-Cyano-pyridin-2-ylmethyl)-1H-pyrazol-3-yl]-2-[4-(3-fluoro-oxetan-3-yl)-phenyl]-acetamide | 0.74 min; 392.14; conditions 3 |
| 247 | N-[1-(5-Cyano-pyridin-2-ylmethyl)-1H-pyrazol-3-yl]-2-[4-(oxetan-3-yloxy)-phenyl]-acetamide | 0.71 min; 390.07; conditions 3 |
| 248 | N-[1-(5-Cyano-pyridin-2-ylmethyl)-1H-pyrazol-3-yl]-2-[4-(3-fluoro-oxetan-3-ylmethoxy)-phenyl]-acetamide | 0.75 min; 422.16; conditions 3 |
| 249 | N-[1-(5-Cyano-pyridin-2-ylmethyl)-1H-pyrazol-3-yl]-2-(1-methyl-1H-indazol-5-yl)-acetamide | 0.71 min; 372.22; conditions 3 |
| 250 | N-[1-(4-Cyano-benzyl)-1H-pyrazol-3-yl]-2-[4-(3-fluoro-oxetan-3-yl)-phenyl]-acetamide | 0.80 min; 391.18; conditions 3 |
| 251 | N-[1-(4-Cyano-benzyl)-1H-pyrazol-3-yl]-2-[4-(oxetan-3-yloxy)-phenyl]-acetamide | 0.78 min; 389.19; conditions 3 |
| 252 | N-[1-(4-Cyano-benzyl)-1H-pyrazol-3-yl]-2-(1-methyl-1H-indazol-5-yl)-acetamide | 0.78 min; 371.11; conditions 3 |
| 253 | N-[1-(4-Cyano-3-fluoro-benzyl)-1H-pyrazol-3-yl]-2-[4-(3-fluoro-oxetan-3-yl)-phenyl]-acetamide | 0.82 min; 409.16; conditions 3 |

| Example No | Name | LC-MS (t$_R$; MH⁺; conditions) |
|---|---|---|
| 254 | N-[1-(4-Cyano-3-fluoro-benzyl)-1H-pyrazol-3-yl]-2-[4-(oxetan-3-yloxy)-phenyl]-acetamide | 0.80 min; 407.13; conditions 3 |
| 255 | N-[1-(4-Cyano-3-fluoro-benzyl)-1H-pyrazol-3-yl]-2-(1-methyl-1H-indazol-5-yl)-acetamide | 0.80 min; 389.16; conditions 3 |
| 256 | N-[1-(4-Cyano-benzyl)-1H-pyrazol-3-yl]-2-[4-(3-fluoro-oxetan-3-ylmethoxy)-phenyl]-acetamide | 0.81 min; 421.17; conditions 3 |
| 257 | N-[1-(4-Cyano-3-fluoro-benzyl)-1H-pyrazol-3-yl]-2-[4-(3-fluoro-oxetan-3-ylmethoxy)-phenyl]-acetamide | 0.83 min; 439.12; conditions 3 |
| 258 | N-[1-(3,4-Difluoro-benzyl)-1H-pyrazol-3-yl]-2-[6-(3-methoxy-oxetan-3-yl)-pyridin-3-yl]-acetamide | 0.70 min; 415.10; conditions 3 |
| 259 | N-[1-(3,4-Difluoro-benzyl)-1H-pyrazol-3-yl]-2-(1,3-dimethyl-1H-indol-6-yl)-acetamide | 0.91 min; 395.10; conditions 3 |
| 260 | N-[1-(3,4-Difluoro-benzyl)-1H-pyrazol-3-yl]-2-(1,3-dimethyl-1H-indol-5-yl)-acetamide | 0.91 min; 395.11; conditions 3 |
| 261 | N-[1-(4-Cyano-3-fluoro-benzyl)-1H-pyrazol-3-yl]-2-[4-(3,3-difluoro-cyclobutoxy)-phenyl]-acetamide | 0.90 min; 441.05; conditions 3 |
| 262 | N-[1-(4-Cyano-3-fluoro-benzyl)-1H-pyrazol-3-yl]-2-[4-(oxetan-3-ylmethoxy)-phenyl]-acetamide | 0.80 min; 421.07; conditions 3 |
| 263 | N-[1-(4-Cyano-3-fluoro-benzyl)-1H-pyrazol-3-yl]-2-[4-(3-methyl-oxetan-3-ylmethoxy)-phenyl]-acetamide | 0.84 min; 435.03; conditions 3 |
| 264 | 2-(4-tert-Butyl-phenyl)-N-[1-(4-cyano-3-fluoro-benzyl)-1H-pyrazol-3-yl]-acetamide | 0.94 min; 391.14; conditions 3 |
| 265 | N-[1-(4-Cyano-3-fluoro-benzyl)-1H-pyrazol-3-yl]-2-[4-(1-trifluoromethyl-cyclopropyl)-phenyl]-acetamide | 0.93 min; 443.05; conditions 3 |
| 266 | N-[1-(4-Cyano-3-fluoro-benzyl)-1H-pyrazol-3-yl]-2-(4-isopropyl-phenyl)-acetamide | 0.91 min; 377.09; conditions 3 |
| 267 | N-[1-(3-Cyano-4-fluoro-benzyl)-1H-pyrazol-3-yl]-2-[4-(3-fluoro-oxetan-3-ylmethoxy)-phenyl]-acetamide | 0.82 min; 439.07; conditions 4 |
| 268 | N-[1-(3-Cyano-4-fluoro-benzyl)-1H-pyrazol-3-yl]-2-(1-methyl-1H-indazol-5-yl)-acetamide | 0.78 min; 388.49; conditions 4 |
| 269 | N-[1-(3-Cyano-4-fluoro-benzyl)-1H-pyrazol-3-yl]-2-[4-(oxetan-3-yloxy)-phenyl]-acetamide | 0.80 min; 406.92; conditions 4 |
| 270 | N-[1-(3-Cyano-4-fluoro-benzyl)-1H-pyrazol-3-yl]-2-(4-(3-fluoro-oxetan-3-yl)-phenyl]-acetamide | 0.82 min; 408.48; conditions 4 |
| 271 | 2-(4-tert-Butyl-phenyl)-N-[1-(4-cyano-benzyl)-1H-pyrazol-3-yl]-acetamide | 0.92 min; 373.15; conditions 3 |
| 272 | 2-(4-tert-Butyl-phenyl)-N-[1-(5-cyano-pyridin-2-ylmethyl)-1H-pyrazol-3-yl]-acetamide | 0.87 min; 374.20; conditions 3 |
| 273 | N-[1-(4-Cyano-benzyl)-1H-pyrazol-3-yl]-2-[4-(3,3-difluoro-cyclobutoxy)-phenyl]-acetamide | 0.88 min; 423.00; conditions 3 |
| 274 | N-[1-(5-Cyano-pyridin-2-ylmethyl)-1H-pyrazol-3-yl]-2-[4-(3,3-difluoro-cyclobutoxy)-phenyl]-acetamide | 0.83 min; 424.10; conditions 3 |
| 275 | N-[1-(4-Cyano-3-fluoro-benzyl)-1H-pyrazol-3-yl]-2-(6-pyrrolidin-1-yl-pyridin-3-yl)-acetamide | 0.64 min; 405.12; conditions 3 |
| 276 | N-[1-(5-Cyano-pyridin-2-ylmethyl)-1H-pyrazol-3-yl]-2-(6-pyrrolidin-1-yl-pyridin-3-yl)-acetamide | 0.56 min; 388.12; conditions 3 |
| 277 | N-[1-(4-Cyano-benzyl)-1H-pyrazol-3-yl]-2-[4-(1-trifluoromethyl-cyclopropyl)-phenyl]-acetamide | 0.92 min; 425.10; conditions 3 |
| 278 | N-[1-(5-Cyano-pyridin-2-ylmethyl)-1H-pyrazol-3-yl]-2-[4-(1-trifluoromethyl-cyclopropyl)-phenyl]-acetamide | 0.87 min; 426.14; conditions 3 |
| 279 | N-[1-(3-Cyano-4-fluoro-benzyl)-1H-pyrazol-3-yl]-2-[4-(oxetan-3-ylmethoxy)-phenyl]-acetamide | 0.80 min; 421.10; conditions 3 |
| 280 | N-[1-(3-Cyano-4-fluoro-benzyl)-1H-pyrazol-3-yl]-2-[4-(3-methyl-oxetan-3-ylmethoxy)-phenyl]-acetamide | 0.84 min; 435.09; conditions 3 |
| 281 | N-[1-(3-Cyano-4-fluoro-benzyl)-1H-pyrazol-3-yl]-2-[4-(3,3-difluoro-cyclobutoxy)-phenyl]-acetamide | 0.90 min; 441.06; conditions 3 |
| 282 | N-[1-(3-Cyano-4-fluoro-benzyl)-1H-pyrazol-3-yl]-2-(4-isopropyl-phenyl)-acetamide | 0.91 min; 377.17; conditions 3 |
| 283 | 2-(4-tert-Butyl-phenyl)-N-[1-(3-cyano-4-fluoro-benzyl)-1H-pyrazol-3-yl]-acetamide | 0.94 min; 391.14; conditions 3 |
| 284 | N-[1-(5-Cyano-pyridin-2-ylmethyl)-1H-pyrazol-3-yl]-2-[4-(3-methyl-oxetan-3-ylmethoxy)-phenyl]-acetamide | 0.76 min; 418.00; conditions 3 |
| 285 | N-[1-(4-Cyano-benzyl)-1H-pyrazol-3-yl]-2-[4-(3-methyl-oxetan-3-ylmethoxy)-phenyl]-acetamide | 0.82 min; 417.07; conditions 3 |
| 286 | N-[1-(4-Cyano-benzyl)-1H-pyrazol-3-yl]-2-[4-(oxetan-3-ylmethoxy)-phenyl]-acetamide | 0.78 min; 403.07; conditions 3 |
| 287 | N-[1-(5-Cyano-pyridin-2-ylmethyl)-1H-pyrazol-3-yl]-2-[4-(oxetan-3-ylmethoxy)-phenyl]-acetamide | 0.72 min; 404.10; conditions 3 |
| 288 | N-[1-(4-Cyano-3-fluoro-benzyl)-1H-pyrazol-3-yl]-2-[4-(3,3-difluoro-cyclobutyl)-phenyl]-acetamide | 0.91 min; 425.11; conditions 3 |
| 289 | N-[1-(4-Cyano-3-fluoro-benzyl)-1H-pyrazol-3-yl]-2-[4-(3,3-difluoro-cyclobutylmethoxy)-phenyl]-acetamide | 0.92 min; 455.02; conditions 3 |
| 290 | N-[1-(4-Cyano-3-fluoro-benzyl)-1H-pyrazol-3-yl]-2-[4-(3,3-difluoro-1-methyl-cyclobutylmethoxy)-phenyl]-acetamide | 0.95 min; 468.76; conditions 3 |
| 291 | N-[1-(4-Cyano-3-fluoro-benzyl)-1H-pyrazol-3-yl]-2-(1-methyl-1H-indazol-6-yl)-acetamide | 0.80 min; 389.06; conditions 3 |

| Example No | Name | LC-MS ($t_R$; MH+; conditions) |
|---|---|---|
| 292 | N-[1-(4-Cyano-3-fluoro-benzyl)-1H-pyrazol-3-yl]-2-(1-methyl-1H-indol-5-yl)-acetamide | 0.85 min; 387.99; conditions 3 |
| 293 | N-[1-(4-Cyano-3-fluoro-benzyl)-1H-pyrazol-3-yl]-2-(1-methyl-1H-indol-6-yl)-acetamide | 0.86 min; 388.02; conditions 3 |
| 294 | N-[1-(4-Cyano-3-fluoro-benzyl)-1H-pyrazol-3-yl]-2-[6-(3,3-difluoro-pyrrolidin-1-yl)-pyridin-3-yl]-acetamide | 0.66 min; 441.07; conditions 3 |
| 295 | N-[1-(4-Cyano-benzyl)-1H-pyrazol-3-yl]-2-(1-methyl-1H-indazol-6-yl)-acetamide | 0.78 min; 371.11; conditions 3 |
| 296 | N-[1-(4-Cyano-benzyl)-1H-pyrazol-3-yl]-2-(1-methyl-1H-indol-5-yl)-acetamide | 0.83 min; 370.11; conditions 3 |
| 297 | N-[1-(4-Cyano-benzyl)-1H-pyrazol-3-yl]-2-(1-methyl-1H-indol-6-yl)-acetamide | 0.84 min; 369.98; conditions 3 |
| 298 | N-[1-(4-Cyano-benzyl)-1H-pyrazol-3-yl]-2-[4-(3,3-difluoro-1-methyl-cyclobutylmethoxy)-phenyl]-acetamide | 0.94 min; 451.06; conditions 3 |
| 299 | N-[1-(4-Cyano-benzyl)-1H-pyrazol-3-yl]-2-[4-(3,3-difluoro-cyclobutylmethoxy)-phenyl]-acetamide | 0.90 min; 437.07; conditions 3 |
| 300 | N-[1-(4-Cyano-benzyl)-1H-pyrazol-3-yl]-2-[4-(3,3-difluoro-cyclobutyl)-phenyl]-acetamide | 0.89 min; 406.97; conditions 3 |
| 301 | N-[1-(5-Cyano-pyridin-2-ylmethyl)-1H-pyrazol-3-yl]-2-(1-methyl-1H-indol-5-yl)-acetamide | 0.78 min; 371.07; conditions 3 |
| 302 | N-[1-(5-Cyano-pyridin-2-ylmethyl)-1H-pyrazol-3-yl]-2-(1-methyl-1H-indol-6-yl)-acetamide | 0.77 min; 371.08; conditions 3 |
| 303 | N-[1-(5-Cyano-pyridin-2-ylmethyl)-1H-pyrazol-3-yl]-2-[4-(3,3-difluoro-1-methyl-cyclobutylmethoxy)-phenyl]-acetamide | 0.89 min; 452.06; conditions 3 |
| 304 | N-[1-(5-Cyano-pyridin-2-ylmethyl)-1H-pyrazol-3-yl]-2-[4-(3,3-difluoro-cyclobutylmethoxy)-phenyl]-acetamide | 0.86 min; 438.07; conditions 3 |
| 305 | N-[1-(5-Cyano-pyridin-2-ylmethyl)-1H-pyrazol-3-yl]-2-[4-(3,3-difluoro-cyclobutyl)-phenyl]-acetamide | 0.85 min; 408.13; conditions 3 |
| 306 | N-[1-(3-Cyano-4-fluoro-benzyl)-1H-pyrazol-3-yl]-2-[6-(3,3-difluoro-pyrrolidin-1-yl)-pyridin-3-yl]-acetamide | 0.66 min; 441.06; conditions 3 |
| 307 | N-[1-(3-Cyano-4-fluoro-benzyl)-1H-pyrazol-3-yl]-2-(6-pyrrolidin-1-yl-pyridin-3-yl)-acetamide | 0.64 min; 405.14; conditions 3 |
| 308 | N-[1-(3-Cyano-4-fluoro-benzyl)-1H-pyrazol-3-yl]-2-(1-methyl-1H-indazol-6-yl)-acetamide | 0.80 min; 389.09; conditions 3 |
| 309 | N-[1-(3-Cyano-4-fluoro-benzyl)-1H-pyrazol-3-yl]-2-(1-methyl-1H-indol-6-yl)-acetamide | 0.85 min; 388.09; conditions 3 |
| 310 | N-[1-(3-Cyano-4-fluoro-benzyl)-1H-pyrazol-3-yl]-2-(1-methyl-1H-indol-5-yl)-acetamide | 0.85 min; 388.07; conditions 3 |
| 311 | N-[1-(3-Cyano-4-fluoro-benzyl)-1H-pyrazol-3-yl]-2-[4-(3,3-difluoro-1-methyl-cyclobutylmethoxy)-phenyl]-acetamide | 0.95 min; 468.93; conditions 3 |
| 312 | N-[1-(3-Cyano-4-fluoro-benzyl)-1H-pyrazol-3-yl]-2-[4-(3,3-difluoro-cyclobutyl)-phenyl]-acetamide | 0.91 min; 425.10; conditions 3 |
| 313 | N-[1-(3-Cyano-4-fluoro-benzyl)-1H-pyrazol-3-yl]-2-[4-(3,3-difluoro-cyclobutylmethoxy)-phenyl]-acetamide | 0.92 min; 455.02; conditions 3 |
| 314 | N-[1-(3-Cyano-4-fluoro-benzyl)-1H-pyrazol-3-yl]-2-[4-(1-trifluoromethyl-cyclopropyl)-phenyl]-acetamide | 0.93 min; 443.05; conditions 3 |
| 315 | N-[1-(3,4-Difluoro-benzyl)-1H-pyrazol-3-yl]-2-[6-(3-fluoro-oxetan-3-yl)-pyridin-3-yl]-acetamide | 0.77 min; 403.05; conditions 3 |
| 316 | N-[1-(3-Cyano-4-fluoro-benzyl)-1H-pyrazol-3-yl]-2-[4-(3-methyl-oxetan-3-yl)-phenyl]-acetamide | 0.82 min; 405.12; conditions 3 |
| 317 | N-[1-(4-Cyano-benzyl)-1H-pyrazol-3-yl]-2-[4-(3-methyl-oxetan-3-yl)-phenyl]-acetamide | 0.80 min; 387.15; conditions 3 |
| 318 | N-[1-(5-Cyano-pyridin-2-ylmethyl)-1H-pyrazol-3-yl]-2-[4-(3-methyl-oxetan-3-yl)-phenyl]-acetamide | 0.73 min; 388.15; conditions 3 |
| 319 | rac-N-[1-(3-Cyano-4-fluoro-benzyl)-1H-pyrazol-3-yl]-2-[4-(1-methoxy-ethyl)-phenyl]-acetamide | 0.83 min; 393.14; conditions 3 |
| 320 | rac-N-[1-(4-Cyano-benzyl)-1H-pyrazol-3-yl]-2-[4-(1-methoxy-ethyl)-phenyl]-acetamide | 0.82 min; 375.16; conditions 3 |
| 321 | N-[1-(3-Cyano-4-fluoro-benzyl)-1H-pyrazol-3-yl]-2-(1,3-dimethyl-1H-pyrrolo[2,3-b]pyridin-5-yl)-acetamide | 0.72 min; 403.12; conditions 3 |
| 322 | N-[1-(5-Cyano-pyridin-2-ylmethyl)-1H-pyrazol-3-yl]-2-(1,3-dimethyl-1H-pyrrolo[2,3-b]pyridin-5-yl)-acetamide | 0.63 min; 386.05; conditions 3 |
| 323 | N-[1-(5-Cyano-pyridin-2-ylmethyl)-1H-pyrazol-3-yl]-2-(3-cyclobutyl-1-methyl-1H-indol-5-yl)-acetamide | 0.89 min; 425.19; conditions 3 |
| 324 | N-[1-(5-Cyano-pyridin-2-ylmethyl)-1H-pyrazol-3-yl]-2-(3-isopropyl-1-methyl-1H-indol-5-yl)-acetamide | 0.88 min; 413.19; conditions 3 |
| 325 | 2-(3-Cyano-1-methyl-1H-indol-5-yl)-N-[1-(5-cyano-pyridin-2-ylmethyl)-1H-pyrazol-3-yl]-acetamide | 0.75 min; 396.14; conditions 3 |
| 326 | N-[1-(5-Cyano-pyridin-2-ylmethyl)-1H-pyrazol-3-yl]-2-(1-methyl-3-trifluoromethyl-1H-indol-5-yl)-acetamide | 0.85 min; 439.09; conditions 3 |
| 327 | N-[1-(3-Cyano-4-fluoro-benzyl)-1H-pyrazol-3-yl]-2-(3-cyclobutyl-1-methyl-1H-indol-5-yl)-acetamide | 0.95 min; 442.11; conditions 3 |
| 328 | N-[1-(3-Cyano-4-fluoro-benzyl)-1H-pyrazol-3-yl]-2-(3-isopropyl-1-methyl-1H-indol-5-yl)-acetamide | 0.94 min; 430.14; conditions 3 |
| 329 | N-[1-(3-Cyano-4-fluoro-benzyl)-1H-pyrazol-3-yl]-2-(3-cyano-1-methyl-1H-indol-5-yl)-acetamide | 0.83 min; 413.15; conditions 3 |

-continued

| Example No | Name | LC-MS ($t_R$; MH+; conditions) |
|---|---|---|
| 330 | N-[1-(3-Cyano-4-fluoro-benzyl)-1H-pyrazol-3-yl]-2-(1,3-dimethyl-1H-indol-6-yl)-acetamide | 0.89 min; 402.05; conditions 3 |
| 331 | N-[1-(5-Cyano-pyridin-2-ylmethyl)-1H-pyrazol-3-yl]-2-(1,3-dimethyl-1H-indol-6-yl)-acetamide | 0.82 min; 385.09; conditions 3 |
| 332 | N-[1-(3-Cyano-4-fluoro-benzyl)-1H-pyrazol-3-yl]-2-[4-fluoro-2-(2,2,2-trifluoro-ethoxy)-phenyl]-acetamide | 0.89 min; 451.04; conditions 3 |
| 333 | N-[1-(5-Cyano-pyridin-2-ylmethyl)-1H-pyrazol-3-yl]-2-[4-fluoro-2-(2,2,2-trifluoro-ethoxy)-phenyl]-acetamide | 0.82 min; 433.94; conditions 3 |
| 334 | N-(1-(3-cyano-4-fluorobenzyl)-1H-pyrazol-3-yl)-2-(4-(pentafluoro-$\lambda^6$-sulfanyl)phenyl)acetamide | 0.91 min; 460.87; conditions 3 |
| 335 | 2-[4-(Cyano-dimethyl-methyl)-phenyl]-N-[1-(3-cyano-4-fluoro-benzyl)-1H-pyrazol-3-yl]-acetamide | 0.86 min; 402.05; conditions 3 |
| 336 | N-(1-((5-cyanopyridin-2-yl)methyl)-1H-pyrazol-3-yl)-2-(4-(pentafluoro-$\lambda^6$-sulfanyl)phenyl)acetamide | 0.85 min; 444.02; conditions 3 |
| 337 | 2-[4-(Cyano-dimethyl-methyl)-phenyl]-N-[1-(5-cyano-pyridin-2-ylmethyl)-1H-pyrazol-3-yl]-acetamide | 0.78 min; 385.09; conditions 3 |
| 338 | N-[1-(5-Cyano-pyridin-2-ylmethyl)-1H-pyrazol-3-yl]-2-(4-trifluoromethyl-phenyl)-acetamide | 0.82 min; 386.01; conditions 3 |
| 339 | N-[1-(5-Cyano-pyridin-2-ylmethyl)-1H-pyrazol-3-yl]-2-[3-methyl-4-(2,2,2-trifluoro-ethoxy)-phenyl]-acetamide | 0.86 min; 430.11; conditions 3 |
| 340 | N-[1-(3-Cyano-4-fluoro-benzyl)-1H-pyrazol-3-yl]-2-(5-fluoro-6-pyrrolidin-1-yl-pyridin-3-yl)-acetamide | 0.67 min; 423.17; conditions 3 |
| 341 | N-[1-(5-Cyano-pyridin-2-ylmethyl)-1H-pyrazol-3-yl]-2-(5-fluoro-6-pyrrolidin-1-yl-pyridin-3-yl)-acetamide | 0.58 min; 406.18; conditions 3 |
| 342 | N-[1-(3-Cyano-4-fluoro-benzyl)-1H-pyrazol-3-yl]-2-(4-trifluoromethyl-phenyl)-acetamide | 0.89 min; 403.01; conditions 3 |
| 343 | N-[1-(3-Cyano-4-fluoro-benzyl)-1H-pyrazol-3-yl]-2-[3-methyl-4-(2,2,2-trifluoro-ethoxy)-phenyl]-acetamide | 0.91 min; 447.08; conditions 3 |
| 344 | N-[1-(4-Cyano-3,5-difluoro-benzyl)-1H-pyrazol-3-yl]-2-(1-methyl-1H-indazol-5-yl)-acetamide | 0.82 min; 407.15; conditions 3 |
| 345 | N-[1-(4-Cyano-3,5-difluoro-benzyl)-1H-pyrazol-3-yl]-2-[4-(3,3-difluoro-cyclobutoxy)-phenyl]-acetamide | 0.91 min; 449.04; conditions 3 |
| 346 | N-[1-(4-Cyano-3,5-difluoro-benzyl)-1H-pyrazol-3-yl]-2-(1-methyl-1H-indazol-6-yl)-acetamide | 0.82 min; 407.14; conditions 3 |
| 347 | N-[1-(4-Cyano-3,5-difluoro-benzyl)-1H-pyrazol-3-yl]-2-[4-(3-fluoro-oxetan-3-yl)-phenyl]-acetamide | 0.83 min; 427.11; conditions 3 |
| 348 | N-[1-(4-Cyano-3,5-difluoro-benzyl)-1H-pyrazol-3-yl]-2-(1,3-dimethyl-1H-indazol-5-yl)-acetamide | 0.83 min; 421.15; conditions 3 |
| 349 | N-[1-(4-Cyano-3,5-difluoro-benzyl)-1H-pyrazol-3-yl]-2-[6-(3,3-difluoro-pyrrolidin-1-yl)-pyridin-3-yl]-acetamide | 0.67 min; 459.03; conditions 3 |
| 350 | N-[1-(4-Cyano-3,5-difluoro-benzyl)-1H-pyrazol-3-yl]-2-[4-(1-trifluoromethyl-cyclopropyl)-phenyl]-acetamide | 0.94 min; 461.03; conditions 3 |
| 351 | N-[1-(4-Cyano-3,5-difluoro-benzyl)-1H-pyrazol-3-yl]-2-(6-pyrrolidin-1-yl-pyridin-3-yl)-acetamide | 0.66 min; 423.16; conditions 3 |
| 352 | 2-(4-tert-Butyl-phenyl)-N-[1-(4-cyano-3,5-difluoro-benzyl)-1H-pyrazol-3-yl]-acetamide | 0.95 min; 409.18; conditions 3 |
| 353 | N-[1-(4-Cyano-3,5-difluoro-benzyl)-1H-pyrazol-3-yl]-2-(4-isopropyl-phenyl)-acetamide | 0.93 min; 395.18; conditions 3 |
| 354 | 2-[4-(1-Cyano-cyclopropyl)-phenyl]-N-[1-(5-cyano-pyridin-2-ylmethyl)-1H-pyrazol-3-yl]-acetamide | 0.77 min; 383.17; conditions 3 |
| 355 | 2-[4-(1-Cyano-cyclopropyl)-phenyl]-N-[1-(3-cyano-4-fluoro-benzyl)-1H-pyrazol-3-yl]-acetamide | 0.84 min; 400.17; conditions 3 |
| 356 | N-[1-(5-Cyano-pyridin-2-ylmethyl)-1H-pyrazol-3-yl]-2-[4-(1-hydroxy-cyclopropyl)-phenyl]-acetamide | 0.55 min; 374.19; conditions 3 |
| 357 | N-[1-(4-Cyano-3,5-difluoro-benzyl)-1H-pyrazol-3-yl]-2-(1-ethyl-1H-indazol-5-yl)-acetamide | 0.84 min; 421.14; conditions 3 |
| 358 | N-[1-(4-Cyano-3,5-difluoro-benzyl)-1H-pyrazol-3-yl]-2-(1,3-dimethyl-1H-indol-5-yl)-acetamide | 0.90 min; 420.14; conditions 3 |
| 359 | N-[1-(4-Cyano-3,5-difluoro-benzyl)-1H-pyrazol-3-yl]-2-[4-(3-methoxy-oxetan-3-yl)-phenyl]-acetamide | 0.81 min; 439.10; conditions 3 |
| 360 | N-[1-(4-Cyano-3,5-difluoro-benzyl)-1H-pyrazol-3-yl]-2-[4-(oxetan-3-ylmethoxy)-phenyl]-acetamide | 0.82 min; 439.10; conditions 3 |
| 361 | N-[1-(4-Cyano-3,5-difluoro-benzyl)-1H-pyrazol-3-yl]-2-[4-(3-fluoro-oxetan-3-ylmethoxy)-phenyl]-acetamide | 0.84 min; 457.04; conditions 3 |
| 362 | N-[1-(4-Cyano-3,5-difluoro-benzyl)-1H-pyrazol-3-yl]-2-[4-(3-methyl-oxetan-3-ylmethoxy)-phenyl]-acetamide | 0.86 min; 453.07; conditions 3 |
| 363 | N-[1-(4-Cyano-3,5-difluoro-benzyl)-1H-pyrazol-3-yl]-2-[4-(3,3-difluoro-cyclobutylmethoxy)-phenyl]-acetamide | 0.93 min; 473.10; conditions 3 |
| 364 | N-[1-(4-Cyano-3,5-difluoro-benzyl)-1H-pyrazol-3-yl]-2-[4-(3,3-difluoro-1-methyl-cyclobutylmethoxy)-phenyl]-acetamide | 0.96 min; 487.01; conditions 3 |
| 365 | N-[1-(6-Cyano-5-fluoro-pyridin-2-ylmethyl)-1H-pyrazol-3-yl]-2-[4-(1-trifluoromethyl-cyclopropyl)-phenyl]-acetamide | 0.91 min; 444.08; conditions 3 |
| 366 | N-[1-(6-Cyano-5-methyl-pyridin-2-ylmethyl)-1H-pyrazol-3-yl]-2-[6-(3,3-difluoro-pyrrolidin-1-yl)-pyridin-3-yl]-acetamide | 0.63 min; 438.14; conditions 3 |
| 367 | N-[1-(6-Cyano-5-methyl-pyridin-2-ylmethyl)-1H-pyrazol-3-yl]-2-[3-methyl-4-(2,2,2-trifluoro-ethoxy)-phenyl]-acetamide | 1.40 min; 444.07; conditions 1 |

| Example No | Name | LC-MS ($t_R$; MH+; conditions) |
| --- | --- | --- |
| 368 | N-[1-(6-Cyano-5-methyl-pyridin-2-ylmethyl)-1H-pyrazol-3-yl]-2-(1,3-dimethyl-1H-indazol-5-yl)-acetamide | 1.03 min; 400.13; conditions 1 |
| 369 | N-[1-(6-Cyano-5-methyl-pyridin-2-ylmethyl)-1H-pyrazol-3-yl]-2-(1,3-dimethyl-1H-indol-5-yl)-acetamide | 1.28 min; 399.09; conditions 1 |
| 370 | N-[1-(6-Cyano-5-methyl-pyridin-2-ylmethyl)-1H-pyrazol-3-yl]-2-(1-ethyl-1H-indazol-5-yl)-acetamide | 1.07 min; 400.01; conditions 1 |
| 371 | 2-(4-tert-Butyl-phenyl)-N-[1-(6-cyano-5-methyl-pyridin-2-ylmethyl)-1H-pyrazol-3-yl]-acetamide | 1.47 min; 388.16; conditions 1 |
| 372 | N-[1-(6-Cyano-5-methyl-pyridin-2-ylmethyl)-1H-pyrazol-3-yl]-2-[4-(1-trifluoromethyl-cyclopropyl)-phenyl]-acetamide | 1.44 min; 440.01; conditions 1 |
| 373 | N-[1-(6-Cyano-5-methyl-pyridin-2-ylmethyl)-1H-pyrazol-3-yl]-2-(6-pyrrolidin-1-yl-pyridin-3-yl)-acetamide | 1.10 min; 402.14; conditions 1 |
| 374 | N-[1-(6-Cyano-5-methyl-pyridin-2-ylmethyl)-1H-pyrazol-3-yl]-2-[4-(3,3-difluoro-cyclobutoxy)-phenyl]-acetamide | 1.33 min; 438.05; conditions 1 |
| 375 | N-[1-(5-Cyano-pyridin-2-ylmethyl)-1H-pyrazol-3-yl]-2-[4-(1-methyl-cyclopropyl)-phenyl]-acetamide | 0.85 min; 472.20; conditions 3 |
| 376 | N-[1-(5-Cyano-pyridin-2-ylmethyl)-1H-pyrazol-3-yl]-2-[4-(2,2,2-trifluoro-1,1-dimethyl-ethyl)-phenyl]-acetamide | 0.87 min; 428.17; conditions 3 |
| 377 | N-[1-(6-Cyano-5-methyl-pyridin-2-ylmethyl)-1H-pyrazol-3-yl]-2-[4-(1-methyl-cyclopropyl)-phenyl]-acetamide | 0.89 min; 386.12; conditions 3 |
| 378 | N-[1-(5-Cyano-pyridin-2-ylmethyl)-1H-pyrazol-3-yl]-2-(2,2-dimethyl-2,3-dihydro-benzofuran-5-yl)-acetamide | 0.80 min; 388.18; conditions 3 |
| 379 | N-[1-(5-Cyano-pyridin-2-ylmethyl)-1H-pyrazol-3-yl]-2-(3,3-dimethyl-2,3-dihydro-benzofuran-5-yl)-acetamide | 0.80 min; 388.19; conditions 3 |
| 380 | N-[1-(5-Cyano-pyridin-2-ylmethyl)-1H-pyrazol-3-yl]-2-(2,2-dimethyl-2,3-dihydro-benzofuran-6-yl)-acetamide | 0.80 min; 388.19; conditions 3 |
| 381 | N-[1-(5-Cyano-pyridin-2-ylmethyl)-1H-pyrazol-3-yl]-2-[4-methyl-3-(2,2,2-trifluoro-ethoxy)-phenyl]-acetamide | 0.86 min; 430.13; conditions 3 |
| 382 | N-[1-(5-Cyano-pyridin-2-ylmethyl)-1H-pyrazol-3-yl]-2-[3-fluoro-4-(2,2,2-trifluoro-ethoxy)-phenyl]-acetamide | 0.83 min; 433.98; conditions 3 |
| 383 | rac-N-[1-(5-Cyano-pyridin-2-ylmethyl)-1H-pyrazol-3-yl]-2-[4-((1R*,2R*)-2-trifluoromethyl-cyclopropyl)-phenyl]-acetamide | 0.87 min; 426.17; conditions 3 |
| 384 | N-[1-(5-Cyano-pyridin-2-ylmethyl)-1H-pyrazol-3-yl]-2-[4-(1-methoxy-cyclopropyl)-phenyl]-acetamide | 0.78 min; 388.19; conditions 3 |

Example 385: N-[1-(5-Cyano-6-difluoromethyl-pyridin-2-ylmethyl)-1H-pyrazol-3-yl]-2-(4-isopropyl-phenyl)-acetamide and Example 386: N-[1-(5-cyano-4-difluoromethyl-pyridin-2-ylmethyl)-1H-pyrazol-3-yl]-2-(4-isopropyl-phenyl)-acetamide To a sol. of Example 71 (205 mg, 0.57 mmol) and zinc difluoromethanesulfinate (355 mg, 1.14 mmol) in DMSO (3.2 mL), is added trifluoroacetic acid (0.0446 mL, 0.57 mmol) at rt. Luperox® TBH70X (tert-butyl hydroperoxide; 70% weight sol. in water, 0.23 mL, 1.71 mmol) is added slowly with vigorous stirring. The mixture is stirred at rt overnight. Zinc difluoromethanesulfinate (355 mg, 1.14 mmol) and Luperox® TBH70X are added again. The mixture was stirred at r.t over 4 nights. The reaction mixture was partitioned between CH$_2$Cl$_2$ (5 mL) and aq. sat. NaHCO$_3$ (5 mL). The layers are separated, and the aq. phase is extracted with CH$_2$Cl$_2$ (3×5 mL). The combined org. layers are dried over MgSO$_4$, filtered, and the solvents are removed under reduced pressure. Purification of the residue by prep. HPLC (column: Waters XBridge, 30×75 mm, 10 um, UV/MS, basic conditions) yields the title products. LC-MS: $t_R$=0.90 min, MH+=410.18 and $t_R$=0.89 min, MH+=410.19 respectively (conditions 3).

2-(1λ4-Diazenylidene)-1-(3,3-dimethyl-2,3-dihydrobenzofuran-6-yl)ethan-1-one and (rac.)-2-(1λ4-diazenylidene)-1-(3-methylchroman-7-yl)ethan-1-one To a mixture of 3,3-dimethyl-2,3-dihydrobenzofuran-6-carboxylic acid (710 mg, 3.69 mmol) in CH$_2$Cl$_2$ (20 mL) at −5° C., are added oxalyl chloride, (0.474 mL, 5.54 mmol) and 4 drops of DMF. The mixture is allowed to warm up to rt over 2 h. The mixture is concentrated in vacuo (backfilled with N2). The resulting oil is dissolved in THF (20 mL) and cooled to −5° C. (Trimethylsilyl)diazomethane (2.0 M in hexanes, 4.15 mL, 8.31 mmol) is added and the mixture is allowed to warm to rt overnight. The solvents are removed under reduced pressure. Purification of the residue by automated FC (Combiflash, heptane→EtOAc/heptane 1:3, column: 80 g, flow: 60 mL/min,) yields a mixture of the two title products. LC-MS: $t_R$=0.80 min, MH+=217.20 for the mixture (conditions 3).

Ethyl 2-(3,3-dimethyl-2,3-dihydrobenzofuran-6-yl)acetate and (rac.)-ethyl 2-(3-methylchroman-7-yl)acetate To a sol. of the previous mixture (280 mg, 1.29 mmol) in EtOH (30 mL), a sol. of silver benzoate (178 mg, 0.777 mmol) in Et$_3$N (5.0 mL) is added dropwise. The resulting black sol. is stirred at rt for 19 h. The black suspension is filtered through Celite. The pad is rinsed with EtOAc. The filtrate is concentrated in vacuo. Purification of the crude by HPLC yielded the two separated title products. LC-MS: $t_R$=0.90 min, MH+=235.22 and $t_R$=0.90 min, respectively (conditions 3).

(rac.)-2-(3-Methylchroman-7-yl)acetic acid

To a sol. of (rac.)-ethyl 2-(3-methylchroman-7-yl)acetate (38 mg, 0.162 mmol) in DMF (1.00 mL) is added aq. NaOH (1M, 0.5 mL). The resulting sol. is stirred at rt for 4 h. The sol. is neutralized with formic acid (0.5 mL), filtered and then purified by prep. HPLC to yield the crude title product. LC-MS: $t_R$=0.74 min (conditions 3).

5-Bromo-3-fluoro-2-((3-nitro-1H-pyrazol-1-yl) methyl)pyridine

Prepared according to general procedure 4 with $K_2CO_3$ (1.87 g, 13.6 mmol), 5-bromo-2-(bromomethyl)-3-fluoropyridine (760 mg, 2.71 mmol), and 5-nitro-1H-pyrazole (313 mg, 2.71 mmol) in acetone (25 mL). The reaction is complete after 2 h. The crude is not purified. LC-MS: $t_R$=0.78 min, MH$^+$=302.98 (conditions 3).

5-Fluoro-6-((3-nitro-1H-pyrazol-1-yl)methyl)nicotinonitrile

To a sol. of 5-bromo-3-fluoro-2-((3-nitro-1H-pyrazol-1-yl)methyl)pyridine (1.02 g, 3.04 mmol) in N,N-dimethylacetamide (6.2 mL), are added in sequence $Zn(CN)_2$ (196 mg, 1.67 mmol), $Pd_2(dba)_3$ (60.7 mg, 0.066 mmol), 1,1'-bis-(diphenylphosphino)-ferrocene (45.5 mg, 0.082 mmol) and poly(methylhydrosiloxane) (PMHS) (0.067 mL). The resulting mixture is stirred at 150° C. in a microwave during 40 min. The mixture is allowed to cool to rt, filtered over Celite, and the filtrate is concentrated in vacuo. Purification of the residue by automated FC (Combiflash, EtOAc/heptane 0:100→40:60, column 24 g, flow 35 mL/min) yields the title product. LC-MS: $t_R$=0.70 min, MH$^+$=248.17 (conditions 3).

6-((3-Amino-1H-pyrazol-1-yl)methyl)-5-fluoronicotinonitrile

To a sol. of 5-fluoro-6-((3-nitro-1H-pyrazol-1-yl)methyl) nicotinonitrile (260 mg, 0.899 mmol) in EtOAc (9.22 mL) under $N_2$, is added Pd (10 wt. % on activated charcoal, 52 mg, 0.489 mmol). The flask is carefully evacuated and backfilled with $H_2$ (3×). The black suspension was stirred at rt under an $H_2$ atmosphere for 30 h. The black suspension is filtered through Celite, and the Celite is rinsed with EtOAc. The filtrate is concentrated in vacuo. To a sol. of the previous residue in THF (9.22 mL) under $N_2$, Pd (10 wt. % on activated charcoal, 52 mg, 0.49 mmol) is added. The flask is carefully evacuated and backfilled with $H_2$ (3×). The black suspension is stirred at rt under an $H_2$ atmosphere overnight. Purification of the residue by HPLC yields the title product. LC-MS: $t_R$=0.40 min, MH$^+$=218.16 (conditions 3).

tert-Butyl 2-(4-(1-cyano-3,3-difluorocyclobutyl) phenyl)acetate

Prepared according to general procedure 6 from 1-(4-bromophenyl)-3,3-difluorocyclobutane-1-carbonitrile (WO2012027322, 92.7 mg, 0.337 mmol), (2-(tert-butoxy)-2-oxoethyl)zinc(II) chloride (0.5M in $Et_2O$, 1.4 mL, 0.70 mmol), $Pd_2(dba)_3$ (15.4 mg, 0.017 mmol), and X-Phos (8.3 mg, 0.017 mmol) in THF (2.9 mL). The reaction is complete overnight at 45° C. Purification of the crude by HPLC yields the title product. LC-MS: $t_R$=0.95 min, MH$^+$=308.13 (conditions 3).

2-(4-(1-Cyano-3,3-difluorocyclobutyl)phenyl)acetic acid

Prepared according to general procedure 7 from tert-Butyl 2-(4-(1-cyano-3,3-difluorocyclobutyl)phenyl)acetate (42 mg, 0.13 mmol) in TFA (0.15 mL) and $CH_2Cl_2$ (0.15 mL) The reaction is complete after 3 h at 0° C. LC-MS: $t_R$=0.74 min (conditions 3).

2-Bromo-3-fluoro-6-((3-nitro-1H-pyrazol-1-yl) methyl)pyridine

Prepared according to general procedure 4 with $K_2CO_3$ (2.01 g, 14.6 mmol), 2-bromo-6-(bromomethyl)-3-fluoropyridine (799 mg, 2.91 mmol), and 5-nitro-1H-pyrazole (336 mg, 2.91 mmol) in acetone (26 mL). The reaction is complete after 2 h. The crude is not purified. LC-MS: $t_R$=0.80 (conditions 3).

3-Fluoro-6-((3-nitro-1H-pyrazol-1-yl)methyl)picolinonitrile

To a sol. of 2-bromo-3-fluoro-6-((3-nitro-1H-pyrazol-1-yl)methyl)pyridine (1.13 g, 3.51 mmol) in N,N-Dimethylacetamide (7.2 mL), are added in sequence $Zn(CN)_2$ (226 mg, 1.93 mmol), $Pd_2(dba)_3$ (70.1 mg, 0.0766 mmol), 1,1'-bis-(diphenylphosphino)-ferrocene (52.6 mg, 0.0948 mmol), and poly(methylhydrosiloxane) (PMHS) (0.077 mL). The mixture is stirred at 150° C. in a microwave for 40 min. The mixture is filtered over Celite, and the Celite is rinsed with EtOAc. The filtrate is concentrated in vacuo. Purification of the residue by automated FC (Combiflash, EtOAc/heptane 0:100→30:70, column 24 g, flow 35 mL/min) yields the title product. LC-MS: $t_R$=0.74, MH$^+$=248.20 (conditions 3).

6-((3-Amino-1H-pyrazol-1-yl)methyl)-3-fluoropicolinonitrile

To a sol. of 3-fluoro-6-((3-nitro-1H-pyrazol-1-yl)methyl) picolinonitrile (320 mg, 1.08 mmol) in EtOAc (11.1 mL) under $N_2$, is added Pd (10 wt. % on activated charcoal, 64 mg, 0.56 mmol). The flask is carefully evacuated and backfilled with $H_2$ (3×). The black suspension was stirred at rt under an $H_2$ atmosphere overnight. The black suspension is filtered through Celite, and the Celite is rinsed with EtOAc. The filtrate is concentrated in vacuo. Purification of the residue by HPLC yields the title product. LC-MS: $t_R$=0.48 min, MH$^+$=218.18 (conditions 3).

tert-Butyl 2-(3-cyano-4-isobutylphenyl)acetate

Prepared according to general procedure 6 from 5-bromo-2-isobutylbenzonitrile (136 mg, 0.57 mmol), (2-(tert-butoxy)-2-oxoethyl)zinc(II) chloride (0.5M in $Et_2O$, 1.24 mL, 0.62 mmol), $Pd_2(dba)_3$ (26.2 mg, 0.0286 mmol), and Q-Phos (41.1 mg, 0.0571 mmol) in dioxane (1.5 mL). The reaction is complete after 30 min at 85° C. Purification by automated FC (Combiflash, EtOAc/heptane 0:100→60:40) yields the title product. LC-MS: $t_R$=1.00 min, MH$^+$=273.97 (conditions 4).

2-(3-Cyano-4-isobutylphenyl)acetic acid

Prepared according to general procedure 7 from tert-butyl 2-(3-cyano-4-isobutylphenyl)acetate (33 mg, 0.12 mmol) in HCl (4M in dioxane, 7 mL) and $CH_2Cl_2$ (1.4 mL) The reaction is complete overnight at rt. LC-MS: $t_R$=0.73 min (conditions 3).

The following examples were prepared according to general procedure 3, from the appropriate carboxylic acids and aminopyrazoles:

| Example No | Name | LC-MS ($t_R$; MH+; conditions) |
|---|---|---|
| 387 | N-[1-(5-Cyano-pyridin-2-ylmethyl)-1H-pyrazol-3-yl]-2-(3,3-dimethyl-2,3-dihydro-benzofuran-6-yl)-acetamide | 0.81 min; 388.19; conditions 3 |
| 388 | rac-N-[1-(5-Cyano-pyridin-2-ylmethyl)-1H-pyrazol-3-yl]-2-(3-methyl-chroman-7-yl)-acetamide | 0.81 min; 388.17; conditions 3 |
| 389 | N-[1-(5-Cyano-3-fluoro-pyridin-2-ylmethyl)-1H-pyrazol-3-yl]-2-[4-(1-trifluoromethyl-cyclopropyl)-phenyl]-acetamide | 0.89 min; 444.07; conditions 3 |
| 390 | 2-[4-(1-Cyano-3,3-difluoro-cyclobutyl)-phenyl]-N-[1-(5-cyano-pyridin-2-ylmethyl)-1H-pyrazol-3-yl]-acetamide | 0.81 min; 433.01; conditions 3 |
| 391 | N-[1-(6-Cyano-5-fluoro-pyridin-2-ylmethyl)-1H-pyrazol-3-yl]-2-[3-methyl-4-(2,2,2-trifluoro-ethoxy)-phenyl]-acetamide | 0.89 min; 448.08; conditions 3 |
| 392 | 2-(3-Cyano-4-isobutyl-phenyl)-N-[1-(5-cyano-pyridin-2-ylmethyl)-1H-pyrazol-3-yl]-acetamide | 0.86 min; 399.17; conditions 3 |
| 393 | 2-(3-Cyano-4-isobutyl-phenyl)-N-[1-(3,4-difluoro-benzyl)-1H-pyrazol-3-yl]-acetamide | 0.94 min; 409.16; conditions 3 |

Example 394: N-[1-(5-Azetidin-1-yl-pyridin-2-ylmethyl)-1H-pyrazol-3-yl]-2-(4-isopropyl-phenyl)-acetamide To a degased mixture of Example 94 (80 mg, 0.192 mmol), $Pd_2(dba)_3$ (17.5 mg, 0.02 mmol), RuPhos (17.9 mg, 0.04 mmol), NaOtBu (37 mg, 0.38 mmol), and molecular sieve (4 A powder, 100 mg) in toluene (2.00 mL) is added azetidine (0.04 mL, 0.57 mmol). The reaction is stirred in a closed vial at 95° C. for 17 h. The mixture is allowed to cool to rt, and the solvents are removed under reduced pressure. Purification of the crude by HPLC yields the title product. LC-MS: $t_R$=0.74 min, MH+=390.20 (conditions 3).

Example 395: 2-(4-Isopropyl-phenyl)-N-[1-(5-pyrrolidin-1-yl-pyridin-2-ylmethyl)-1H-pyrazol-3-yl]-acetamide To a degased mixture of Example 94 (80 mg, 0.192 mmol), $Pd_2(dba)_3$ (17.5 mg, 0.02 mmol), RuPhos (17.9 mg, 0.04 mmol), NaOtBu (37 mg, 0.38 mmol), and molecular sieve (4 A powder, 100 mg) in toluene (2.00 mL) is added pyrrolidine (0.05 mL, 0.57 mmol). The reaction is stirred in a closed vial at 110° C. for 17 h. The mixture is allowed to cool to rt, and the solvents are removed under reduced pressure. Purification of the crude by HPLC yields the title product. LC-MS: $t_R$=0.75 min, MH+=404.23 (conditions 3).

Example 396: N-{1-[5-(3,3-Difluoro-pyrrolidin-1-yl)-pyridin-2-ylmethyl]-1H-pyrazol-3-yl}-2-(4-isopropyl-phenyl)-acetamide To a degased mixture of Example 94 (80 mg, 0.192 mmol), $Pd_2(dba)_3$ (17.5 mg, 0.02 mmol), RuPhos (17.9 mg, 0.04 mmol), NaOtBu (37 mg, 0.38 mmol), and molecular sieve (4 A powder, 100 mg) in toluene (2.00 mL) is added 3,3-difluoropyrrolidine hydrochloride (57.6 mg, 0.57 mmol). The reaction is stirred in a closed vial at 110° C. for 17 h. The mixture is allowed to cool to rt, and the solvents are removed under reduced pressure. Purification of the crude by HPLC yields the title product. LC-MS: $t_R$=0.78 min, MH+=440.17 (conditions 3).

tert-Butyl 2-(4-(cyclopropylmethoxy)-3-(trifluoromethoxy)phenyl)acetate

Prepared according to general procedure 6 from 4-bromo-1-(cyclopropylmethoxy)-2-(trifluoromethoxy)benzene (146 mg, 0.47 mmol), (2-(tert-butoxy)-2-oxoethyl)zinc(II) chloride (0.5M in $Et_2O$, 1.04 mL, 0.52 mmol), $Pd_2(dba)_3$ (22 mg, 0.020 mmol), and Q-Phos (34 mg, 0.050 mmol) in dioxane (1.5 mL). The reaction is complete after 1 h at 85° C. Purification by automated FC (Combiflash, EtOAc/heptane 0:100→60:40) yields the title product. LC-MS: $t_R$=1.04 min, MH+=223.23 (conditions 4).

2-(4-(Cyclopropylmethoxy)-3-(trifluoromethoxy)phenyl)acetic acid

Prepared according to general procedure 7 from tert-butyl 2-(4-(cyclopropylmethoxy)-3-(trifluoromethoxy)phenyl)acetate (30 mg, 0.087 mmol) in HCOOH (0.60 mL) The reaction is complete after 2 h at rt.

4-Bromo-5-fluoro-2-methylpyridine 1-oxide

To a stirred solution of acetyl bromide (10.7 mL, 143 mmol) in AcOH (22.3 mL), is added portionwise 5-fluoro-2-methyl-4-nitropyridine 1-Oxide (2500 mg, 14.5 mmol). The mixture is stirred at for 2.5 h at rt. The mixture is carefully poured onto ice, and solid $K_2CO_3$ is carefully added in portions. The aq. layer is extracted with EtOAc (95 mL) and the org. layer is washed with brine (20 mL). The combined aq. layers are saturated with NaCl, and $CH_2Cl_2$/iPrOH 3/1 (100 mL) is added. The mixture is stirred at rt for 2 h. The layers are separated, and the aq. phase is extracted with $CH_2Cl_2$/iPrOH 3/1 (2×100 mL) and $CH_2Cl_2$ (1×200 mL). The combined org. layers are dried over $MgSO_4$, filtered, and the solvents are removed under reduced pressure to yield the crude title product. LC-MS: $t_R$=0.51 min, MH+=206.06 (conditions 3).

(4-Bromo-5-fluoropyridin-2-yl)methyl acetate

To $Ac_2O$ (7.39 mL, 77.5 mmol) at 120° C. is added 4-bromo-5-fluoro-2-methylpyridine 1-oxide (2.98 g, 13.6 mmol). The resulting sol. is stirred at 120° C. for 5 min, and at reflux for 30 min. The mixture is allowed to cool down to rt, and is poured onto ice (57 g). The mixture is neutralized with $NaHCO_3$. $Et_2O$ (60 mL) is added, and the layers are separated. The aq. phase is extracted with $Et_2O$ (2×30 mL), and the combined org. layers are washed with brine, dried over $MgSO_4$, filtered and the solvents are removed under reduced pressure. Purification by automated FC (Combiflash, EtOAc/heptane 0:100→30:70, column 80 g, flow 60 mL/min) yields the title product. LC-MS: $t_R$=0.73 min, MH+=248.08 (conditions 3).

(4-Bromo-5-fluoropyridin-2-yl)methanol $K_2CO_3$ (25.9 mg, 0.187 mmol) is added to a sol. of (4-bromo-5-fluoropyridin-2-yl)methyl acetate (1680 mg, 5.82 mmol) in MeOH (7.8 mL). The resulting mixture is stirred overnight at rt. $K_2CO_3$ (1674 mg, 12.1 mmol, 2.082 eq) is added again, and the mixture is stirred at rt for 1 h. Water (16 mL) is added, and the mixture is neutralized with aq. 5% AcOH. $CH_2Cl_2$ is added, and the layers are separated. The aq. phase is extracted with $CH_2Cl_2$ (2×), and the combined org. layers are washed with brine, dried over $MgSO_4$, filtered, and the solvents are removed under reduced pressure to yield the crude title product. LC-MS: $t_R$=0.55 min, $MH^+$=206.06 (conditions 3).

4-Bromo-2-(bromomethyl)-5-fluoropyridine

To a warmed (50° C.) mixture of (4-bromo-5-fluoropyridin-2-yl)methanol (810 mg, 3.76 mmol) in DMF (4.8 mL) is added $PBr_3$ (0.389 mL, 4.14 mmol). The mixture is stirred at 50° C. for 1.5 h. The mixture is allowed to cool down to rt, is diluted with water (240 mL) and is basified with aq. sat. $NaHCO_3$. EtOAc is added, and the layers are separated. The aq. layer is extracted with EtOAc (2×), and the combined org. layers are washed with brine, dried over $MgSO_4$, filtered and concentrated in vacuo to give the crude title product. LC-MS: $t_R$=0.78 min, $MH^+$=269.97 (conditions 3).

4-Bromo-5-fluoro-2-((3-nitro-1H-pyrazol-1-yl)methyl)pyridine

Prepared according to general procedure 4 with $K_2CO_3$ (2.38 g, 17.3 mmol), 4-bromo-2-(bromomethyl)-5-fluoropyridine (952 mg, 3.45 mmol), and 5-nitro-1H-pyrazole (399 mg, 3.45 mmol) in acetone (31 mL). The reaction is complete after 3 h. The crude is not purified. LC-MS: $t_R$=0.78, $MH^+$=301.02 (conditions 3).

5-Fluoro-2-((3-nitro-1H-pyrazol-1-yl)methyl)isonicotinonitrile

To a sol. of 4-bromo-5-fluoro-2-((3-nitro-1H-pyrazol-1-yl)methyl)pyridine (1.38 g, 4.15 mmol) in N,N-Dimethylacetamide (8.5 mL), are added in sequence $Zn(CN)_2$ (268 mg, 2.28 mmol), $Pd_2(dba)_3$ (83 mg, 0.091 mmol), 1,1'-bis-(diphenylphosphino)-ferrocene (62.3 mg, 0.112 mmol) and poly(methylhydrosiloxane) (0.091 mL). The mixture is stirred at 150° C. in a microwave for 40 min. The mixture is filtered over Celite, and the Celite is rinsed with EtOAc. The filtrate is concentrated in vacuo. Purification of the residue by automated FC (Combiflash, EtOAc/heptane 0:100→70:30, column 24 g, flow 35 mL/min) yields the title product. LC-MS: $t_R$=0.72 (conditions 3).

2-((3-Amino-1H-pyrazol-1-yl)methyl)-5-fluoroisonicotinonitrile

To a sol. of 5-fluoro-2-((3-nitro-1H-pyrazol-1-yl)methyl)isonicotinonitrile (815 mg, 2.35 mmol) in EtOAc (24 mL) is added Pd on charcoal (10 wt. %, 163 mg, 1.53 mmol). The flask is carefully evacuated and backfilled with $H_2$ (3×). The black suspension is stirred at rt under an $H_2$ atmosphere overnight. The black suspension is filtered through Celite. The Celite is rinsed with EtOAc. The filtrate is concentrated in vacuo. Ca. 300 mg of the residue is purified by HPLC. The resulting fractions are combined and $CH_2Cl_2$ is added. The layers are separated, and the aq. phase is extracted with $CH_2Cl_2$ (2×). The combined org. layers are dried over $MgSO_4$, filtered, and the solvents are concentrated in vacuo to give the crude title product. LC-MS: $t_R$=0.45, $MH^+$=218.18 (conditions 3).

tert-Butyl 2-(4-(1-cyanocyclopropyl)-3-(trifluoromethyl)phenyl)acetate

Prepared according to general procedure 6 from 1-(4-bromo-2-(trifluoromethyl)phenyl)cyclopropane-1-carbonitrile (WO2006018725, 170 mg, 0.59 mmol), (2-(tert-butoxy)-2-oxoethyl)zinc(II) chloride (0.5M in $Et_2O$, 1.28 mL, 0.64 mmol), $Pd_2(dba)_3$ (27 mg, 0.029 mmol), and Q-Phos (42 mg, 0.059 mmol) in dioxane (1.5 mL). The reaction is complete after 1 h at 85° C. Purification by automated FC (Combiflash, EtOAc/heptane 0:100→50:50) yields the title product. LC-MS: $t_R$=0.91 min, $MH^+$=326.04 (conditions 4).

2-(4-(1-Cyanocyclopropyl)-3-(trifluoromethyl)phenyl)acetic acid

Prepared according to general procedure 7 from tert-butyl 2-(4-(1-cyanocyclopropyl)-3-(trifluoromethyl)phenyl)acetate (36 mg, 0.11 mmol) in TFA (0.36 mL) and $CH_2Cl_2$ (0.35 mL). The reaction is complete after 2.5 h at 0° C. LC-MS: $t_R$=0.65 (conditions 4).

Methyl 2-(3-methyl-4-(3,3,3-trifluoropropoxy)phenyl)acetate

To a sol. of 2-(4-hydroxy-3-methylphenyl)acetic acid methyl ester (200 mg, 1.11 mmol) in DMF (3 mL) is added $Cs_2CO_3$ (470 mg, 1.44 mmol). The mixture is cooled to 0° C., and 3,3,3-trifluoropropyl methanesulfonate (853 mg, 4.44 mmol) is added dropwise. The mixture is stirred overnight while warming up to rt. $Cs_2CO_3$ (1.88 g, 5.76 mmol) and 3,3,3-trifluoropropyl methanesulfonate (853 mg, 4.44 mmol) are added again. The mixture is stirred overnight. Water is added, and the mixture is extracted with EtOAc (2×). The solvents are removed under reduced pressure. Purification of the residue by FC (EtOAc/heptane 10:90→20:80→25:75→50:50-75:25-100:0) yields the title product.

2-(3-Methyl-4-(3,3,3-trifluoropropoxy)phenyl)acetic acid

To a sol. of methyl 2-(3-methyl-4-(3,3,3-trifluoropropoxy)phenyl)acetate (50.0 mg, 0.18 mmol) in THF (1.00 mL) and MeOH (0.15 mL), is added 1M aq. NaOH (0.23 mL). The mixture is stirred overnight at rt, and the organic volatiles are removed in vacuo. The residue is diluted with water and washed with EtOAc (1×). The aq. layer is acidified with aq. 1M HCl. The mixture is extracted with $CH_2CO_2$ (3×). The comb. org. layers are dried over $MgSO_4$, filtered, and the solvents are removed under reduced pressure to yield the crude title product.

4-Bromo-2-cyclopropyl-1-(2,2,2-trifluoroethoxy)benzene

To a sol. of 4-bromo-2-cyclopropylphenol (240 mg, 1.13 mmol) in DMF (5 mL) are added $Cs_2CO_3$ (550 mg, 1.69 mmol) and 1,1,1-trifluoro-2-iodoethane (0.555 mL, 5.63 mmol). The mixture is stirred for 2 h at 90° C., and is allowed to cool to rt. Water is added, and the mixture is extracted with EtOAc (3×). The combined org. layers are washed with water and with brine, are dried over MgSO4, filtered, and the solvents are removed under reduced pressure. Purification of the crude by automated FC (Combiflash, EtOAc/heptane 1:1) yields the title product.

tert-Butyl 2-(3-cyclopropyl-4-(2,2,2-trifluoroethoxy) phenyl)acetate

Prepared according to general procedure 6 from 4-bromo-2-cyclopropyl-1-(2,2,2-trifluoroethoxy)benzene (144 mg, 0.488 mmol), (2-(tert-butoxy)-2-oxoethyl)zinc(II) chloride (0.5M in Et$_2$O, 2.20 mL, 1.10 mmol), Pd$_2$(dba)$_3$ (22 mg, 0.024 mmol), and Q-Phos (23 mg, 0.049 mmol) in dioxane (3.0 mL). The reaction is complete overnight at 85° C. Purification by automated FC (Combiflash, EtOAc/heptane 0:100→50:50) yields the title product.

2-(3-Cyclopropyl-4-(2,2,2-trifluoroethoxy)phenyl) acetic acid

Prepared according to general procedure 7 from tert-butyl 2-(3-cyclopropyl-4-(2,2,2-trifluoroethoxy)phenyl)acetate (30 mg, 0.091 mmol) in HCOOH (0.80 mL). The reaction is complete after 2.5 h at rt. LC-MS: t$_R$=0.77 (conditions 4).

tert-Butyl 2-(3-methyl-4-(trifluoromethoxy)phenyl)acetate

Prepared according to general procedure 6 from 4-bromo-2-methyl-1-(trifluoromethoxy)benzene (300 mg, 1.18 mmol), (2-(tert-butoxy)-2-oxoethyl)zinc(II) chloride (0.5M in Et$_2$O, 3.40 mL, 1.70 mmol), Pd$_2$(dba)$_3$ (54 mg, 0.059 mmol), and Q-Phos (56 mg, 0.118 mmol) in dioxane (3.0 mL). The reaction is complete overnight at 85° C. Purification by automated FC (Combiflash, EtOAc/heptane 0:100→100:0) yields the title product. LC-MS: t$_R$=1.02 (conditions 4).

2-(3-Methyl-4-(trifluoromethoxy)phenyl)acetic acid

Prepared according to general procedure 7 from tert-butyl 2-(3-methyl-4-(trifluoromethoxy)phenyl)acetate (32 mg, 0.11 mmol) in HCOOH (0.80 mL). The reaction is complete after 2.5 h at rt. LC-MS: t$_R$=0.77 (conditions 4).

4-Bromo-2-ethyl-1-(2,2,2-trifluoroethoxy)benzene

To a sol. of 4-bromo-2-ethylphenol (300 mg, 1.49 mmol) in DMF (3 mL) is added Cs$_2$CO$_3$ (632 mg, 1.94 mmol). The mixture is cooled to 0° C., and 2,2,2-trifluoroethyl trifluoromethanesulfonate (0.215 mL, 1.49 mmol) is added. The mixture is stirred for 90 min while warming up to rt. Water is added, and the mixture is extracted with EtOAc (3×). The combined org. layers are washed with water and brine, dried over MgSO$_4$, filtered, and the solvents are removed under reduced pressure to yield the crude title product. LC-MS: t$_R$=0.99 (conditions 3).

tert-Butyl 2-(3-ethyl-4-(2,2,2-trifluoroethoxy)phenyl)acetate

Prepared according to general procedure 6 from 4-bromo-2-ethyl-1-(2,2,2-trifluoroethoxy)benzene (100 mg, 0.353 mmol), (2-(tert-butoxy)-2-oxoethyl)zinc(II) chloride (0.5M in Et$_2$O, 1.40 mL, 0.70 mmol), Pd$_2$(dba)$_3$ (16 mg, 0.018 mmol), and X-Phos (17 mg, 0.035 mmol) in dioxane (3.0 mL). The reaction is complete overnight at 85° C. Purification by automated FC (Combiflash, EtOAc/heptane 0:100→80:20) yields the title product. LC-MS: t$_R$=1.02 (conditions 4).

2-(3-Ethyl-4-(2,2,2-trifluoroethoxy)phenyl)acetic acid

Prepared according to general procedure 7 from tert-butyl 2-(3-ethyl-4-(trifluoromethoxy)phenyl)acetate (86 mg, 0.27 mmol) in HCOOH (2.0 mL). The reaction is complete after 2.5 h at rt. LC-MS: t$_R$=0.77 (conditions 4).

5-Bromo-1,3-dimethyl-2-(2,2,2-trifluoroethoxy)benzene

To a sol. of 4-bromo-2,6-xylenol (300 mg, 1.49 mmol, 1 eq) in DMF (3 mL) is added Cs$_2$CO$_3$ (632 mg, 1.94 mmol). The mixture is cooled to 0° C., and 2,2,2-trifluoroethyl trifluoromethanesulfonate (0.215 mL, 1.49 mmol) is added. The mixture is stirred overnight while warming up to rt. Water is added, and the mixture is extracted with EtOAc (3×). The combined org. layers are washed with water and brine, dried over MgSO4, filtered, and the solvents are removed under reduced pressure. Purification of the crude by automated FC (Combiflash, EtOAc/heptane 0:100→100:0) yields the title product.

tert-Butyl 2-(3,5-dimethyl-4-(2,2,2-trifluoroethoxy) phenyl)acetate

Prepared according to general procedure 6 from 5-bromo-1,3-dimethyl-2-(2,2,2-trifluoroethoxy)benzene (100 mg, 0.353 mmol), (2-(tert-butoxy)-2-oxoethyl)zinc(II) chloride (0.5M in Et$_2$O, 1.40 mL, 0.70 mmol), Pd$_2$(dba)$_3$ (16 mg, 0.018 mmol), and X-Phos (17 mg, 0.035 mmol) in dioxane (3.0 mL). The reaction is complete overnight at 85° C. Purification by automated FC (Combiflash, EtOAc/heptane 0:100→80:20) yields the title product. LC-MS: t$_R$=1.01 (conditions 4).

2-(3,5-Dimethyl-4-(2,2,2-trifluoroethoxy)phenyl) acetic acid

Prepared according to general procedure 7 from tert-butyl 2-(3,5-dimethyl-4-(2,2,2-trifluoroethoxy)phenyl)acetate (96 mg, 0.30 mmol) in HCOOH (2.2 mL). The reaction is complete after 2.5 h at rt. LC-MS: t$_R$=0.76 (conditions 4).

tert-Butyl 2-(5-methyl-6-(2,2,2-trifluoroethoxy)pyridin-3-yl)acetate

Prepared according to general procedure 6 from 5-bromo-3-methyl-2-(2,2,2-trifluoroethoxy)pyridine (334 mg, 1.17 mmol), (2-(tert-butoxy)-2-oxoethyl)zinc(II) chloride (0.5M in Et$_2$O, 3.40 mL, 1.70 mmol), Pd$_2$(dba)$_3$ (54 mg, 0.058 mmol), and X-Phos (56 mg, 0.117 mmol) in dioxane (3.0 mL). The reaction is complete overnight at 85° C. Purification by automated FC (Combiflash, EtOAc/heptane 0:100→80:20) yields the title product. LC-MS: t$_R$=0.97 (conditions 4).

2-(5-Methyl-6-(2,2,2-trifluoroethoxy)pyridin-3-yl) acetic acid

Prepared according to general procedure 7 from tert-butyl 2-(5-methyl-6-(2,2,2-trifluoroethoxy)pyridin-3-yl)acetate (92 mg, 0.30 mmol) in HCOOH (2.2 mL). The reaction is complete after 2.5 h at rt. LC-MS: t$_R$=0.70 (conditions 4).

The following examples were prepared according to general procedure 3, from the appropriate carboxylic acids and aminopyrazoles:

| Example No | Name | LC-MS ($t_R$; MH+; conditions) |
|---|---|---|
| 397 | N-[1-(5-Cyano-pyridin-2-ylmethyl)-1H-pyrazol-3-yl]-2-(4-cyclopropylmethoxy-3-trifluoromethoxy-phenyl)-acetamide | 0.90 min; 472.01; conditions 3 |
| 398 | 2-(4-Cyclopropylmethoxy-3-trifluoromethoxy-phenyl)-N-[1-(3,4-difluoro-benzyl)-1H-pyrazol-3-yl]-acetamide | 0.97 min; 481.76; conditions 3 |
| 399 | N-[1-(4-Cyano-5-fluoro-pyridin-2-ylmethyl)-1H-pyrazol-3-yl]-2-[3-methyl-4-(2,2,2-trifluoro-ethoxy)-phenyl]-acetamide | 0.88 min; 448.06; conditions 3 |
| 400 | 2-(4-tert-Butyl-phenyl)-N-[1-(4-cyano-5-fluoro-pyridin-2-ylmethyl)-1H-pyrazol-3-yl]-acetamide | 0.90 min; 392.18; conditions 3 |
| 401 | N-[1-(4-Cyano-5-fluoro-pyridin-2-ylmethyl)-1H-pyrazol-3-yl]-2-(4-isopropyl-phenyl)-acetamide | 0.88 min; 378.16; conditions 3 |
| 402 | N-[1-(4-Cyano-5-fluoro-pyridin-2-ylmethyl)-1H-pyrazol-3-yl]-2-[4-(1-trifluoromethyl-cyclopropyl)-phenyl]-acetamide | 0.90 min; 444.07; conditions 3 |
| 403 | 2-[4-(1-Cyano-cyclopropyl)-3-trifluoromethyl-phenyl]-N-[1-(5-cyano-pyridin-2-ylmethyl)-1H-pyrazol-3-yl]-acetamide | 0.71 min; 451.04; conditions 4 |
| 404 | 2-[4-(1-Cyano-cyclopropyl)-3-trifluoromethyl-phenyl]-N-[1-(3,4-difluoro-benzyl)-1H-pyrazol-3-yl]-acetamide | 0.82 min; 460.99; conditions 4 |
| 405 | N-[1-(5-Cyano-pyridin-2-ylmethyl)-1H-pyrazol-3-yl]-2-[3-methyl-4-(3,3,3-trifluoro-propoxy)-phenyl]-acetamide | 0.78 min; 444.10; conditions 4 |
| 406 | N-[1-(5-Cyano-pyridin-2-ylmethyl)-1H-pyrazol-3-yl]-2-[3-cyclopropyl-4-(2,2,2-trifluoro-ethoxy)-phenyl]-acetamide | 0.80 min; 456.01; conditions 4 |
| 407 | N-[1-(5-Cyano-pyridin-2-ylmethyl)-1H-pyrazol-3-yl]-2-(3-methyl-4-trifluoromethoxy-phenyl)-acetamide | 0.78 min; 416.10; conditions 4 |
| 408 | N-[1-(6-Cyano-5-fluoro-pyridin-2-ylmethyl)-1H-pyrazol-3-yl]-2-[3-cyclopropyl-4-(2,2,2-trifluoro-ethoxy)-phenyl]-acetamide | 0.84 min; 473.76; conditions 4 |
| 409 | N-[1-(4-Cyano-5-fluoro-pyridin-2-ylmethyl)-1H-pyrazol-3-yl]-2-[3-cyclopropyl-4-(2,2,2-trifluoro-ethoxy)-phenyl]-acetamide | 0.83 min; 473.89; conditions 4 |
| 410 | N-[1-(6-Cyano-5-fluoro-pyridin-2-ylmethyl)-1H-pyrazol-3-yl]-2-(3-methyl-4-trifluoromethoxy-phenyl)-acetamide | 0.83 min; 433.94; conditions 4 |
| 411 | N-[1-(5-Cyano-pyridin-2-ylmethyl)-1H-pyrazol-3-yl]-2-[3-ethyl-4-(2,2,2-trifluoro-ethoxy)-phenyl]-acetamide | 0.80 min; 444.07; conditions 4 |
| 412 | N-[1-(6-Cyano-5-fluoro-pyridin-2-ylmethyl)-1H-pyrazol-3-yl]-2-[3-ethyl-4-(2,2,2-trifluoro-ethoxy)-phenyl]-acetamide | 0.85 min; 462.03; conditions 4 |
| 413 | N-[1-(4-Cyano-5-fluoro-pyridin-2-ylmethyl)-1H-pyrazol-3-yl]-2-[3-ethyl-4-(2,2,2-trifluoro-ethoxy)-phenyl]-acetamide | 0.84 min; 461.97; conditions 4 |
| 414 | N-[1-(5-Cyano-pyridin-2-ylmethyl)-1H-pyrazol-3-yl]-2-[3,5-dimethyl-4-(2,2,2-trifluoro-ethoxy)-phenyl]-acetamide | 0.79 min; 444.05; conditions 4 |
| 415 | N-[1-(6-Cyano-5-fluoro-pyridin-2-ylmethyl)-1H-pyrazol-3-yl]-2-[3,5-dimethyl-4-(2,2,2-trifluoro-ethoxy)-phenyl]-acetamide | 0.84 min; 462.05; conditions 4 |
| 416 | N-[1-(4-Cyano-5-fluoro-pyridin-2-ylmethyl)-1H-pyrazol-3-yl]-2-[3,5-dimethyl-4-(2,2,2-trifluoro-ethoxy)-phenyl]-acetamide | 0.82 min; 461.94; conditions 4 |
| 417 | N-[1-(5-Cyano-pyridin-2-ylmethyl)-1H-pyrazol-3-yl]-2-[5-methyl-6-(2,2,2-trifluoro-ethoxy)-pyridin-3-yl]-acetamide | 0.75 min; 431.04; conditions 4 |
| 418 | N-[1-(6-Cyano-5-fluoro-pyridin-2-ylmethyl)-1H-pyrazol-3-yl]-2-[5-methyl-6-(2,2,2-trifluoro-ethoxy)-pyridin-3-yl]-acetamide | 0.80 min; 448.93; conditions 4 |
| 419 | N-[1-(4-Cyano-5-fluoro-pyridin-2-ylmethyl)-1H-pyrazol-3-yl]-2-[5-methyl-6-(2,2,2-trifluoro-ethoxy)-pyridin-3-yl]-acetamide | 0.79 min; 449.01; conditions 4 |
| 420 | N-[1-(6-Cyano-5-fluoro-pyridin-2-ylmethyl)-1H-pyrazol-3-yl]-2-[3-methyl-4-(3,3,3-trifluoro-propoxy)-phenyl]-acetamide | 0.82 min; 461.98; conditions 4 |
| 421 | N-[1-(4-Cyano-5-fluoro-pyridin-2-ylmethyl)-1H-pyrazol-3-yl]-2-[3-methyl-4-(3,3,3-trifluoro-propoxy)-phenyl]-acetamide | 0.81 min; 462.03; conditions 4 |

In Vitro Methods—Measurement of Calcium Channel Flux by Means of FLIPR Assays.

HEK293 cells recombinantly expressing either voltage-dependent T-type calcium channel subunit alpha-1G (Cav3.2) or voltage-dependent L-type calcium channel subunit alpha-1C (Cav1.2) are assayed for calcium flux using the calcium indicator dye Fluo-4-AM (Molecular Devices) and FLIPR technology (Fluorometric Imaging Plate Reader, Molecular Devices) (Xie X, Van Deusen A L, Vitko I, Babu D A, Davies L A, Huynh N, Cheng H, Yang N, Barrett P Q, Perez-Reyes E. Validation of high throughput screening assays against three subtypes of Ca(v)3 T-type channels using molecular and pharmacologic approaches. Assay and Drug Development Technologies 2007, 5(2), 191-203). The HEK293 cells recombinantly expressing Cav3.2 are maintained in DMEM growth medium (Life Technologies) supplemented with 10% Fetal Bovine Serum (FBS), 100 U/ml penicillin (Life Technologies), 100 µg/ml streptomycin (Life Technologies) and 1 mg/ml G418 (Life Technologies). HEK293 cells recombinantly expressing Cav1.2 are maintained in DMEM growth medium (Life technologies) supplemented with 10% FBS, 0.1 mg/ml G418 (Life Technologies), 0.1 mg/ml hygromycin (Life Technologies) and 40 ug/ml zeocin (Life Technologies).

Cells are washed once with PBS, then dissociated in 0.25% trypsin/EDTA (Life Technologies) and seeded into poly-D-lysine coated 384-well black, clear bottom plates (BD Biosciences) at a density of 30,000 cells/well. The seeded plates are incubated overnight at 37° C.

Immediately prior to performing the assay, medium is removed and cells are treated for 1 hour at 37° C. with loading buffer containing HBSS 1× (137 mM NaCl; 5.4 mM KCl; 0.25 mM Na2HPO4; 1.3 mM CaCl2; 0.4 mM MgSO4; 0.5 mM MgCl2; 0.4 mM KH2PO4, pH 7.4), 0.375 g/L NaHCO3, 20 mM Hepes, supplemented with 3 µM Fluo-4-AM and 0.15% Pluronic (Life Technologies). The cells are then washed three times with assay buffer (HBSS 1×; 0.375 g/L NaHCO3; 20 mM Hepes; 1% FBS; pH 7.4) and allowed to rest in 50 µl of wash buffer for 30 minutes.

Stock solutions of test compounds are prepared to a concentration of 10 mM in DMSO. For the Cav3.2 assay, serial dilutions of the compounds are prepared in TEAC buffer (100 mM tetraethylammonium chloride; 20 mM Hepes; 2.5 mM CaCl2; 5 mM KCl; 1 mM MgCl2; 1% FBS; pH 7.2), for the Cav1.2 assay serial dilutions are prepared in assay buffer. Test compounds are added to the cells to give a 3-fold dilution range from 10 μM to 0.05 nM. The compounds are incubated with the cells for 3 minutes and Ca2+ entry is stimulated by adding either CaCl2 to a final concentration of 10 mM (Cav3.2 assay) or by adding KCl to a final concentration of 20 mM (Cav1.2 assay). The kinetics of fluorescence increase are recorded for every well and the area under the fluorescence trace for every compound concentration is used to generate inhibition curves using non-linear regression sigmoidal concentration-response curve analysis with in-house software. $IC_{50}$ values are calculated and represent the compound concentration required to inhibit 50% of the signal that is obtained in the presence of vehicle instead of test compound. In analogy, antagonistic activities ($IC_{50}$ values) of all exemplified compounds have been measured for the for the Cav3.1- and the Cav3.3-channel. Antagonistic activities ($IC_{50}$ values) of all exemplified compounds are in the range of 0.3 to 1210 nM with respect to Cav3.1; and in the range of 0.8 to 1280 nM with respect to Cav3.3.

In the following table, $IC_{50}$-values generated for the Cav3.2-channel are presented.

| Example | IC50 (nM) |
|---|---|
| 1 | 14 |
| 2 | 4.1 |
| 3 | 12 |
| 4 | 82 |
| 5 | 20 |
| 6 | 6.6 |
| 7 | 7.9 |
| 8 | 47 |
| 9 | 12 |
| 10 | 10 |
| 11 | 5.4 |
| 12 | 20 |
| 13 | 133 |
| 14 | 650 |
| 15 | 374 |
| 16 | 10 |
| 17 | 12 |
| 18 | 25 |
| 19 | 10 |
| 20 | 5.1 |
| 21 | 3.4 |
| 22 | 5.0 |
| 23 | 6.4 |
| 24 | 13 |
| 25 | 64 |
| 26 | 5.4 |
| 27 | 61 |
| 28 | 8.0 |
| 29 | 25 |
| 30 | 8.6 |
| 31 | 4.0 |
| 32 | 7.6 |
| 33 | 101 |
| 34 | 91 |
| 35 | 43 |
| 36 | 160 |
| 37 | 29 |
| 38 | 39 |
| 39 | 49 |
| 40 | 16 |
| 41 | 38 |
| 42 | 19 |
| 43 | 82 |
| 44 | 372 |
| 45 | 33 |
| 46 | 26 |
| 47 | 37 |
| 48 | 138 |
| 49 | 9.2 |
| 50 | 11 |
| 51 | 16 |
| 52 | 2.6 |
| 53 | 6.7 |
| 54 | 28 |
| 55 | 33 |
| 56 | 46 |
| 57 | 14 |
| 58 | 285 |
| 59 | 136 |
| 60 | 4.7 |
| 61 | 3.4 |
| 62 | 3.8 |
| 63 | 38 |
| 64 | 80 |
| 65 | 74 |
| 66 | 19 |
| 67 | 3.4 |
| 68 | 4.8 |
| 69 | 16 |
| 70 | 11 |
| 71 | 60 |
| 72 | 46 |
| 73 | 7.9 |
| 74 | 14 |
| 75 | 5.2 |
| 76 | 6.1 |
| 77 | 9.1 |
| 78 | 275 |
| 79 | 218 |
| 80 | 92 |
| 81 | 131 |
| 82 | 33 |
| 83 | 26 |
| 84 | 18 |
| 85 | 301 |
| 86 | 140 |
| 87 | 157 |
| 88 | 109 |
| 89 | 61 |
| 90 | 75 |
| 91 | 23 |
| 92 | 48 |
| 93 | 39 |
| 94 | 8.3 |
| 95 | 99 |
| 96 | 53 |
| 97 | 31 |
| 98 | 38 |
| 99 | 48 |
| 100 | 60 |
| 101 | 925 |
| 102 | 7050 |
| 103 | 145 |
| 104 | 4520 |
| 105 | 31 |
| 106 | 15 |
| 107 | 338 |
| 108 | 322 |
| 109 | 22 |
| 110 | 14 |
| 111 | 1330 |
| 112 | 21 |
| 113 | 4.8 |
| 114 | 14 |
| 115 | 57 |
| 116 | 75 |
| 117 | 332 |
| 118 | 97 |
| 119 | 137 |
| 120 | 6.7 |
| 121 | 68 |
| 122 | 19 |
| 123 | 1270 |

| Example | IC50 (nM) |
|---|---|
| 124 | 9.9 |
| 125 | 64 |
| 126 | 3.4 |
| 127 | 27 |
| 128 | 9.7 |
| 129 | 128 |
| 130 | 293 |
| 131 | 88 |
| 132 | 51 |
| 133 | 191 |
| 134 | 428 |
| 135 | 247 |
| 136 | 1570 |
| 137 | 313 |
| 138 | 756 |
| 139 | 36 |
| 140 | 176 |
| 141 | 35 |
| 142 | 185 |
| 143 | 19 |
| 144 | 160 |
| 145 | 44 |
| 146 | 136 |
| 147 | 13 |
| 148 | 7.6 |
| 149 | 85 |
| 150 | 682 |
| 151 | 649 |
| 152 | 1160 |
| 153 | 21 |
| 154 | 78 |
| 155 | 70 |
| 156 | 179 |
| 157 | 34 |
| 158 | 11 |
| 159 | 1180 |
| 160 | 29 |
| 161 | 258 |
| 162 | 64 |
| 163 | 345 |
| 164 | 568 |
| 165 | 13 |
| 166 | 86 |
| 167 | 21 |
| 168 | 113 |
| 169 | 104 |
| 170 | 191 |
| 171 | 980 |
| 172 | 15 |
| 173 | 188 |
| 174 | 319 |
| 175 | 17 |
| 176 | 67 |
| 177 | 18 |
| 178 | 99 |
| 179 | 2500 |
| 180 | 33 |
| 181 | 272 |
| 182 | 65 |
| 183 | 530 |
| 184 | 490 |
| 185 | 7.7 |
| 186 | 41 |
| 187 | 15 |
| 188 | 60 |
| 189 | 88 |
| 190 | 21 |
| 191 | 93 |
| 192 | 133 |
| 193 | 78 |
| 194 | 61 |
| 195 | 47 |
| 196 | 176 |
| 197 | 54 |
| 198 | 16 |
| 199 | 74 |
| 200 | 67 |
| 201 | 30 |
| 202 | 16 |
| 203 | 1260 |
| 204 | 79 |
| 205 | 288 |
| 206 | 50 |
| 207 | 5.3 |
| 208 | 88 |
| 209 | 53 |
| 210 | 8.0 |
| 211 | 3.1 |
| 212 | 35 |
| 213 | 31 |
| 214 | 164 |
| 215 | 599 |
| 216 | 269 |
| 217 | 15 |
| 218 | 79 |
| 219 | 14 |
| 220 | 3.1 |
| 221 | 5.0 |
| 222 | 117 |
| 223 | 8.4 |
| 224 | 21 |
| 225 | 13 |
| 226 | 25 |
| 227 | 4.3 |
| 228 | 44 |
| 229 | 3.8 |
| 230 | 255 |
| 231 | 21 |
| 232 | 5.8 |
| 233 | 8.1 |
| 234 | 6 |
| 235 | 42 |
| 236 | 18 |
| 237 | 6.1 |
| 238 | 32 |
| 239 | 2.4 |
| 240 | 11 |
| 241 | 34 |
| 242 | 39 |
| 243 | 37 |
| 244 | 33 |
| 245 | 30 |
| 246 | 705 |
| 247 | 2590 |
| 248 | 1810 |
| 249 | 295 |
| 250 | 127 |
| 251 | 303 |
| 252 | 56 |
| 253 | 57 |
| 254 | 100 |
| 255 | 52 |
| 256 | 251 |
| 257 | 76 |
| 258 | 934 |
| 259 | 4.1 |
| 260 | 3.1 |
| 261 | 15 |
| 262 | 155 |
| 263 | 97 |
| 264 | 5.4 |
| 265 | 15 |
| 266 | 6.6 |
| 267 | 90 |
| 268 | 35 |
| 269 | 162 |
| 270 | 51 |
| 271 | 3.4 |
| 272 | 7.5 |
| 273 | 35 |
| 274 | 133 |
| 275 | 14 |
| 276 | 188 |
| 277 | 15 |

-continued

| Example | IC50 (nM) |
|---------|-----------|
| 278 | 18 |
| 279 | 275 |
| 280 | 138 |
| 281 | 21 |
| 282 | 12 |
| 283 | 9.5 |
| 284 | 3070 |
| 285 | 208 |
| 286 | 393 |
| 287 | 9480 |
| 288 | 4.7 |
| 289 | 23 |
| 290 | 39 |
| 291 | 80 |
| 292 | 6.5 |
| 293 | 6.6 |
| 294 | 22 |
| 295 | 308 |
| 296 | 17 |
| 297 | 20 |
| 298 | 43 |
| 299 | 37 |
| 300 | 7.5 |
| 301 | 71 |
| 302 | 39 |
| 303 | 51 |
| 304 | 118 |
| 305 | 29 |
| 306 | 17 |
| 307 | 42 |
| 308 | 263 |
| 309 | 27 |
| 310 | 13 |
| 311 | 81 |
| 312 | 10 |
| 313 | 45 |
| 314 | 32 |
| 315 | 240 |
| 316 | 36 |
| 317 | 56 |
| 318 | 378 |
| 319 | 66 |
| 320 | 99 |
| 321 | 91 |
| 322 | 856 |
| 323 | 36 |
| 324 | 31 |
| 325 | 893 |
| 326 | 33 |
| 327 | 37 |
| 328 | 33 |
| 329 | 80 |
| 330 | 4.8 |
| 331 | 9.6 |
| 332 | 600 |
| 333 | 2790 |
| 334 | 21 |
| 335 | 20 |
| 336 | 34 |
| 337 | 168 |
| 338 | 61 |
| 339 | 7.0 |
| 340 | 8.5 |
| 341 | 64 |
| 342 | 40 |
| 343 | 4.5 |
| 344 | 52 |
| 345 | 34 |
| 346 | 159 |
| 347 | 85 |
| 348 | 29 |
| 349 | 23 |
| 350 | 69 |
| 351 | 65 |
| 352 | 22 |
| 353 | 30 |
| 354 | 248 |

-continued

| Example | IC50 (nM) |
|---------|-----------|
| 355 | 26 |
| 356 | 327 |
| 357 | 34 |
| 358 | 20 |
| 359 | 212 |
| 360 | 360 |
| 361 | 80 |
| 362 | 117 |
| 363 | 51 |
| 364 | 62 |
| 365 | 18 |
| 366 | 147 |
| 367 | 10 |
| 368 | 301 |
| 369 | 64 |
| 370 | 578 |
| 371 | 13 |
| 372 | 38 |
| 373 | 349 |
| 374 | 107 |
| 375 | 9.9 |
| 376 | 20 |
| 377 | 25 |
| 378 | 249 |
| 379 | 658 |
| 380 | 214 |
| 381 | 54 |
| 382 | 114 |
| 383 | 36 |
| 384 | 128 |
| 385 | 44 |
| 386 | 69 |
| 387 | 122 |
| 388 | 30 |
| 389 | 506 |
| 390 | 47 |
| 391 | 2.1 |
| 392 | 101 |
| 393 | 51 |
| 394 | 126 |
| 395 | 315 |
| 396 | 369 |
| 397 | 44 |
| 398 | 39 |
| 399 | 60 |
| 400 | 49 |
| 401 | 126 |
| 402 | 106 |
| 403 | 97 |
| 404 | 14 |
| 405 | 18 |
| 406 | 15 |
| 407 | 25 |
| 408 | 8.5 |
| 409 | 43 |
| 410 | 17 |
| 411 | 7.8 |
| 412 | 5.3 |
| 413 | 30 |
| 414 | 6.4 |
| 415 | 4.9 |
| 416 | 17 |
| 417 | 37 |
| 418 | 94 |
| 419 | 9430 |
| 420 | 8.7 |
| 421 | 41 |

The invention claimed is:

1. A method of decreasing burst firing discharges in a neuronal cell by blocking calcium T-channels; said method comprising the administration to a subject in need thereof of a compound of Formula (I)

Formula (I)

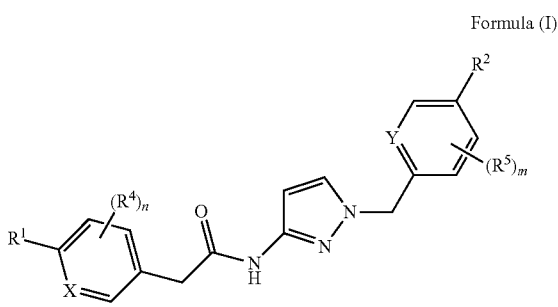

wherein
X represents a ring carbon or a ring nitrogen atom;
R$^1$ represents
(C$_{2-6}$)alkyl;
(C$_{2-4}$)alkyl mono-substituted with cyano, or (C$_{1-3}$)alkoxy;
(C$_{1-4}$)fluoroalkyl;
(C$_{1-3}$)fluoroalkoxy;
pentafluoro-sulfanyl;
(C$_{3-6}$)cycloalkyl-L$^1$- wherein
said (C$_{3-6}$)cycloalkyl optionally contains one ring oxygen atom; wherein said (C$_{3-6}$)cycloalkyl is unsubstituted, or mono-substituted with fluoro, (C$_{1-3}$)alkyl, (C$_{1-3}$)alkoxy, hydroxy, cyano, or (C$_{1-3}$)fluoroalkyl, or di-substituted with fluoro, or tri-substituted with two fluoro substituents and a substituent selected from (C$_{1-3}$)alkyl and cyano; and
the linker L$^1$ represents a direct bond, (C$_{1-2}$)alkylene, oxygen, or (C$_{1-2}$)alkylene-oxy;
5- or 6-membered heteroaryl, independently optionally mono-substituted with (C$_{1-3}$)alkyl;
NR$^{11}$R$^{12}$, wherein
R$^{11}$ and R$^{12}$ independently represent hydrogen, (C$_{1-3}$)alkyl, (C$_{2-3}$)fluoroalkyl, (C$_{3-6}$)cycloalkyl, (C$_{3-6}$)cycloalkyl mono- or di-substituted with fluoro, (C$_{3-6}$)cycloalkyl-(C$_{1-3}$)alkyl, (C$_{1-3}$)alkoxy-(C$_{2-3}$)alkyl;
or R$^{11}$ and R$^{12}$, together with the nitrogen atom to which they are attached, form a 4- to- 6 membered ring optionally mono- or di-substituted with fluoro; a 2-oxo-pyrrolidinyl group; or a morpholinyl group;
and (R$^4$)$_n$ represents one or two optional substituents independently selected from (C$_{1-4}$)alkyl, (C$_{3-6}$)cycloalkyl, (C$_{1-4}$)alkoxy, (C$_{1-3}$)fluoroalkyl, (C$_{1-3}$)fluoroalkoxy, halogen, and cyano;
or R$^1$ together with (R$^4$)n forms a non-aromatic 5- or 6-membered ring which is fused to the phenyl/pyridine ring; wherein said 5- or 6-membered ring optionally contains one or two heteroatoms independently selected from oxygen and nitrogen; wherein said fused 5- or 6-membered non-aromatic ring independently is optionally further mono-substituted with oxo or (C$_{1-3}$)alkyl; di-substituted with (C$_{1-3}$)alkyl; or di-, tri-, or tetra-substituted wherein one substituent is oxo and the remaining are (C$_{1-3}$)alkyl;
or R$^1$ together with (R$^4$)$_n$ forms an aromatic 5- or 6-membered ring which is fused to the phenyl/pyridine ring; wherein said 5- or 6-membered ring optionally contains one or two nitrogen atoms, wherein said fused 5- or 6-membered aromatic ring independently is optionally further mono- or di-substituted wherein the substituents are independently selected from (C$_{1-3}$)alkyl, (C$_{3-6}$)cycloalkyl, (C$_1$)fluoroalkyl, or cyano;
or R$^1$ represents methyl, or halogen; and (R$^4$)$_n$ represents one substituent selected from (C$_{1-3}$)fluoroalkoxy which is attached to the phenyl/pyridinyl ring in ortho- or meta-position to the point of attachment of the —CH$_2$—CO—NH— group;
Y represents a ring carbon or a ring nitrogen atom; and
R$^2$ represents (C$_{1-4}$)alkyl; (C$_{3-6}$)cycloalkyl; (C$_{1-4}$)alkoxy; (C$_{3-6}$)cycloalkyl-oxy; (C$_{1-3}$)fluoroalkyl; (C$_{1-3}$)fluoroalkoxy; (C$_{1-3}$)alkoxy-(C$_{2-3}$)alkoxy; halogen; cyano; or —NR$^{21}$R$^{22}$, wherein R$^{21}$ and R$^{22}$ independently represent hydrogen, or (C$_{1-3}$)alkyl, or R$^{21}$ and R$^{22}$, together with the nitrogen atom to which they are attached, form a 4- to- 6 membered ring optionally mono- or di-substituted with fluoro, or a morpholinyl group;
and
(R$^5$)$_m$ represents one or two optional substituents independently selected from (C$_{1-4}$)alkyl; (C$_{3-6}$)cycloalkyl; (C$_{1-4}$)alkoxy; halogen; cyano; (C$_{1-3}$)fluoroalkyl; and (C$_{1-3}$)fluoroalkoxy;
or a pharmaceutically acceptable salt of such a compound.

2. A method according to claim 1, said method comprising the administration to a subject in need thereof of a compound of Formula (I), wherein X represents a ring carbon atom; or a pharmaceutically acceptable salt of such a compound.

3. A method according to claim 1, said method comprising the administration to a subject in need thereof of a compound of Formula (I), wherein R$^1$ represents
(C$_{2-6}$)alkyl;
(C$_{2-4}$)alkyl mono-substituted with cyano, or (C$_{1-3}$)alkoxy;
(C$_{1-4}$)fluoroalkyl;
(C$_{1-33}$)fluoroalkoxy;
pentafluoro-sulfanyl;
(C$_{3-6}$)cycloalkyl-L$^1$- wherein
said (C$_{3-6}$)cycloalkyl optionally contains one ring oxygen atom; wherein said (C$_{3-6}$)cycloalkyl is unsubstituted, or mono-substituted with fluoro, (C$_{1-3}$)alkyl, (C$_{1-3}$)alkoxy, hydroxy, cyano, or (C$_{1-3}$)fluoroalkyl, or di-substituted with fluoro, or tri-substituted with two fluoro substituents and a (C$_{1-3}$)alkyl substituent; and
the linker L$^1$ represents a direct bond, (C$_{1-2}$)alkylene, oxygen, or (C$_{1-2}$)alkylene-oxy;
5- or 6-membered heteroaryl selected from oxadiazolyl, pyrazinyl, pyrimidinyl, and pyridinyl; wherein said heteroaryl independently is optionally mono-substituted with (C$_{1-3}$)alkyl; or
—NR$^{11}$R$^{12}$, wherein
R$^{11}$ and R$^{12}$ independently represent hydrogen, (C$_{1-3}$)alkyl, (C$_{2-3}$)fluoroalkyl, (C$_{3-6}$)cycloalkyl, (C$_{3-6}$)cycloalkyl mono- or di-substituted with fluoro, (C$_{3-6}$)cycloalkyl-(C$_{1-3}$)alkyl, (C$_{1-3}$)alkoxy-(C$_{2-3}$)alkyl;
or R$^{11}$ and R$^{12}$, together with the nitrogen atom to which they are attached, form an azetidinyl or a pyrrolidinyl ring, both independently optionally mono- or di-substituted with fluoro; or a 2-oxo-pyrrolidinyl group;
and (R$^4$)$_n$ represents one optional substituent selected from (C$_{1-4}$)alkyl, (C$_{1-4}$)alkoxy, (C$_{1-3}$)fluoroalkyl, (C$_{1-3}$)fluoroalkoxy, halogen, and cyano;
or R$^1$ together with (R$^4$)$_n$ forms a non-aromatic 5- or 6-membered ring which is fused to the phenyl/pyridine ring to form a bicyclic ring system; wherein said bicyclic ring system is selected from 2,3-dihydrobenzoxazolyl, 3,4-dihydro-2H-benzo[1,4]oxazinyl, 2,3-dihydro-1H-indolyl, and 2,3-dihydro-benzofuranyl; wherein said non-aromatic 5- or 6-membered ring part of said bicyclic ring system independently is optionally further mono-substituted with oxo; or di-, tri-, or tetra-substituted wherein one substituent is oxo and the remaining are $(C_{1-3})$alkyl;

or $R^1$ together with $(R^4)_n$ forms an aromatic 5- or 6-membered ring which is fused to the phenyl/pyridine ring to form a bicyclic aromatic ring system selected from pyrrolo[2,3-b]pyridinyl, indolyl, indazolyl, quinoxalinyl, benzimidazolyl, and quinolinyl; wherein said fused 5- or 6-membered aromatic ring part of said aromatic bicyclic ring system independently is optionally further mono- or di-substituted wherein the substituents are independently selected from $(C_{1-3})$alkyl, $(C_{3-6})$cycloalkyl, $(C_1)$fluoroalkyl, or cyano;

or $R^1$ represents methyl, or halogen; and $(R^4)_n$ represents one substituent selected from $(C_{1-3})$fluoroalkoxy which is attached to the phenyl/pyridinyl ring in ortho- or meta-position to the point of attachment of the —$CH_2$—CO—NH— group;

or a pharmaceutically acceptable salt of such a compound.

4. A method according to claim 2, said method comprising the administration to a subject in need thereof of a compound of Formula (I), wherein $R^1$ represents $(C_{2-6})$alkyl;

$(C_{1-4})$fluoroalkyl;

$(C_{1-3})$fluoroalkoxy;

$(C_{3-6})$cycloalkyl wherein said $(C_{3-6})$cycloalkyl optionally contains one ring oxygen atom; wherein said $(C_{3-6})$cycloalkyl is mono-substituted with fluoro or $(C_{1-3})$fluoroalkyl, or di-substituted with fluoro; or $(C_{3-6})$cycloalkyl-oxy- wherein said $(C_{3-6})$cycloalkyl optionally contains one ring oxygen atom; wherein said $(C_{3-6})$cycloalkyl is unsubstituted, or di-substituted with fluoro;

and $(R^4)_n$ represents one optional substituent selected from $(C_{1-4})$alkyl, or halogen;

or a pharmaceutically acceptable salt of such a compound.

5. A method according to claim 1, said method comprising the administration to a subject in need thereof of a compound of Formula (I), wherein the fragment

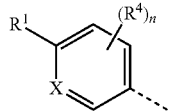

represents 4-cyclopropyl-phenyl, 4-isopropyl-phenyl, 4-dimethylamino-phenyl, 4-trifluoromethyl-phenyl, 4-tert-butyl-phenyl, 4-isobutyl-phenyl, 4-(1-methoxy-ethyl)-phenyl, 4-(1-methyl-cyclopropyl)-phenyl, 4-(cyclopropyl-methyl)-phenyl, 4-(1-hydroxy-cyclopropyl)-phenyl, 4-(cyclopropyl-oxy)-phenyl, 4-(azetidin-1-yl)-phenyl, 4-(oxetan-3-yl-oxy)-phenyl, 4-(3-hydroxy-oxetan-3-yl)-phenyl, 4-(3-fluoro-oxetan-3-yl)-phenyl, 4-(cyclobutyl-oxy)-phenyl, 4-(3-methyl-oxetan-3-yl)-phenyl, 4-([1,2,4]oxadiazol-3-yl)-phenyl, 4-(5-methyl-[1,2,4]oxadiazol-3-yl)-phenyl, 4-(3-fluoro-azetidin-1-yl)-phenyl, 4-(1-cyano-cyclopropyl)-phenyl, 4-(1-cyano-1-methyl-ethyl)-phenyl, 4-(diethylamino)-phenyl, 4-(pentafluoro-sulfanyl)-phenyl, 4-(2,2,2-trifluoroethoxy)-phenyl, 3-methyl-4-(2,2,2-trifluoroethoxy)-phenyl, 3-fluoro-4-(2,2,2-trifluoroethoxy)-phenyl, 4-((2-methoxyethyl)-methyl-amino)-phenyl, 4-(3,3-difluoro-cyclobutyl)-phenyl, 4-(3-methoxy-oxetan-3-yl)-phenyl, 4-(oxetan-3-yl-methoxy)-phenyl, 4-(pyrazin-2-yl)-phenyl, 4-(3-methyl-pyrazin-2-yl)-phenyl, 4-(pyrimidin-4-yl)-phenyl, 4-(5-methyl-pyrimidin-4-yl)-phenyl, 4-(pyrimidin-2-yl)-phenyl, 4-(pyrimidin-5-yl)-phenyl, 4-(pyridin-4-yl)-phenyl, 4-(pyridin-3-yl)-phenyl, 4-(pyridin-2-yl)-phenyl, 4-(3-fluoro-pyrrolidin-1-yl)-phenyl, 4-(3,3-difluoro-azetidin-1-yl)-phenyl, 4-(2-oxo-pyrrolidin-1-yl)-phenyl, 4-(2-trifluoromethyl-cyclopropyl)-phenyl, 4-(1-trifluoromethyl-cyclopropyl)-phenyl, 4-((3-fluoro-oxetan-3-yl)-methoxy)-phenyl, 4-(3,3-difluoro-cyclobutyl-oxy)-phenyl, 4-(2,2,2-trifluoro-1,1-dimethyl-ethyl)-phenyl, 4-((3,3-difluoro-cyclobutyl)-methoxy)-phenyl, 4-((3,3-difluoro-1-methyl-cyclobutyl)-methoxy)-phenyl, 2-cyclopropyl-pyridin-5-yl, 2-dimethylamino-pyridin-5-yl, 2-isopropyl-pyridin-5-yl, 2-(ethyl-methyl-amino)-pyridin-5-yl, 2-(3-fluoro-azetidin-1-yl)-pyridin-5-yl, 2-(pyrrolidin-1-yl)-pyridin-5-yl, 2-(cyclopropyl-methyl-amino)-pyridin-5-yl, 2-(3-fluoro-oxetan-3-yl)-pyridin-5-yl, 2-(diethylamino)-pyridin-5-yl, 2-((2,2-difluoro-ethyl)-methyl-amino)-pyridin-5-yl, 2-((2-methoxyethyl)-methyl-amino)-pyridin-5-yl, 2-(2,2,2-trifluoroethoxy)-pyridin-5-yl, 3-fluoro-2-(2,2,2-trifluoroethoxy)-pyridin-5-yl, 3-fluoro-2-(pyrrolidin-1-yl)-pyridin-5-yl, 2-(3-fluoro-pyrrolidin-1-yl)-pyridin-5-yl, 2-((cyclopropylmethyl)-methyl-amino)-pyridin-5-yl, 2-(3,3-difluoro-azetidin-1-yl)-pyridin-5-yl, 2-(3-methoxy-oxetan-3-yl)-pyridin-5-yl, 2-(3,3-difluoro-pyrrolidin-1-yl)-pyridin-5-yl, 2-oxo-2,3-dihydro-benzoxazol-6-yl, 3-oxo-3,4-dihydro-2H-benzo[1,4]oxazin-7-yl, 4-methyl-3-oxo-3,4-dihydro-2H-benzo[1,4]oxazin-7-yl, 3-methyl-2-oxo-2,3-dihydro-benzoxazol-6-yl, 3,3-dimethyl-2-oxo-2,3-dihydro-1H-indol-5-yl, 1,3,3-trimethyl-2-oxo-2,3-dihydro-1H-indol-5-yl, 2,2-dimethyl-2,3-dihydro-benzofuran-6-yl, 2,2-dimethyl-2,3-dihydro-benzofuran-5-yl, 3,3-dimethyl-2,3-dihydro-benzofuran-5-yl, 1-methyl-1H-pyrrolo[2,3-b]pyridin-5-yl, 1,3-dimethyl-1H-pyrrolo[2,3-b]pyridin-5-yl, 1H-indol-5-yl, 1H-indol-6-yl, 1-methyl-1H-indazol-5-yl, 1-methyl-1H-indazol-6-yl, 1-ethyl-1H-indazol-5-yl, 1-ethyl-1H-indazol-6-yl, 1,3-dimethyl-1H-indazol-5-yl, 1-methyl-1H-indol-5-yl, 1-methyl-1H-indol-6-yl, 1,3-dimethyl-1H-indol-5-yl, 1,3-dimethyl-1H-indol-6-yl, 3-cyano-1-methyl-1H-indol-5-yl, 3-isopropyl-1-methyl-1H-indol-5-yl, 3-cyclobutyl-1-methyl-1H-indol-5-yl, 1-methyl-3-trifluoromethyl-1H-indol-5-yl, quinoxalin-6-yl, 2-methyl-1H-benzimidazol-6-yl, 1-methyl-1H-benzimidazol-5-yl, 1-methyl-1H-benzimidazol-6-yl, quinolin-7-yl, 4-methyl-3-(2,2,2-trifluoroethoxy)-phenyl, or 4-fluoro-2-(2,2,2-trifluoroethoxy)-phenyl;

or a pharmaceutically acceptable salt of such a compound.

6. A method according to claim 1, said method comprising the administration to a subject in need thereof of a compound of Formula (I), wherein Y represents a ring nitrogen atom; and $R^2$ represents $(C_{1-4})$alkyl; $(C_{3-6})$cycloalkyl; $(C_{1-4})$alkoxy; $(C_{1-3})$fluoroalkyl; $(C_{1-3})$fluoroalkoxy; $(C_{1-3})$alkoxy-$(C_{2-3})$alkoxy; halogen; or cyano; and $(R^5)_m$ represents one optional substituent independently selected from the group consisting of $(C_{1-4})$alkyl; $(C_{3-6})$cycloalkyl; $(C_{1-4})$alkoxy; halogen; cyano; $(C_{1-3})$fluoroalkyl; and $(C_{1-3})$fluoroalkoxy;

or

Y represents a ring carbon atom; and $R^2$ represents $(C_{1-4})$alkyl; $(C_{3-6})$cycloalkyl; $(C_{1-4})$alkoxy; $(C_{3-6})$cycloalkyl-oxy; $(C_{1-3})$fluoroalkyl; $(C_{1-3})$fluoroalkoxy; halogen; or cyano; and $(R^5)_m$ represents one or two optional substituents independently selected from the group consisting of ($C_{1-4}$)alkyl; ($C_{1-4}$)alkoxy; halogen; cyano; ($C_{1-3}$)fluoroalkyl, and ($C_{1-3}$)fluoroalkoxy;

or a pharmaceutically acceptable salt of such a compound.

7. A method according to claim 1, said method comprising the administration to a subject in need thereof of a compound of Formula (I), wherein Y represents a ring nitrogen atom; and $R^2$ represents ($C_{1-4}$)alkyl; ($C_{3-6}$)cycloalkyl; ($C_{1-4}$)alkoxy; ($C_{1-3}$)fluoroalkyl; ($C_{1-3}$)fluoroalkoxy; ($C_{1-3}$)alkoxy-($C_{2-3}$)alkoxy; halogen; or cyano; and $(R^5)_m$ represents one optional substituent independently selected from the group consisting of ($C_{1-4}$)alkyl; ($C_{3-6}$)cycloalkyl; ($C_{1-4}$)alkoxy; halogen; cyano; ($C_{1-3}$)fluoroalkyl, and ($C_{1-3}$)fluoroalkoxy;

or a pharmaceutically acceptable salt of such a compound.

8. A method according to claim 1, said method comprising the administration to a subject in need thereof of a compound of Formula (I), wherein X represents a ring carbon or a ring nitrogen atom;

$R^1$ represents ($C_{2-6}$)alkyl;

($C_{2-4}$)alkyl mono-substituted with cyano;

($C_{1-4}$)fluoroalkyl;

($C_{3-6}$)cycloalkyl-$L^1$- wherein said ($C_{3-6}$)cycloalkyl optionally contains one ring oxygen atom; wherein said ($C_{3-6}$)cycloalkyl is unsubstituted, or mono-substituted with fluoro, ($C_{1-3}$)alkyl, ($C_{1-3}$)alkoxy, hydroxy, cyano, or ($C_{1-3}$)fluoroalkyl, or di-substituted with fluoro; and the linker $L^1$ represents a direct bond, or ($C_{1-2}$)alkylene; or 5- or 6-membered heteroaryl, independently optionally mono-substituted with ($C_{1-3}$)alkyl;

and $(R^4)_n$ represents one or two optional substituents independently selected from ($C_{1-4}$)alkyl, ($C_{3-6}$)cycloalkyl, ($C_{1-3}$)fluoroalkyl, halogen, and cyano;

or $R^1$ together with $(R^4)_n$ forms an aromatic 5- or 6-membered ring which is fused to the phenyl/pyridine ring to form a bicyclic aromatic ring system selected from indolyl, indazolyl and quinolinyl; wherein said fused 5- or 6-membered aromatic ring part of said aromatic bicyclic ring system independently is optionally further mono- or di-substituted wherein the substituents are independently selected from ($C_{1-3}$)alkyl, ($C_{3-6}$)cycloalkyl, ($C_1$)fluoroalkyl, or cyano;

Y represents a ring carbon or a ring nitrogen atom; and $R^2$ represents ($C_{1-4}$)alkyl; ($C_{3-6}$)cycloalkyl; ($C_{1-4}$)alkoxy; ($C_{3-6}$)cycloalkyl-oxy; ($C_{1-3}$)fluoroalkyl; ($C_{1-3}$)fluoroalkoxy; halogen; or cyano;

and $(R^5)_m$ represents one or two optional substituents independently selected from ($C_{1-4}$)alkyl; ($C_{3-6}$)cycloalkyl; ($C_{1-4}$)alkoxy; halogen; cyano; ($C_{1-3}$)fluoroalkyl; and ($C_{1-3}$)fluoroalkoxy;

or a pharmaceutically acceptable salt of such a compound.

9. A method according to claim 1, said method comprising the administration to a subject in need thereof of a compound of Formula (I), wherein the fragment

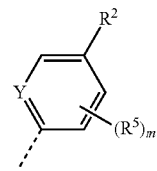

represents 4-fluorophenyl, 4-chlorophenyl, 4-bromophenyl, 4-methylphenyl, 4-ethylphenyl, 3-fluoro-4-methyl-phenyl, 4-fluoro-3-methyl-phenyl, 4-fluoro-3-cyano-phenyl, 4-fluoro-3,5-dimethylphenyl, 4-chloro-3-fluorophenyl, 3-chloro-4-fluorophenyl, 3,4-difluorophenyl, 3,5-difluoro-4-methoxy-phenyl, 4-cyano-3,5-difluoro-phenyl, 4-methoxyphenyl, 4-cyanophenyl, 4-cyclopropyl-phenyl, 3,4,5-trifluorophenyl, 4-tert.-butyl-phenyl, 4-isopropyl-phenyl, 4-(cyclopropyl-oxy)-phenyl, 4-chloro-3-trifluoromethyl-phenyl, 4-fluoro-3-trifluoromethyl-phenyl, 4-methoxy-3-trifluoromethyl-phenyl, 4-difluoromethoxy-phenyl, 4-trifluoromethoxy-phenyl, 4-chloro-3-trifluoromethoxy-phenyl, 4-fluoro-3-trifluoromethoxy-phenyl, 5-fluoro-pyridin-2-yl, 5-bromo-pyridin-2-yl, 5-cyano-pyridin-2-yl, 5-methyl-pyridin-2-yl, 5-ethyl-pyridin-2-yl, 5-methoxy-pyridin-2-yl, 6-chloro-5-fluoro-pyridin-2-yl, 5-cyclopropyl-pyridin-2-yl, 6-cyano-5-fluoro-pyridin-2-yl, 5-cyano-6-fluoro-pyridin-2-yl, 6-chloro-5-cyano-pyridin-2-yl, 5-chloro-6-cyano-pyridin-2-yl, 5-cyano-6-methyl-pyridin-2-yl, 5-cyano-4-methyl-pyridin-2-yl, 6-cyano-5-methyl-pyridin-2-yl, 5-cyano-6-isobutyl-pyridin-2-yl, 5-cyano-6-methoxy-pyridin-2-yl, 5-cyano-6-isopropoxy-pyridin-2-yl, 5-trifluoromethyl-pyridin-2-yl, 5-(2,2,2-trifluoroethoxy)-pyridin-2-yl, 5-cyano-6-(2,2,2-trifluoroethoxy)-pyridin-2-yl, 5-isobutyl-pyridin-2-yl, 5-isopropoxy-pyridin-2-yl, 5-dimethylamino-pyridine-2-yl, 4-cyclopropyl-5-cyano-pyridin-2-yl, 5-(2-methoxy-ethoxy)-pyridin-2-yl, or 5-(3-fluoropyrrolidin-1-yl)-pyridin-2-yl;

or a pharmaceutically acceptable salt of such a compound.

10. A method according to claim 1, said method comprising the administration to a subject in need thereof of a compound selected from the group consisting of N-[1-(4-Chloro-benzyl)-1H-pyrazol-3-yl]-2-(4-isopropyl-phenyl)-acetamide;

N-[1-(4-Chloro-benzyl)-1H-pyrazol-3-yl]-2-(4-dimethylamino-phenyl)-acetamide;

2-(4-Dimethylamino-phenyl)-N-[1-(4-fluoro-benzyl)-1H-pyrazol-3-yl]-acetamide;

N-[1-(4-Chloro-benzyl)-1H-pyrazol-3-yl]-2-(6-dimethylamino-pyridin-3-yl)-acetamide;

N-[1-(4-Fluoro-benzyl)-1H-pyrazol-3-yl]-2-(4-isopropyl-phenyl)-acetamide;

2-(4-Isopropyl-phenyl)-N-[1-(4-methoxy-benzyl)-1H-pyrazol-3-yl]-acetamide;

2-(4-Dimethylamino-phenyl)-N-[1-(4-methoxy-benzyl)-1H-pyrazol-3-yl]-acetamide;

2-(4-Isopropyl-phenyl)-N-[1-(4-methyl-benzyl)-1H-pyrazol-3-yl]-acetamide;

2-(4-Dimethylamino-phenyl)-N-[1-(4-methyl-benzyl)-1H-pyrazol-3-yl]-acetamide;

N-[1-(4-Cyano-benzyl)-1H-pyrazol-3-yl]-2-(4-isopropyl-phenyl)-acetamide;

N-[1-(4-Cyano-benzyl)-1H-pyrazol-3-yl]-2-(4-dimethylamino-phenyl)-acetamide;

2-(4-Dimethylamino-phenyl)-N-[1-(4-ethyl-benzyl)-1H-pyrazol-3-yl]-acetamide;

2-(4-Dimethylamino-phenyl)-N-[1-(4-isopropyl-benzyl)-1H-pyrazol-3-yl]-acetamide;

N-[1-(4-tert-Butyl-benzyl)-1H-pyrazol-3-yl]-2-(4-dimethylamino-phenyl)-acetamide;
N-[1-(4-Difluoromethoxy-benzyl)-1H-pyrazol-3-yl]-2-(4-dimethylamino-phenyl)-acetamide;
2-(4-Dimethylamino-phenyl)-N-[1-(4-trifluoromethoxy-benzyl)-1H-pyrazol-3-yl]-acetamide;
N-[1-(3,4-Difluoro-benzyl)-1H-pyrazol-3-yl]-2-(4-dimethylamino-phenyl)-acetamide;
2-(4-Dimethylamino-phenyl)-N-[1-(4-fluoro-3-trifluoromethoxy-benzyl)-1H-pyrazol-3-yl]-acetamide;
2-(4-Dimethylamino-phenyl)-N-[1-(4-fluoro-3-trifluoromethyl-benzyl)-1H-pyrazol-3-yl]-acetamide;
2-(4-Dimethylamino-phenyl)-N-[1-(3,4,5-trifluoro-benzyl)-1H-pyrazol-3-yl]-acetamide;
2-(4-Dimethylamino-phenyl)-N-[1-(4-fluoro-3,5-dimethyl-benzyl)-1H-pyrazol-3-yl]-acetamide;
N-[1-(4-Chloro-3-fluoro-benzyl)-1H-pyrazol-3-yl]-2-(4-dimethylamino-phenyl)-acetamide;
N-[1-(4-Chloro-3-trifluoromethyl-benzyl)-1H-pyrazol-3-yl]-2-(4-dimethylamino-phenyl)-acetamide;
N-[1-(3,5-Difluoro-4-methoxy-benzyl)-1H-pyrazol-3-yl]-2-(4-dimethylamino-phenyl)-acetamide;
2-(4-Dimethylamino-phenyl)-N-[1-(4-methoxy-3-trifluoromethyl-benzyl)-1H-pyrazol-3-yl]-acetamide;
2-(4-Dimethylamino-phenyl)-N-[1-(4-fluoro-3-methyl-benzyl)-1H-pyrazol-3-yl]-acetamide;
N-[1-(3-Chloro-4-fluoro-benzyl)-1H-pyrazol-3-yl]-2-(4-dimethylamino-phenyl)-acetamide;
2-(4-Dimethylamino-phenyl)-N-[1-(3-fluoro-4-methyl-benzyl)-1H-pyrazol-3-yl]-acetamide;
2-(6-Dimethylamino-pyridin-3-yl)-N-[1-(4-ethyl-benzyl)-1H-pyrazol-3-yl]-acetamide;
2-(6-Dimethylamino-pyridin-3-yl)-N-[1-(4-trifluoromethoxy-benzyl)-1H-pyrazol-3-yl]-acetamide;
2-(6-Dimethylamino-pyridin-3-yl)-N-[1-(3-fluoro-4-methyl-benzyl)-1H-pyrazol-3-yl]-acetamide;
2-(6-Dimethylamino-pyridin-3-yl)-N-[1-(4-fluoro-3-methyl-benzyl)-1H-pyrazol-3-yl]-acetamide;
N-[1-(3-Chloro-4-fluoro-benzyl)-1H-pyrazol-3-yl]-2-(6-dimethylamino-pyridin-3-yl)-acetamide;
2-(6-Dimethylamino-pyridin-3-yl)-N-[1-(3,4,5-trifluoro-benzyl)-1H-pyrazol-3-yl]-acetamide;
N-[1-(4-Chloro-3-fluoro-benzyl)-1H-pyrazol-3-yl]-2-(6-dimethylamino-pyridin-3-yl)-acetamide;
N-[1-(4-Methoxy-benzyl)-1H-pyrazol-3-yl]-2-[4-(2,2,2-trifluoro-ethoxy)-phenyl]-acetamide;
N-[1-(4-Fluoro-benzyl)-1H-pyrazol-3-yl]-2-[4-(2,2,2-trifluoro-ethoxy)-phenyl]-acetamide;
N-[1-(4-Cyano-benzyl)-1H-pyrazol-3-yl]-2-[4-(2,2,2-trifluoro-ethoxy)-phenyl]-acetamide;
2-[4-(3,3-Difluoro-azetidin-1-yl)-phenyl]-N-[1-(4-fluoro-benzyl)-1H-pyrazol-3-yl]-acetamide;
N-[1-(4-Cyano-benzyl)-1H-pyrazol-3-yl]-2-[4-(3,3-difluoro-azetidin-1-yl)-phenyl]-acetamide;
2-[4-(3,3-Difluoro-azetidin-1-yl)-phenyl]-N-[1-(4-methoxy-benzyl)-1H-pyrazol-3-yl]-acetamide;
2-[4-(3,3-Difluoro-azetidin-1-yl)-phenyl]-N-[1-(3,4-difluoro-benzyl)-1H-pyrazol-3-yl]-acetamide;
2-(4-Azetidin-1-yl-phenyl)-N-[1-(4-fluoro-benzyl)-1H-pyrazol-3-yl]-acetamide;
2-(4-Azetidin-1-yl-phenyl)-N-[1-(4-cyano-benzyl)-1H-pyrazol-3-yl]-acetamide;
2-(4-Azetidin-1-yl-phenyl)-N-[1-(4-methoxy-benzyl)-1H-pyrazol-3-yl]-acetamide;
N-[1-(3,4-Difluoro-benzyl)-1H-pyrazol-3-yl]-2-(6-dimethylamino-pyridin-3-yl)-acetamide;
N-[1-(4-Cyano-3-fluoro-benzyl)-1H-pyrazol-3-yl]-2-(4-dimethylamino-phenyl)-acetamide;
2-(4-Azetidin-1-yl-phenyl)-N-[1-(3,4-difluoro-benzyl)-1H-pyrazol-3-yl]-acetamide;
N-[1-(3,4-Difluoro-benzyl)-1H-pyrazol-3-yl]-2-[4-((S)-3-fluoro-pyrrolidin-1-yl)-phenyl]-acetamide;
N-[1-(3,4-Difluoro-benzyl)-1H-pyrazol-3-yl]-2-[4-(3-fluoro-azetidin-1-yl)-phenyl]-acetamide;
2-(4-Cyclopropoxy-phenyl)-N-[1-(4-fluoro-benzyl)-1H-pyrazol-3-yl]-acetamide;
2-(4-Cyclopropoxy-phenyl)-N-[1-(4-methoxy-benzyl)-1H-pyrazol-3-yl]-acetamide;
2-(4-Cyclopropoxy-phenyl)-N-[1-(3,4-difluoro-benzyl)-1H-pyrazol-3-yl]-acetamide;
N-[1-(3,4-Difluoro-benzyl)-1H-pyrazol-3-yl]-2-[4-(3,3-difluoro-pyrrolidin-1-yl)-phenyl]-acetamide;
N-[1-(3,4-Difluoro-benzyl)-1H-pyrazol-3-yl]-2-[4-((R)-3-fluoro-pyrrolidin-1-yl)-phenyl]-acetamide;
N-[1-(4-Cyano-benzyl)-1H-pyrazol-3-yl]-2-[4-((R)-3-fluoro-pyrrolidin-1-yl)-phenyl]-acetamide;
N-[1-(4-Fluoro-benzyl)-1H-pyrazol-3-yl]-2-[4-((R)-3-fluoro-pyrrolidin-1-yl)-phenyl]-acetamide;
N-[1-(5-Cyano-pyridin-2-ylmethyl)-1H-pyrazol-3-yl]-2-(4-isopropyl-phenyl)-acetamide;
N-[1-(4-Cyano-benzyl)-1H-pyrazol-3-yl]-2-[4-(3-fluoro-azetidin-1-yl)-phenyl]-acetamide;
2-[4-(3-Fluoro-azetidin-1-yl)-phenyl]-N-[1-(4-fluoro-benzyl)-1H-pyrazol-3-yl]-acetamide;
N-[1-(4-Cyano-benzyl)-1H-pyrazol-3-yl]-2-[4-((S)-3-fluoro-pyrrolidin-1-yl)-phenyl]-acetamide;
N-[1-(4-Fluoro-benzyl)-1H-pyrazol-3-yl]-2-[4-((S)-3-fluoro-pyrrolidin-1-yl)-phenyl]-acetamide;
N-[1-(4-Cyano-benzyl)-1H-pyrazol-3-yl]-2-[4-(3,3-difluoro-pyrrolidin-1-yl)-phenyl]-acetamide;
2-[4-(3,3-Difluoro-pyrrolidin-1-yl)-phenyl]-N-[1-(4-fluoro-benzyl)-1H-pyrazol-3-yl]-acetamide;
N-[1-(4-Fluoro-benzyl)-1H-pyrazol-3-yl]-2-(4-pyridin-2-yl-phenyl)-acetamide;
N-[1-(4-Fluoro-benzyl)-1H-pyrazol-3-yl]-2-(4-pyridin-3-yl-phenyl)-acetamide;
N-[1-(4-Fluoro-benzyl)-1H-pyrazol-3-yl]-2-(4-pyridin-4-yl-phenyl)-acetamide;
N-[1-(5-Cyano-pyridin-2-ylmethyl)-1H-pyrazol-3-yl]-2-4-((R)-3-fluoro-pyrrolidin-1-yl)-phenyl]-acetamide;
N-[1-(5-Cyano-pyridin-2-ylmethyl)-1H-pyrazol-3-yl]-2-[4-(3,3-difluoro-pyrrolidin-1-yl)-phenyl]-acetamide;
N-[1-(4-Fluoro-benzyl)-1H-pyrazol-3-yl]-2-[4-(5-methyl-pyrimidin-4-yl)-phenyl]-acetamide;
2-(4-Isopropyl-phenyl)-N-{1-[5-(2,2,2-trifluoro-ethoxy)-pyridin-2-ylmethyl]-1H-pyrazol-3-yl}-acetamide;
N-[1-(5-Bromo-pyridin-2-ylmethyl)-1H-pyrazol-3-yl]-2-(4-isopropyl-phenyl)-acetamide;
N-[1-(5-Cyclopropyl-pyridin-2-ylmethyl)-1H-pyrazol-3-yl]-2-(4-isopropyl-phenyl)-acetamide;
2-(4-Isopropyl-phenyl)-N-[1-(5-methyl-pyridin-2-ylmethyl)-1H-pyrazol-3-yl]-acetamide;
N-[1-(5-Isobutyl-pyridin-2-ylmethyl)-1H-pyrazol-3-yl]-2-(4-isopropyl-phenyl)-acetamide;
2-(6-Azetidin-1-yl-pyridin-3-yl)-N-[1-(3,4-difluoro-benzyl)-1H-pyrazol-3-yl]-acetamide;
N-[1-(5-Ethyl-pyridin-2-ylmethyl)-1H-pyrazol-3-yl]-2-(4-isopropyl-phenyl)-acetamide;
N-[1-(5-Isopropoxy-pyridin-2-ylmethyl)-1H-pyrazol-3-yl]-2-(4-isopropyl-phenyl)-acetamide;
N-[1-(5-Fluoro-pyridin-2-ylmethyl)-1H-pyrazol-3-yl]-2-(4-isopropyl-phenyl)-acetamide;

2-(4-Isopropyl-phenyl)-N-[1-(5-trifluoromethyl-pyridin-2-ylmethyl)-1H-pyrazol-3-yl]-acetamide;
N-[1-(6-Chloro-5-cyano-pyridin-2-ylmethyl)-1H-pyrazol-3-yl]-2-(4-isopropyl-phenyl)-acetamide;
2-(4-Diethylamino-phenyl)-N-[1-(4-methoxy-benzyl)-1H-pyrazol-3-yl]-acetamide;
2-(4-Diethylamino-phenyl)-N-[1-(3,4-difluoro-benzyl)-1H-pyrazol-3-yl]-acetamide;
N-[1-(4-Cyano-benzyl)-1H-pyrazol-3-yl]-2-(4-diethylamino-phenyl)-acetamide;
N-[1-(5-Cyano-6-ethyl-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-[6-(3,3-difluoro-pyrrolidin-1-yl)-pyridin-3-yl]-acetamide;
N-[1-(4-Cyano-benzyl)-1H-pyrazol-3-yl]-2-[6-(3,3-difluoro-pyrrolidin-1-yl)-pyridin-3-yl]-acetamide;
2-[6-(3,3-Difluoro-pyrrolidin-1-yl)-pyridin-3-yl]-N-[1-(4-fluoro-benzyl)-1H-pyrazol-3-yl]-acetamide;
2-(6-Diethylamino-pyridin-3-yl)-N-[1-(3,4-difluoro-benzyl)-1H-pyrazol-3-yl]-acetamide;
N-[1-(4-Methoxy-benzyl)-1H-pyrazol-3-yl]-2-{4-[(2-methoxy-ethyl)-methyl-amino]-phenyl}-acetamide;
N-[1-(3,4-Difluoro-benzyl)-1H-pyrazol-3-yl]-2-{4-[(2-methoxy-ethyl)-methyl-amino]-phenyl}-acetamide;
N-[1-(4-Cyano-benzyl)-1H-pyrazol-3-yl]-2-{4-[(2-methoxy-ethyl)-methyl-amino]-phenyl}-acetamide;
N-[1-(4-Fluoro-benzyl)-1H-pyrazol-3-yl]-2-{4-[(2-methoxy-ethyl)-methyl-amino]-phenyl}-acetamide;
N-[1-(5-Cyano-6-methyl-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-[6-((R)-3-fluoro-pyrrolidin-1-yl)-pyridin-3-yl]-acetamide;
N-[1-(4-Fluoro-benzyl)-1H-pyrazol-3-yl]-2-[6-((R)-3-fluoro-pyrrolidin-1-yl)-pyridin-3-yl]-acetamide;
2-[6-(3,3-Difluoro-azetidin-1-yl)-pyridin-3-yl]-N-[1-(3,4-difluoro-benzyl)-1H-pyrazol-3-yl]-acetamide;
2-[6-(3,3-Difluoro-azetidin-1-yl)-pyridin-3-yl]-N-[1-(4-fluoro-benzyl)-1H-pyrazol-3-yl]-acetamide;
N-[1-(4-Fluoro-benzyl)-1H-pyrazol-3-yl]-2-(4-isobutyl-phenyl)-acetamide;
N-[1-(5-Cyano-6-fluoro-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-[6-((S)-3-fluoro-pyrrolidin-1-yl)-pyridin-3-yl]-acetamide;
N-[1-(4-Fluoro-benzyl)-1H-pyrazol-3-yl]-2-[6-((S)-3-fluoro-pyrrolidin-1-yl)-pyridin-3-yl]-acetamide;
N-[1-(4-Chloro-5-cyano-pyridin-2-ylmethyl)-1H-pyrazol-3-yl]-2-(4-isopropyl-phenyl)-acetamide;
2-(4-Cyclopropylmethyl-phenyl)-N-[1-(4-fluoro-benzyl)-1H-pyrazol-3-yl]-acetamide;
N-[1-(3,4-Difluoro-benzyl)-1H-pyrazol-3-yl]-2-[6-(3-fluoro-azetidin-1-yl)-pyridin-3-yl]-acetamide;
2-[6-(3-Fluoro-azetidin-1-yl)-pyridin-3-yl]-N-[1-(4-fluoro-benzyl)-1H-pyrazol-3-yl]-acetamide;
2-[6-(Cyclopropyl(methyl)amino)-pyridin-3-yl]-N-[1-(3,4-difluoro-benzyl)-1H-pyrazol-3-yl]-acetamide;
2-[6-(Cyclopropyl(methyl)amino)-pyridin-3-yl]-N-[1-(4-fluoro-benzyl)-1H-pyrazol-3-yl]-acetamide;
N-[1-(3,4-Difluoro-benzyl)-1H-pyrazol-3-yl]-2-[6-(ethyl-methyl-amino)-pyridin-3-yl]-acetamide;
N-[1-(3,4-Difluoro-benzyl)-1H-pyrazol-3-yl]-2-(6-pyrrolidin-1-yl-pyridin-3-yl)-acetamide;
N-[1-(4-Cyano-benzyl)-1H-pyrazol-3-yl]-2-(6-pyrrolidin-1-yl-pyridin-3-yl)-acetamide;
N-[1-(4-Fluoro-benzyl)-1H-pyrazol-3-yl]-2-(6-pyrrolidin-1-yl-pyridin-3-yl)-acetamide;
N-[1-(3,4-Difluoro-benzyl)-1H-pyrazol-3-yl]-2-{6-[(2-methoxy-ethyl)-methyl-amino]-pyridin-3-yl}-acetamide;
N-[1-(4-Fluoro-benzyl)-1H-pyrazol-3-yl]-2-{6-[(2-methoxy-ethyl)-methyl-amino]-pyridin-3-yl}-acetamide;
2-[6-(Cyclopropylmethyl-methyl-amino)-pyridin-3-yl]-N-[1-(3,4-difluoro-benzyl)-1H-pyrazol-3-yl]-acetamide;
N-[1-(4-Cyano-benzyl)-1H-pyrazol-3-yl]-2-[6-(cyclopropylmethyl-methyl-amino)-pyridin-3-yl]-acetamide;
2-[6-(Cyclopropylmethyl-methyl-amino)-pyridin-3-yl]-N-[1-(4-fluoro-benzyl)-1H-pyrazol-3-yl]-acetamide;
2-[6-(Cyclopropylmethyl-methyl-amino)-pyridin-3-yl]-N-[1-(4-methoxy-benzyl)-1H-pyrazol-3-yl]-acetamide;
2-(6-Diethylamino-pyridin-3-yl)-N-[1-(4-fluoro-benzyl)-1H-pyrazol-3-yl]-acetamide;
N-[1-(3-Chloro-4-fluoro-benzyl)-1H-pyrazol-3-yl]-2-(6-cyclopropyl-pyridin-3-yl)-acetamide;
N-[1-(4-Cyclopropoxy-benzyl)-1H-pyrazol-3-yl]-2-(4-isopropyl-phenyl)-acetamide;
N-[1-(4-Cyano-benzyl)-1H-pyrazol-3-yl]-2-(4-cyclobutoxy-phenyl)-acetamide;
2-(4-Cyclobutoxy-phenyl)-N-[1-(4-fluoro-benzyl)-1H-pyrazol-3-yl]-acetamide;
2-(4-Cyclobutoxy-phenyl)-N-[1-(4-methoxy-benzyl)-1H-pyrazol-3-yl]-acetamide;
2-(4-Cyclobutoxy-phenyl)-N-[1-(5-fluoro-pyridin-2-ylmethyl)-1H-pyrazol-3-yl]-acetamide;
N-[1-(4-Fluoro-benzyl)-1H-pyrazol-3-yl]-2-[4-(1-methoxy-ethyl)-phenyl]-acetamide;
N-[1-(3,4-Difluoro-benzyl)-1H-pyrazol-3-yl]-2-[4-(1-methoxy-ethyl)-phenyl]-acetamide;
N-[1-(3,4-Difluoro-benzyl)-1H-pyrazol-3-yl]-2-quinolin-7-yl-acetamide;
N-[1-(3,4-Difluoro-benzyl)-1H-pyrazol-3-yl]-2-(1H-indol-6-yl)-acetamide;
N-[1-(3,4-Difluoro-benzyl)-1H-pyrazol-3-yl]-2-(4-methyl-3-oxo-3,4-dihydro-2H-benzo[1,4]oxazin-7-yl)-acetamide;
N-[1-(6-Cyano-5-fluoro-pyridin-2-ylmethyl)-1H-pyrazol-3-yl]-2-(4-isopropyl-phenyl)-acetamide;
N-[1-(6-Chloro-5-fluoro-pyridin-2-ylmethyl)-1H-pyrazol-3-yl]-2-(4-isopropyl-phenyl)-acetamide;
N-[1-(3,4-Difluoro-benzyl)-1H-pyrazol-3-yl]-2-(1-methyl-1H-pyrrolo [2,3-b]pyridin-5-yl)-acetamide;
N-[1-(4-Fluoro-benzyl)-1H-pyrazol-3-yl]-2-(1-methyl-1H-pyrrolo [2,3-b]pyridin-5-yl)-acetamide;
N-[1-(3,4-Difluoro-benzyl)-1H-pyrazol-3-yl]-2-(3-methyl-2-oxo-2,3-dihydro-benzoxazol-6-yl)-acetamide;
N-[1-(3,4-Difluoro-benzyl)-1H-pyrazol-3-yl]-2-(1H-indol-5-yl)-acetamide;
N-[1-(3,4-Difluoro-benzyl)-1H-pyrazol-3-yl]-2-(1-methyl-1H-indol-5-yl)-acetamide;
N-[1-(3,4-Difluoro-benzyl)-1H-pyrazol-3-yl]-2-(1-methyl-1H-indol-6-yl)-acetamide;
N-[1-(3,4-Difluoro-benzyl)-1H-pyrazol-3-yl]-2-(1-methyl-1H-indazol-5-yl)-acetamide;
N-[1-(3,4-Difluoro-benzyl)-1H-pyrazol-3-yl]-2-(1-methyl-1H-indazol-6-yl)-acetamide;
N-[1-(3,4-Difluoro-benzyl)-1H-pyrazol-3-yl]-2-[4-(3-fluoro-oxetan-3-yl)-phenyl]-acetamide;
N-[1-(3,4-Difluoro-benzyl)-1H-pyrazol-3-yl]-2-[4-(3-hydroxy-oxetan-3-yl)-phenyl]-acetamide;

N-[1-(3,4-Difluoro-benzyl)-1H-pyrazol-3-yl]-2-[4-(3-methyl-oxetan-3-yl)-phenyl]-acetamide;
N-[1-(3,4-Difluoro-benzyl)-1H-pyrazol-3-yl]-2-(3,3-dimethyl-2-oxo-2,3-dihydro-1H-indol-5-yl)-acetamide;
N-[1-(3,4-Difluoro-benzyl)-1H-pyrazol-3-yl]-2-(1,3,3-trimethyl-2-oxo-2,3-dihydro-1H-indol-5-yl)-acetamide;
N-[1-(3,4-Difluoro-benzyl)-1H-pyrazol-3-yl]-2-[4-(3-methoxy-oxetan-3-yl)-phenyl]-acetamide;
N-[1-(3,4-Difluoro-benzyl)-1H-pyrazol-3-yl]-2-[4-((R)-1-methoxy-ethyl)-phenyl]-acetamide;
N-[1-(3,4-Difluoro-benzyl)-1H-pyrazol-3-yl]-2-[4-((S)-1-methoxy-ethyl)-phenyl]-acetamide;
N-[1-(3,4-Difluoro-benzyl)-1H-pyrazol-3-yl]-2-(4-isopropyl-phenyl)-acetamide;
N-[1-(3,4-Difluoro-benzyl)-1H-pyrazol-3-yl]-2-[4-(5-methyl-[1,2,4]oxadiazol-3-yl)-phenyl]-acetamide;
N-[1-(3,4-Difluoro-benzyl)-1H-pyrazol-3-yl]-2-(4-[1,2,4]oxadiazol-3-yl-phenyl)-acetamide;
N-[1-(3,4-Difluoro-benzyl)-1H-pyrazol-3-yl]-2-[4-(3,3-difluoro-cyclobutyl)-phenyl]-acetamide;
N-[1-(3,4-Difluoro-benzyl)-1H-pyrazol-3-yl]-2-[4-(oxetan-3-yloxy)-phenyl]-acetamide;
N-[1-(4-Bromo-benzyl)-1H-pyrazol-3-yl]-2-(4-dimethylamino-phenyl)-acetamide;
N-[1-(3,4-Difluoro-benzyl)-1H-pyrazol-3-yl]-2-[4-(3,3-difluoro-cyclobutoxy)-phenyl]-acetamide;
N-[1-(3,4-Difluoro-benzyl)-1H-pyrazol-3-yl]-2-[4-(3-methyl-oxetan-3-ylmethoxy)-phenyl]-acetamide;
N-[1-(3,4-Difluoro-benzyl)-1H-pyrazol-3-yl]-2-[4-(oxetan-3-ylmethoxy)-phenyl]-acetamide;
N-[1-(3,4-Difluoro-benzyl)-1H-pyrazol-3-yl]-2-[4-(3,3-difluoro-1-methyl-cyclobutylmethoxy)-phenyl]-acetamide;
N-[1-(3,4-Difluoro-benzyl)-1H-pyrazol-3-yl]-2-[4-(3,3-difluoro-cyclobutylmethoxy)-phenyl]-acetamide;
N-[1-(3,4-Difluoro-benzyl)-1H-pyrazol-3-yl]-2-[4-(3-fluoro-oxetan-3-ylmethoxy)-phenyl]-acetamide;
N-[1-(4-Cyano-benzyl)-1-pyrazol-3-yl]-2-(1-methyl-1H-indazol-5-yl)-acetamide;
N-[1-(4-Cyano-3-fluoro-benzyl)-1H-pyrazol-3-yl]-2-[4-(3-fluoro-oxetan-3-yl)-phenyl]-acetamide;
N-[1-(4-Cyano-3-fluoro-benzyl)-1H-pyrazol-3-yl]-2-(1-methyl-1H-indazol-5-yl)-acetamide;
N-[1-(3,4-Difluoro-benzyl)-1H-pyrazol-3-yl]-2-(1,3-dimethyl-1H-indol-6-yl)-acetamide;
N-[1-(3,4-Difluoro-benzyl)-1H-pyrazol-3-yl]-2-(1,3-dimethyl-1H-indol-5-yl)-acetamide;
N-[1-(4-Cyano-3-fluoro-benzyl)-1H-pyrazol-3-yl]-2-[4-(3,3-difluoro-cyclobutoxy)-phenyl]-acetamide;
2-(4-tert-Butyl-phenyl)-N-[1-(4-cyano-3-fluoro-benzyl)-1H-pyrazol-3-yl]-acetamide;
N-[1-(4-Cyano-3-fluoro-benzyl)-1H-pyrazol-3-yl]-2-[4-(1-trifluoromethyl-cyclopropyl)-phenyl]-acetamide;
N-[1-(4-Cyano-3-fluoro-benzyl)-1H-pyrazol-3-yl]-2-(4-isopropyl-phenyl)-acetamide;
N-[1-(3-Cyano-4-fluoro-benzyl)-1H-pyrazol-3-yl]-2-(1-methyl-1H-indazol-5-yl)-acetamide;
N-[1-(3-Cyano-4-fluoro-benzyl)-1H-pyrazol-3-yl]-2-[4-(3-fluoro-oxetan-3-yl)-phenyl]-acetamide;
2-(4-tert-Butyl-phenyl)-N-[1-(4-cyano-benzyl)-1H-pyrazol-3-yl]-acetamide;
2-(4-tert-Butyl-phenyl)-N-[1-(5-cyano-pyridin-2-ylmethyl)-1H-pyrazol-3-yl]-acetamide;
N-[1-(4-Cyano-benzyl)-1H-pyrazol-3-yl]-2-[4-(3,3-difluoro-cyclobutoxy)-phenyl]-acetamide;
N-[1-(4-Cyano-3-fluoro-benzyl)-1H-pyrazol-3-yl]-2-(6-pyrrolidin-1-yl-pyridin-3-yl)-acetamide;
N-[1-(4-Cyano-benzyl)-1H-pyrazol-3-yl]-2-[4-(1-trifluoromethyl-cyclopropyl)-phenyl]-acetamide;
N-[1-(5-Cyano-pyridin-2-ylmethyl)-1H-pyrazol-3-yl]-2-[4-(1-trifluoromethyl-cyclopropyl)-phenyl]-acetamide;
N-[1-(3-Cyano-4-fluoro-benzyl)-1H-pyrazol-3-yl]-2-[4-(3,3-difluoro-cyclobutoxy)-phenyl]-acetamide;
N-[1-(3-Cyano-4-fluoro-benzyl)-1H-pyrazol-3-yl]-2-(4-isopropyl-phenyl)-acetamide;
2-(4-tert-Butyl-phenyl)-N-[1-(3-cyano-4-fluoro-benzyl)-1H-pyrazol-3-yl]-acetamide;
N-[1-(4-Cyano-3-fluoro-benzyl)-1H-pyrazol-3-yl]-2-[4-(3,3-difluoro-cyclobutyl)-phenyl]-acetamide;
N-[1-(4-Cyano-3-fluoro-benzyl)-1H-pyrazol-3-yl]-2-[4-(3,3-difluoro-cyclobutylmethoxy)-phenyl]-acetamide;
N-[1-(4-Cyano-3-fluoro-benzyl)-1H-pyrazol-3-yl]-2-[4-(3,3-difluoro-1-methyl-cyclobutylmethoxy)-phenyl]-acetamide;
N-[1-(4-Cyano-3-fluoro-benzyl)-1H-pyrazol-3-yl]-2-(1-methyl-1H-indol-5-yl)-acetamide;
N-[1-(4-Cyano-3-fluoro-benzyl)-1H-pyrazol-3-yl]-2-(1-methyl-1H-indol-6-yl)-acetamide;
N-[1-(4-Cyano-3-fluoro-benzyl)-1H-pyrazol-3-yl]-2-[6-(3,3-difluoro-pyrrolidin-1-yl)-pyridin-3-yl]-acetamide;
N-[1-(4-Cyano-benzyl)-1H-pyrazol-3-yl]-2-(1-methyl-1H-indol-5-yl)-acetamide;
N-[1-(4-Cyano-benzyl)-1H-pyrazol-3-yl]-2-(1-methyl-1H-indol-6-yl)-acetamide;
N-[1-(4-Cyano-benzyl)-1H-pyrazol-3-yl]-2-[4-(3,3-difluoro-1-methyl-cyclobutylmethoxy)-phenyl]-acetamide;
N-[1-(4-Cyano-benzyl)-1H-pyrazol-3-yl]-2-[4-(3,3-difluoro-cyclobutylmethoxy)-phenyl]-acetamide;
N-[1-(4-Cyano-benzyl)-1H-pyrazol-3-yl]-2-[4-(3,3-difluoro-cyclobutyl)-phenyl]-acetamide;
N-[1-(5-Cyano-pyridin-2-ylmethyl)-1H-pyrazol-3-yl]-2-(1-methyl-1H-indol-5-yl)-acetamide;
N-[1-(5-Cyano-pyridin-2-ylmethyl)-1H-pyrazol-3-yl]-2-(1-methyl-1H-indol-6-yl)-acetamide;
N-[1-(5-Cyano-pyridin-2-ylmethyl)-1H-pyrazol-3-yl]-2-[4-(3,3-difluoro-1-methyl-cyclobutylmethoxy)-phenyl]-acetamide;
N-[1-(5-Cyano-pyridin-2-ylmethyl)-1H-pyrazol-3-yl]-2-[4-(3,3-difluoro-cyclobutyl)-phenyl]-acetamide;
N-[1-(3-Cyano-4-fluoro-benzyl)-1H-pyrazol-3-yl]-2-[6-(3,3-difluoro-pyrrolidin-1-yl)-pyridin-3-yl]-acetamide;
N-[1-(3-Cyano-4-fluoro-benzyl)-1H-pyrazol-3-yl]-2-(6-pyrrolidin-1-yl-pyridin-3-yl)-acetamide;
N-[1-(3-Cyano-4-fluoro-benzyl)-1H-pyrazol-3-yl]-2-(1-methyl-1H-indol-6-yl)-acetamide;
N-[1-(3-Cyano-4-fluoro-benzyl)-1H-pyrazol-3-yl]-2-(1-methyl-1H-indol-5-yl)-acetamide;
N-[1-(3-Cyano-4-fluoro-benzyl)-1H-pyrazol-3-yl]-2-[4-(3,3-difluoro-cyclobutyl)-phenyl]-acetamide;
N-[1-(3-Cyano-4-fluoro-benzyl)-1H-pyrazol-3-yl]-2-[4-(3,3-difluoro-cyclobutylmethoxy)-phenyl]-acetamide;
N-[1-(3-Cyano-4-fluoro-benzyl)-1H-pyrazol-3-yl]-2-[4-(1-trifluoromethyl-cyclopropyl)-phenyl]-acetamide;
N-[1-(3-Cyano-4-fluoro-benzyl)-1H-pyrazol-3-yl]-2-[4-(3-methyl-oxetan-3-yl)-phenyl]-acetamide;
N-[1-(4-Cyano-benzyl)-1H-pyrazol-3-yl]-2-[4-(3-methyl-oxetan-3-yl)-phenyl]-acetamide;
N-[1-(3-Cyano-4-fluoro-benzyl)-1H-pyrazol-3-yl]-2-[4-(1-methoxy-ethyl)-phenyl]-acetamide;
N-[1-(3-Cyano-4-fluoro-benzyl)-1H-pyrazol-3-yl]-2-(1,3-dimethyl-1H-pyrrolo[2,3-b]pyridin-5-yl)-acetamide;

N-[1-(5-Cyano-pyridin-2-ylmethyl)-1H-pyrazol-3-yl]-2-(3-cyclobutyl-1-methyl-1H-indol-5-yl)-acetamide;
N-[1-(5-Cyano-pyridin-2-ylmethyl)-1H-pyrazol-3-yl]-2-(3-isopropyl-1-methyl-1H-indol-5-yl)-acetamide;
N-[1-(5-Cyano-pyridin-2-ylmethyl)-1H-pyrazol-3-yl]-2-(1-methyl-3-trifluoromethyl-1H-indol-5-yl)-acetamide;
N-[1-(3-Cyano-4-fluoro-benzyl)-1H-pyrazol-3-yl]-2-(3-cyclobutyl-1-methyl-1H-indol-5-yl)-acetamide;
N-[1-(3-Cyano-4-fluoro-benzyl)-1H-pyrazol-3-yl]-2-(3-isopropyl-1-methyl-1H-indol-5-yl)-acetamide;
N-[1-(3-Cyano-4-fluoro-benzyl)-1H-pyrazol-3-yl]-2-(1,3-dimethyl-1H-indol-6-yl)-acetamide;
N-[1-(5-Cyano-pyridin-2-ylmethyl)-1H-pyrazol-3-yl]-2-(1,3-dimethyl-1H-indol-6-yl)-acetamide;
N-(1-(3-cyano-4-fluorobenzyl)-1H-pyrazol-3-yl)-2-(4-(pentafluoro-$\lambda^6$-sulfanyl)phenyl)acetamide;
2-[4-(Cyano-dimethyl-methyl)-phenyl]-N-[1-(3-cyano-4-fluoro-benzyl)-1H-pyrazol-3-yl]-acetamide;
N-(1-((5-cyanopyridin-2-yl)methyl)-1H-pyrazol-3-yl)-2-(4-(pentafluoro-$\lambda^6$-sulfanyl)phenyl)acetamide;
N-[1-(5-Cyano-pyridin-2-ylmethyl)-1H-pyrazol-3-yl]-2-(4-trifluoromethyl-phenyl)-acetamide;
N-[1-(5-Cyano-pyridin-2-ylmethyl)-1H-pyrazol-3-yl]-2-[3-methyl-4-(2,2,2-trifluoro-ethoxy)-phenyl]-acetamide;
N-[1-(3-Cyano-4-fluoro-benzyl)-1H-pyrazol-3-yl]-2-(5-fluoro-6-pyrrolidin-1-yl-pyridin-3-yl)-acetamide;
N-[1-(5-Cyano-pyridin-2-ylmethyl)-1H-pyrazol-3-yl]-2-(5-fluoro-6-pyrrolidin-1-yl-pyridin-3-yl)-acetamide;
N-[1-(3-Cyano-4-fluoro-benzyl)-1H-pyrazol-3-yl]-2-(4-trifluoromethyl-phenyl)-acetamide;
N-[1-(3-Cyano-4-fluoro-benzyl)-1H-pyrazol-3-yl]-2-[3-methyl-4-(2,2,2-trifluoro-ethoxy)-phenyl]-acetamide;
N-[1-(4-Cyano-3,5-difluoro-benzyl)-1H-pyrazol-3-yl]-2-[4-(3,3-difluoro-cyclobutoxy)-phenyl]-acetamide;
N-[1-(4-Cyano-3,5-difluoro-benzyl)-1H-pyrazol-3-yl]-2-(1,3-dimethyl-1H-indazol-5-yl)-acetamide;
N-[1-(4-Cyano-3,5-difluoro-benzyl)-1H-pyrazol-3-yl]-2-[6-(3,3-difluoro-pyrrolidin-1-yl)-pyridin-3-yl]-acetamide;
N-[1-(4-Cyano-3,5-difluoro-benzyl)-1H-pyrazol-3-yl]-2-(6-pyrrolidin-1-yl-pyridin-3-yl)-acetamide;
2-(4-tert-Butyl-phenyl)-N-[1-(4-cyano-3,5-difluoro-benzyl)-1H-pyrazol-3-yl]-acetamide;
N-[1-(4-Cyano-3,5-difluoro-benzyl)-1H-pyrazol-3-yl]-2-(4-isopropyl-phenyl)-acetamide;
2-[4-(1-Cyano-cyclopropyl)-phenyl]-N-[1-(3-cyano-4-fluoro-benzyl)-1H-pyrazol-3-yl]-acetamide;
N-[1-(4-Cyano-3,5-difluoro-benzyl)-1H-pyrazol-3-yl]-2-(1-ethyl-1H-indazol-5-yl)-acetamide;
N-[1-(4-Cyano-3,5-difluoro-benzyl)-1H-pyrazol-3-yl]-2-(1,3-dimethyl-1H-indol-5-yl)-acetamide;
N-[1-(4-Cyano-3,5-difluoro-benzyl)-1H-pyrazol-3-yl]-2-[4-(3,3-difluoro-cyclobutylmethoxy)-phenyl]-acetamide;
N-[1-(6-Cyano-5-fluoro-pyridin-2-ylmethyl)-1H-pyrazol-3-yl]-2-[4-(1-trifluoromethyl-cyclopropyl)-phenyl]-acetamide;
N-[1-(6-Cyano-5-methyl-pyridin-2-ylmethyl)-1H-pyrazol-3-yl]-2-[3-methyl-4-(2,2,2-trifluoro-ethoxy)-phenyl]-acetamide;
2-(4-tert-Butyl-phenyl)-N-[1-(6-cyano-5-methyl-pyridin-2-ylmethyl)-1H-pyrazol-3-yl]-acetamide;
N-[1-(6-Cyano-5-methyl-pyridin-2-ylmethyl)-1H-pyrazol-3-yl]-2-[4-(1-trifluoromethyl-cyclopropyl)-phenyl]-acetamide;
N-[1-(5-Cyano-pyridin-2-ylmethyl)-1H-pyrazol-3-yl]-2-[4-(1-methyl-cyclopropyl)-phenyl]-acetamide;
N-[1-(5-Cyano-pyridin-2-ylmethyl)-1H-pyrazol-3-yl]-2-[4-(2,2,2-trifluoro-1,1-dimethyl-ethyl)-phenyl]-acetamide;
N-[1-(6-Cyano-5-methyl-pyridin-2-ylmethyl)-1H-pyrazol-3-yl]-2-[4-(1-methyl-cyclopropyl)-phenyl]-acetamide;
N-[1-(5-Cyano-pyridin-2-ylmethyl)-1H-pyrazol-3-yl]-2-[4-methyl-3-(2,2,2-trifluoro-ethoxy)-phenyl]-acetamide; and
N-[1-(5-Cyano-pyridin-2-ylmethyl)-1H-pyrazol-3-yl]-2-[4-((1S*,2S*)-2-trifluoromethyl-cyclopropyl)-phenyl]-acetamide;

or a pharmaceutically acceptable salt of such a compound.

11. A method according to claim 1, said method comprising the administration to a subject in need thereof of a compound selected from the group consisting of:

N-[1-(5-Cyano-pyridin-2-ylmethyl)-1H-pyrazol-3-yl]-2-[4-(1-methoxy-cyclopropyl)-phenyl]-acetamide;
N-[1-(5-Cyano-6-difluoromethyl-pyridin-2-ylmethyl)-1H-pyrazol-3-yl]-2-(4-isopropyl-phenyl)-acetamide;
N-[1-(5-cyano-4-difluoromethyl-pyridin-2-ylmethyl)-1H-pyrazol-3-yl]-2-(4-isopropyl-phenyl)-acetamide;
N-[1-(5-Cyano-pyridin-2-ylmethyl)-1H-pyrazol-3-yl]-2-(3,3-dimethyl-2,3-dihydro-benzofuran-6-yl)-acetamide;
N-[1-(5-Cyano-pyridin-2-ylmethyl)-1H-pyrazol-3-yl]-2-(3-methyl-chroman-7-yl)-acetamide;
N-[1-(5-Cyano-3-fluoro-pyridin-2-ylmethyl)-1H-pyrazol-3-yl]-2-[4-(1-trifluoromethyl-cyclopropyl)-phenyl]-acetamide;
2-[4-(1-Cyano-3,3-difluoro-cyclobutyl)-phenyl]-N-[1-(5-cyano-pyridin-2-ylmethyl)-1H-pyrazol-3-yl]-acetamide;
N-[1-(6-Cyano-5-fluoro-pyridin-2-ylmethyl)-1H-pyrazol-3-yl]-2-[3-methyl-4-(2,2,2-trifluoro-ethoxy)-phenyl]-acetamide;
2-(3-Cyano-4-isobutyl-phenyl)-N-[1-(5-cyano-pyridin-2-ylmethyl)-1H-pyrazol-3-yl]-acetamide;
2-(3-Cyano-4-isobutyl-phenyl)-N-[1-(3,4-difluoro-benzyl)-1H-pyrazol-3-yl]-acetamide;
N-[1-(5-Azetidin-1-yl-pyridin-2-ylmethyl)-1H-pyrazol-3-yl]-2-(4-isopropyl-phenyl)-acetamide;
2-(4-Isopropyl-phenyl)-N-[1-(5-pyrrolidin-1-yl-pyridin-2-ylmethyl)-1H-pyrazol-3-yl]-acetamide;
N-{1-[5-(3,3-Difluoro-pyrrolidin-1-yl)-pyridin-2-ylmethyl]-1H-pyrazol-3-yl}-2-(4-isopropyl-phenyl)-acetamide;
N-[1-(5-Cyano-pyridin-2-ylmethyl)-1H-pyrazol-3-yl]-2-(4-cyclopropylmethoxy-3-trifluoromethoxy-phenyl)-acetamide;
2-(4-Cyclopropylmethoxy-3-trifluoromethoxy-phenyl)-N-[1-(3,4-difluoro-benzyl)-1H-pyrazol-3-yl]-acetamide;
N-[1-(4-Cyano-5-fluoro-pyridin-2-ylmethyl)-1H-pyrazol-3-yl]-2-[3-methyl-4-(2,2,2-trifluoro-ethoxy)-phenyl]-acetamide;
2-(4-tert-Butyl-phenyl)-N-[1-(4-cyano-5-fluoro-pyridin-2-ylmethyl)-1H-pyrazol-3-yl]-acetamide;
N-[1-(4-Cyano-5-fluoro-pyridin-2-ylmethyl)-1H-pyrazol-3-yl]-2-(4-isopropyl-phenyl)-acetamide;
N-[1-(4-Cyano-5-fluoro-pyridin-2-ylmethyl)-1H-pyrazol-3-yl]-2-[4-(1-trifluoromethyl-cyclopropyl)-phenyl]-acetamide;

2-[4-(1-Cyano-cyclopropyl)-3-trifluoromethyl-phenyl]-N-[1-(5-cyano-pyridin-2-ylmethyl)-1H-pyrazol-3-yl]-acetamide;

2-[4-(1-Cyano-cyclopropyl)-3-trifluoromethyl-phenyl]-N-[1-(3,4-difluoro-benzyl)-1H-pyrazol-3-yl]-acetamide;

N-[1-(5-Cyano-pyridin-2-ylmethyl)-1H-pyrazol-3-yl]-2-[3-methyl-4-(3,3,3-trifluoro-propoxy)-phenyl]-acetamide;

N-[1-(5-Cyano-pyridin-2-ylmethyl)-1H-pyrazol-3-yl]-2-[3-cyclopropyl-4-(2,2,2-trifluoro-ethoxy)-phenyl]-acetamide;

N-[1-(5-Cyano-pyridin-2-ylmethyl)-1H-pyrazol-3-yl]-2-(3-methyl-4-trifluoromethoxy-phenyl)-acetamide;

N-[1-(6-Cyano-5-fluoro-pyridin-2-ylmethyl)-1H-pyrazol-3-yl]-2-[3-cyclopropyl-4-(2,2,2-trifluoro-ethoxy)-phenyl]-acetamide;

N-[1-(4-Cyano-5-fluoro-pyridin-2-ylmethyl)-1H-pyrazol-3-yl]-2-[3-cyclopropyl-4-(2,2,2-trifluoro-ethoxy)-phenyl]-acetamide;

N-[1-(6-Cyano-5-fluoro-pyridin-2-ylmethyl)-1H-pyrazol-3-yl]-2-(3-methyl-4-trifluoromethoxy-phenyl)-acetamide;

N-[1-(5-Cyano-pyridin-2-ylmethyl)-1H-pyrazol-3-yl]-2-[3-ethyl-4-(2,2,2-trifluoro-ethoxy)-phenyl]-acetamide;

N-[1-(6-Cyano-5-fluoro-pyridin-2-ylmethyl)-1H-pyrazol-3-yl]-2-[3-ethyl-4-(2,2,2-trifluoro-ethoxy)-phenyl]-acetamide;

N-[1-(4-Cyano-5-fluoro-pyridin-2-ylmethyl)-1H-pyrazol-3-yl]-2-[3-ethyl-4-(2,2,2-trifluoro-ethoxy)-phenyl]-acetamide;

N-[1-(5-Cyano-pyridin-2-ylmethyl)-1H-pyrazol-3-yl]-2-[3,5-dimethyl-4-(2,2,2-trifluoro-ethoxy)-phenyl]-acetamide;

N-[1-(6-Cyano-5-fluoro-pyridin-2-ylmethyl)-1H-pyrazol-3-yl]-2-[3,5-dimethyl-4-(2,2,2-trifluoro-ethoxy)-phenyl]-acetamide;

N-[1-(4-Cyano-5-fluoro-pyridin-2-ylmethyl)-1H-pyrazol-3-yl]-2-[3,5-dimethyl-4-(2,2,2-trifluoro-ethoxy)-phenyl]-acetamide;

N-[1-(5-Cyano-pyridin-2-ylmethyl)-1H-pyrazol-3-yl]-2-[5-methyl-6-(2,2,2-trifluoro-ethoxy)-pyridin-3-yl]-acetamide;

N-[1-(6-Cyano-5-fluoro-pyridin-2-ylmethyl)-1H-pyrazol-3-yl]-2-[5-methyl-6-(2,2,2-trifluoro-ethoxy)-pyridin-3-yl]-acetamide;

N-[1-(6-Cyano-5-fluoro-pyridin-2-ylmethyl)-1H-pyrazol-3-yl]-2-[3-methyl-4-(3,3,3-trifluoro-propoxy)-phenyl]-acetamide; and N-[1-(4-Cyano-5-fluoro-pyridin-2-ylmethyl)-1H-pyrazol-3-yl]-2-[3-methyl-4-(3,3,3-trifluoro-propoxy)-phenyl]-acetamide;

or a pharmaceutically acceptable salt of such a compound.

12. A method according to claim 8, said method comprising the administration to a subject in need thereof of a compound of Formula (I), wherein X represents a ring carbon atom;

or a pharmaceutically acceptable salt of such a compound.

13. A method according to claim 12, said method comprising the administration to a subject in need thereof of a compound of Formula (I), wherein $R^1$ represents cyclopropyl wherein said cyclopropyl is unsubstituted, or mono-substituted with methyl, methoxy, cyano, or trifluoromethyl;

or a pharmaceutically acceptable salt of such a compound.

14. A method according to claim 4, said method comprising the administration to a subject in need thereof of a compound of Formula (I), wherein Y represents a ring nitrogen atom;

$R^2$ represents $(C_{1-4})$alkyl; $(C_{3-6})$cycloalkyl; $(C_{1-4})$alkoxy; $(C_{1-3})$fluoroalkyl; $(C_{1-3})$fluoroalkoxy; halogen; or cyano; and $(R^5)_m$ represents one optional substituent selected from the group consisting of $(C_{1-4})$alkyl; $(C_{3-6})$cycloalkyl; $(C_{1-4})$alkoxy; halogen; cyano; $(C_{1-3})$fluoroalkyl; and $(C_{1-3})$fluoroalkoxy;

or a pharmaceutically acceptable salt of such a compound.

15. A method according to claim 13, said method comprising the administration to a subject in need thereof of a compound of Formula (I), wherein Y represents a ring nitrogen atom;

$R^2$ represents $(C_{1-4})$alkyl; $(C_{3-6})$cycloalkyl; $(C_{1-4})$alkoxy; $(C_{1-3})$fluoroalkyl; $(C_{1-3})$fluoroalkoxy; halogen; or cyano; and $(R^5)_m$ represents one optional substituent selected from the group consisting of $(C_{1-4})$alkyl; $(C_{3-6})$cycloalkyl; $(C_{1-4})$alkoxy; halogen; cyano; $(C_{1-3})$fluoroalkyl; and $(C_{1-3})$fluoroalkoxy;

or a pharmaceutically acceptable salt of such a compound.

16. A method according to claim 14, said method comprising the administration to a subject in need thereof of a compound of Formula (I), wherein $(R^5)_m$ is absent (i.e. m=0);

or a pharmaceutically acceptable salt of such a compound.

17. A method according to claim 15, said method comprising the administration to a subject in need thereof of a compound of Formula (I), wherein $(R^5)_m$ is absent (i.e. m=0);

or a pharmaceutically acceptable salt of such a compound.

18. A method according to claim 1, said method comprising the administration to a subject in need thereof of the compound 2-(4-tert-Butyl-phenyl)-N-[1-(5-cyano-pyridin-2-ylmethyl)-1H-pyrazol-3-yl]-acetamide;

or a pharmaceutically acceptable salt of the compound.

19. A method according to claim 1, said method comprising the administration to a subject in need thereof of the compound N-[1-(5-Cyano-pyridin-2-yl-methyl)-1H-pyrazol-3-yl]-2-[4-(1-trifluoromethyl-cyclopropyl)-phenyl]-acetamide;

or a pharmaceutically acceptable salt of the compound.

20. A method according to claim 1, said method comprising the administration to a subject in need thereof of the compound N-[1-(5-Cyano-pyridin-2-yl-methyl)-1H-pyrazol-3-yl]-2-[3-methyl-4-(2,2,2-trifluoro-ethoxy)-phenyl]-acetamide;

or a pharmaceutically acceptable salt of the compound.

21. A method according to claim 1, said method comprising the administration to a subject in need thereof of the compound N-[1-(5-Cyano-pyridin-2-yl-methyl)-1H-pyrazol-3-yl]-2-[3-methyl-4-(3,3,3-trifluoro-propoxy)-phenyl]-acetamide;

or a pharmaceutically acceptable salt of the compound.

22. A method according to claim 1, said method comprising the administration to a subject in need thereof of the compound N-[1-(5-Cyano-pyridin-2-yl-methyl)-1H-pyrazol-3-yl]-2-(3-methyl-4-trifluoromethoxy-phenyl)-acetamide;

or a pharmaceutically acceptable salt of the compound.

23. A method according to claim 1, said method comprising the administration to a subject in need thereof of the compound
N-[1-(5-Cyano-pyridin-2-yl-methyl)-1H-pyrazol-3-yl]-2-[3-ethyl-4-(2,2,2-trifluoro-ethoxy)-phenyl]-acetamide;
or a pharmaceutically acceptable salt of the compound.

24. A method of treating idiopathic generalized epilepsy, said method comprising the administration to a subject in need thereof of a compound of Formula (I)

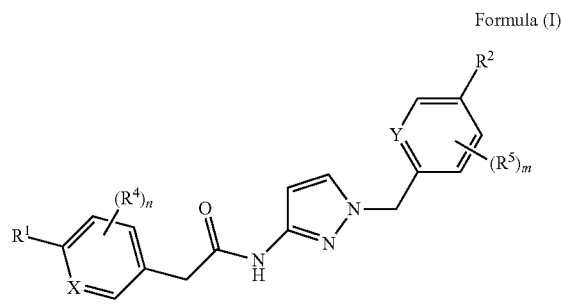

Formula (I)

wherein
X represents a ring carbon or a ring nitrogen atom;
$R^1$ represents
  $(C_{2-6})$alkyl;
  $(C_{2-4})$alkyl mono-substituted with cyano, or $(C_{1-3})$alkoxy;
  $(C_{1-4})$fluoroalkyl;
  $(C_{1-3})$fluoroalkoxy;
  pentafluoro-sulfanyl;
  $(C_{3-6})$cycloalkyl-$L^1$- wherein
    said $(C_{3-6})$cycloalkyl optionally contains one ring oxygen atom; wherein said $(C_{3-6})$cycloalkyl is unsubstituted, or mono-substituted with fluoro, $(C_{1-3})$alkyl, $(C_{1-3})$alkoxy, hydroxy, cyano, or $(C_{1-3})$fluoroalkyl, or di-substituted with fluoro, or tri-substituted with two fluoro substituents and a substituent selected from $(C_{1-3})$alkyl and cyano; and
    the linker $L^1$ represents a direct bond, $(C_{1-2})$alkylene, oxygen, or $(C_{1-2})$alkylene-oxy;
  5- or 6-membered heteroaryl, independently optionally mono-substituted with $(C_{1-3})$alkyl;
  $NR^{11}R^{12}$, wherein
    $R^{11}$ and $R^{12}$ independently represent hydrogen, $(C_{1-3})$alkyl, $(C_{2-3})$fluoroalkyl, $(C_{3-6})$cycloalkyl, $(C_{3-6})$cycloalkyl mono- or di-substituted with fluoro, $(C_{3-6})$cycloalkyl-$(C_{1-3})$alkyl, $(C_{1-3})$alkoxy-$(C_{2-3})$alkyl;
    or $R^{11}$ and $R^{12}$, together with the nitrogen atom to which they are attached, form a 4- to- 6 membered ring optionally mono- or di-substituted with fluoro; a 2-oxo-pyrrolidinyl group; or a morpholinyl group;
  and $(R^4)_n$ represents one or two optional substituents independently selected from $(C_{1-4})$alkyl, $(C_{3-6})$cycloalkyl, $(C_{1-4})$alkoxy, $(C_{1-3})$fluoroalkyl, $(C_{1-3})$fluoroalkoxy, halogen, and cyano;
  or $R^1$ together with $(R^4)_n$ forms a non-aromatic 5- or 6-membered ring which is fused to the phenyl/pyridine ring; wherein said 5- or 6-membered ring optionally contains one or two heteroatoms independently selected from oxygen and nitrogen; wherein said fused 5- or 6-membered non-aromatic ring independently is optionally further mono-substituted with oxo or $(C_{1-3})$alkyl; di-substituted with $(C_{1-3})$alkyl; or di-, tri-, or tetra-substituted wherein one substituent is oxo and the remaining are $(C_{1-3})$alkyl;
  or $R^1$ together with $(R^4)_n$ forms an aromatic 5- or 6-membered ring which is fused to the phenyl/pyridine ring; wherein said 5- or 6-membered ring optionally contains one or two nitrogen atoms, wherein said fused 5- or 6-membered aromatic ring independently is optionally further mono- or di-substituted wherein the substituents are independently selected from $(C_{1-3})$alkyl, $(C_{3-6})$cycloalkyl, $(C_1)$fluoroalkyl, or cyano;
  or $R^1$ represents methyl, or halogen; and $(R^4)_n$ represents one substituent selected from $(C_{1-3})$fluoroalkoxy which is attached to the phenyl/pyridinyl ring in ortho or meta-position to the point of attachment of the —$CH_2$—CO—NH— group;
Y represents a ring carbon or a ring nitrogen atom; and
$R^2$ represents $(C_{1-4})$alkyl; $(C_{3-6})$cycloalkyl; $(C_{1-4})$alkoxy; $(C_{3-6})$cycloalkyl-oxy; $(C_{1-3})$fluoroalkyl; $(C_{1-3})$fluoroalkoxy; $(C_{1-3})$alkoxy-$(C_{2-3})$alkoxy; halogen; cyano; or —$NR^{21}R^{22}$, wherein $R^{21}$ and $R^{22}$ independently represent hydrogen, or $(C_{1-3})$alkyl, or $R^{21}$ and $R^{22}$, together with the nitrogen atom to which they are attached, form a 4- to- 6 membered ring optionally mono- or di-substituted with fluoro, or a morpholinyl group;
and
$(R^5)_m$ represents one or two optional substituents independently selected from $(C_{1-4})$alkyl; $(C_{3-6})$cycloalkyl; $(C_{1-4})$alkoxy; halogen; cyano; $(C_{1-3})$fluoroalkyl; and $(C_{1-3})$fluoroalkoxy;
or a pharmaceutically acceptable salt of such a compound.

25. A method according to claim 24, said method comprising the administration to a subject in need thereof of the compound
2-(4-tert-Butyl-phenyl)-N-[1-(5-cyano-pyridin-2-ylmethyl)-1H-pyrazol-3-yl]-acetamide;
or a pharmaceutically acceptable salt of the compound.

26. A method according to claim 24, said method comprising the administration to a subject in need thereof of the compound
N-[1-(5-Cyano-pyridin-2-ylmethyl)-1H-pyrazol-3-yl]-2-[4-(1-trifluoromethyl-cyclopropyl)-phenyl]-acetamide;
or a pharmaceutically acceptable salt of the compound.

27. A method according to claim 24, said method comprising the administration to a subject in need thereof of the compound
N-[1-(5-Cyano-pyridin-2-ylmethyl)-1H-pyrazol-3-yl]-2-[3-methyl-4-(2,2,2-trifluoro-ethoxy)-phenyl]-acetamide;
or a pharmaceutically acceptable salt of the compound.

28. A method according to claim 24, said method comprising the administration to a subject in need thereof of the compound
N-[1-(5-Cyano-pyridin-2-ylmethyl)-1H-pyrazol-3-yl]-2-[3-methyl-4-(3,3,3-trifluoro-propoxy)-phenyl]-acetamide;
or a pharmaceutically acceptable salt of the compound.

29. A method according to claim 24, said method comprising the administration to a subject in need thereof of the compound
N-[1-(5-Cyano-pyridin-2-ylmethyl)-1H-pyrazol-3-yl]-2-(3-methyl-4-trifluoromethoxy-phenyl)-acetamide;
or a pharmaceutically acceptable salt of the compound.

30. A method according to claim 24, said method comprising the administration to a subject in need thereof of the compound
N-[1-(5-Cyano-pyridin-2-ylmethyl)-1H-pyrazol-3-yl]-2-[3-ethyl-4-(2,2,2-trifluoro-ethoxy)-phenyl]-acetamide; or a pharmaceutically acceptable salt of the compound.

\* \* \* \* \*

UNITED STATES PATENT AND TRADEMARK OFFICE
CERTIFICATE OF CORRECTION

PATENT NO. : 10,065,929 B2
APPLICATION NO. : 15/847611
DATED : September 4, 2018
INVENTOR(S) : Siegrist et al.

Page 1 of 1

It is certified that error appears in the above-identified patent and that said Letters Patent is hereby corrected as shown below:

In the Claims

Column 149, Line 52, Claim 1; delete "$(R^4)n$" and insert -- $(R^4)_n$ --, therefore.

Column 150, Line 35, Claim 3; delete "$(C_{1-33})$fluoroalkoxy" and insert -- $(C_{1-3})$fluoroalkoxy --, therefore.

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*